US009650425B2

(12) United States Patent
Dale et al.

(10) Patent No.: US 9,650,425 B2
(45) Date of Patent: May 16, 2017

(54) GROUP A STREPTOCOCCAL M-RELATED PROTEINS AND METHODS OF USE

(71) Applicant: University of Tennessee Research Foundation, Knoxville, TN (US)

(72) Inventors: James B. Dale, Memphis, TN (US); Harry S. Courtney, West Memphis, AR (US)

(73) Assignee: UNIVERSITY OF TENNESSEE RESEARCH FOUNDATION, Knoxville, TN (US)

(*) Notice: Subject to any disclaimer, the term of this patent is extended or adjusted under 35 U.S.C. 154(b) by 0 days.

(21) Appl. No.: 14/178,021

(22) Filed: Feb. 11, 2014

(65) Prior Publication Data

US 2014/0227313 A1   Aug. 14, 2014

Related U.S. Application Data

(60) Provisional application No. 61/918,460, filed on Dec. 19, 2013, provisional application No. 61/764,771, filed on Feb. 14, 2013, provisional application No. 61/763,314, filed on Feb. 11, 2013.

(51) Int. Cl.
    *A61K 39/00*  (2006.01)
    *C07K 14/315* (2006.01)
    *A61K 38/16*  (2006.01)
    *A61K 39/09*  (2006.01)

(52) U.S. Cl.
    CPC .......... *C07K 14/315* (2013.01); *A61K 38/164* (2013.01); *A61K 39/092* (2013.01); *A61K 2039/55505* (2013.01); *A61K 2039/58* (2013.01); *A61K 2039/6081* (2013.01); *A61K 2039/70* (2013.01); *C07K 2319/00* (2013.01)

(58) Field of Classification Search
    None
    See application file for complete search history.

(56) References Cited

U.S. PATENT DOCUMENTS

| 4,284,537 A | 8/1981 | Beachey |
| 4,454,121 A | 6/1984 | Beachey |
| 4,521,334 A | 6/1985 | Beachey |
| 4,597,967 A | 7/1986 | Beachey |
| 4,705,684 A | 11/1987 | Beachey |
| 4,919,930 A | 4/1990 | Beachey et al. |
| 5,124,153 A | 6/1992 | Beachey et al. |
| 6,063,386 A | 5/2000 | Dale et al. |
| 6,419,932 B1 | 7/2002 | Dale |
| 6,716,433 B1 | 4/2004 | Dale |
| 7,063,850 B1 | 6/2006 | Dale |
| 7,074,416 B2 | 7/2006 | Dale |
| 7,160,547 B2 | 1/2007 | Dale |
| 7,255,863 B2 | 8/2007 | Dale |
| 7,270,827 B2 | 9/2007 | Reddish et al. |
| 7,402,316 B2 | 7/2008 | Dale |
| 7,407,664 B2 | 8/2008 | Beall et al. |
| 7,638,136 B2 * | 12/2009 | Meinke et al. ............ 424/244.1 |
| 7,811,585 B2 | 10/2010 | Martin et al. |
| 7,883,710 B2 | 2/2011 | Beall et al. |
| 2009/0035259 A1 | 2/2009 | Dale |
| 2012/0321657 A1 | 12/2012 | Dale |

FOREIGN PATENT DOCUMENTS

WO      00/37648 A1      6/2000
WO   2012/174455 A2    12/2012

OTHER PUBLICATIONS

Colman (Res. Immunol., 145:33-36, 1994).*
Ahmed et al., "Streptococcal protective antigens (Spa): a new family of type-specific proteins of group A streptococci," *European Journal of Clinical Microbiology & Infectious Diseases* 29(1):51-57, Jan. 2010.
Bessen et al., "Genetic Correlates of Throat and Skin Isolates of Group A Streptococci," *The Journal of Infectious Diseases* 173:896-900, 1996.
Bisno et al., "M Proteins of Group G Streptococci Isolated from Bacteremic Human Infections," *Infection and Immunity* 55(3):753-757, Mar. 1987.
Bisno et al., "M Proteins of Group C Streptococci Isolated from Patients with Acute Pharyngitis," *Journal of Clinical Microbiology* 34(10): 2511-2515, Oct. 1996.
Brandt et al., "Human Infections Due to *Streptococcus dysgalactiae* Subspecies *equisimilis*," *Emerging Infections* 49(5):766-772, Sep. 2009.
Bronze et al., "Epitopes of streptococcal M proteins that evoke antibodies that cross-react with human brain," *Journal of Immunology* 151(5):2820-2828, Sep. 1, 1993.
Broyles et al., "Population-Based Study of Invasive Disease Due to β-Hemolytic Streptococci of Groups Other than A and B," *Clinical Infectious Diseases* 48:706-712, Mar. 2009.
Carapetis et al., "The global burden of group A streptococcal diseases," *The Lancet Infectious Diseases* 5(11):685-594, Nov. 2005.
Collins et al., "Group G Streptococcal M Protein Exhibits Structural Features Analogous to Those of Class I M Protein of Group A Streptococci," *Infection and Immunity* 60(9):3689-3696, Sep. 1992.
Courtney et al., "Anti-phagocytic mechanisms of *Streptococcus pyogenes*: binding of fibrinogen to M-related protein," *Molecular Microbiology* 59(3):936-947, 2006.
Cunningham, "Pathogenesis of Group A Streptococcal Infections," *Clin. Microbiol. Rev.* 13(3):470-511, 2000.
Dale, "Current Status of Group A Streptococcal Vaccine Development," *Advances in Experimental Medicine and Biology* 609:53-63, 2008.
Dale, "Group A streptococcal vaccines," *Infectious Disease Clinics of North America* 13(1):227-243, Mar. 1999, 18 pages.
Dale et al., "Multiple, heart-cross-reactive epitopes of streptococcal M proteins," *Journal of Experimental Medicine* 161(1):113-122, Jan. 1, 1985.

(Continued)

*Primary Examiner* — Brian J Gangle
(74) *Attorney, Agent, or Firm* — Seed IP Law Group LLP

(57) ABSTRACT

Immunogenic group A streptococcus M-related polypeptides and peptides and immunogenic compositions comprising these M-related polypeptides and peptides are provided herein that evoke cross-opsonic and cross-protective anti-GAS and anti-SDSE antibodies in animals. Also provided are preparations comprising immunogenic compositions that comprise M-related polypeptides, peptides, or fusion proteins and that further comprise at least one additional group A streptococcus immunogen, such as an M peptide or Spa peptide.

32 Claims, 17 Drawing Sheets

(56) References Cited

OTHER PUBLICATIONS

Dale et al., "Multivalent Group A Streptococcal Vaccine Elicits Bactericidal Antibodies against Variant M Subtypes," *Clinical and Diagnostic Laboratory Immunology* 12(7):833-836, Jul. 2005.
Dale et al., "New 30-Valent M Protein-Based Vaccine Evokes Cross-Opsonic Antibodies Against Non-Vaccine Serotypes of Group A Streptococci," *Vaccine*. Oct. 26, 2011; 29(46):8175-8178. doi:10.1016/j.vaccine.2011.09.005., 9 pages.
Dale et al., "New protective antigen of group A streptococci," *Journal of Clinical Investigation* 103(9):1261-1268, May 1, 1999.
Dale et al., "Protective antigenic determinant of streptococcal M protein shared with sarcolemmal membrane protein of human heart," *Journal of Experimental Medicine* 156(4):1165-1176, Oct. 1, 1982.
Efstratiou, "Pyogenic Streptococci of Lancefield Groups C and G as Pathogens in Man," *Journal of Applied Microbiology Symposium Supplement* 83:72S-79S, 1997.
Facklam et al., "*emm* Typing and Validation of Provisional M Types for Group A Streptococci," *Emerging Infectious Diseases* 5(2):247-253, Apr.-Jun. 1999.
Fritzer et al., "Novel Conserved Group A Streptococcal Proteins Identified by the Antigenome Technology as Vaccine Candidates for a Non-M Protein-Based Vaccine," *Infection and Immunity* 78(9):4051-4067, Sep. 2010.
Hu et al., "Immunogenicity of a 26-Valent Group A Streptococcal Vaccine," *Infection and Immunity* 70(4):2171-2177, Apr. 2002.
Husmann et al., "Expression of the Arp protein, a member of the M protein family, is not sufficient to inhibit phagocytosis of *Streptococcus pyogenes*," *Infection and Immunity* 63(1):345-348, Jan. 1995.
Johnsson et al., "Identification of the IgA-binding region in streptococcal protein Arp," *Journal of Immunology* 153(8):3557-3564, Oct. 15, 1994.
Kellermayer et al., "Release of Potassium, Lipids, and Proteins From Nonionic Detergent Treated Chicken Red Blood Cells," *Journal of Cellular Physiology* 159:197-204, 1994.
Kotloff et al., "Safety and Immunogenicity of a Recombinant Multivalent Group A Streptococcal Vaccine in Healthy Adults," (Reprinted) *Journal of the American Medical Association* 292(6):709-715, Aug. 11, 2004.
Lei et al., "Identification of New Candidate Vaccine Antigens Made by *Streptococcus pyogenes*: Purification and Characterization of 16 Putative Extracellular Lipoproteins," *The Journal of Infectious Diseases* 189:79-89, 2004.
Luca-Harari et al., "Clinical and Microbiological Characteristics of Severe *Streptococcus pyogenes* Disease in Europe," *Journal of Clinical Microbiology* 47(4):1155-1165, Apr. 2009.
McLellan et al., "Spa Contributes to the Virulence of Type 18 Group A Streptococci," *Infection and Immunity* 69(5):2943-2949, May 2001.
McNeil et al., "Safety and Immunogenicity of 26-Valent Group A *Streptococcus* Vaccine in Healthy Adult Volunteers," *Clinical Infectious Diseases* 41:000-000, Oct. 15, 2005, 9 pages.
O'Loughlin et al., "The Epidemiology of Invasive Group A Streptococcal Infection and Potential Vaccine Implications: United States, 2000-2004," *Clinical Infectious Diseases* 45(7):853-862, Oct. 1, 2007.
Severin et al., "Proteomic Analysis and Identification of *Streptococcus pyogenes* Surface-Associated Proteins," *Journal of Bacteriology* 189(5):1514-1522, Mar. 2007.
Shulman et al., "Group A Streptococcal Pharyngitis Serotype Surveillance in North America, 2000-2002," *Clinical Infectious Diseases* 39(3):325-332, Aug. 1, 2004.
Shulman et al., "Seven-Year Surveillance of North American Pediatric Group A Streptococcal Pharyngitis Isolates", *Clinical Infectious Diseases* 49(1):78-84, Jul. 1, 2009.
Steer et al., "Global *emm* type distribution of group A streptococci: systematic review and implications for vaccine development," *The Lancet Infectious Diseases* 9(10):611-616, Oct. 2009.
Steer et al., "Group A streptococcal vaccines: facts versus fantasy," *Current Opinion in Infectious Diseases* 22(6):544-552, 2009.
Vandamme et al., "Taxonomic Study of Lancefield Groups C, G, and L (*Streptococcus dysgalactiae*) and Proposal of *S. dysgalactiae* subsp. *equisimilis* subsp. nov.," *International Journal of Systematic Bacteriology* 46(3):774-781, Jul. 1996.
Yung et al., "DNA Sequencing and Gene Expression of the emm Gene Cluster in an M50 Group A *Streptococcus* Strain Virulent for Mice," *Infection and Immunity* 64(6):2193-2200, 1996.
Green et al., "Genome Sequence of a Serotype M28 Strain of Group A *Streptococcus*: Potential New Insights into Puerperal Sepsis and Bacterial Disease Specificity," *JID* 192: 760-770, Sep. 1, 2005.
Heath et al., "Fc-receptor and M-protein genes of group A streptococci are products of gene duplication" *Proc. Natl. Acad. Sci. USA* 86: 4741-4745, Jun. 1989.
Krebs et al., "Different alleles of the *fcrA/mrp* gene of *Streptococcus pyogenes* encode M-related proteins exhibiting an identical immunoglobulin-binding pattern," *Med. Microbiol. Immunol .185*: 39-47, 1996.
O'Toole et al., "Two major classes in the M protein family in group A streptococci," *Proc. Natl. Acad. Sci. USA* 89: 8661-8665, Sep. 1992.
Podbielski et al., "Immunoglobulin-biinding FcrA and Enn proteins and M proteins of group A streptococci evolved independently from a common ancestral protein," *Med. Microbiol. Immunol. 183*: 33-42, 1994.
Podbielski et al., "The Group A Streptococcal *virR49* Gene Controls Expression of Four Structural *vir* Regulon Genes," *Infection and Immunity* 63(1): 9-20, Jan. 1995.
Podbielski et al., "M-related protein (Mrp) contributes to group A streptococcal resistance to phagocytosis by human granulocytes," *Molecular Microbiology* 19(3):429-441, 1996.

* cited by examiner

```
Mrp2, 425 amino acids
MSKRNPNKHY SLRKLKTGTA SVAVALTVGG TGLANTTDVK AETVGRFSDE QVRKAREKAI
EDVFDGYTGA RSVYQSGNLP NRLTPTKLSK LMQQMYKETL QKKEELDTLS KALTHTIEKK
IESENAYKKE LGQLKAAAEA EAQKALDALN NKNKQISDLT TENAQLKEAI EGYVQTIQNA
SREIAAKQQE LAAAKSQLEA KNAEIEALKQ QDASKTEELA KLQSEAATLE NLLGSAKREL
TELQAKLDTA TAEKAKLESQ VTTLENLLGS AKRELTDLQA KLDAANAEKE KLQSQAAALE
KQLEATKKEL ADLQAKLAAT NQGKEKLEAE AKALKEQLAK QAEELAKLKA DKASGGQKPD
TKPGNKEVPT RPSQTRTNTN KAPMAQTKRQ LPSTGEETTN PFFTAAALTV IASAGVLALK
RKEEN
```

*FIG. 1A*

```
Mrp2U, 99 amino acids
METVGRFSDE QVRKAREKAI EDVFDGYTGA RSVYQSGNLP NRLTPTKLSK LMQQMYKETL
QKKEELDTLS KALTHTIEKK IESENAKLAA ALEHHHHHH
```

*FIG. 1B*

```
Mrp49, 415 amino acids
MSTRNPNKHY SLRKLKTGTA SVAVALTVLG TGLANTTDVK ADLSTQEHPR VTKAREEALE
EVLRSWDYGS VKAALAGSYR KNLQLENTIK QKDKELSFLS KVLDEAAKKY RESSDKYKQE
IGQLKAAAEA EAQKALDALN NKNKQISDLT NENAQLKEAI EGYVQTIQNA SREIAAKQQE
LAAVKSQLEA KNAEIEDLKQ QDASKTEEIA NLQSEAATLE NLLGSAKHEL TDLQAKLDTA
TAEKAKLESQ ETTLENLLGS AKRELTDLQA KLDDANAEKE KLQSQAAALE KQLEATKKEL
ADLQAKLAAT NQEKEKLEAE AKALKEQLAK QVEELAKLKA DKASGAQKPD TKPDNKEVPT
RPSQTRTNTN KAPMPQTKRQ LPSTGEETTN PFFTAAALTV IASAGVLALK RKEEN
```

*FIG. 1C*

```
Mrp49U, 89 amino acids
MDLSTQEHPR VTKAREEALE EVLRSWDYGS VKAALAGSYR KNLQLENTIK QKDKELSFLS
KVLDEAAKKY RESSDKKLAA ALEHHHHHH
```

*FIG. 1D*

```
Mrp4, 388 amino acids
MSKRNPNKLYSLRKLKTGTASVAVALTVLGTGLANTTDVKAESRRYQAPPRVLLQGKEANKVFEERK
ALEKQARDLGDTINHMSQTISEQSRKIAALKSEAELKNQQALEALNNKNKQISDLTNENAQLKEAIE
GYVQTIQNASREIAAKQQELAAAKSQLEAKNAEIEALKQQDASKTEEIAKLQSEAATLENLLGSAKR
ELTELQAKLDTATAEKAKLESQVTTLENLLGSAKRELTDLQAKLDAANAEKEKLQSQAATLEKQLEA
TKKELADLQAKLAATNQEKEKLEAEAKALKEQLAKQAEELAKLKADKASGAQKPDTKPGNKEVPTRP
SQTRTNTNKAPMAQTKRQLPSTGEETTNPFFTAAALTVIASAGVLALKRKEEN
```

*FIG. 1E*

```
Mrp4U, 145 amino acids
mggshhhhhh  gmasmtggqq  mgrdlydddd  kdrwgsESRR   40
YQAPPRVLLQ  GKEANKVFEE  RKALEKQARD  LGDTINHMSQ   80
TISEQSRKIA  ALKSEAELKN  QQALEALNNK  NKQISDLgse  120
leicswyhmg  irslavlade  rrfsa
```

*FIG. 1F*

```
Mrp2U
atgGAGACCG  TAGGTCGCTT  TAGTGATGAA  CAAGTTAGAA   40
AGGCTCGTGA  AAAAGCAATC  GAAGACGTGT  TTGATGGCTA   80
TACTGGAGCT  CGTTCTGTTT  ATCAATCTGG  GAATCTGCCT  120
AATAGGTTAA  CTCCTACAAA  ACTTAGCAAA  TTAATGCAAC  160
AGATGTATAA  GGAGACTTTA  CAAAAGAAAG  AAGAACTGGA  200
TACCCTATCT  AAAGCTCTTA  CGCACACTAT  TGAGAAAAAG  240
ATTGAGTCAG  AAAATGCTct  cgagttggcc  gcactcgagc  280
accaccacca  ccaccactga  300
```

*FIG. 1G*

```
Mrp4U
ATGGGGGGTT CTCATCATCA TCATCATCAT GGTATGGCTA   40
GCATGACTGG TGGACAGCAA ATGGGTCGGG ATCTGTACGA   80
CGATGACGAT AAGGATCGAT GGggatccGA GAGTCGTCGT  120
TATCAGGCAC CTCCTCGTGT GTTACTGCAA GGCAAAGAAG  160
CTAACAAAGT ATTCGAAGAG CGCAAAGCCT TGGAAAAACA  200
AGCACGTGAT TTGGGTGACA CTATTAACCA CATGTCACAA  240
ACCATTAGCG AGCAAAGCCG CAAGATTGCA GCACTAAAGT  280
CTGAAGCAGA ACTTAAAAAC CAACAAGCTC TTGAAGCTTT  320
AAACAATAAA AACAAGCAAA TCTCAGATTT AggatccGAG  360
CTCGAGATCT GCAGCTGGTA CCATATGGGA ATTCGAAGCT  400
TGGCTGTTTT GGCGGATGAG AGAAGATTTT CAGCCTGA   438
```

FIG. 1H

```
Mrp49U
atgGACTTAA GTACTCAGGA ACATCCTAGA GTAACAAAAG   40
CGAGAGAAGA AGCTCTCGAG GAAGTTTTAC GTAGTTGGGA   80
TTATGGATCT GTAAAAGCTG CTTTGGCAGG CTCTTATCGT  120
AAAAACTTAC AACTTGAAAA CACTATTAAG CAGAAAGATA  160
AAGAATTATC TTTCTTATCC AAAGTTTTGG ATGAGGCTGC  200
AAAAAAATAT AGAGAATCTA GCGACAAGaa gcttgcggcc  240
gcactcgagc accaccacca ccaccactga   270
```

FIG. 1I

```
Mrp101        ESRG-YQVPPRVLLPGKEA------------------------------------NKVFEERKALEKQARELGDTINHMSQTISEQSRKIAALKSEAELKNQQALEA
MrpAla49      ESRG-YQVPPRVLLPGKEA------------------------------------NKVFEERKALEKQARELGDTINHMSQTISEQSRKIAALKSEAELKNQQALEA
Mrp100.2      ESRG-YQVPPRVLLPGKEA------------------------------------NKVFEERKALEKQARELGDTINHMSQTISEQSRKIAALKSEAELKNQQALEA
Mrp80         ESRG-YQVPPRVLLPGKEA------------------------------------NKVFEERKALEKQARELGDTINHMSQTISEQSRKIAALKSEAELKNQQALEA
Mrp64         ESRG-YQVPPRVLLPGKEA------------------------------------NKVFEERKALEKQARELGDTINHMSQTISEQSRKIAALKSEAELKNQQALEA
Mrp116        ESRG-YQAPPRVLLPGKEA------------------------------------NKVFEERKALEKQARELGDTINHMSQTISEQSRKIAALKSEAELKNQQALEA
Mrp121        ESRG-YQAPPRVLLPGKEA------------------------------------NKVFEERKALEKQARELGDTINHMSQTISEQSRKIAALKSEAELKNQQALEA
MrpNS88.2     ESRG-YQAPPRVLLPGKEA------------------------------------NKVFEERKALEKQARELGDTINHMSQTISEQSRKIAALKSEAELKNQQALEA
Mrp15         EGRG-YQVPPRAPLPGKEA------------------------------------NKVFEERKALEKQARDLGDTINHMSQTISEQSRKIAALKSEAELKNQQALEA
Mrp15B106     EGRG-YQVPPRVLLPGKEA------------------------------------NKVFEERKALEKQARDLGDTINHMSQTISEQSRKIAALKSEAELKNQQALEA
MrpST4547     ESRG-YQVPPRVLLPGKEA------------------------------------NKVFEERKALEKQARDLGDTINHMSQTISEQSRKIAALKSEAELKNQQALEA
Mrp4          ESRR-YQAPPRVLLQGKEA------------------------------------NKVFEERKALEKQARDLGDTINHMSQTISEQSRKIAALKSEAELKNQQALEA
Mrp22         ESRR-YQAPPRVLLQGKEA------------------------------------NKVFEERKALEKQAHDLGDTINHMSQIISEKSRKIAALKSEAELKNQQALEA
Mrp25         ET------EHLDVVLSAKEA------------------------------------NKVFEERKALEKQAHDLGDTINHMSQIISEKSRKIAALKSEAELKNQQALEA
Mrp81.2       ET------EHLDVVLSAKEA------------------------------------NKVFEERKALEKQARDLGDTINHMSQTISEQSRKIAALKSEAELKNQQALEA
Mrp8          ET------EHVDVVLSAKEA------------------------------------NKVFEERKALEKQARDLGDTINHMSQTISEQSRKIAALKSEAELKNQQALEA
Mrp28         ET------EHLDVVLSAKEA------------------------------------NKVFEERKALEKQARDLGDTINHMSQTISEQSRKIAALKSEAELKNQQALEA
Mrp67         KT------EHLDVVLSAKEA------------------------------------NKVFEERKALEKQARDLGDTINHMSQTISEQSRKIAALKSEAELKNQQALEA
Mrp124        KT------EHLDVVLSAKEA------------------------------------NKVFEERKALEKQARDLGDTINHMSQTISEQSRKIAALKSEAELKNQQALEA
Mrp2          ETVG-RFSDEQVRKAREKAIEDVFDGYTGARSVYQSGNLPNRLTPTKLSKLMQQMYKETLQKKEELDTLSKALTHTIEKKIESENAYKKELGQLKAAAEAEAQKALDA
Mrp76         ETVG-RFSDEQVRKAREKAIEDVFDGYTGARSVYQSGNLPNRLTPTKLSKLMQQMYKETLQKKEELDTLSKALTHTIEKKIESENAYKKELGQLKAAAEAEAQKALDA
Mrp50         ETVG-RFSDEQVRKAREKAIEDVFDGYTGARSVYQSGNLPNRLTPTKLSKLMQQMYKETLQKKEELDTLSKALTDTIEKKIESENAYKKELGQLKAAAEAEAQKALDA
Mrp42         ETLG-RFSDEQVRKAREKAIEDVFDGYTGARSVYQSGDLPNRLTPTKLSKLMQQMYKETLQKKEELDTLSKAPTDTIEKKIESENAYKKELGQLKAAAEAEAQKALDA
Mrp65         ETLG-RFSDEQVRKAREKAIEDVFDGYTGARSVYQSGDLPNRLTPTKLSKLMQQMYKETLQKKEELDTLSKALTDTIEKKIESENVYKKELGQLKAAAEAEAQKALDA
Mrp13         ENRTPRFTAEEFKKAREKVIKEMFDDYTGATSRHYSNGYQ-RMTPSQLSNLMQGMFRETLQKKEELDTLSKALTHTIEKKIESENAYKKELGQLKAAAEAEAQKALDA
Mrp9          DLS--TQENPRVTEAREKALEEVIAKMP------FEELQHTLAGSYRKNR--ELEKTIEKKDSEASFLSKVLDETAKKYRESSDKYKQEIGQLKAAAEAEAQKALDA
Mrp123        DFS--TQENPRVTEAREKALEEVITNMS------LEELQHTLAGSYRKNR--ELEKTIEKKDGEASFLSKVLDETAKRYRESSDKYKQEIGQLKAAAEAEAQKALDA
Mrp49         DLS--TQEHPRVTKAREEALEEVLRSWD------YGSVKAALAGSYRKNL--QLENTIKQDKELSFLSKVLDEAAKKYRESSDKYKQEIGQLKAAAEAEAQKALDA
Mrp52         DLS--TQEHPRVTKAREEALEEVLRSWD------YGSVKAALAGSYRKNL--QLENTIKQDKELSFLSKVLDEAAKKYRESSDKYKQEIGQLKAAAEAEAQKALDA
Mrp59         DLS--TQEHPRVTKAREEALEEVLRSWD------YGSVRAALAGSYRKNL--QLENTIKQDKELSFLSKVLDEAAKKYRESSDKYKQEIGQLKAAAEAEAQKALDA
```

*FIG. 2*

```
            10        20        30        40        50        60
Mrp2    ETVGRFSDEQVRKAREKAIEDVFDGYTGARSVYQSGNLPNRLTPTKLSKLMQQMYKETLQ
        ..:::...:.:.:.:.....::  ::::  :.:.: :   .:  :::.::.::  ::.. :
stL1929 QSVGRFNEDQIREARDKVLKEMFDDYTGATSIYNS-NGYGRKTPTELSNLMQGMYRDLLA
            30        40        50        60        70        80

70        80
Mrp2    KKEELDTLSKALTHTIEKKIESENA
        :::::.  :.   :..::.:::::.::
stL1929 KKEELSFLNDELSRTIDKKIESDNA
            90        100
```

FIG. 14A

```
            50        60        70        80
Mrp2    LTPTKLSKLMQQMYKETLQKKEELDTLSKALTHTIEKKIESE
        :    ...:....  ..  ...::  .::::.:  :  .:...  ::   .:
stG1389 LLNKRINKLQEDLANKEQESKETIDTLNKILDETVKDKIAKE
            50        60        70        80
```

FIG. 14B

```
            40        50        60        70        80
Mrp4    QARDLGDTINHMSQTISEQSRKIAALKSEAELKNQQALEALNNKNKQISD
        .:  :::...  ::   . .  .  :.   :::....:   :.::::: .:  .:   ::
stG7882 RANDLNSQRNHEIERLEDLKSKFEKLKAHSEKYFQEALEAEENFDKYTSD
            30        40        50        60
```

FIG. 14C

```
          10        20        30        40        50        60
Mrp49   DLSTQEHPRVTKAREEALEEVLRSWDYGSVKAALAGSYRKNLQLENTIKQKDKELSFLSK
        ......:. :. .:.:.::.::::.  :  ..: : ::..::: .::.::..:...: ::.
stG6792 EVKAEENERLRQAKEQALQEVLRNTPYDDLKNAYAGAFRKNDELEKTIQEKNRDLESLSQ
            20        30        40        50        60
70
             70
        VLDEAAKKYRESSDK
         ::.....:. :::::
stG6792 ELDKTVSKHIESSDK
             80
```

FIG. 14D

```
          20        30        40        50        60        70
Mrp49   VTKAREEALEEVLRSWDYGSVKAALAGSYRKNLQLENTIKQKDKELSFLSKVLDEAAKKY
        . : :::::.::.  :::... .:::::.:.:  :..::::.  .: :::. :::....:.
stG643  IEKIREEALKEVIGRMDYGQLSNTLAGSFRENSALKETIKQKEGDLEFLSQELDKTVSKH
          30        40        50        60        70        80

Mrp49   RESSDK
        :::::
stG643  IESSDK
           90
```

FIG. 14E

```
              10        20        30        40
M1            NGDGNPREVIEDLAANNPAIQNIRLRHENKDLKARLENAMEVAGRD
              : .:.::::::.:::.::.::::::: ::. :: :::::.:::::
stG866 VLGAGFTNQTEVKANENGSPREVIEELAAKNPVIQNIRLRSENQKLKESLENAMDVAGRD
       10        20        30        40        50        60
```

FIG. 15A

```
              10        20        30        40
M1            NGDGNPREVIEDLAANNPAIQNIRLRHENKDLKARLENAMEVA
              .:::: :..:: ::..::::::: ::. ::: :::::...:
stC7505VAVALCVLGAGLASQTEVKAQDPREVTEEIAARNPVVQNIRLRSENEKLKASLENAIDIA
       10        20        30        40        50        60
```

FIG. 15B

```
              10        20        30        40
M114          NSKNPAPAPASAVPVKKEATKLSEAELYNKIQELEEGKAELFDKLEKV
              :. :. .. .    :.: :::::.::. ... : :.: :.
stC5345VALTVLGAGLASGQIVKADSSDVAIVVQPQSIEKEIADLNNKIQKLEKENSLLNDSLLKT
       10        20        30        40        50        60
```

FIG. 15C

```
              10        20        30        40
M118          AEKKVEVADSNASSVAKLYNQIADLTDKNGEYLERIEELEERQKNL
              ::  ... .  :  :. ..: ::::. ...:
stG866 NENGSPREVIEELAAKNPVIQNIRLRSENQKLKESLENAMDVAGRDFKRAEELEKAKQDL
          20        30        40        50        60        70
```

FIG. 15D

```
            10        20        30
M12         DHSDLVAEKQRLEDLGQKFERLKQRSELYLQQYYDNK
              : .::::: .:::.:: .:: :.:.   . .
stG7882SVAVALTVLGAGLVAGQTVRANDLNSQRNHEIERLEDLKSKFEKLKAHSEKYFQEALEAE
       10        20        30        40        50        60
```

*FIG. 15E*

```
              10        20        30        40
M3            DARSVNGEFPRHVKLKNEIENLLDQVTQLYTKHNSNYQQYNA
         :. .::::. ::.:::.:::.::::::::.::. :: :::.:..
stG211 GALSVLGAGLVAGQTVKADVGNVNGEYHRHTKLKSEIEDLLDQVTELYSTHNHNYQRYDS
       10        20        30        40        50        60
```

*FIG. 15F*

```
                10        20
M6              RVFPRGTVENPDKARELLNKYDVEN
            ::. :...:.::.::::::. : : :
stC9431ASVAVALSVLGAGLVVNTNEVSARVYTRSVVNNPEKARELIYKLDSEVIALEKEKESLNK
       10        20        30        40        50        60
```

*FIG. 15G*

GROUP A STREPTOCOCCAL M-RELATED PROTEINS AND METHODS OF USE

CROSS-REFERENCE TO RELATED APPLICATIONS

This application claims benefit under 35 U.S.C. §119(e) of U.S. Provisional Patent Application No. 61/763,314 filed Feb. 11, 2013; U.S. Provisional Patent Application No. 61/764,771 filed Feb. 14, 2013; and U.S. Provisional Patent Application No. 61/918,460 filed Dec. 19, 2013, which applications are all incorporated herein by reference in their entirety.

STATEMENT OF GOVERNMENT INTEREST

This invention was made with government support under Grant No. AI095852 awarded by National Institute of Allergy and Infectious Diseases and Grant No. AI010085 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920098_415_SEQUENCE LISTING.txt. The text file is 109 KB, was created on Feb. 10, 2014 and is being submitted electronically via EFS-Web.

BACKGROUND

Technical Field

Compositions and methods for treating and preventing beta (β)-hemolytic streptococcus infections are described herein.

Description of the Related Art

Human pathogens expressing the β-hemolytic phenotype are a heterogeneous group of organisms that includes groups A, C, G, and L streptococci. Group A streptococcal infections result in approximately 500,000 deaths per year worldwide, with invasive infections and rheumatic heart disease as the major contributors to mortality. Group A streptococci (GAS) are ubiquitous human pathogens that cause a wide spectrum of clinical syndromes. The acute infections range from uncomplicated pharyngitis, cellulitis, and pyoderma to life-threatening infections that include necrotizing fasciitis, sepsis, pneumonia, and streptococcal toxic shock syndrome (see, e.g., Bronze et al., *Am. J. Med. Sci.* 1996; 311:41-54). Mild and even asymptomatic infections can be followed by serious autoimmune diseases; acute rheumatic fever (ARF) and rheumatic heart disease (RHD) are the most significant. Although GAS infections are global in distribution, a distinct dichotomy exists in the burden of GAS infections and their sequelae between economically developed and developing countries of the world. In the United States, Western Europe, and other developed countries, the majority of GAS infections present as uncomplicated pharyngitis or pyoderma.

The greatest overall burden of disease caused by GAS infections is ARF and RHD and serious invasive infections that have a very high mortality rate. The vast majority of afflicted persons live in economically disadvantaged countries. Previous estimates indicated that 350,000 people die each year from complications of RHD, and approximately 12 million people currently suffer from RHD (see, e.g., Carapetis et al., *The Lancet Infectious Diseases* 2005; 5(11): 685-94; Bisno et al., *Clin. Infect. Dis.* 2005; 41(8):1150-56). An estimated 663,000 cases of invasive infections worldwide result in 163,000 deaths each year. In 2002, the World Health Organization web site listed GAS as the ninth most common single-pathogen cause of death in the world. For the more common mortality-associated pathogens (i.e., tuberculosis, pneumococcus, hepatitis B, *Haemophilus influenzae* type B, measles, rotavirus), vaccines are available, or very intensive, well-funded vaccine development programs (e.g., HIV, malaria) are ongoing. Recent studies have shown that the prevalence of RHD in children and young adults in developing countries may actually be five times higher than previously predicted (see, e.g., Paar et al., *Am. J. Cardiol.* 2010; 105(12):1809-14; Marijon et al., *N. Engl. J. Med.* 2007; 357(5):470-76; Anabwani et al., *East Afr. Med. J.* 1996; 73(4):215-17; Beaton et al., *Circulation* 2012; 125(25):3127-32), potentially placing GAS fourth on the list of single-organism causes of death, just behind HIV, tuberculosis, and malaria.

Vaccines designed to prevent the GAS infections that trigger ARF and those that cause serious invasive infections could have a major impact on the health of millions of people, as well as reducing the economic burden of this devastating disease.

Recent taxonomic studies have classified the large-colony group C, G and L streptococcal human pathogens as belonging to the species *Streptococcus dysgalactiae* subspecies *equisimilus* (SDSE) to differentiate them from animal pathogens belonging to the same Lancefield groups (see, e.g., Vandamme et al., *Int. J. Syst. Bacteriol.* 1996; 46(3):774-81). Once considered commensal bacteria of the human microbiome, SDSE have emerged as important human pathogens that cause a spectrum of disease similar to that of group A streptococci (see, e.g., Efstratiou et al., *Soc. Appl. Bacteriol. Symp. Ser.* 1997; 26: 72S-9S). SDSE are not uncommon colonizers of the human upper respiratory, gastrointestinal, female genital tracts, as well as the skin. These sites most likely represent the portal of entry leading to subsequent infection and serve as the reservoir for human-to-human transmission. The infections range from superficial skin and mucosal infections to life-threatening bacteremia and toxic shock syndrome. SDSE has been associated with outbreaks of pharyngitis in children (see, e.g., Gerber et al., *Pediatrics* 1991; 87(5): 598-603) and is an established cause of acute post-streptococcal glomerulonephritis (see, e.g., Reid H A, *Vet. Rec.* 1985; 117(24): 641). Although a potential etiologic role for SDSE in acute rheumatic fever has been proposed (see, e.g., Haidan et al., *Lancet* 2000; 356(9236):1167-79), a convincing study has not yet been performed.

Recent epidemiologic studies have defined the prominent role of SDSE in serious human infections, the incidence of which equals or exceeds that caused by GAS (see, e.g., Broyles et al., *Clin. Infect. Dis.* 2009; 48(6):706-12). The pathogenesis of SDSE infections is mediated by virulence determinants that are similar or identical to those expressed by GAS, including streptolysin O, streptolysin S, fibronectin-binding proteins, plasminogen-binding proteins, and pyrogenic exotoxins (see, e.g., Brandt et al., *Clin. Infect. Dis.* 2009; 49(5):766-72). A major distinguishing factor between human and animal pathogens of group C and G streptococci is that the human pathogens express a surface M protein, which has a function in virulence similar to that of the M protein of GAS (see, e.g., Bisno et al., *Infect. Immun.* 1987; 55(3):753-57; Collins et al., *Infect. Immun.* 1992; 60(9): 3689-96).

In view of the increasing incidence of SDSE in human populations and the seriousness of infections caused by SDSE and by group A streptococci, a vaccine that evokes a protective immune response against both group A streptococci and SDSE would provide significant benefit to millions of people.

BRIEF SUMMARY

Provided herein are group A streptococcus Mrp polypeptides and immunogenic fragments thereof, fusion polypeptides comprising the Mrp polypeptides and immunogenic fragments thereof, and immunogenic compositions comprising Mrp polypeptides and immunogenic fragments thereof that are used in methods for prophylaxis (prevention) and treatment of beta-hemolytic streptococcal infections, including group A streptococcus infections and SDSE infections. In certain embodiments, an immunogenic composition comprising Mrp polypeptides further comprises at least one additional group A streptococcus immunogen such as an amino-terminal fragment of a group A streptococcus M polypeptide. As described in greater detail herein, the following embodiments are provided.

In one embodiment provided herein, is an isolated Mrp polypeptide selected from: (a) an isolated polypeptide consisting of an amino acid sequence at least 70% identical to the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55; (b) an isolated polypeptide consisting of an amino acid sequence at least 80% identical to the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55; (c) an isolated polypeptide consisting of an amino acid sequence at least 90% identical to the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55; (d) an isolated polypeptide consisting of an amino acid sequence at least 95% identical to the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55; (e) an isolated polypeptide consisting of the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55; (f) an isolated polypeptide comprising an immunogenic fragment that comprises at least 15 contiguous amino acids of SEQ ID NO:12, SEQ ID NO:13, SEQ ID NO:16, SEQ ID NO:17, SEQ ID NO:20, SEQ ID NO:39, SEQ ID NO:47; or SEQ ID NO:55; and (g) an isolated polypeptide that is a variant of a polypeptide consisting of the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55, wherein the variant has no more than 10 amino acid additions, deletions, or substitutions in the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55, and wherein the isolated polypeptide evokes an immune response specific for a beta-hemolytic streptococcus selected from group A streptococcus and *Streptococcus dysgalactiae* subspecies *equisimilus* (SDSE). In certain embodiments, the isolated polypeptide evokes an immune response specific for group A streptococcus. In other certain embodiments, the isolated polypeptide evokes an immune response specific for SDSE. In certain embodiments, the isolated polypeptide evokes an immune response specific for group A streptococcus and SDSE. Additional embodiments of the isolated polypeptide are described herein. Also provided are immunogenic compositions comprising a pharmaceutically acceptable excipient and the isolated polypeptide. In certain embodiments, the immunogenic composition may further comprise a pharmaceutically acceptable adjuvant. Additional embodiments of the immunogenic compositions are described herein.

In another embodiment, a fusion polypeptide is provided that comprises any one of the Mrp polypeptides of the above embodiment and as described herein, wherein the fusion polypeptide evokes an immune response specific for a beta-hemolytic streptococcus selected from group A streptococcus and *Streptococcus dysgalactiae* subspecies *equisimilus* (SDSE). In certain embodiments, the fusion polypeptide evokes an immune response specific for group A streptococcus. In other certain embodiments, the fusion polypeptide evokes an immune response specific for SDSE. In certain embodiments, the fusion polypeptide evokes an immune response specific for group A streptococcus and SDSE. In certain embodiments, the fusion polypeptide further comprises at least one immunogenic peptide that comprises at least 25 contiguous amino acids from the amino terminal portion of a group A streptococcus M protein or a group A streptococcus Spa protein. In a more particular embodiment, the at least one M protein is selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18. Additional embodiments of the fusion polypeptide are described above and herein. Also provided are immunogenic compositions comprising a pharmaceutically acceptable excipient and the fusion polypeptide. In certain embodiments, the immunogenic composition may further comprise a pharmaceutically acceptable adjuvant. Additional embodiments of immunogenic compositions are described herein.

In another embodiment, a preparation is provided wherein the preparation comprises (a) a first immunogenic composition that comprises at least one Mrp polypeptide as described above and herein, the fusion polypeptide comprising any one of the Mrp polypeptides described above and herein; and (b) a second immunogenic composition comprising at least one other group A streptococcus immunogen and a pharmaceutically acceptable excipient, wherein the first composition and the second immunogenic compositions each induce an immune response against a beta-hemolytic streptococcus selected from group A streptococcus and *Streptococcus dysgalactiae* subspecies equisimilus (SDSE). In certain embodiments, the first immunogenic composition evokes an immune response specific for group A streptococcus. In other certain embodiments, the first immunogenic composition evokes an immune response specific for SDSE. In certain embodiments, the first immunogenic composition evokes an immune response specific for group A streptococcus and SDSE. In other particular embodiments, the second immunogenic composition evokes an immune response specific for group A streptococcus. In other certain embodiments, the second immunogenic composition evokes an immune response specific for SDSE. In certain embodiments, the second immunogenic composition evokes an immune response specific for group A streptococcus and SDSE. In particular embodiments, the at least one other group A streptococcus immunogen comprises an immunogenic peptide comprising at least 25 contiguous amino acids from the amino terminal portion of a group A streptococcus (GAS) serotype M protein or a Spa protein. In a more particular embodiment, the at least one M protein is selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18. In certain embodiments, the first, second, or first and second immunogenic compositions may further comprise a pharmaceutically acceptable adjuvant. Additional embodiments of the preparation are described herein.

Also provided herein are methods of evoking (i.e., inducing) an immune response against a beta-hemolytic streptococcus selected from GAS and SDSE by administering to a subject any one of the polypeptides, fusion polypeptides, immunogenic compositions, or preparations described above and herein. Methods are also provided for treating or preventing a beta-hemolytic streptococcus infection such as a GAS infection and/or an SDSE infection by administering to a subject any one of the polypeptides, fusion polypeptides, immunogenic compositions, or preparations described above and herein. Also provided are uses of the Mrp polypeptides, fusion polypeptides, immunogenic compositions, and preparations for manufacturing a medicament for inducing an immune response to GAS and/or SDSE. In other embodiments, uses of the Mrp polypeptides, fusion polypeptides, immunogenic compositions, and preparations are provided for the manufacture of a medicament to treat or prevent either one or both of a GAS infection and an SDSE infection.

In another embodiment, methods and uses are provided for inducing an immune response in a subject against *Streptococcus dysgalactiae* subspecies equisimilus (SDSE) with an immunogenic composition comprising a pharmaceutically acceptable excipient and an immunogenic peptide comprising at least 25 contiguous amino acids from the amino terminal portion of a group A streptococcus (GAS) serotype M protein or a Spa protein. In other embodiments, methods and uses are provided for treating or preventing an SDSE infection by administering to a subject an immunogenic composition comprising a pharmaceutically acceptable excipient and an immunogenic peptide comprising at least 25 contiguous amino acids from the amino terminal portion of a group A streptococcus (GAS) serotype M protein or a Spa protein. In certain particular embodiments of these methods, the at least one M protein is selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18. Various embodiments of these methods and uses are described in greater detail herein.

As used herein and in the appended claims, the singular forms "a," "and," and "the" include plural referents unless the context clearly dictates otherwise. Thus, for example, reference to "a polypeptide" may refer to one or more polypeptides, or a plurality of such polypeptides, and reference to "a cell" or "the cell" includes reference to one or more cells and equivalents thereof (e.g., plurality of cells) known to those skilled in the art, and so forth. Similarly, reference to "a composition" includes a plurality of such compositions, and refers to one or more compositions unless the context clearly dictates otherwise. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. It should also be noted that the term "or" is generally employed in its sense including "and/or" unless the content clearly dictates otherwise. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

As used herein, the term "isolated" means that a material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such a nucleic acid could be part of a vector, or such nucleic acid or polypeptide could be part of a composition, and still be isolated in that the vector or composition is not part of the natural environment for the nucleic acid or polypeptide, respectively. The term "gene" means the segment of DNA involved in producing a polypeptide chain; it includes regions preceding and following the coding region "leader and trailer," as well as intervening sequences (introns) between individual coding segments (exons) when applicable. Amino acids may be referred to herein according to the single letter and three letter codes, which are understood according to common textbook knowledge in the art, and as such a person skilled in the art is familiar with the meanings of the abbreviations. Immunogenic fragments comprise polypeptides and peptides of the proteins described herein. In the art, the number of amino acids covalently bonded to form a "peptide" and the number of amino acids that form a "polypeptide," varies. A peptide may be defined as having less than about 50 amino acids or may be defined as having less than about 100 amino acids, respectively. Accordingly, a polypeptide would have greater than about 50 amino acids or greater than having about 100 amino acids. Usually, but not necessarily, as used herein a peptide has less than about 100 amino acids and a polypeptide has greater than about 100 amino acids. In specific embodiments, the number of amino acids comprising a peptide or polypeptide is stated. The term "fusion polypeptide" used herein may also be used interchangeably with "fusion protein," and unless specifically indicated otherwise, the two terms are not meant to indicate molecules that have distinguishable properties or characteristics.

BRIEF DESCRIPTION OF THE DRAWINGS

FIG. 1A-1I present representative full-length Mrp polypeptide, N-terminal amino acid sequences, and polynucleotide sequences encoding the Mrp N-terminal amino acid sequences. FIG. 1A: Amino acid sequence of Mrp2 (SEQ ID NO:10). FIG. 1B: Amino acid sequence of a polypeptide comprising N-terminal Mrp2U portion, N-terminal methionine residue, and His-6 tag (SEQ ID NO:11). FIG. 1C: Amino acid sequence of Mrp49 (SEQ ID NO:14). FIG. 1D: Amino acid sequence of a polypeptide comprising N-terminal Mrp49U portion, N-terminal methionine residue, and His-6 tag (SEQ ID NO:15). FIG. 1E: Amino acid sequence of Mrp4 (SEQ ID NO:18). FIG. 1F: Amino acid sequence of a polypeptide comprising N-terminal Mrp4U portion. Uncapitalized letters correspond to non-Mrp4U amino acids, including His-6 tag (positions 5-10) (SEQ ID NO:19). FIG. 1G: Nucleotide sequence encoding N-terminal Mrp2U. Uncapitalized letters correspond to non-Mrp2U nucleotides (SEQ ID NO:21). FIG. 1H: Nucleotide sequence encoding N-terminal Mrp4U (SEQ ID NO:22). FIG. 1I: Nucleotide sequence encoding N-terminal Mrp49U. Uncapitalized letters correspond to non-Mrp49U nucleotides (SEQ ID NO:23).

FIG. 2 presents an alignment of N-terminal amino acid sequences of 30 Mrp polypeptides (SEQ ID NO: 28-57) from heterologous emm types of group A streptococcus (GAS).

FIG. 14A-14E presents amino acid sequence homologies between Mrp of GAS and M proteins of SDSE. FIG. 14A compares GAS Mrp2 (SEQ ID NO:104) and SDSE stL1929 (SEQ ID NO:105), which have 55% identity and 85% similarity between the peptides shown. FIG. 14B compares GAS Mrp2 (SEQ ID NO:106) and SDSE stG1389 SEQ ID NO:107), which have 33% identity and 73% similarity between the peptides shown. FIG. 14C compares GAS Mrp4 (SEQ ID NO:108) and SDSE stG7882 (SEQ ID NO:109), which have 36% identity and 64% similarity between the peptides shown. FIG. 14D compares GAS Mrp49 (SEQ ID NO:110) and SDSE stG6792 (SEQ ID NO:111), which have 45% identity and 84% similarity between the peptides shown. FIG. 14E compares GAS Mrp49 (SEQ ID NO:112) and SDSE stG643 (SEQ ID NO:113), which have 53% identity and 82% similarity between the peptides shown.

FIG. 15A-15G shows sequence homologies between 30-valent vaccine peptides and SDSE M proteins. FIG. 15A compares M1 (SEQ ID NO: 114) and SDSE stG866 (SEQ ID NO: 115), which have 76% identity between the peptides shown. FIG. 15B compares GAS M1 (SEQ ID NO:116) and SDSE stC7505 (SEQ ID NO:117), which have 67.4% identity between the peptides shown. FIG. 15C compares GAS M114 (SEQ ID NO:118) and SDSE stC5345 (SEQ ID NO:119), which have 38.5% identity between the peptides shown. FIG. 15D compares GAS M118 (SEQ ID NO:120) and SDSE stG866 (SEQ ID NO:121), which have 37.5% identity between the peptides shown. FIG. 15E compares GAS M12 (SEQ ID NO:122) and SDSE stG7882 (SEQ ID NO:123), which have 47.6% identity between the peptides shown. FIG. 15F compares GAS M3 (SEQ ID NO:124) and SDSE stG211 (SEQ ID NO:125), which have 67.3% identity between the peptides shown. FIG. 15G compares GAS M6 (SEQ ID NO:126) and SDSE stC9431 (SEQ ID NO:127), which have 58.3% identity between the peptides shown.

DETAILED DESCRIPTION

Figure 3:
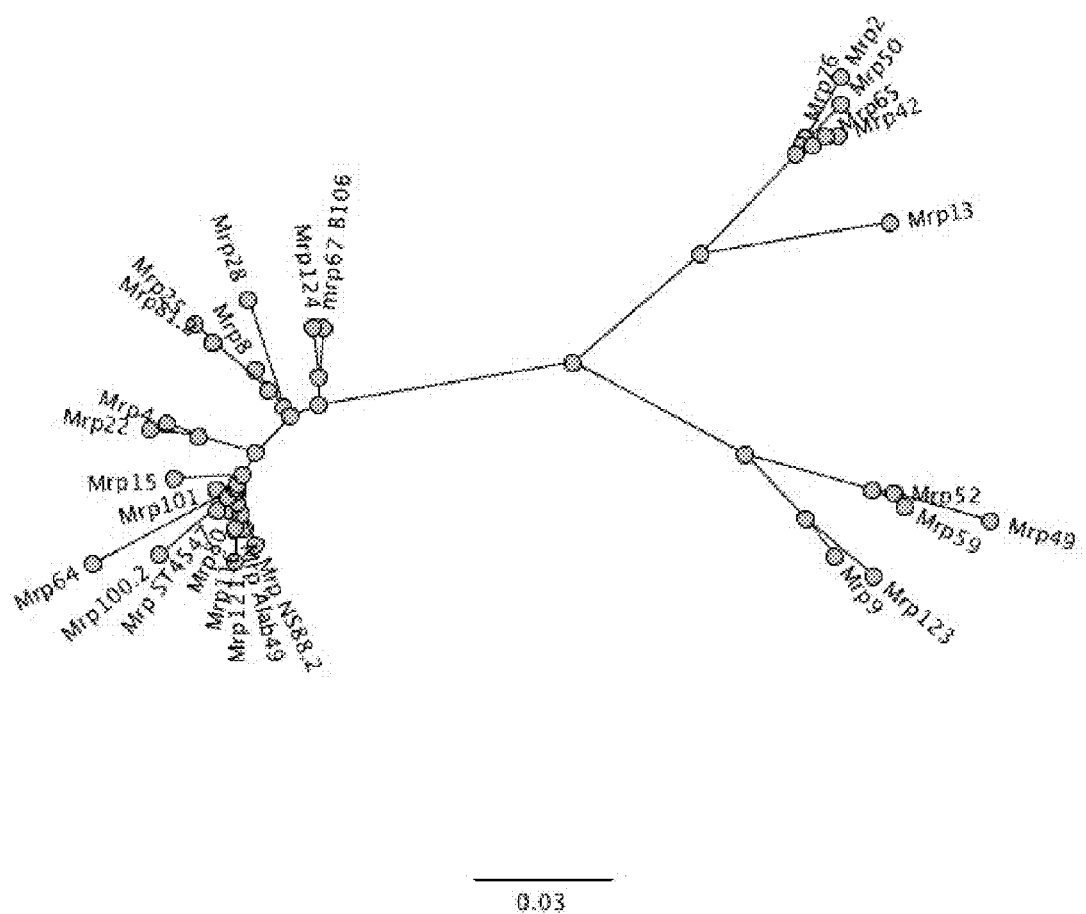
FIG. 3 illustrates a phylogenetic tree analysis of Mrp sequences indicating three related families based on the amino acid sequences of the N-terminal semi-conserved regions.

Provided herein are immunogenic group A streptococcus (GAS) M-related polypeptides and peptides and immunogenic compositions comprising these M-related polypeptides and peptides that have relatively conserved structures across serotypes and evoke cross-opsonic and cross-protective antibodies in animals. The M-related proteins (Mrps) were previously thought not to be useful immunogens. The Mrp polypeptides and peptides, immunogenic compositions, and methods of using same therefore provide unexpected protective M related protein-based vaccines that broaden GAS immune coverage in developing countries of the world. The Mrp polypeptides and peptides and immunogenic compositions comprising same, and a GAS M protein immunogenic composition, each alone or together, evoke an immune response that includes bactericidal antibodies that kill not only GAS but other beta-hemolytic streptococci, including the species *Streptococcus dysgalactiae* subspecies *equisimilus* (SDSE).

Previous studies have focused on the development of multivalent M protein-based vaccines that are designed to prevent the most common infections in North America and Europe (see, e.g., Shulman et al., *Clin. Infect. Dis.* 2009; 49(1):78-84; O'Loughlin et al., *Clin. Infect. Dis.* 2007; 45(7):853-62; Luca-Harari et al., *J. Clin. Microbiol.* 2009; 47(4):1155-65). These vaccines have been evaluated in clinical trials and were found to be safe, well-tolerated and immunogenic (see, e.g., McNeil et al., *International Congress Series* 2005; 1289:303-306; McNeil et al., *Clin. Infect. Dis.* 2005; 41(8):1114-22). However, because of divergent epidemiology of GAS infections in resource-poor countries and type-specific immunity against the M protein peptides, multivalent vaccines likely provide sub-optimal protection in areas of the world where the burden of ARF and RHD is greatest (see, e.g., Steer et al., *The Lancet Infectious Diseases* 2009; 9(10):611-16).

The finding that SDSE harbors emm genes that are comparable in overall structure and function to those of GAS (see, e.g., Campo et al., *J. Infect. Dis.* 1995; 171(3): 601-16; Bisno et al., *J. Clin. Microbiol* 0.1996; 34(10): 2511-15) suggests that antibodies against the SDSE surface proteins could potentially confer protection against infection. Like GAS emm genes, those of SDSE display variable sequences in their 5' regions that represent ~100 distinct sequence types (see, e.g., CDC Streptococcal Reference Page. Available at the Internet at the CDC web site, (see, e.g., /pub/infectious_diseases/biotech/tstransl/). Bactericidal activity of M protein antibodies has been correlated with protection against GAS infection (see, e.g., Lancefield R C, *J. Immunol.* 1962; 89:307-13); Wannamaker et al., *AMA Am J Dis Child* 1953; 86(3):347-48). While some research has suggested that SDSE may have acquired genetic material from GAS via horizontal transfer, until the disclosure herein, no reports compare the emm sequences of SDSE to those of GAS, and no studies have determined if antibodies against GAS M protein-based vaccines and M-related protein (Mrp) vaccines may mediate cross-reactive opsonization and bactericidal killing of clinical isolates of SDSE. As provided in this disclosure, the GAS vaccines described herein could be efficacious in preventing or treating SDSE infections in humans.

As described herein, the GAS surface protein, M-related protein (Mrp), has potential as a vaccine component that may broaden the coverage of current M protein-based vaccines. Sequence analyses of 30 mrp genes indicated three families of structurally related Mrps (see FIG. 3). N-terminal peptides of three polypeptides, Mrp2, Mrp4 and Mrp49, representing the three families, were cloned and purified. Rabbit antisera against these Mrps were assayed by immunoassays (e.g., ELISA) and in bactericidal assays to assess the cross-protective potential against multiple serotypes of GAS. The anti-Mrp rabbit antisera reacted specifically with the homologous Mrp, as determined by ELISA, and cross-reactivity against some heterologous Mrps was also observed. The Mrp antisera were bactericidal against homologous and heterologous serotypes, indicating the presence of cross-opsonic (i.e., shared) epitopes on the surface of multiple GAS serotypes. As described herein, combinations of M and Mrp antisera showed greater bactericidal activity than either antiserum alone, indicating an additive functional role for each antibody population. Furthermore, Mrp is immunogenic in humans following natural infection: normal sera from adults contained significant levels of antibodies against one or more of the three N-terminal Mrp peptides; the antibodies are acquired in a age-related fashion; and human Mrp antibodies are bactericidal against GAS. Taken together, these results indicate that GAS immunogenic compositions (i.e., GAS vaccines) comprising Mrp peptides may provide immunoprotection against a broad range of GAS serotypes that are prevalent around the world.

As described herein, GAS Mrp immunogens not only induce a protective immune response against the GAS M serotype strain that expresses the particular Mrp polypeptide but induced cross-protection against additional GAS M serotypes. Accordingly, in one embodiment, an immunogenic composition is provided that comprises polypeptides or immunogenic peptides representing Mrp2, Mrp4, and Mrp49 expressing strains and which evokes an immune response against about 80% of all GAS M serotype strains. In another embodiment, preparations are provided that comprise these Mrp immunogenic compositions and that further comprise a second immunogenic composition that comprises at least one additional GAS immunogen (e.g., an immunogenic peptide comprising at least 25 contiguous amino acids from the amino terminal portion of a GAS serotype M protein or Spa protein).

Moreover, GAS Mrp immunogens and GAS M serotype M protein and Spa protein immunogens as described herein evoke antibodies that are bactericidal against SDSE strains. Accordingly, provided herein are peptides, fusion polypeptides, immunogenic compositions comprising these peptides and fusion polypeptides, and methods that are useful for evoking an immune response against beta-hemolytic streptococci (e.g., group A streptococcus and *Streptococcus dysgalactiae* subspecies equisimilus (SDSE)). The β-hemolytic phenotype includes a heterogeneous group of organisms such as group A, C, G, and L streptococci. Large-colony group C, G and L human pathogens are classified as belonging to the species *Streptococcus dysgalactiae* subspecies *equisimilus* (SDSE). Accordingly, provided herein are GAS Mrp immunogens, GAS M serotype M protein and Spa protein immunogens, and compositions comprising one or more of these immunogens that are useful for evoking an immune response against GAS and SDSE that includes bactericidal antibodies and which immune response protects an immunized host against either one or both of GAS infection and SDSE infection.

These immunogenic compositions, preparations, methods, and uses are discussed in greater detail herein.

Group A *Streptococcus* Immunogens

Group A *Streptococcus* M-Related Proteins (Mrp)

As long known in the art, protection of a host against GAS infection generally correlates with the production of opsonizing antibodies against GAS serotype-specific M protein (see, e.g., Lancefield, *J. Immunol.* 89:307, 1962). The cell surface M protein of group A streptococci (GAS) is one of the major virulence factors for this pathogen. The M protein, which is encoded by the emm gene, extends from the cell surface as an α-helical coiled-coil dimer that appears as a fibril on the surface of a GAS bacterium. The M proteins form an antigenically diverse group, and GAS strains have been serologically categorized according to M protein serotypes. More than 120 M protein serotypes have been identified, and within some serotypes, subtypes have also been identified. By way of illustration, the M proteins of GAS serotype 3 include related subtypes, which are designated as 3.0, 3.1, 3.2, etc.

As described herein, Mrp is another important virulence determinant expressed on the surface of GAS. In strains of GAS that express both M protein and Mrp, conferring resistance to phagocytosis and expression of opsonic epitopes are functions that are shared by Mrp and M protein. Mrp has been virtually ignored as a potential GAS vaccine antigen. All previously described large-scale proteomic, reverse vaccinology, and/or antigenome approaches failed to identify immunogenic Mrp as a common protective antigen (see, e.g., Severin et al., *J. Bacteriol.* 2007; 189(5):1514-22; Rodriguez-Ortega et al., *Nat. Biotechnol.* 2006; 24(2):191-97; Fritzer et al., *Infect. Immun.* 2010; 78(9):4051-67; Lei et al., *J. Infect. Dis.* 2004; 189(1):79-89). Therefore, until the present disclosure, Mrp had not been identified as a potential vaccine component by any of these modern vaccinology techniques.

Provided herein are Mrp polypeptides, which are GAS cell wall proteins that are useful as immunogens for evoking an immune response against group A streptococcus and/or SDSE. M-related proteins of GAS have semi-conserved N-terminal sequences that comprise three distinct structural families. Mrp's are expressed on the surface of the majority of GAS serotypes (see, e.g., Bessen et al., *J. Infect. Dis.*

1996; 173(4):896-900) and function as virulence determinants in concert with M proteins (see, e.g., Courtney et al., *Mol. Microbiol.* 2006; 59(3):936-47). The proteins range from 38-42 kDa in size, are largely alpha-helical, and are anchored to the cell wall via an LPSTGE (SEQ ID NO:1) motif (see FIG. 1). An Mrp present in GAS bacteria may promote GAS infection; for example, Mrp4 binds human plasma fibrinogen, which prevents the activation and deposition of complement on the surface of the organism (see, e.g., Courtney et al., supra). Mrp's also bind human IgG (see, e.g., Krebs et al., *Med. Microbiol. Immunol.* 1996; 185(1):39-47), a function that is localized to repeating segments located in the middle of the molecule.

Of the 125 defined M/emm serotypes (i.e., the GAS strains that have been assigned a number), 83% are Mrp-positive. Representative amino acid sequences of full-length Mrp polypeptides are described herein, and certain amino acid sequences of Mrp polypeptides are described in the art (see, for example, publically available databases such as GenBank, Swiss Prot, and GenEMBL). Sequence analyses of 30 mrp genes indicated that Mrps belong to one of three families of structurally related Mrps (see Example 1; amino acid sequences from the N-terminal portion of Mrps, which represent each family, from heterologous emm-genotypes of GAS are shown in FIG. 3). As exemplified herein, the amino acid sequences of the amino terminal portion of an Mrp from M serotype 2 (called Mrp2), the amino terminal portion of an Mrp from M serotype 4 (called Mrp4), and the amino terminal portion of an Mrp from M serotype 49 (called Mrp49) represent Mrps of each of three Mrp families (see FIG. 3). Comparison of the N-terminal portion of the sequences within each of the three families indicates that the sequences may vary from each other by about 0% to 30% (see FIGS. 2 and 3; Examples; Sequence Listing). In other words, the amino terminal portions of the proteins of the Mrp2 family of which Mrp2 is representative share at least 70% (i.e., 70%-100%) amino acid sequence identity. Similarly, the amino terminal portions of the proteins of the Mrp4 family of which Mrp4 is representative share at least 70% (i.e., 70%-100%) amino acid sequence identity, and the amino terminal portions of the proteins of the Mrp49 family of which Mrp49 is representative share at least 70% (i.e., 70%-100%) amino acid sequence identity. Accordingly, the Mrp2 family comprises polypeptides at least 70% identical to the full-length Mrp2 protein (SEQ ID NO:10) including peptides from the amino terminal portion of Mrp2 that are at least 70% identical to SEQ ID NO:13 or 47; the Mrp4 family comprises polypeptides at least 70% identical to the full-length Mrp4 protein (SEQ ID NO:18) including peptides from the amino terminal portion of Mrp4 that are at least 70% identical to SEQ ID NO:20 or 39; the Mrp49 family comprises polypeptides at least 70% identical to the full-length Mrp49 protein (SEQ ID NO:14) including peptides from the amino terminal portion of Mrp49 that are at least 70% identical to SEQ ID NO:17 or 55. (See Table 1.)

In certain embodiments, immunogenic fragments of the Mrp polypeptides are provided herein. In particular embodiments, the immunogenic Mrp fragment is obtained from the amino terminal portion of an Mrp polypeptide. The term "amino terminal portion" of an Mrp protein is readily understood by a person having ordinary skill in the art as the portion or region of a polypeptide that is located in the amino terminal half of the polypeptide. (Amino terminal may also be called N-terminal or $NH_2$-terminal herein and in the art.) In certain embodiments, the Mrp immunogenic polypeptides or peptides comprise amino acids from the amino terminal portion of an Mrp from which all or a portion of the signal peptide sequence of the Mrp has been removed. As is well understood in the art, polypeptides that are secreted or that are membrane bound proteins are translocated through or to the membrane, respectively, by a translocation apparatus that interacts with a signal peptide at the amino terminal end of a nascent polypeptide. In bacteria, a signal peptide sequence is typically cleaved from a nascently translated polypeptide in vivo by a bacterial protease to form the mature polypeptide. A full-length polypeptide from which the signal peptide sequence has been cleaved (i.e., deleted, removed) is called herein the "mature" polypeptide.

Mrp polypeptides useful as immunogens include Mrp2 polypeptides, Mrp4 polypeptides, and Mrp49 polypeptides, which are representative of each of the three Mrp families. Additional Mrps in each family may also be used as immunogens; representative polypeptides/peptides are listed in Table 1 and FIG. 2, (see also Sequence Listing). An example of an amino acid sequence representing a full-length Mrp2 polypeptide is provided in SEQ ID NO:10; an amino acid sequence representing a full-length Mrp4 polypeptide is provided in SEQ ID NO:18; and an amino acid sequence representing full-length Mrp49 polypeptide is provided in SEQ ID NO:14 (see Table 1 below; Sequence Listing). As discussed in greater detail herein, immunogenic compositions comprising one or more of Mrp2, Mrp4, and Mrp49 polypeptides, or immunogenic fragments thereof, are useful for evoking in a subject an immune response that is specific for the respective polypeptide and for Mrp polypeptides that share one or more epitopes with the respective Mrp2, Mrp4, or Mrp49 immunogenic polypeptides or fragments thereof. Therefore, the immunogenic compositions described herein are useful for treatment or prophylaxis of a GAS infection. As discussed in greater detail herein these immunogenic compositions are also useful for treatment or prophylaxis of a SDSE infection.

TABLE 1

REPRESENTATIVE MRPS AND IMMUNOGENIC FRAGMENTS THEREOF

| Mrp Family | Mrp | SEQ ID NO | Description |
|---|---|---|---|
| Mrp2 Family | Mrp2 | 10 | Full-length Mrp2 |
| | Mrp2U | 11 | residues 42-126 of SEQ ID NO: 10 plus Met at N-terminus and KLAAALE (SEQ ID NO: 65) spacer and 6-His tag at carboxy terminus |
| | Mrp2U | 12 | residues 42-126 of SEQ ID NO: 10 plus KLAAALE (SEQ ID NO: 65) spacer |
| | Mrp2U | 13 | residues 42-126 of SEQ ID NO: 10 |
| | N Mrp2 | 47 | N-terminal peptide sequence: residues 42-148 of SEQ ID NO: 10 |

TABLE 1-continued

REPRESENTATIVE MRPS AND IMMUNOGENIC FRAGMENTS THEREOF

| Mrp Family | Mrp | SEQ ID NO | Description |
|---|---|---|---|
| | N Mrp76 | 48 | N-terminal peptide sequence |
| | N Mrp50 | 49 | N-terminal peptide sequence |
| | N Mrp42 | 50 | N-terminal peptide sequence |
| | N Mrp65 | 51 | N-terminal peptide sequence |
| | N Mrp13 | 52 | N-terminal peptide sequence |
| | N Mrp9 | 53 | N-terminal peptide sequence |
| | N Mrp123 | 54 | N-terminal peptide sequence |
| Mrp4 Family | Mrp4 | 18 | Full-length Mrp4 |
| | Mrp4U | 19 | residues 42-122 of SEQ ID NO: 18 plus plasmid sequences at N-terminus and carboxy terminus |
| | Mrp4U | 20 | residues 42-122 of SEQ ID NO: 18 |
| | N Mrp101 | 28 | N-terminal peptide sequence |
| | N MrpAlab49 | 29 | N-terminal peptide sequence |
| | N Mrp100.2 | 30 | N-terminal peptide sequence |
| | N Mrp80 | 31 | N-terminal peptide sequence |
| | N Mrp64 | 32 | N-terminal peptide sequence |
| | N Mrp116 | 33 | N-terminal peptide sequence |
| | N Mrp121 | 34 | N-terminal peptide sequence |
| | N MrpNS88.2 | 35 | N-terminal peptide sequence |
| | N Mrp15 | 36 | N-terminal peptide sequence |
| | N Mrp15B106 | 37 | N-terminal peptide sequence |
| | N MrpST4547 | 38 | N-terminal peptide sequence |
| | N Mrp4 | 39 | Residues 42-111 of SEQ ID NO: 18 |
| | N Mrp22 | 40 | N-terminal peptide sequence |
| | N Mrp25 | 41 | N-terminal peptide sequence |
| | N Mrp81.2 | 42 | N-terminal peptide sequence |
| | N Mrp8 | 43 | N-terminal peptide sequence |
| | N Mrp28 | 44 | N-terminal peptide sequence |
| | N Mrp67 | 45 | N-terminal peptide sequence |
| | N Mrp124 | 46 | N-terminal peptide sequence |
| Mrp49 Family | Mrp49 | 14 | Full-length Mrp49 |
| | Mrp49U | 15 | residues 42-116 of SEQ ID NO: 14 plus Met at N-terminus and KLAAALE (SEQ ID NO: 65) spacer and 6-His tag at carboxy terminus |
| | Mrp49U | 16 | residues 42-116 of SEQ ID NO: 14 plus KLAAALE (SEQ ID NO: 65) spacer |
| | Mrp49U | 17 | residues 42-116 of SEQ ID NO: 14 |
| | N Mrp49 | 55 | residues 42-138 of SEQ ID NO: 14 |
| | N Mrp52 | 56 | N-terminal peptide sequence |
| | N Mrp59 | 57 | N-terminal peptide sequence |

In certain embodiments are provided polypeptides that comprise immunogenic polypeptide and peptide fragments of Mrps. Immunogenic fragments comprise a sufficient number of contiguous amino acids of an Mrp that form at least one epitope that induces an immune response specific for the fragment, for the full-length and mature polypeptides from which the fragment is derived, and for GAS bacteria that express a polypeptide comprising the immunogenic fragment. The immune response may also be specific for and cross-reactive with SDSE bacteria that express a polypeptide comprising at least one epitope sufficiently similar to the at least one epitope of the Mrp protein that induces the immune response. An immunogenic peptide or polypeptide (which peptide or polypeptide may called an immunogenic fragment) may comprise at least 5, 6, 8, 10, 15, 20, 25, 30, 35, 40, 45, 50, 55, 60, 65, 70, 75, 80, 85, 90, 95, or 100 or longer (or any integer of amino acids between 5-25, 5-50, 5-10, 10-15, 15-20, 20-25, 25-30, 25-50, 30-35, 35-40, 40-45, 45-50, 50-55, 55-60, 60-65, 65-70, 70-75, 75-80, 85-90, 90-95, 95-100, 100-105, 105-110, or 110-120) contiguous amino acids of an Mrp polypeptide of interest. A person skilled in the vaccine and immunology arts readily appreciates that certain epitopes may comprise two or more non-contiguous regions of a polypeptide and which epitopes form when the polypeptide folds into a three-dimensional structure. An immunogenic fragment of an Mrp polypeptide comprising such a three-dimensional epitope comprises a sufficient number of contiguous amino acids of the full-length (or mature) polypeptide to form the epitope. Alternatively, a fusion polypeptide may be prepared that comprises regions of the GAS polypeptide that form an epitope and which are fused in frame with spacer sequences that are non-GAS polypeptide sequences but provide the necessary architecture for a three-dimensional epitope to form upon folding of the fusion polypeptide. In particular embodiments, the immunogenic fragments are derived from the amino terminal portion of an Mrp polypeptide. Examples of Mrp immunogenic fragments include an Mrp2 polypeptide called Mrp2U herein, which is represented by SEQ ID NO:13, and the Mrp2 immunogenic fragment set forth in SEQ ID NO:47 (N Mrp2). Examples of Mrp immunogenic fragments include an Mrp4 polypeptide called Mrp4U herein, which is represented by SEQ ID NO:20, and the Mrp4 immunogenic fragment set forth in SEQ ID NO:39 (N Mrp4). Examples of Mrp immunogenic fragments also include an Mrp49 polypeptide called Mrp49U herein, which is represented by SEQ ID NO:17, and the Mrp49 immunogenic fragment set forth in SEQ ID NO:55 (N Mrp49). (See Table 1; FIG. 2.)

The amino acid sequences of several Mrp proteins are available in the art or provided herein. Databases may be accessed to determine the variability in the amino acid sequences within Mrps of each of the three Mrp families. Alignment tools for comparison of the amino terminal portions of Mrps can be used to identify amino acid residues within the amino terminal portion or throughout the full-length protein that may be variable. Examples of alignment tools (which may also be useful for comparing nucleotide sequences, such as those encoding an Mrp protein) include, without limitation, software programs such as BlastP, BLAST, tBLAST, and MegAlign. Other software programs are provided in the Lasergene bioinformatics computing suite (DNASTAR® Madison, Wis.); CLUSTALW program (see, e. g., Thompson et al., *Nucleic Acids Res.* 22:4673-80 (1991)); and "GeneDoc" (Nicholas et al., *EMBNEW* News 4:14 (1991)). References for algorithms such as ALIGN or BLAST may be found in, for example, Altschul, *J. Mol. Biol.* 219:555-565, 1991; and Henikoff and Henikoff, *Proc. Natl. Acad. Sci. USA* 89:10915-10919, 1992. Algorithms including the Align and BLAST algorithms are available at the NCBI website (see [online] Internet at ncbi.nlm.nih.gov/cgi-bin/BLAST). Default parameters may be used. Additional methods available in the art for comparing nucleotide or amino acid sequences and determining optimal alignment include methods described, for example, in Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology*, pages 123-151 (CRC Press, Inc. 1997); and Bishop (ed.), *Guide to Human Genome Computing*, 2nd Ed. (Academic Press, Inc. 1998).

The amino acid sequences of the Mrp immunogenic polypeptides and peptides and fusion polypeptides described herein are examples, and immunogenic polypeptide and peptide fragments and fusion polypeptides useful for inducing an immune response against GAS or SDSE or GAS and SDSE may include substitutions, insertions, and deletions of one or more amino acids that do not adversely affect (i.e., decrease or reduce in a statistically significant manner or biologically or clinical significant manner) the immunogenicity of the immunogenic peptide or fusion polypeptide. Immunogenicity of a variant polypeptide or peptide or variant fusion polypeptide that is substantially similar in a statistically, biologically, or clinically significant manner to the immunogenicity of an immunogenic peptide or fusion polypeptide, respectively, described herein is desired. Mrp polypeptide and peptide species (i.e., Mrp polypeptide and peptide variants) are described in greater detail herein.

In another embodiment, fusion proteins are provided that comprise at least one Mrp polypeptide, or immunogenic fragment (polypeptide or peptide), or immunogenic variant of the polypeptide or fragment. As described in greater detail herein, a fusion protein comprising at least one Mrp polypeptide, immunogenic fragment, or variant thereof may be fused in frame with a detectable moiety, an immunogenicity enhancing moiety, a tag moiety useful for purification purposes (such as multiple histidine residues), another GAS immunogenic polypeptide or peptide, or any combination of the aforementioned. A fusion protein comprising an Mrp polypeptide or immunogenic fragment thereof may further comprise a non-GAS polypeptide or peptide that is useful for enhancing an immune response to the Mrp of interest. Examples of non-GAS proteins (sometimes called carrier protein in the art), include but are not limited to tetanus toxoid, cholera toxoid, other bacterial toxoids, keyhole limpet hemocyanin, or other protein or protein fragment, used in the art to enhance an immune response to an antigen of interest. See, for example, U.S. Pat. Nos. 6,716,433 and 7,402,316.

In certain embodiments, an Mrp polypeptide or immunogenic fragment or peptide thereof is fused in frame with another Mrp polypeptide or immunogenic fragment or peptide. In other embodiments, the fusion polypeptide comprises three different Mrps (or immunogenic fragments, peptides, or variants thereof), which in particular embodiments, the three different Mrps are representative polypeptides of each of the three Mrp families. For naming convenience when a fusion protein comprises two or more different Mrps (or immunogenic fragments, peptides, or variants thereof), the different Mrps may be called a first Mrp polypeptide (or fragment) and a second Mrp polypeptide (or fragment), etc. In other specific embodiments, a fusion protein may comprise one immunogenic fragment of one Mrp and a second immunogenic fragment of the same Mrp, which fragments may be, but not necessarily, linked by a non-immunogenic spacer amino acid sequence. In other specific embodiments, two or more immunogenic fragments of different Mrps within the same Mrp family may be fused in frame, with or without a spacer sequence, to form a fusion protein. In other embodiments, fusion proteins are provided that comprise at least one Mrp polypeptide or immunogenic fragment or peptide or variant thereof fused in frame to another GAS immunogenic polypeptide. In particular embodiments, an Mrp polypeptide or immunogenic fragment or peptide or variant thereof may be fused in frame with a GAS M protein or amino-terminal immunogenic fragment thereof. GAS M proteins and immunogenic fragments thereof that may be fused with Mrps in the fusion proteins or combined in immunogenic compositions are described in greater detail herein. Fusion proteins that comprise an Mrp protein or immunogenic peptide or polypeptide thereof (e.g., an immunogenic fragment from the N-terminal end of an Mrp mature protein) may comprise at least one of the Mrp proteins or immunogenic fragment thereof in duplicate. In a particular embodiment, the duplicates are directly linked in tandem (i.e., the carboxyl terminal amino acid of one duplicate is directly linked to the amino terminal amino acid of the second duplicate).

By way of example, in more specific embodiments, a fusion protein is provided that comprises at least two, three, four, five, six, seven, or eight, or more different Mrp polypeptides or immunogenic fragments thereof. In a particular embodiment, a fusion protein comprises at least two Mrp polypeptides or immunogenic fragments thereof that each belong to two different Mrp families. In another particular embodiment, a fusion protein comprises three Mrp polypeptides or immunogenic fragments thereof, and each of the three Mrp polypeptides (or immunogenic fragments thereof) belong to one of the three different Mrp families (e.g., Mrp2, Mrp4, and Mrp49 families). In another embodiment, the fusion protein comprises two or more immunogenic fragments from one Mrp family member. In more specific embodiments, a fusion protein comprises at least two of (a) an Mrp2 family polypeptide (e.g., SEQ ID NOS:10-13, 47-54) or immunogenic fragment or variant thereof; (b) an Mrp4 family polypeptide (e.g., SEQ ID NOS:18-20, 28-46) or immunogenic fragment or variant thereof; and (c) an Mrp49 family polypeptide (e.g., SEQ ID NOS:14-17, 55-57) or immunogenic fragment or variant thereof. In other specific embodiments, a fusion protein comprises at least one of an Mrp2 family polypeptide (e.g., SEQ ID NOS:10-13, 47-54) or immunogenic fragment or variant thereof; at least one of an Mrp4 family polypeptide (e.g., SEQ ID NOS:18-20, 28-46) or immunogenic fragment or variant thereof; and at least one of an Mrp49 family polypeptide (e.g., SEQ ID NOS:14-17, 55-57) or immunogenic fragment or variant thereof. An immunogenic fragment may comprise at least 5, 6, 8, 10, 15, 20, 25, 30, 35, 40, 45, 50, 55, 60, 65, 70, 75, 80, 85, 90, 95, or 100 or longer (or any integer of amino acids between 5-25, 5-50, 5-10, 10-15, 15-20, 20-25, 25-30, 25-50, 30-35, 35-40, 40-45, 45-50, 50-55, 55-60, 60-65, 65-70, 70-75, 75-80, 85-90, 90-95, 95-100, 100-105, 105-110, or 110-120) contiguous amino acids of an Mrp polypeptide of interest.

In other embodiments, any one of these fusion proteins may further comprise at least one immunogenic peptide that comprises at least 25 contiguous amino acids from the amino terminal portion of a group A streptococcus M protein or a group A streptococcus Spa protein. Examples of M and Spa immunogenic peptides that may be fused in frame with at least one Mrp immunogenic polypeptide or peptide are described in greater detail below. In certain specific embodiments, the at least one M protein is selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18. In still other specific embodiments, the at least one M immunogenic peptide is an M4 immunogenic peptide.

Variants of individual immunogenic polypeptides, peptides and of fusion polypeptides comprising immunogenic polypeptides and peptides, can be prepared without altering a biological activity of the resulting molecule (i.e., without altering one or more immunogenic activities in a statistically significant, clinically significant, or biologically significant manner). As described in greater detail herein, for example, substitutions of one amino acid for another are generally made by interchanging an amino acid with another amino acid that is included within the same group, such as the group of polar residues, charged residues, hydrophobic residues, and/or small residues, and the like. The effect of any amino acid substitution may be determined empirically merely by testing the resulting modified peptide or fusion polypeptide for the ability to function in a biological assay (e.g., bactericidal or opsonophagocytosis assays or animal models), or to bind to a cognate ligand or target molecule, such as a monoclonal or polyclonal antibody.

The fusion polypeptides described herein may further comprise a heterologous peptide or polypeptide that acts as a spacer between two different moieties, which may be between two different Mrp polypeptide or peptides; between an Mrp polypeptide or peptide and a different GAS immunogenic polypeptide or peptide (such as an M protein or Spa protein or immunogenic fragment thereof); or between a GAS immunogenic moiety and a heterologous peptide or polypeptide at either the amino or carboxy terminus that facilitates expression, solubilization, stabilization, isolation, and/or detection of the fusion protein. A polypeptide spacer typically comprises from 5 to 100 amino acid residues. Examples of spacers include the amino acid sequence KLAAALE (SEQ ID NO:65), and Gly-Ser spacers such as $(Gly_4Ser)_n$ ((SEQ ID NO: 99)$_n$) wherein n=1-12.

Each of these immunogenic polypeptides, peptides, and fusion proteins may each be chemically synthesized or may be recombinantly produced according to techniques and methods described in greater detail herein and in the art. Individual polypeptides, peptides, and/or fusion proteins may then be combined together and formulated in an immunogenic composition. Also as described in greater detail herein, the immunogenic compositions may further comprise one or more pharmaceutically suitable excipients, and may further comprise one or more pharmaceutically suitable adjuvants.

Given the description in the art and herein regarding regions of Mrps that exhibit immunogenic activity, persons skilled in the art can readily determine which amino acids in the full-length and in the amino terminal portions of Mrps may be more amenable to alteration (i.e., substitution, deletion, or addition of one or more amino acids) and which amino acids may not be amenable to change. Also given the description herein and given the many molecular biology, protein expression, and protein isolation techniques and methods routinely practiced in the art for introducing mutations in a peptide or polypeptide, isolating these peptides and polypeptides and variants thereof, and analyzing same, a polypeptide or peptide variant having the desired immunogenicity can be made readily and without undue experimentation. Retention of immunogenicity includes the capability to evoke an immune response against GAS, such as production of antibodies that specifically bind to the cognate immunogenic peptide and/or fusion polypeptide, cognate mature Mrp (either isolated or present on the cell surface of GAS bacteria), or cognate full-length Mrp, and which antibodies include those with bactericidal or phagocytic activity. Retention of immunogenicity may also include the capability to evoke an immune response against SDSE, which may include production of antibodies that specifically bind to SDSE and which antibodies may have bactericidal activity or phagocytic activity.

Assays for assessing whether a variant of an immunogenic polypeptide or peptide of an Mrp, or a fusion polypeptide comprising the immunogenic peptide(s), folds into a conformation comparable to the non-variant peptide or fusion polypeptide include, for example, the ability of the polypeptide, peptide or fusion polypeptide to react with mono- or polyclonal antibodies that are specific for native or unfolded epitopes, the retention of ligand-binding functions, immunologic function, and the sensitivity or resistance of the mutant polypeptide, peptide or fusion polypeptide to digestion with proteases (see Sambrook et al., supra). Immunogenic polypeptide and peptide variants and fusion polypeptide variants as described herein can be identified, characterized, and/or made according to these methods described herein or other methods known in the art, which are routinely practiced by persons skilled in the art.

Group A *Streptococcus* M and Spa Proteins

The cell surface M protein of GAS is a major virulence factor for this pathogen. The M protein, which is encoded by the emm gene, extends from the cell surface as an α-helical coiled-coil dimer that appears as a fibril on the surface of a GAS bacterium. The M proteins form an antigenically diverse group, and GAS strains have been serologically categorized according to M protein serotypes. More than 120 M protein serotypes have been identified, and within some serotypes, subtypes have also been identified. By way of example, the M proteins of GAS serotype 3 include related subtypes, which are designated as 3.0, 3.1, 3.2, etc. Antibodies to the M protein can facilitate opsonophagocytosis by phagocytic cells present in blood. As used herein, when referring to GAS bacteria according to serotype, the bacteria may be called, for example, GAS serotype 3, GAS M serotype 3, or GAS serotype M3. When referring to the M protein of a particular serotype, the designation of the GAS serotype from which the M protein is derived, such as M3, is typically followed by the word protein or immunogenic peptide depending on the context (i.e., M3 protein or M3 immunogenic peptide).

Distinct from M protein, a polypeptide designated Spa (Streptococcal protective antigen) contains epitopes that induce production of opsonic, protective antibodies. Spa polypeptides may be serotype specific, such as the Spa polypeptide from GAS serotype 36, whereas other Spa polypeptides, such as Spa polypeptide isolated from GAS serotype 18, evoke antibodies that bind to multiple GAS serotypes. The Spa polypeptide of GAS serotype 18 induces antibodies that bind to and are protective against serotypes 3 and 28 as well as serotype 18 (see, e.g., U.S. Pat. No. 7,063,850; Ahmed et al., *Eur. J. Clin. Microbiol. Infect. Dis.* 29:51-57 (2010) Epub 2009 Oct. 29; McLellan et al., *Infect. Immun.* 69:2943-49 (2001); Dale et al., *J. Clin. Invest.* 103:1261-68 (1999)).

Fusion proteins may comprise at least one of the more than 120 GAS M proteins or a GAS Spa protein, or immunogenic fragment thereof. In other embodiments, a fusion protein may comprise at least one Mrp or immunogenic fragment thereof and may further comprise at least one of the more than 120 GAS M proteins or a GAS Spa protein, or immunogenic fragment thereof. Also provided herein are immunogenic compositions comprising such a fusion protein. Alternatively, in another embodiment, immunogenic compositions (or preparations as described herein) for use in evoking an immune response against GAS or SDSE or both may comprise one or more MRP proteins or immunogenic fragments thereof, one or more fusion proteins comprising one or more MRP proteins or immunogenic fragments thereof, and one or more immunogenic fragments of GAS M protein(s) or Spa protein or one or more fusion proteins comprising one or more immunogenic fragments of GAS M protein(s) or Spa protein. Selection of M protein serotypes to include may be based on available epidemiology and serotype prevalence of GAS infections in North America and Europe (see, e.g., Shulman et al., *Clin. Infect. Dis.* 39:325-32 (2004)); Shulman et al., *Clin. Infect. Dis.* 49:78-84 (2009); O'Loughlin et al., *Clin. Infect. Dis.* 45:853-62 (2007); Luca-Harari et al., *J. Clin. Microbiol.* 47:1155-65 (2009)), and in developing countries (see, e.g., Steer et al., *The Lancet Infectious Diseases* 9:611-16 (2009)).

In a particular embodiment, immunogenic compositions are provided that comprise at least one of the more than 120 GAS M proteins or a GAS Spa protein, or immunogenic fragment thereof. These fusion proteins and immunogenic compositions may also contain an immunogenic peptide from a Spa protein. These compositions comprising GAS M and/or Spa proteins, or immunogenic fragments thereof, may be used alone (i.e., in the absence of an at least one Mrp protein or immunogenic fragment thereof or composition comprising same) for evoking an immune response against GAS and/or SDSE.

The amino terminal regions of M proteins have been shown to evoke antibodies with the greatest bactericidal (protective) activity and are least likely to cross-react with human tissues (see, e.g., Dale, *Adv. Exp. Med. Biol.* 609: 53-63 (2008)). One approach has been to construct recombinant hybrid proteins containing M protein peptides combined into multivalent vaccines designed to elicit opsonic antibodies against epidemiologically important serotypes of group A streptococci (see, e.g., Dale, *Inf. Dis. Clin. N. Amer.* 13:227-43 (1999); Hu et al., *Infect. Immun.* 70:2171-77 (2002)).

The amino acid sequences of M proteins and subtypes of M proteins are available in protein databases, such as GenBank, GenEMBL, and Swiss Prot databases. M protein sequences are also available at the Center for Disease Control (CDC) emm typing center website that may be found by accessing the Internet at cdc.gov/ncidod/biotech/strep/emmtypes. Criteria for subtyping of GAS M serotypes as currently used in the art is described by Facklam et al., *Emerg. Infect. Dis.* 5:247-53 (1999).

The amino acid sequences of Spa polypeptides are also available in public databases and described in Dale et al., *J. Clin. Invest.* 103:1261-68 (1999); U.S. Pat. No. 7,063,850; and International Patent Application Publication No. WO 00/37648. The amino-terminal peptide fragment of Spa18, a protective antigen that is expressed by several serotypes of group A streptococci, such as but not limited to, GAS serotype 18, GAS serotype 3, and GAS serotype 28.

Also long known in the art, region(s) of M proteins comprise amino acid sequences that induce antibodies that cross-react with host tissue, for example, human heart (see, e.g., Dale et al., *J. Exp. Med.* 156:1165-76 (1982); Dale et al., *J. Exp. Med.* 161:113-22 (1985)), brain (see, e.g., Bronze et al., *J. Immunol.* 151:2820-28 (1993)), muscle, kidney, and cartilage. Accordingly, the design of fusion proteins and immunogenic compositions described herein, which may be used in combination with at least one Mrp protein or immunogenic fragment thereof, includes analysis of amino acid sequences of M proteins to determine if an M protein has five or more contiguous amino acids in common with one or more human proteins and which therefore could potentially induce antibodies that might bind to human tissue. Immunogenic peptides of M proteins and fusion polypeptides comprising these immunogenic peptides described herein lack regions that comprise five or more contiguous amino acids that are identical to five or more contiguous amino acids of a known human protein.

Comparison of the amino acid sequences of M proteins with human proteins can be accomplished using one or more of the several alignment programs available to a person skilled in the art. Such alignment tools (which may also be useful for comparing nucleotide sequences, such as those encoding an M protein) include, without limitation, software programs such as BlastP, BLAST, tBLAST, and MegAlign. Other software programs are provided in the Lasergene bioinformatics computing suite (DNASTAR® Madison, Wis.); CLUSTALW program (see, e. g., Thompson et al., *Nucleic Acids Res.* 22:4673-80 (1991)); and "GeneDoc" (Nicholas et al., EMBNEW News 4:14 (1991)). References for algorithms such as ALIGN or BLAST may be found in, for example, Altschul, *J. Mol. Biol.* 219:555-565, 1991; and Henikoff and Henikoff, *Proc. Natl. Acad. Sci. USA* 89:10915-10919, 1992. Algorithms including the Align and BLAST algorithms are available at the NCBI website (see [online] Internet at ncbi.nlm.nih.gov/cgi-bin/BLAST). Default parameters may be used. Additional methods available in the art for comparing nucleotide or amino acid sequences and determining optimal alignment include methods described, for example, in Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology*, pages 123-151 (CRC Press, Inc. 1997); and Bishop (ed.), *Guide to Human Genome Computing*, 2nd Ed. (Academic Press, Inc. 1998).

A GAS M or Spa immunogenic peptide, which may be used in the compositions and fusion proteins in combination with an Mrp polypeptide, peptide, or fusion protein, comprises an immunogenic portion of a full-length GAS polypeptide and may comprise at least 20, 25, 30, 35, 40, 45, 50, 55, or 60 or more contiguous amino acids (or any number of amino acids between 20-45, 20-50, 25-45, 25-50, 25-60, 25-30, 30-35, 35-40, 40-45, 45-50, 40-55, or 55-60, or more than 60 contiguous amino acids) of the mature polypeptide (i.e., the polypeptide from which the signal peptide sequence has been removed). In certain particular embodiments, the M or Spa immunogenic peptide comprises at least 25, 30, 35, 40, 45, 50, 55, or 60 or more contiguous amino acids from the amino terminal portion of the M protein or the Spa protein (or any number of amino acids between 25-45, 25-50, 25-60, 25-30, 30-35, 35-40, 40-45, 45-50, 40-55, or 55-60, or more than 60 contiguous amino acids from the amino terminal portion of the protein). An immunogenic portion of a mature or full-length GAS M or Spa polypeptide has one or more epitopes that induces an immune response, which includes production of antibodies that specifically bind to the immunogenic peptide, and to the immunogenic portion within the mature and full-length polypeptide, and to GAS bacteria that express the polypeptide. As described herein, the immune response may include production of antibodies that bind to SDSE. In more particular embodiments, an M or Spa immunogenic peptide comprises at least 25 or at least 50 contiguous amino acids from the amino terminal portion of the M protein or the Spa protein, respectively.

In certain specific embodiments, a fusion protein comprising two or more of the M immunogenic peptides or Spa immunogenic peptides may be used in combination with an at least one Mrp polypeptide, peptide or a fusion protein comprising at least one Mrp immunogenic polypeptide or peptide (or composition comprising same). Fusion proteins that comprise an M immunogenic peptide or Spa immunogenic peptide comprising at least 25 contiguous amino acids from the amino terminal portion of the respective M protein or a Spa protein may comprise at least one of the M or Spa peptides in duplicate. In a particular embodiment, the duplicates are directly linked in tandem. In other words and by way of illustration, if the immunogenic region selected includes amino acid residues 1-25 of the amino terminal portion of an M protein or Spa protein, the immunogenic peptide in duplicate includes amino acid residues 1-25 linked in tandem to a second repeat of amino acids 1-25 (i.e., amino acid residue 25 of the first duplicate bonds directly to amino acid residue 1 of the second duplicate).

Immunogenic compositions that comprise one or more M immunogenic peptides may be obtained from or derived from at least 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, or more different GAS serotypes. In a more specific embodiment, one of the GAS serotypes represented in an immunogenic composition is M4, and the immunogenic composition comprises an M4 immunogenic peptide comprising at least 25 contiguous amino acids from the amino terminal portion of the M4 protein. In other certain embodiments, an immunogenic composition comprises at least 25-31 immunogenic peptides that are representative of at least 24-30 different GAS serotypes. In more particular embodiments, an immunogenic composition comprises at least 31 different immunogenic M and Spa peptides; the amino acid sequence of each of the 31 immunogenic peptides is different and each comprises at least 25, 30, 35, 40, 45, 50, 55, or 60 or more contiguous amino acids (or any number of amino acids between 25-45, 25-50, 25-60, 25-30, 30-35, 35-40, 40-45, 45-50, 40-55, or 55-60, or more than 60 contiguous amino acids). In certain embodiments, the 31 immunogenic peptides are obtained or derived from the amino terminal portion of the M protein from one of GAS serotypes (1) M1; (2) M2; (3) M3; (4) M4; (5) M5; (6) M6; (7) M11; (8) M12; (9) M14; (10) M18; (11) M19; (12) M22; (13) M24; (14) M28; (15) M29; (16) M44; (17) M49; (18) M58; (19) M73; (20) M75; (21) M77; (22) M78; (23) M81; (24) M82; (25) M83; (26) M87; (27) M89; (28) M92; (29) M114; (30) M118, and (31) from the amino terminal portion of the Spa protein from GAS serotype, for example, such as GAS serotype M18. In another more specific embodiment, one or more of the immunogenic peptides comprises at least 25 contiguous amino acids in duplicate. In another specific embodiment one or more of the immunogenic peptides comprises at least 40, at least 45, or at least 50 contiguous amino acids.

In other certain embodiments, an immunogenic composition may comprise 32, 33, 34, 35, 36, 37, 38, 39, 40, 41, 42, 43, 44, 45, or more different M and Spa immunogenic peptides. The different immunogenic peptides may include the 31 immunogenic peptides from the amino terminal portions of the M proteins from GAS M serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118, and Spa protein from the GAS serotype 18 (as described above) and further comprise immunogenic peptides from the amino terminal portions of M proteins from at least one additional, different GAS serotype or subtype and/or one or more additional, different immunogenic peptide(s) from the amino terminal portion of a Spa protein. Selection of additional immunogenic peptides may be informed by one or more of epidemiology data; the lack of shared identity of 5 or more contiguous amino acids of the GAS protein with a human protein; immunogenicity, bactericidal, and/or protection data, including the capability of the one or more additional immunogenic peptides to increase the number of non-represented GAS serotypes recognized by antibodies produced in response to immunization with such an immunogenic composition.

As described herein and known to a person skilled in the art, the amino terminal portion of M proteins and Spa proteins comprise the regions of M proteins and Spa proteins that have one or more immunogenic epitopes which evoke a protective immune response against the beta-hemolytic streptococci, GAS or SDSE or both, but do not induce antibodies that cross-react with proteins expressed by human cells and tissues. As used herein the amino terminal portion of an M protein or a Spa protein refers to the mature protein, which is the expressed protein lacking the signal peptide sequence.

Accordingly, unless specified otherwise, a description herein of an M or Spa immunogenic peptide as an immunogenic peptide comprising the amino acid sequence of residues 1-50 of an M protein (for example), residue 1 is at the amino terminus of the M protein in the absence of the signal peptide sequence. Exemplary amino acid sequences for immunogenic peptides are provided in SEQ ID NOS: 66-96 (see Sequence Listing and Table 2).

The term "amino terminal portion" of an M protein or a Spa protein is readily understood by a person having ordinary skill in the art as the portion or region of an polypeptide located in the amino terminal half of the polypeptide. The immunogenic peptides described herein that comprise amino acids from the amino terminal portion of an M protein or a Spa protein may, but not necessarily, comprise at least 25 contiguous amino acids from the amino terminal end of the respective M protein or Spa protein (i.e., amino acids 1-25 of the mature polypeptide). In other instances, an immunogenic peptide may comprise at least 25 contiguous amino acids derived from the amino terminal portion of an M protein or Spa protein that lack one or more amino acids located at the amino terminus of the mature protein (e.g., amino acids 2-26, 3-27, 4-28 and the like of the mature polypeptide). In other embodiments, and by way of example, the at least 25 contiguous amino acids may be derived from the amino terminal portion of the M protein or Spa protein that begins at amino acid position 5, 6, 7, 8, 9, 10, 11, 12, 13, 14, 15, 16, 17, 18, 19, 20, 21, 22, 23, 24, or 25. As described herein, the amino acid sequence of each immunogenic peptide is selected, at least in part, on the basis of the presence of at least one immunogenic epitope and the lack of at least five contiguous amino acids that are identical to at least five contiguous amino acids present in a known human protein.

In one embodiment, the immunogenic composition comprising at least 31 different immunogenic peptides contains each of the individual immunogenic peptides as separate peptides. In certain embodiments, the immunogenic composition may comprise 31, 32, 33, 34, 35, 36, 37, 38, 39, 40, 41, 42, 43, 44, 45, or more different immunogenic peptides and contains each of the individual immunogenic peptides as a separate peptide. Each of these immunogenic peptides may be chemically synthesized or may be recombinantly produced according to techniques and methods described in greater detail herein and in the art. The individual peptides are then combined together and formulated in an immunogenic composition. Also as described in greater detail herein, the immunogenic compositions may comprise one or more pharmaceutically suitable excipients, and may further comprise one or more pharmaceutically suitable adjuvants. In still another embodiment, an immunogenic composition that comprises M and Spa immunogenic peptides comprises the at least 31 different M and Spa immunogenic peptides as a combination of individual immunogenic peptides, dimeric peptides, and/or trimeric peptides.

In still other embodiments, at least four different immunogenic peptides may be linked together in tandem to form a fusion polypeptide for inclusion in an immunogenic composition. In certain embodiments, the immunogenic composition comprising at least 31 different M and Spa immunogenic peptides may include at least one, two, three, four, five, six, seven, or more fusion polypeptides, wherein each fusion polypeptide comprises at least 4, 5, 6, 7, 8, 9, 10, 11, 12, 13, 14, or 15, different and individual M and Spa immunogenic peptides linked together in tandem. In certain particular embodiments, the immunogenic composition comprises 31, 32, 33, 34, 35, 36, 37, 38, 39, 40, 41, 42, 43, 44, 45, or more different immunogenic peptides and may include at least one, two, three, four, five, six, seven or more fusion polypeptides, wherein each fusion polypeptide comprises at least 4, 5, 6, 7, 8, 9, 10, 11, 12, 13, 14, or 15, different and individual M and Spa immunogenic peptides linked together in tandem. In even more specific embodiments described herein, an immunogenic composition comprises at least 31 different immunogenic peptides, each from the amino terminal portion of a GAS M protein or Spa protein, and at least six, seven, eight or nine different immunogenic peptides are linked together in a manner that provides four fusion polypeptides. Stated another way, each of the at least 31 different immunogenic peptides is included in one of these four fusion polypeptides. Such compositions may be combined with an immunogenic composition comprising at least one Mrp protein or immunogenic fragment thereof to form a preparation. Each composition of the preparation may be administered concurrently or each composition of the preparation may be administered sequentially to a subject, thereby evoking an immune response to GAS, SDSE, or both GAS and SDSE.

In more specific embodiments, an immunogenic composition comprises at least 31 different M and Spa immunogenic peptides (e.g., immunogenic peptides from the amino terminal portions of the M proteins from GAS M serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118, and Spa protein from GAS serotype 18), wherein at least six, seven, eight, or nine different immunogenic peptides are linked together in tandem to form at least four fusion polypeptides. In one particular embodiment, each of the four fusion polypeptides comprises at least 7 or at least 8 different immunogenic peptides. In one embodiment, the immunogenic composition comprises four fusion polypeptides (which for convenience may be called a first fusion polypeptide, a second fusion polypeptide, a third fusion polypeptide, and a fourth fusion polypeptide) and each fusion polypeptide comprises 7 or 8 different immunogenic peptides independently selected from the at least 31 different immunogenic peptides. Which immunogenic peptides are included on each of the first, second, third, and fourth fusion polypeptides and the order with which the immunogenic peptides are linked may be readily determined by a person skilled in the art using methods and techniques described herein and routinely practiced in the art and does not require undue empirical, trial and error analysis to ensure optimization of the immunogenicity of each polypeptide. To determine that the amino acids located at the junction where two different immunogenic peptides are tandemly linked does not introduce a contiguous 5-amino acid sequence that shares identity with a human protein, the amino acid sequence of each fusion polypeptide is compared with the sequences of human proteins available in databases described herein and known to the person skilled in the art.

Fusion polypeptides comprising three or more different immunogenic peptides from the amino terminal portions of the M proteins and Spa proteins from GAS serotypes are constructed so that the immunogenic peptide located at the amino terminal end is repeated (i.e., duplicated) at the carboxy terminal end of the fusion polypeptide. In the absence of a duplicate immunogenic peptide at the carboxy terminal end of the fusion polypeptide, the immunogenicity of the penultimate and carboxy terminal peptide may be reduced or compromised. Without wishing to be bound by theory, repetition of the amino terminal peptide at the carboxy terminal end preserves the immunogenicity of all peptides included in the fusion protein and reduces or abrogates the need for inclusion of a non-GAS carrier protein, such as tetanus toxoid, keyhole limpet hemocyanin, or other protein or protein fragment, used in the art to enhance an immune response to an antigen of interest. See U.S. Pat. Nos. 6,716,433 and 7,402,316.

As described herein, the amino acid sequences of M proteins and Spa proteins are readily available in the art. M and Spa immunogenic peptide species or a fusion polypeptide species comprising the immunogenic peptides described herein includes immunogenic peptide species and fusion polypeptide species, respectively, that have one or more amino acid substitutions, insertions, or deletions (also called herein a variant). Databases, such as provided at the CDC emm typing center website, may be accessed to determine the variability in the amino acid sequences within an M protein from a GAS serotype (referred to herein and in the art as GAS subtypes) or within a Spa protein from a GAS serotype (see, e.g., Dale et al., *Clin. Diagn. Lab. Immunol.* 12:833-36 (2005); Facklam et al., *Emerg. Infect. Dis.* 5:247-53 (1999)). Alignment tools for comparison of the amino terminal portions of M proteins (or Spa proteins) can be used to identify amino acid residues within the amino terminal portion that may be variable. The amino acid sequences of the immunogenic peptides and fusion polypeptides described herein are examples, and immunogenic peptides and fusion polypeptides useful for inducing an immune response against GAS may include substitutions, insertions, and deletions of one or more amino acids that do not adversely affect (i.e., do not decrease or reduce in a statistically significant manner or biologically or clinical significant manner) the immunogenicity of the immunogenic peptide or fusion polypeptide. Fusion polypeptide variants include species comprising at least one immunogenic peptide variant. Immunogenicity of a variant peptide or variant fusion polypeptide that is substantially similar in a statistically, biologically, or clinically significant manner to the immunogenicity of an immunogenic peptide or fusion polypeptide, respectively, described herein is desired. Table 2 provides examples of amino acid sequences for immunogenic peptides from the amino terminal portions of the M proteins from GAS M serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118, and Spa protein from GAS serotype 18.

Also provided herein in more specific embodiments are immunogenic compositions that may be used in particular geographic regions. By way of example, in certain embodiments immunogenic compositions are provided that comprise at least 23 different immunogenic peptides (e.g., immunogenic peptides from the amino terminal portions of the M proteins from GAS M serotypes 1; 2; 3; 4; 5; 6; 11; 12; 14; 18; 19; 22; 24; 28; 29; 44; 58; 73; 75; 77; 78; 89; 118, and Spa protein from GAS serotype 18), wherein at least six, seven, eight, or nine different immunogenic peptides are linked together in tandem to form at least three or at least four fusion polypeptides (which for convenience may be called a first fusion polypeptide, a second fusion polypeptide, a third fusion polypeptide, a fourth fusion polypeptide), and each fusion polypeptide comprises 7 or 8 different immunogenic peptides. This exemplary immunogenic composition comprises GAS serotypes that are more prevalent in GAS infections in North America than in other global regions, such as Europe. GAS M serotypes, such as 49, 81, 82, 83, 87, 92 and 114, are identified in Europe more frequently than in North America as the cause of a GAS infection.

A person having ordinary skill in the art will readily appreciate that the GAS M and Spa polypeptides and peptides described herein include variants of the described amino acid sequences, which variants comprise at least one amino acid deletion, insertion, or substitution when compared with the amino acid sequence provided herein that is the "wildtype" or the "parent" sequence. Variants of M and Spa immunogenic peptides (and Mrp polypeptides and peptides) are described in greater detail herein.

Given the description in the art and herein regarding regions of M proteins and Spa proteins that exhibit immunogenic activity and lack undesirable epitopes that induce antibodies that cross-react with proteins expressed on human cells, persons skilled in the art can readily determine which amino acids in the amino terminal portions of M proteins and Spa proteins may be more amenable to alteration (i.e., substitution, deletion, or addition of one or more amino acids) and which amino acids may not be amenable to change. Also given the description herein and given the many molecular biology, protein expression, and protein isolation techniques and methods routinely practiced in the art for introducing mutations in a peptide or polypeptide, isolating these peptides and polypeptides and variants thereof and analyzing same with the desired immunogenicity can be accomplished readily and without undue experimentation. Retention of immunogenicity includes the capability to evoke an immune response against GAS, such as production of antibodies that specifically bind to the cognate immunogenic peptide and/or fusion polypeptide, cognate mature M protein or Spa protein (either isolated or present on the cell surface of GAS bacteria), or cognate full-length M protein or Spa protein, and which antibodies include those with bactericidal and phagocytic activity. In certain embodiments, retention of immunogenic includes the capability to evoke an immune response against SDSE, such as production of antibodies that specifically bind to SDSE, and which antibodies include those with bactericidal and phagocytic activity.

Assays for assessing whether a variant of an immunogenic peptide of an M protein or of a Spa protein, or a fusion polypeptide comprising the immunogenic peptides, folds into a conformation comparable to the non-variant peptide or fusion polypeptide include, for example, the ability of the peptide or fusion polypeptide to react with mono- or polyclonal antibodies that are specific for native or unfolded epitopes, the retention of ligand-binding functions, retention of immunogenic activity, and the sensitivity or resistance of the mutant peptide or fusion polypeptide to digestion with proteases (see Sambrook et al., supra). Immunogenic peptide variants and fusion polypeptide variants as described herein can be identified, characterized, and/or made according to these methods described herein or other methods known in the art, which are routinely practiced by persons skilled in the art.

Variants of individual immunogenic peptides and of fusion polypeptides comprising immunogenic peptides, can be prepared without altering a biological activity of the resulting molecule (i.e., without altering one or more immunogenic activities in a statistically significant, clinically significant, or biologically significant manner). As described in greater detail herein, for example, such substitutions are generally made by interchanging an amino acid with another amino acid that is included within the same group, such as the group of polar residues, charged residues, hydrophobic residues, and/or small residues, and the like. The effect of any amino acid substitution may be determined empirically merely by testing the resulting modified peptide or fusion polypeptide for the ability to function in a biological assay, or to bind to a cognate ligand or target molecule, such as a monoclonal or polyclonal antibody.

Examples of immunogenic compositions comprising M and Spa immunogenic peptides include the following. In one embodiment, an immunogenic composition comprises 31 different immunogenic peptides, and each immunogenic peptide is incorporated into one of four fusion polypeptides. Each immunogenic peptide is from the amino terminal portion of the M protein from one of GAS M serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118, or from the amino terminal portion of Spa protein from GAS serotype 18. Three fusion polypeptides (for convenience, called a first, second, and third fusion polypeptide, respectively) each comprise at least 8 different immunogenic peptides linked in tandem, and the fourth fusion polypeptide comprises at least 7 different immunogenic peptides linked in tandem. Each immunogenic peptide in each of the first, second, third, and fourth fusion polypeptides may comprise independently at least 25, 30, 35, 40, 45, 50, 55, or 60 or more contiguous amino acids from the amino terminal portion of the respective M protein or Spa protein (or any number of amino acids between 25-40, 25-50, 25-60, 25-30, 30-35, 35-40, 40-45, 45-50, 40-55, or 55-60, or more than 60 contiguous amino acids from the amino terminal portion of the respective M protein or Spa protein). In another more specific embodiment, one or more of the immunogenic peptides comprises at least 25 contiguous amino acids in duplicate and each duplicate is in tandem (i.e., not separated by one or more immunogenic peptides from a different M or Spa protein of the fusion protein). In another specific embodiment one or more of the immunogenic peptides comprises at least 40, at least 45, or at least 50 contiguous amino acids from the amino terminal portion of the respective M protein or Spa protein.

In a particular embodiment, the first fusion polypeptide comprises 8 immunogenic peptides, which are different, and each immunogenic peptide comprises at least 25 contiguous amino acids from the amino terminal portion of the M protein from one of GAS M serotypes 1, 2, 3, 6, 12, 18, 28, and from the amino terminal portion of the Spa protein from GAS serotype 18. Stated another way, a first fusion polypeptide comprises at least 8 different immunogenic peptides linked in tandem, and each immunogenic peptide comprises at least 25 contiguous amino acids from the amino terminal portion of one of M1 protein, M2 protein, M3 protein, M6 protein, M12 protein, M18 protein, M28 protein, and Spa 18 protein (i.e., the fusion polypeptide therefore comprises an immunogenic peptide from the amino terminal portion of M1 protein, an immunogenic peptide from the amino terminal portion of M2 protein, an immunogenic peptide from the amino terminal portion of M3 protein etc.). One of the immunogenic peptides is repeated at each of the amino and carboxy terminal ends of the fusion polypeptide. In a more particular embodiment, the first fusion polypeptide comprises duplicates (repeats) of the immunogenic peptide comprising at least 25 contiguous amino acids from the amino terminal portion of the M protein from GAS serotype 1; one duplicate is located at the amino terminal end of the fusion polypeptide and the second duplicate is located at the carboxy terminal end of the fusion polypeptide.

In one embodiment, the second fusion polypeptide comprises at least 8 different immunogenic peptides linked in tandem, and each immunogenic peptide comprises at least 25 contiguous amino acids from the amino terminal portion of one of M4 protein, M5 protein, M11 protein, M14 protein, M19 protein, M24 protein, M29 protein, and M75 protein. One of the immunogenic peptides is repeated at each of the amino and carboxy terminal ends of the second fusion polypeptide. In a more particular embodiment, the second fusion polypeptide comprises duplicates (repeats) of the immunogenic peptide comprising at least 25 contiguous amino acids from the amino terminal portion of the M protein from GAS serotype 4; one duplicate is located at the amino terminal end of the fusion polypeptide and the second duplicate is located at the carboxy terminal end of the fusion polypeptide.

In certain embodiments, the third fusion polypeptide comprises at least 8 different immunogenic peptides linked in tandem, and each immunogenic peptide comprises at least 25 contiguous amino acids from the amino terminal portion of one of M22 protein, M44 protein, M58 protein, M73 protein, M77 protein, M78 protein, M89 protein, and M118 protein. One of the immunogenic peptides is repeated at each of the amino and carboxy terminal ends of the third fusion polypeptide. In a more particular embodiment, the third fusion polypeptide comprises duplicates (repeats) of the immunogenic peptide comprising at least 25 contiguous amino acids from the amino terminal portion of the M protein from GAS serotype 77; one duplicate is located at the amino terminal end of the fusion polypeptide and the second duplicate is located at the carboxy terminal end of the fusion polypeptide.

The fourth fusion polypeptide in certain embodiments comprises at least 7 different immunogenic peptides linked in tandem, and each immunogenic peptide comprises at least 25 contiguous amino acids from the amino terminal portion of one of M49 protein, M81 protein, M82 protein, M83 protein, M87 protein, M92 protein, and M114 protein. One of the immunogenic peptides is repeated at each of the amino and carboxy terminal ends of the fourth fusion polypeptide. In a more particular embodiment, the fourth fusion polypeptide comprises duplicates (repeats) of the immunogenic peptide comprising at least 25 contiguous amino acids from the amino terminal portion of the M protein from GAS serotype 83; one duplicate is located at the amino terminal end of the fusion polypeptide and the second duplicate is located at the carboxy terminal end of the fusion polypeptide.

In certain specific embodiments, as discussed herein, the immunogenic peptides may be derived from subtypes of the respective M protein. For example, in certain specific embodiments, the immunogenic peptide from the M protein of GAS serotype 3 is from GAS serotype 3.1. In other specific embodiments, the immunogenic peptide from the M protein of GAS serotype 6 is from GAS serotype 6.4. In still another specific embodiment, the immunogenic peptide from the M protein of GAS serotype 5 is from GAS serotype 5.0 (parent subtype). In a certain particular embodiment, the immunogenic peptide from the M protein of GAS serotype 14 is from GAS serotype 14.3. In yet another specific embodiment, the immunogenic peptide from the M protein of GAS serotype 29 is from GAS serotype 29.2. In still yet another specific embodiment, the immunogenic peptide from the M protein of GAS serotype 49 is from GAS serotype 49.1. In still another specific embodiment, the immunogenic peptide from the M protein of GAS serotype 83 is from GAS serotype 83.1. If no subtype is designated, the M protein is derived from the subtype considered in the art as the "parent" subtype, such as, by way of illustration, M12.0, M18.0, M28.0, and the like.

In a more specific embodiment, the first fusion polypeptide comprising eight immunogenic peptides, which immunogenic peptides are independently from the amino terminal portion of the M protein from one of GAS M serotypes 1, 2, 3, 6, 12, 18, 28, and from the amino terminal portion of the Spa protein from GAS serotype 18 as described above, are linked in tandem in the following order from amino terminal to carboxy terminal: M1, M3.1, M6.4, M2, M18, M28, M12, Spa, and M1. Each of the M1, M18, M28, M12, and Spa immunogenic peptides comprises amino acid residues 1-50 from each of the respective mature M proteins or Spa protein. The immunogenic peptide representing the GAS serotype 3.1 comprises amino acid residues at positions 22-71 of the mature M3.1 protein. Each of the immunogenic peptides of the M3.1 protein and the M6.4 protein include amino acid residues 1-25 of the respective mature M protein linked directly in tandem to a duplicate (i.e., repeat) of residues 1-25. The immunogenic peptide of the M2 protein include amino acid residues 2-26 of the respective mature M protein linked directly in tandem to a duplicate (i.e., repeat) of residues 2-26. The second fusion polypeptide comprising eight immunogenic peptides, which immunogenic peptides are independently from the amino terminal portion of the M protein from one of GAS M serotypes 4, 5, 11, 14, 19, 24, 29, and 75, are linked in tandem in the following order from amino terminal to carboxy terminal: M4, M5.0, M11, M75, M19, M29.2, M14.3, M24, and M4. Each of the M4, M11, M75, M29.2, M14.3, and M24 immunogenic peptides comprises amino acid residues 1-50 from the amino terminal portion of the respective mature M protein. Each of the immunogenic peptides of the M5.0 protein and the M19 protein includes amino acid residues 1-25 of the respective mature M protein linked directly in tandem to a duplicate (i.e., repeat) of residues 1-25. The third fusion polypeptide comprising eight immunogenic peptides, which immunogenic peptides are independently from the amino terminal portion of the M protein from one of GAS M serotypes 22, 44, 58, 73, 77, 78, 89, and 118, are linked in tandem in the following order from amino terminal to carboxy terminal: M77, M22, M73, M89, M58, M44, M78, M118, and M77. Each of these M protein immunogenic peptides comprises amino acid residues 1-50 at the amino terminal portion of the respective mature M proteins. The fourth fusion polypeptide comprising seven immunogenic peptides, which immunogenic peptides are independently from the amino terminal portion of the M protein from one of GAS M serotypes 49, 81, 82, 83, 87, 92, and 114, are linked in tandem in the following order from amino terminal to carboxy terminal: M83.1, M82, M81, M87, M49.1, M92, M114, and M83.1. Each of these M protein immunogenic peptides comprises amino acid residues 1-50 at the amino terminal portion of the respective mature M proteins.

Examples of amino acid sequences for each of the specific embodiments of a first, second, third, and fourth fusion polypeptides are provided in SEQ ID NOS: 24, 25, 26, and 27, respectively. Any of the immunogenic peptides and fusion polypeptides, including the exemplary fusion polypeptides described herein may further comprise a heterologous peptide or polypeptide at either the amino or carboxy terminus or both to facilitate expression, solubilization, stabilization, isolation, and/or detection. For example, when immunogenic polypeptides, peptides, or fusion polypeptides are produced according to recombinant methods, an initiating methionine residue at the amino terminus is typically included, and which are described in greater detail herein. A fusion polypeptide variant includes a fusion polypeptide, that has at least 70%, 80%, 85%, 90%, 92%, 95%, 97%, 98%, or 99% amino acid sequence identity to any of the exemplary fusion polypeptide amino acid sequences provided herein, including in the sequence listing (e.g., SEQ ID NOS:24-27). Fusion polypeptides useful for inducing an immune response against GAS may include substitutions, insertions, and deletions of one or more amino acids of any of the aforementioned amino acid sequences and that do not adversely affect or alter (decrease or reduce) the immunogenicity of the fusion polypeptide in a statistically, biologically, or clinically significant manner. Stated another way, a variant of a fusion polypeptide described herein retains immunogenicity exhibited by the parent or non-variant fusion polypeptide. As described herein, retention of immunogenicity includes the capability to evoke an immune response against GAS, such as production of antibodies that specifically bind to the cognate immunogenic peptide and/or fusion polypeptide, cognate mature or full-length M protein or Spa protein (either isolated or present on the cell surface of GAS bacteria), and which antibodies include those with bactericidal and phagocytic activity against GAS or SDSE or both.

In one embodiment, an immunogenic composition comprising at least one Mrp polypeptide, peptide, or fusion protein (or a variant of Mrp polypeptide, peptide or fusion protein) may be combined with an immunogenic composition comprising at least one M immunogenic peptide or Spa immunogenic peptide as described above. In certain embodiments, an Mrp containing immunogenic composition is used in conjunction with a 30-valent GAS vaccine comprising each of the above described examples of first, second, third, and fourth fusion polypeptides. An immunogenic composition comprising these four GAS M and Spa fusion proteins evokes production of bactericidal antibodies that specifically bind to each GAS serotype represented by an M protein immunogenic peptide and Spa immunogenic peptide (i.e., GAS serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118) (see also, e.g., International Patent Application Publication No. WO 2012/174455). Another example of an immunogenic composition comprising GAS M protein immunogenic fragments and a Spa immunogenic fragment is a 26-valent composition (i.e., vaccine) that may be combined with an immunogenic composition comprising an Mrp protein, Mrp immunogenic polypeptide or peptide or other Mrp immunogenic fragment, or an Mrp containing fusion protein (see, e.g., U.S. Pat. No. 7,270,827; Hu et al., *Infect. Immun.* 70:2171-77 (2002)).

Immunization of animals with a 30-valent vaccine evoked production of bactericidal antibodies that specifically bound to each GAS serotype represented by an M immunogenic peptide and Spa immunogenic peptide in one of the fusion polypeptides (i.e., GAS serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118) (see International Patent Application Publication No. WO 2012/174455). In addition, antisera from immunized animals was bactericidal against more than half of GAS serotypes for which an immunogenic peptide from an M protein or Spa protein was not represented in any one of the fusion polypeptides (see WO 2012/174455, supra). When compared with a 26-valent vaccine (see, e.g., U.S. Pat. No. 7,270,827; Hu et al., supra), the particular combination of 31 M and Spa immunogenic peptides described herein induced an immune response that recognized more non-vaccine GAS serotypes (see WO 2012/174455). Serotypes represented in the 30-valent immunogenic composition that were not included in the 26-valent composition include GAS M serotypes 4, 29, 58, 44, 49, 73, 78, 81, 82, 83, 87, 118. Serotypes in the 26-valent composition not represented by immunogenic peptides in the 30-valent composition include GAS M serotypes 1.2, 13, 33, 43, 59, 76, and 101.

TABLE 2

AMINO ACID SEQUENCES OF M PROTEIN IMMUNOGENIC PEPTIDES

| M protein ($NH_2$ terminal residues) | Amino Acid Sequence | Fusion Protein Location | Sequence Identifier |
|---|---|---|---|
| M1 (1-50) | NGDGNPREVI EDLAANNPAI QNIRLRHENK DLKARLENAM EVAGRDFKRA | 1-50 and 401-450 of SEQ ID NO: 24 | SEQ ID NO: 66 |

TABLE 2-continued

AMINO ACID SEQUENCES OF M PROTEIN IMMUNOGENIC PEPTIDES

| M protein (NH$_2$ terminal residues) | Amino Acid Sequence | Fusion Protein Location | Sequence Identifier |
|---|---|---|---|
| M3.1 (22-71) | LLDQVTQLYT KHNSNYQQYN AQAGRLDLRQ KAEYLKGLND WAERLLQELN | 51-100 of SEQ ID NO: 24 | SEQ ID NO: 67 |
| M6.4 (1-25)$_2$ | RVFPRGTVEN PDKARELLNK YDVENRVFPR GTVENPDKAR ELLNKYDVEN | 101-150 of SEQ ID NO: 24 | SEQ ID NO: 68 |
| M2 (2-26)$_2$ | SKNPVPVKKE AKLSEAELHD KIKNLSKNPV PVKKEAKLSE AELHDKIKNL | 151-200 of SEQ ID NO: 24 | SEQ ID NO: 69 |
| M18 (1-50) | APLTRATADN KDELIKRAND YEIQNHQLTV ENKKLKTDKE QLTKENDDLK | 201-250 of SEQ ID NO: 24 | SEQ ID NO: 70 |
| M28 (1-50) | AESPKSTETS ANGADKLADA YNTLLTEHEK LRDEYYTLID AKEEEPRYKA | 251-300 of SEQ ID NO: 24 | SEQ ID NO: 71 |
| M12 (1-50) | DHSDLVAEKQ RLEDLGQKFE RLKQRSELYL QQYYDNKSNG YKGDWYVQQL | 301-350 of SEQ ID NO: 24 | SEQ ID NO: 72 |
| SPA (1-50) | DSVSGLEVAD PSDSKKLIEL GLAKYLNDKL PFKTKEDSEI LSELRDVLKN | 351-400 of SEQ ID NO: 24 | SEQ ID NO: 73 |
| M4 (1-50) | AEIKKPQADS AWNWPKEYNA LLKENEELKV EREKYLSYAD DKEKDPQYRA | 1-50 and 401-450 of SEQ ID NO: 25 | SEQ ID NO: 74 |
| M5.0 (1-25)$_2$ | AVTRGTINDP QRAKEALDKY ELENHAVTRG TINDPQRAKE ALDKYELENH | 51-100 of SEQ ID NO: 25 | SEQ ID NO: 75 |
| M11 (1-50) | TEVKAAGQSA PKGTNVSADL YNSLWDENKT LREKQEEYIT KIQNEETKNK | 101-150 of SEQ ID NO: 25 | SEQ ID NO: 76 |
| M75 (1-50) | EEERTFTELP YEARYKAWKS ENDELERENYR RTLDKFNTEQ GKTTRLEEQN | 151-200 of SEQ ID NO: 25 | SEQ ID NO: 77 |
| M19 (1-25)$_2$ | RVRYTRHTPE DKLKKIIDDL DAKEHRVRYT RHTPEDKLKK IIDDLDAKEH | 201-250 of SEQ ID NO: 25 | SEQ ID NO: 78 |
| M29.2 (1-50) | RVYITRRMTK EDVEKIANDL DTENHGLKQQ NEQLSTEKQG LEEQNKQLST | 251-300 of SEQ ID NO: 25 | SEQ ID NO: 79 |
| M14.3 (1-50) | DRVSRSMSRD DLLNRAQDLE AKNHGLEHQN TKLSTENKTL QEQAEARQKE | 301- of SEQ ID NO: 25 | SEQ ID NO: 80 |
| M24 (1-50) | VATRSQTDTL EKVQERADKF EIENNTLKLK NSDLSFNNKA LKDHNDELTE | 351-400 of SEQ ID NO: 25 | SEQ ID NO: 81 |
| M77 (1-50) | EGVSVGSDAS LHNRITDLEE EREKLLNKLD KVEEEHKKDH EQLEKKSEDV | 1-50 and 401-450 of SEQ ID NO: 26 | SEQ ID NO: 82 |
| M22 (1-50) | ESSNNAESSN ISQESKLINT LTDENEKLRE ELQQYYALSD AKEEEPRYKA | 51-100 of SEQ ID NO: 26 | SEQ ID NO: 83 |
| M73 (1-50) | DNQSPAPVKK EAKKLNEAEL YNKIQELEEG KAELFDKLEK VEEENKKVKE | 101-150 of SEQ ID NO: 26 | SEQ ID NO: 84 |

TABLE 2-continued

AMINO ACID SEQUENCES OF M PROTEIN IMMUNOGENIC PEPTIDES

| M protein (NH₂ terminal residues) | Amino Acid Sequence | Fusion Protein Location | Sequence Identifier |
|---|---|---|---|
| M89 (1-50) | DSDNINRSVS VKDNEKELHN KIADLEEERG EHLDKIDELK EELKAKEKSS | 151-200 of SEQ ID NO: 26 | SEQ ID NO: 85 |
| M58 (1-50) | DSSREVTNEL TASMWKAQAD SAKAKAKELE KQVEEYKKNY ETLEKGYDDL | 201-250 of SEQ ID NO: 26 | SEQ ID NO: 86 |
| M44 (1-50) | AESRSVSQGS VSLELYDKLS DENDILREKQ DEYLTKIDGL DKENKEYASQ | 251-300 of SEQ ID NO: 26 | SEQ ID NO: 87 |
| M78 (1-50) | ESQNSRSITN EQLIDKLVEE NNDLKEERAK YLDLLDNREK DPQYRALMGE | 301-350 of SEQ ID NO: 26 | SEQ ID NO: 88 |
| M118 (1-50) | AEKKVEVADS NASSVAKLYN QIADLTDKNG EYLERIEELE ERQKNLEKLE | 351-400 of SEQ ID NO: 26 | SEQ ID NO: 89 |
| M83.1 (1-50) | DNPRYTDAHN AVTQGRTVPL QNLLHEMDKN GKLRSENEEL KADLQKKEQE | 1-50 and 351-400 of SEQ ID NO: 27 | SEQ ID NO: 90 |
| M82 (1-50) | DSSSRDITEA GVSKFWKSKF DAEQNRANEL EKKLSGYEKD YKTLEQEYEN | 51-100 of SEQ ID NO: 27 | SEQ ID NO: 91 |
| M81 (1-50) | AGSEENVPKQ QYNALWEENE DLRGRERKYI AKLEKEEIQN GELNEKNRKL | 101-150 of SEQ ID NO: 27 | SEQ ID NO: 92 |
| M87 (1-50) | ESPREVTNEL AASVWKKKVE EAKEKASKLE KQLEEAQKDY SEIEGKLEQF | 151-200 of SEQ ID NO: 27 | SEQ ID NO: 93 |
| M49.1 (1-50) | VEKKVEAAEN NVSSVARREK ELYDQIADLT DKNGEYLERI GELEERQKNL | 201-250 of SEQ ID NO: 27 | SEQ ID NO: 94 |
| M92 (1-50) | DDRSVSTNSG SVSTPYNNLL NEYDDLLAKH GELLSEYDAL KEKQDKNQEE | 251-300 of SEQ ID NO: 27 | SEQ ID NO: 95 |
| M114 (1-50) | NSKNPAPAPA SAVPVKKEAT KLSEAELYNK IQELEEGKAE LFDKLEKVEE | 301-350 of SEQ ID NO: 27 | SEQ ID NO: 96 |

Production of Immunogenic Polypeptides, Peptides and Fusion Polypeptides

Each of the immunogenic Mrp, M, and Spa polypeptides and peptides (and variants Mrp, M, and Spa polypeptides and peptides), and fusion polypeptides comprising same may be produced recombinantly or may be chemically synthesized. Alternatively, polynucleotides encoding individual immunogenic polypeptides, peptides, and fusion polypeptides may be constructed by recombinant methods or chemically synthesized, and the constructed or synthesized polynucleotides may be incorporated into expression vectors for production of the respective immunogenic polypeptides, peptides, and fusion polypeptide in a host cell into which the expression vector has been introduced.

Peptides and polypeptides may be chemically synthesized by manual techniques or by automated procedures. Equipment for automated synthesis of polypeptides is commercially available from suppliers such as Perkin-Elmer, Inc. and Applied BioSystems Division (Foster City, Calif.), and may be operated according to the manufacturer's instructions. By way of example, solid phase polypeptide synthesis has been performed since the early 1960's (see, e.g., Merrifield, J. Am. Chem. Soc. 85:2149-2154 (1963)). Numerous improvements to synthesis methods have been developed, and many methods have been automated and chemistries have been developed to protect the terminal ends and other reactive groups (see, e.g., Geysen et al., J. Immun. Meth. 102:259-274 (1987); Miranda et al., Proc. Natl. Acad. Sci. USA 96:1181-86 (1999); Frank et al., Tetrahedron 44:6031-6040 (1988); Hyrup et al., Bioorg. Med. Chem. 4:5-23 (1996); Perry-O'Keefe et al., Proc. Natl. Acad. Sci. USA 93:14670-675 (1996); Schnölzer, et al. Int. J. Pept. Protein Res. 40, 180-193 (1992); Hackeng et al., Proc. Natl. Acad. Sci. USA 94:7845-50 (1997); Creighton, T. E. Protein: Structures and Molecular Properties, pp. 55-60, W. H. Freeman and Co., New York, N.Y. (1984)). Equipment for performing automated synthesis is available from a variety of manufacturers. Synthesized immunogenic polypeptides, peptides, and fusion polypeptides may be obtained from any number of different custom peptide synthesizing manufacturers. If required, synthesized peptides or polypeptides may be purified using preparative reverse phase chromatography, partition chromatography, gel filtration, gel electrophoresis, or ion-exchange chromatography or other methods used in the art.

In certain embodiments, an immunogenic Mrp polypeptide, peptide, and fusion polypeptide described herein includes immunogenic Mrp polypeptide, peptide, or fusion polypeptide species, respectively, that have one or more amino acid substitutions, insertions, or deletions (also called herein a variant). Similarly, M and Spa polypeptides, peptides, and fusion polypeptides described herein includes immunogenic M and Spa polypeptide, peptide, or fusion polypeptide species, respectively, that have one or more amino acid substitutions, insertions, or deletions (also called herein a variant). Mrp, M, and Spa variants may be identified from different GAS strains. Immunogenic polypeptide or peptide variants and fusion polypeptide variants also include those that have amino acid substitutions, deletions, or insertions that may be introduced during chemical synthesis or recombinant production, whichever method is used to produce the particular immunogenic polypeptide, peptide or fusion polypeptide. As described herein, a variant of an immunogenic polypeptide or peptide or of a fusion polypeptide described herein retains immunogenicity exhibited by the non-mutated or "parent" immunogenic polypeptide or peptide or fusion polypeptide, respectively, from which the variant was derived. Retention of immunogenicity includes the capability to evoke an immune response against GAS and/or SDSE, such as production of antibodies that specifically bind to the cognate immunogenic polypeptide, peptide and/or fusion polypeptide, cognate full-length or mature protein (either isolated or present on the cell surface of GAS and/or SDSE bacteria), and which antibodies include those with bactericidal and phagocytic activity.

In certain embodiments, an amino acid substitution that may be included in an immunogenic polypeptide, peptide or a fusion protein is a conservative substitution. Conservative substitutions of amino acids are well known and may occur naturally in an Mrp, M protein, or Spa polypeptide or may be introduced when the peptide or fusion polypeptide is recombinantly produced. A variety of criteria understood by a person skilled in the art indicate whether an amino acid that is substituted at a particular position in an immunogenic polypeptide, peptide or fusion polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine) In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the peptide or polypeptide to the sequence of a second peptide or polypeptide, respectively, using any one of the algorithms, such as Align or the BLAST algorithm, or other algorithms described herein and practiced in the art.

Amino acid substitutions, deletions, and additions may be introduced into an Mrp, M, or Spa immunogenic polypeptide, peptide or fusion polypeptide during chemical synthesis of the polynucleotide that encodes the polypeptide, peptide or fusion polypeptide. Alternatively, amino acid substitutions, deletions, and additions may be introduced into an immunogenic polypeptide, peptide or fusion polypeptide recombinantly using well-known and routinely practiced mutagenesis methods (see, e.g., Sambrook et al. *Molecular Cloning: A Laboratory Manual,* 3d ed., Cold Spring Harbor Laboratory Press, NY 2001)). Oligonucleotide-directed site-specific (or segment specific) mutagenesis procedures may be employed to provide an altered polynucleotide that has particular codons altered according to the substitution, deletion, or insertion desired. Alternatively, random mutagenesis techniques, such as alanine scanning mutagenesis, error prone polymerase chain reaction mutagenesis, and oligonucleotide-directed mutagenesis may be used to prepare immunogenic polypeptide, peptide, and fusion polypeptide variants (see, e.g., Sambrook et al., supra). An immunogenic polypeptide variant, peptide variant or a fusion polypeptide variant includes an immunogenic polypeptide, peptide or fusion polypeptide, respectively, that has at least 70%, 75%, 80%, 85%, 90%, 92%, 95%, 97%, 98%, or 99% amino acid sequence identity to any of the exemplary Mrp, M, and Spa immunogenic polypeptide, peptide and fusion polypeptide amino acid sequences provided herein, including in the sequence listing (see for example, Mrps and fragments thereof listed in Table 1; fusion polypeptides comprising amino-terminal immunogenic M and Spa peptides represented by SEQ ID NOS:24-27; amino-terminal immunogenic M and Spa peptides represented by SEQ ID NOS:66-96). Percent identity of one amino acid sequence to one or more additional sequences may be determined using any one of the alignment tools described herein and used in the art. In other embodiments, an Mrp, M, or Spa immunogenic polypeptide variant, peptide variant or a fusion polypeptide variant includes an immunogenic polypeptide, peptide or fusion polypeptide, respectively, that has no more than 5, no more than 10, no more than 15, no more than 20, no more than 25, or no more than 30 amino acid deletions, additions, or substitutions of the respective Mrp, M, or Spa polypeptide sequence provided herein.

Given the description in the art and herein regarding regions of Mrps, M proteins, and Spa proteins that exhibit immunogenic activity, persons skilled in the art can readily determine which amino acids in the respective mature and full-length polypeptides and within the amino terminal portions of same may be more amenable to alteration (i.e., substitution, deletion, or addition of one or more amino acids) and which amino acids may less amenable to change. Also given the description herein and given the many molecular biology, protein expression, and protein isolation techniques and methods routinely practiced in the art for introducing mutations in a peptide or polypeptide, isolating these peptides and polypeptides and variants thereof, and analyzing same, and obtaining a peptide or polypeptide variant with the desired immunogenicity can be readily accomplished without undue experimentation. Retention of immunogenicity includes the capability to evoke an immune response against GAS, such as production of antibodies that specifically bind to the cognate immunogenic peptide and/or fusion polypeptide, cognate mature Mrp, M, or Spa protein (either isolated or present on the cell surface of GAS bacteria), or cognate full-length Mrp, M, or Spa protein and which antibodies include those with bactericidal and phagocytic activity. In certain embodiments, retention of immunogenicity includes the capability to evoke an immune response against SDSE, which response includes production of antibodies that bind to SDSE and have bactericidal and phagocytic activity.

The effect of any amino acid substitution may be determined empirically merely by testing the resulting modified polypeptide, peptide or fusion polypeptide for the ability to function in a biological assay, or to bind to a cognate ligand or target molecule, such as a monoclonal or polyclonal antibody. Assays for assessing whether a variant of an Mrp, M, or Spa protein or immunogenic fragment thereof, or a fusion polypeptide comprising same, folds into a conformation comparable to the non-variant polypeptide or peptide or fusion polypeptide include, for example, the ability of the polypeptide or peptide or fusion polypeptide to react with mono- or polyclonal antibodies that are specific for native or unfolded epitopes, the retention of ligand-binding functions, retention of immunogenicity, and the sensitivity or resistance of the mutant polypeptide, peptide or fusion polypeptide to digestion with proteases (see Sambrook et al., supra). Immunogenic polypeptide and peptide variants and fusion polypeptide variants as described herein can be identified, characterized, and/or made using these methods described herein or other methods known in the art, which are routinely practiced by persons skilled in the art.

Polynucleotides that encode the polypeptides, peptides, and fusion proteins described herein may be chemically synthesized or may be constructed by recombinant methods familiar to a person skilled in the art. Polynucleotides can also be synthesized using an automatic synthesizer. The nucleotide sequence can be designed with the appropriate codons for the particular amino acid sequence desired. In general, preferred codons may be selected for the intended host in which the nucleotide sequence will be expressed. One recombinant method of preparing a polynucleotide includes assembly from overlapping oligonucleotides prepared by standard methods to provide a complete coding sequence (see, e.g., Au et al., *Biochem. Biophys. Res. Commun.* 248:200-203 (1998); Stemmer et al., *Gene* 164: 49-53 (1995); Ausubel et al. (eds.), *Current Protocols in Molecular Biology*, (Greene Publ. Assoc. Inc. & John Wiley & Sons, Inc., 1993)); Sambrook et al., et al. *Molecular Cloning: A Laboratory Manual,* 3rd Ed., (Cold Spring Harbor Laboratory 2001; and elsewhere). Methods for purifying polynucleotides after either chemical synthesis or recombinant synthesis are known to persons skilled in the art (see, e.g., Ausubel et al., supra; Sambrook et al., supra).

Chemical synthesis of oligonucleotides for primers and probes has long been practiced in the art (see, e.g., Letsinger et al., *J. Am. Chem. Soc.* 98:3655-61 (1976); Matteucci et al., *J. Am. Chem. Soc.* 103:3185-9 (1981)). Improved methods for synthesizing oligonucleotides and polynucleotides, which provide more rapid results, greater yields, and longer polynucleotides, have since been developed and automated (see, e.g., Gao et al., *Biopolymers* 73:579-96 (2004); Mueller et al., *Chem. Biol.* 16:337-47 (2009); Lee et al., *Nucleic Acids Res.* 38:2514-21 (2010)). Polynucleotides that encode the immunogenic polypeptides, peptides, and fusion polypeptides described herein may be synthesized commercially (see, e.g., GENSCRIPT, Piscataway, N.J.).

Polynucleotides that encode an immunogenic polypeptide, peptide, or fusion polypeptide described herein may be recombinantly expressed in a variety of different host cells. Host cells containing recombinant expression constructs may be genetically engineered (transduced, transformed, or transfected) with the vectors and/or expression constructs (for example, a cloning vector, a shuttle vector, or an expression construct). The vector or construct may be in the form of a plasmid, a viral particle, a phage, etc. The engineered host cells can be cultured in conventional nutrient media modified as appropriate for activating promoters, selecting transformants, or amplifying particular genes or encoding-nucleotide sequences. Selection and maintenance of culture conditions for particular host cells, such as temperature, pH and the like, will be readily apparent to the ordinarily skilled artisan. In general, the desired host cell is one that can be adapted to sustained propagation in culture to yield a stable cell line that can express sufficient amount of the immunogenic polypeptide, peptide, or fusion polypeptide. In certain embodiments, the cell line is an immortal cell line, which refers to a cell line that can be repeatedly passaged (at least ten times while remaining viable) in culture following log-phase growth. In other embodiments, the host cell used to generate a cell line is a cell that is capable of unregulated growth, such as a cancer cell, or a transformed cell, or a malignant cell.

Useful bacterial expression constructs are prepared by inserting into an expression vector a structural DNA sequence encoding the desired peptide or polypeptide together with suitable translation initiation and termination signals in an operative reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may also be employed as a matter of choice. Any other plasmid or vector may be used as long as the plasmid or vector is replicable and viable in the host. Thus, for example, the polynucleotides as provided herein may be included in any one of a variety of expression vector constructs as a recombinant expression construct for expressing the immunogenic polypeptides, peptides, and fusion polypeptides. Such vectors and constructs include chromosomal, nonchromosomal, and synthetic DNA sequences, e.g., bacterial plasmids; phage DNA; baculovirus; yeast plasmids; vectors derived from combinations of plasmids and phage DNA; viral DNA, such as vaccinia, adenovirus, fowl pox virus, and pseudorabies.

The appropriate DNA sequence(s) may be inserted into the vector by a variety of procedures with which the skilled person is familiar. In certain instances, the DNA sequence is inserted into an appropriate restriction endonuclease site(s) by procedures known in the art. Notably, the fusion polypeptides described herein lack any restriction enzyme sites between any one of the immunogenic polypeptides and peptides that comprise the fusion polypeptide. The omission of restriction sites and the amino acid sequence encoded by the restriction site is intended to remove the possibility that a desired immunogenic epitope will be adversely altered or that an epitope will be inadvertently added that may have an undesirable immunogenicity (for example, inducing production of an antibody that recognizes a normal, human protein). Standard techniques for cloning, DNA isolation, amplification and purification, for enzymatic reactions involving DNA ligase, DNA polymerase, restriction endonucleases and the like, and various separation techniques are those known and commonly employed by those skilled in the art. Numerous standard techniques are described, for example, in Ausubel et al. (*Current Protocols in Molecular Biology* (Greene Publ. Assoc. Inc. & John Wiley & Sons, Inc., 1993)) and in Sambrook et al. (*Molecular Cloning: A Laboratory Manual,* 3rd Ed., (Cold Spring Harbor Laboratory 2001)).

The DNA sequence encoding a peptide or polypeptide in the expression vector is operatively linked to at least one appropriate expression control sequences (e.g., a promoter or a regulated promoter) to direct mRNA synthesis. Representative examples of such expression control sequences include LTR or SV40 promoter, *E. coli* lac or trp, the phage lambda $P_L$ promoter, and other promoters known to control expression of genes in prokaryotic or eukaryotic cells or their viruses. Promoter regions can be selected from any desired gene using CAT (chloramphenicol transferase) vectors or other vectors with selectable markers. Particular bacterial promoters include lacI, lacZ, T3, T5, T7, gpt, lambda $P_R$, $P_L$, and trp. Eukaryotic promoters include CMV immediate early, HSV thymidine kinase, early and late SV40, LTRs from retroviruses, and mouse metallothionein-I. Selection of the appropriate vector and promoter and preparation of certain recombinant expression constructs comprising at least one promoter or regulated promoter operatively linked to a polynucleotide described herein is well within the level of ordinary skill in the art.

Design and selection of inducible, regulated promoters and/or tightly regulated promoters are known in the art and will depend on the particular host cell and expression system. The pBAD Expression System (Invitrogen Life Technologies, Carlsbad, Calif.) is an example of a tightly regulated expression system that uses the *E. coli* arabinose operon ($P_{BAD}$ or $P_{ARA}$) (see Guzman et al., *J. Bacteriology* 177:4121-30 (1995); Smith et al., *J. Biol. Chem.* 253:6931-33 (1978); Hirsh et al., *Cell* 11:545-50 (1977)), which controls the arabinose metabolic pathway. A variety of vectors employing this system are commercially available. Other examples of tightly regulated promoter-driven expression systems include PET Expression Systems (see U.S. Pat. No. 4,952,496) available from Stratagene (La Jolla, Calif.) or tet-regulated expression systems (Gossen et al., *Proc. Natl. Acad. Sci. USA* 89:5547-51 (1992); Gossen et al., *Science* 268:1766-69 (1995)). The pLP-TRE2 Acceptor Vector (BD Biosciences Clontech, Palo Alto, Calif.) is designed for use with CLONTECH's Creator™ Cloning Kits to rapidly generate a tetracycline-regulated expression construct for tightly controlled, inducible expression of a gene of interest using the site-specific Cre-lox recombination system (see, e.g., Sauer, *Methods* 14:381-92 (1998); Furth, *J. Mamm. Gland Biol. Neoplas.* 2:373 (1997)), which may also be employed for host cell immortalization (see, e.g., Cascio, *Art Organs* 25:529 (2001)).

The polypeptides, peptides, and fusion polypeptides described herein may further comprise a heterologous peptide or polypeptide at either the amino or carboxy terminus or both to facilitate expression, solubilization, stabilization, isolation, and/or detection. For example, when immunogenic polypeptides, peptides, or fusion polypeptides are produced according to recombinant methods, an initiating methionine residue at the amino terminus is typically included. Other amino acid sequences that may be added to an immunogenic polypeptide, peptide, or fusion polypeptide at either the amino or carboxy terminal ends (also called polypeptide tags) are those that facilitate isolation, solubilization, stabilization, and/or detection of the polypeptide, peptide or fusion polypeptide. Examples of amino acid sequences that may be added at either carboxy or amino terminus include polyhistidine tags (e.g., 6-His tag), glutathione-S-transferase (GST), FLAG® epitope tag (DYKDDDDK, SEQ ID NO:97), beta-galactosidase, alkaline phosphatase, chitin binding protein (CBP), XPRESS™ epitope tag (DLYDDDDK, SEQ ID NO: 98; Invitrogen Life Technologies, Carlsbad, Calif.) maltose binding protein (MBP), thioredoxin (a solubilization tag), and poly(NANP) (a solubilization tag) (see, e.g., U.S. Pat. No. 5,011,912; Hopp et al., (*Bio/Technology* 6:1204 (1988)). If the polypeptide, peptide, or fusion polypeptide is recombinantly produced, the affinity sequence may be supplied by a vector, such as, for example, a hexa-histidine tag that is provided in pBAD/His (Invitrogen). Alternatively, the affinity sequence may be added either synthetically or engineered into the primers used to recombinantly generate the nucleic acid coding sequence (e.g., using the polymerase chain reaction). Additional methods and techniques for using polypeptide tags are routinely practiced in the art and available from commercial vendors who manufacture systems and kits for adding tags to a peptide or polypeptide of interest.

A person skilled in the art can readily determine a polynucleotide sequence that encodes any of the polypeptides, peptides, and fusion proteins described herein given the long known genetic code information. Examples of polynucleotide sequences that may be used in recombinant expression of the polypeptides and peptides described herein include the following. Polynucleotide sequences that encode amino terminal fragments, Mrp2U, Mrp4U, and Mrp49U, are provided in SEQ ID NOS:21-23, respectively, which include an ATG codon for the initiating methionine residue and nucleotides at the 3' end that are non-Mrp sequences. Polynucleotides that encode only Mrp2U, Mrp4U, and Mrp49U amino acid sequences are provided in SEQ ID NOS:62-64. Polynucleotide sequences that encode four exemplary M and Spa comprising fusion polypeptides (SEQ ID NOS:24-27) are provided in SEQ ID NOS: 58-61 (sequences include regulatory expression sequences at 5' end) and SEQ ID NOS:100-103, respectively (see also WO 2012/174455).

The nucleotide sequence of an Mrp variant, M variant or Spa variant can be determined and/or identified by comparing the nucleotide sequence of a polynucleotide encoding the variant with a polynucleotide described herein or known in the art that encodes the particular Mrp, M protein, or Spa protein, respectively, using any one of the alignment algorithms described herein and used in the art. The percent identity between two polynucleotides may thus be readily determined. Polynucleotides have 100% nucleotide sequence identity if the nucleotide residues of the two sequences are the same when aligned for maximal correspondence. In particular embodiments, the nucleotide sequence encoding an Mrp, M, or Spa polypeptide or peptide, respectively, is at least 70%, 75%, 80%, 85%, 90%, 95%, 97%, or 98% identical to one or more of the respective polynucleotide sequences that encode the respective immunogenic polypeptide or peptide described herein. Polynucleotide variants also include polynucleotides that differ in nucleotide sequence identity due to the degeneracy of the genetic code. A polynucleotide sequence that is complementary to the encoding polynucleotide can be readily determined by a person skilled in the art. Certain polynucleotides that encode any immunogenic peptide or variant thereof may also be used as probes, primers, short interfering RNA (siRNA), or antisense oligonucleotides. Polynucleotides may be single-stranded DNA or RNA (coding or antisense) or double-stranded RNA (e.g., genomic or synthetic) or DNA (e.g., cDNA or synthetic).

Polynucleotide variants may be identified by alignment procedures described herein and in the art and also may be identified by hybridization methods. Hybridization of two polynucleotides may be performed using methods that incorporate the use of suitable moderately stringent conditions, for example, pre-washing in a solution of 5×SSC, 0.5% SDS, 1.0 mM EDTA (pH 8.0); hybridizing at 50° C.-70° C., 5×SSC for 1-16 hours; followed by washing once or twice at 22-65° C. for 20-40 minutes with one or more each of 2×, 0.5×, and 0.2×SSC containing 0.05-0.1% SDS. For additional stringency, conditions may include a wash in 0.1×SSC and 0.1% SDS at 50-60° C. for 15 minutes. As understood by persons having ordinary skill in the art, variations in stringency of hybridization conditions may be achieved by altering the time, temperature, and/or concentration of the solutions used for pre-hybridization, hybridization, and wash steps. Suitable conditions may also depend in part on the particular nucleotide sequences of the probe used (i.e., for example, the guanine plus cytosine (G/C) versus adenine plus thymidine (A/T) content). Accordingly, a person skilled in the art will appreciate that suitably stringent conditions can be readily selected without undue experimentation when a desired selectivity of the probe is identified.

If desired, immunogenic polypeptide variants, peptide variants, and fusion polypeptide variants may be readily prepared by genetic engineering and recombinant molecular biology methods and techniques. Analysis of the primary and secondary amino acid sequence of the peptides and polypeptides and computer modeling of same to analyze the tertiary structure of the polypeptide or peptide may aid in identifying specific amino acid residues that can be substituted, added, or deleted without altering the structure and as a consequence, potentially the immunogenicity of the peptide or polypeptide or fusion protein. Modification of a polynucleotide, such as DNA, encoding a peptide or polypeptide variant may be performed by a variety of methods, including site-specific or site-directed mutagenesis of the DNA, which methods include DNA amplification using primers to introduce and amplify alterations in the DNA template, such as PCR splicing by overlap extension (SOE). Mutations may be introduced at a particular location by synthesizing oligonucleotides containing a mutant sequence, flanked by restriction sites enabling ligation to fragments of the non-variant sequence. Following ligation, the resulting reconstructed sequence encodes a variant having the desired amino acid insertion, substitution, or deletion. While restriction sites may be introduced during mutagenesis procedures, as described herein, inclusion of amino acids that are encoded by the nucleotide sequences of a restriction site in the encoded peptide or polypeptide is avoided to reduce the likelihood of introducing an undesired epitope.

Site directed mutagenesis of a polynucleotide such that it encodes a variant of an immunogenic polypeptide, peptide or fusion polypeptide may be performed according to any one of numerous methods described herein and practiced in the art (Kramer et al., *Nucleic Acids Res.* 12:9441 (1984); Kunkel *Proc. Natl. Acad. Sci. USA* 82:488-92 (1985); Kunkel et al., *Methods Enzymol.* 154:367-82 (1987)). Random mutagenesis methods to identify residues that, when mutated (e.g., substituted or deleted), alter binding of the immunogenic polypeptide, peptide or fusion polypeptide to a ligand (e.g., a monoclonal or polyclonal antibody) can also be performed according to procedures that are routinely practiced by a person skilled in the art (e.g., alanine scanning mutagenesis; error prone polymerase chain reaction mutagenesis; and oligonucleotide-directed mutagenesis (see, e.g., Sambrook et al. *Molecular Cloning: A Laboratory Manual*, 3rd ed., Cold Spring Harbor Laboratory Press, NY (2001)). When a variant peptide or polypeptide is intended for use in an immunogenic composition to induce an immune response against GAS and/SDSE, the variant desirably retains the capability in a substantially similar manner (i.e., in a statistically, biologically, or clinically significant manner) as the non-variant immunogenic peptide or polypeptide to bind to specific antibodies and to evoke production of antibodies that bind to GAS and/or SDSE bacteria and that are bactericidal.

Characterization of Immunogenic Polypeptides, Peptides, and Fusion Polypeptides

As described in detail herein, the immunogenic Mrp polypeptides, peptides, and fusion polypeptides that comprise one or more of these immunogenic polypeptides or peptides, alone or in combination with at least one other GAS immunogen (e.g., an M immunogenic peptide or Spa immunogenic peptide or fusion polypeptide comprising same as described herein), are intended for use as immunogens to induce an immune response, particularly a protective immune response, against the beta-hemolytic streptococci GAS and SDSE serotypes that cause infections in humans. Also as provided herein, M immunogenic peptides and Spa immunogenic peptide or fusion polypeptide comprising same are intended for use as immunogens to induce an immune response, particularly a protective immune response, against beta-hemolytic streptococci, including GAS and SDSE serotypes that cause infections in humans. To determine and characterize the immunogenicity of immunogens, any number of immunoassays, phagocytosis and bactericidal assays, and animal studies may be performed according to methods described herein and in the art and which are routinely practiced by a person skilled in the art. Additional pre-clinical studies that evaluate the safety of the immunogenic composition(s) to be administered to a subject are typically performed. Ultimately, the safety and efficacy of immunogenic compositions comprising GAS immunogens for human use will be determined by clinical studies, which are monitored by regulatory agencies.

The immunogenicity of an immunogenic polypeptide, peptide, or fusion polypeptide (or immunogenic composition comprising same) may be determined by administering same to a host (i.e., subject, patient) according to immunization protocols described herein and in the art. Typically, after administering an initial dose of the immunogenic polypeptide, peptide, or fusion polypeptide or immunogenic composition comprising same (also called the primary immunization) to a host, one, two or more doses (also called boosting or booster doses) are administered.

In general, to monitor the immune response of an immunized host during pre-clinical studies in animals, sera is obtained from the animals prior to the first dose (i.e., pre-immune sera) and obtained after the final boosting dose. Sera may also be obtained after any one or more of the boosting doses between the primary dose and final boosting dose. To monitor the immune response of an immunized host during clinical studies or during post-marketing studies, sera may also be obtained from humans before the first immunization and after one or more administrations of the immunogenic compositions.

An antibody that specifically binds to an immunogenic polypeptide or peptide (and to a fusion polypeptide, full length or mature protein, or to GAS bacteria expressing the protein, or to SDSE bacteria expressing a protein recognized by the antibody) may belong to any immunoglobulin class, for example IgG, IgE, IgM, IgD, or IgA. For characterizing the immunogenic polypeptides, peptides and fusion polypeptides described herein, use of polyclonal and/or monoclonal antibodies may be desired. The antibody may be obtained from or derived from an animal, for example, fowl (e.g., chicken) and mammals, which include but are not limited to a mouse, rat, hamster, rabbit, or other rodent, a cow, horse, sheep, goat, camel, human, or other primate. As described herein, polyclonal antisera are obtained from an animal by immunizing the animal with an immunogenic composition comprising an immunogenic polypeptide, peptide, plurality of immunogenic polypeptides, peptides or a fusion polypeptide or plurality of fusion polypeptides.

In certain embodiments, immune sera obtained from immunized subjects immunized with the immunogens and immunogenic compositions described herein may be used for passive immunotherapy. The immune sera may be obtained from an immunized human or immunized animal, such as a horse, pig, or bovine. For human use, human immune sera is preferred to avoid inducing an immune response against non-human antibodies, which may result in premature clearing of the immune sera.

Production of immunogen-specific antibodies in an immunized host (including a human host) may include production of any class of immunoglobulin, including IgG, IgA, IgM, and/or IgE, and isotypes within the classes. The presence of specific IgG, IgM, IgE, and IgA (particularly in mucosal secretions) may be detected in a biological sample (e.g., serum, nasal wash, lung lavage, or other tissues) obtained from an immunized host. For detection of immunogenic polypeptide-, peptide-, fusion protein- and GAS- or SDSE-specific antibodies in an immunoassay, the biological sample may be permitted to interact with or contact an antigen that is purified, isolated, partially isolated, or a fragment thereof, or to interact with or contact a microorganism, which may be fixed (such as with ethanol or formaldehyde) or unfixed or non-denatured. Mucosal secretions include those collected from the respiratory tract, including the nasopharynx and lungs. Functional assays may also be performed, such as the capability of an immunogen-specific antibody to facilitate phagocytosis or opsonization of GAS, inhibit growth of GAS or kill the bacteria, or to prevent entry of GAS into a host cell. Such functional assays may also be performed to determine capability of an immunogen-specific antibody to facilitate phagocytosis or opsonization of other beta-hemolytic streptococci such as SDSE, inhibit growth of SDSE or kill the bacteria, or to prevent entry of SDSE into a host cell. Such methods are described herein and are routinely practiced by persons skilled in the art.

Immune sera (i.e., sera obtained from a host after immunization with one or more doses of the immunogenic composition) or other biological sample may be evaluated for the presence of antibodies (immunoglobulins) that specifically bind to any one or more of the immunogenic polypeptides or peptides included in an immune composition (including those that are incorporated into fusion polypeptides). An assay to detect the presence of a specific antibody in a biological sample, such as immunoassays described herein, may also use a mature or full-length protein (e.g., mature or full-length Mrp, M, or Spa) and/or whole GAS bacteria and/or whole SDSE bacteria. The level to which antibodies in the immune sera bind to GAS serotypes represented by an immunogen in the immunogenic composition and the level to which antibodies bind to one or more GAS serotypes not represented by an immunogenic polypeptide or peptide in the composition (also called non-vaccine GAS serotypes), and the level to which antibodies bind to one or more SDSE serotypes may be determined. The level to which antibodies bind to an immunogen or to beta-hemolytic streptococci, such as GAS bacteria and SDSE bacteria (typically referred in the art as titer) can be readily determined using any one or more immunoassays that are routinely practiced by a person having ordinary skill in the art. By way of non-limiting example, immunoassays include ELISA, immunoblot, radioimmunoassay, immunohistochemistry, fluorescence activated cell sorting (FACS), Ouchterlony, and the like. Immunoassays may be performed using one or more of the immunogens included in the immunizing composition, and which may be used in the assays as individual immunogenic polypeptides, peptides, or fusion polypeptides.

In one embodiment, a method is provided for detecting an antibody, which may be a monoclonal antibody or polyclonal antibody, and which may be of any class or isotype, and may be present in or suspected of being present in a biological sample, which antibody binds to any one of the GAS immunogens described herein. The method comprises contacting the biological sample with at least one immunogen of interest under conditions and for a time sufficient for an antibody in the sample to interact with the at least one immunogen (i.e., mixing, combining, or in some manner permitting the biological sample and the immunogen to interact). An antibody present in the biological sample that specifically binds to the immunogen can be detected using any one of the exemplary detection methods described herein and in the art for detecting antibody-antigen binding. By way of non-limiting example, antibody bound to the at least one immunogen may be detected using a reagent specific for a conserved region of the antibody, such as the Fc portion of the antibody, which reagent is typically selected depending on the source of the antibody (i.e., whether the antibody is from an animal, such as a mouse, rat, goat, or sheep, etc or whether the antibody is from a human). These reagents typically comprise a detectable label, such as for example an enzyme, fluorescent label, luminescent label, or radioactive label. Additional exemplary reagents include those that detect a specific isotype or class of antibody. Many such reagents may be obtained from commercial sources.

Immunoassays may also be used to detect the presence of an anti-GAS antibody that specifically binds to an Mrp, an M polypeptide, a Spa polypeptide or to an SDSE polypeptide that is not specifically represented in a particular immunogenic composition. These immunoassays may be used to characterize a heterologous immune response and thereby assist in characterization of an heterologous streptococcal immune response to a particular immunogen.

Conditions for a particular assay include temperature, buffers (including salts, cations, media), and other components, which maintain the integrity of the antibodies within the pre-immune and immune sera and the integrity of the antigen (which may be an immunogenic Mrp, M, or Spa polypeptide, peptide, fusion polypeptide, or bacteria) used in the assay, and which conditions are familiar to a person skilled in the art and/or can be readily determined. A biological sample, such as serum, is contacted (mixed, combined with, or in some manner permitted to interact) with the antigen, under conditions and for a time sufficient to permit interaction between the antigen and antibodies present in the sample. The interaction, or level of binding, of the antigen to an antibody present in an immune serum sample (or other biological sample) may be determined and compared to a level of binding of the respective antigen to antibodies present in a pre-immune sample (or an otherwise suitable negative control). An increase in the level of binding of the antigen to the immune serum sample compared with the pre-immune serum sample indicates that the immunogenic composition evoked production of specific antibodies. As noted herein, the level of binding of an immunogen to antibodies present in a sample from an immunized host is typically referred to in the art as the titer.

Interaction or binding of an antibody to a specific antigen generally involves electrostatic interactions, hydrogen bonding, Van der Waals interactions, and hydrophobic interactions. Any one of these or any combination thereof can play a role in the binding between an antibody and its antigen. As used herein, an antibody is said to be "specific for" or to "specifically bind" an immunogenic polypeptide, peptide, fusion polypeptide comprising the immunogenic polypeptide or peptide, or GAS bacteria when the antibody reacts at a detectable level with the respective immunogen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. The ability of the antibody to bind to its cognate ligand (in this instance, the immunogenic polypeptide peptide, fusion polypeptide, or bacteria) may also be expressed as a dissociation constant $K_D$, and an antibody is said to specifically bind its cognate ligand if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M.

Affinities of an antibody for an immunogenic peptide, a polypeptide, or fusion polypeptide described herein, can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the surface plasmon resonance signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

Several in vitro assays described herein and routinely practiced in the art may be used to determine activity of specific antibodies evoked by the immunogenic polypeptide, peptide, and fusion polypeptides described herein. An exemplary assay is an opsonophagocytosis assay, which detects phagocytosis facilitated by the presence of opsonic antibodies present in test antisera. Briefly, the assay measures the level of phagocytosis of bacterial by neutrophils after pre-incubating the bacteria in the presence of immune sera. Pre-immune sera or other suitable negative control(s) are also included in such an assay. Preincubated bacteria are then mixed with whole blood from a suitable host, such as a host for which opsonic protection is sought (e.g., a human), to determine the percent of neutrophils that associate with the bacterial cells, which is a measure of phagocytic activity facilitated by opsonic antibodies. The percent of neutrophils associated with the bacteria preincubated with immune sera can be compared to the percent of neutrophils associated with the bacteria that is preincubated with preimmune sera (or other suitable sera believed or known not to contain anti-GAS antibodies). A greater percent (i.e., a statistically, biologically, or clinically significant increased percent) of neutrophils associated with the bacteria pre-incubated with immune sera compared with the percent of neutrophils associated with bacteria pre-incubated with pre-immune sera indicates that the test immune sera contains opsonic antibodies.

Another exemplary in vitro assay that determines bactericidal activity of antibodies present in a sample is a bactericidal assay such as described by Hu et al., supra (see also, e.g., Examples herein). GAS bacteria are incubated with immune serum or an appropriate control serum (e.g., pre-immune serum), mixed with (e.g., rotated with or in some manner permitting interaction with) non-immune human blood and then plated on medium that permits growth of GAS (e.g., sheep blood agar). Similarly, when determining bactericidal activity against SDSE strains, SDSE bacteria are incubated with immune serum or an appropriate control serum (e.g., pre-immune serum), mixed with (e.g., rotated with or in some manner permitting interaction with) non-immune human blood, and then plated on medium that permits growth of SDSE (e.g., sheep blood agar). Typically after an overnight incubation, the number of viable bacteria is quantified and the results are expressed as percent killing. A commonly used formula used in an indirect bactericidal assay for expressing percent killing is [(CFU (colony forming units) of bacteria sample pre-incubated with preimmune serum)−(CFU of bacteria sample pre-incubated with immune serum)÷CFU of bacteria sample pre-incubated with preimmune serum]×100.

Opsonization, phagocytosis, and bactericidal assays are art-accepted in vitro methods for characterization of potential streptococci prophylactic and therapeutic treatments (e.g., anti-GAS prophylactic and therapeutic treatments and anti-SDSE prophylactic and therapeutic treatments). Results obtained in one or more of these assays that suggest to a person skilled in the art the usefulness of a vaccine for prophylactic or therapeutic use have been supported by clinical study findings (see, e.g., U.S. Pat. No. 7,270,827; Kotloff et al., supra; McNeil et al., supra). Animal models that may be used for characterizing the immunogenicity of the immunogenic polypeptides, peptides, fusion polypeptides, and immunogenic compositions comprising same include those that are considered direct immunotherapy models (i.e., animals are immunized with a potential candidate immunogenic composition and then challenged with GAS or SDSE) and those that are indirect or passive immunotherapy models (i.e., antiserum, or antibodies purified or isolated from antisera obtained from animals immunized with a candidate immunogenic composition, or a monoclonal antibody that is specific for a beta-hemolytic streptococcal antigen, including a GAS antigen or an SDSE antigen, is administered prior to, subsequent to, or concurrently with the challenge streptococcus bacteria).

Animal models that mimic non-invasive GAS disease, such as pharyngitis, have been difficult to establish in rodent models. A mouse model for studying GAS impetigo has been described by Scaramuzzino et al. (*Infect. Immun.* 68:2880-87 (2000)). An non-human primate model that has been successfully developed for studying pharyngitis includes a cynomolgus macaque model of acute pharyngitis that mimics human disease (see, e.g., Ashbaugh et al., *Cellular Microbiol.* 2:283-92 (2000); Sumby et al., in *Meth. Molec. Biol.* 431:255-67 (DeLeo et al. (ed.) Humana Press, Totowa N.J. (2008))). Other animal models available in the art have been developed to evaluate therapeutics and prophylactics for invasive diseases, such as an invasive soft tissue infection (see, e.g., Ashbaugh et al., *J. Clin. Investig.* 102:550-60 (1998); Boyle et al., *J. Infect. Dis.* 177:991-97 (1998)); sepsis (see, e.g., Goldmann et al., *J. Inf. Dis.* 187:854-61 (2003); Kapur et al., *Microbiol. Pathogenesis* 16:443-50 (1994); Medina et al., *J. Infect. Dis.* 184:846-52 (2001)); and necrotizing fasciitis (Patel et al., *J. Inf. Dis.* 181:230-34 (2000)). These animal models may be adapted by a person skilled in the art for evaluating other beta-hemolytic streptococcal infections and diseases, such SDSE infections and related diseases.

Polyclonal antibodies and immune sera that comprise such polyclonal antibodies that bind specifically to an immunogenic polypeptide or peptide can be prepared using methods described herein and practiced by persons skilled in the art (see, for example, Green et al., "Production of Polyclonal Antisera," in *Immunochemical Protocols* (Manson, ed.), pages 1-5 (Humana Press 1992); Harlow et al., *Antibodies: A Laboratory Manual*, Cold Spring Harbor Laboratory (1988); Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995)). See also, for example, U.S. Pat. Nos. 7,270,827; 6,716,433; 7,402,316; 7,063,850. Although polyclonal antibodies are typically raised in animals such as rats, mice, rabbits, goats, cattle, or sheep, an antibody may also be obtained from a subhuman primate. General techniques for immunizing baboons may be found, for example, in International Patent Application Publication No. WO 91/11465 (1991) and in Losman et al., *Int. J. Cancer* 46:310, 1990.

Non-human animals that may be immunized with any one of the immunogenic polypeptides, peptides, fusion polypeptides, or immunogenic compositions comprising same include by way of non-limiting example, mice, rats, rabbits, hamsters, ferrets, dogs, cats, camels, sheep, cattle, pigs, horses, goats, chickens, and non-human primates (e.g., cynomolgus macaque, chimpanzee, rhesus monkeys, orangutan, and baboon). Any one of the immunogenic compositions described herein may be administered to immunize an animal by a parenteral (e.g., intravenous), intraperitoneal, intramuscular, intradermal, intraocular, or subcutaneous route. The immunogenic composition may further comprise a suitable adjuvant to enhance the immune response to the immunogen. See, e.g., Harlow et al., *Antibodies: A Laboratory Manual*, Cold Spring Harbor Laboratory (1988). Adjuvants typically used for immunization of non-human animals include but are not limited to Freund's complete adjuvant, Freund's incomplete adjuvant, montanide ISA, Ribi Adjuvant System (RAS) (GlaxoSmithKline, Hamilton, Mont.), and nitrocellulose-adsorbed antigen. In general, after the first injection, animals receive one or more booster immunizations according to a preferred schedule that may vary according to, inter alia, the immunogen, the adjuvant (if any), and/or the particular animal species. The immune response may be monitored by periodically bleeding the animal, separating the sera from the collected blood, and analyzing the sera in an immunoassay, such as an ELISA or Ouchterlony diffusion assay, or the like, to determine the specific antibody titer. When an adequate antibody titer is established, the animals may be bled periodically to accumulate the polyclonal antisera.

Polyclonal antibodies that bind specifically to the immunogen may then be purified from immune antisera, for example, by affinity chromatography using protein A or protein G immobilized on a suitable solid support (see, e.g., Coligan, supra, p. 2.7.1-2.7.12; 2.9.1-2.9.3; Baines et al., Purification of Immunoglobulin G (IgG), in *Methods in Molecular Biology*, 10:9-104 (The Humana Press, Inc. (1992)). Alternatively, affinity chromatography may be performed wherein an antibody specific for an Ig constant region of the particular immunized animal species is immobilized on a suitable solid support. Affinity chromatography may also incorporate use of one or more immunogenic polypeptides, peptides, or fusion proteins, which may be useful for separating polyclonal antibodies by their binding activity to a particular immunogen.

Monoclonal antibodies that specifically bind to an immunogen and immortal eukaryotic cell lines (e.g., hybridomas) that produce monoclonal antibodies having the desired binding specificity, may also be prepared, for example, using the technique of Kohler and Milstein (*Nature*, 256:495-97 (1976), *Eur. J. Immunol.* 6:511-19 (1975)) and improvements thereto (see, e.g., Coligan et al. (eds.), *Current Protocols in Immunology*, 1:2.5.1-2.6.7 (John Wiley & Sons 1991); U.S. Pat. Nos. 4,902,614, 4,543,439, and 4,411,993; *Monoclonal Antibodies, Hybridomas: A New Dimension in Biological Analyses*, Plenum Press, Kennett et al. (eds.) (1980); and *Antibodies: A Laboratory Manual*, Harlow and Lane (eds.), Cold Spring Harbor Laboratory Press (1988); see also, e.g., Brand et al., *Planta Med.* 70:986-92 (2004); Pasqualini et al., *Proc. Natl. Acad. Sci. USA* 101:257-59 (2004)). Monoclonal antibodies may be used as reagents to determine and monitor immunogenicity of the immunogens described herein, and immunogenic compositions comprising same.

Monoclonal antibodies may be isolated from the supernatants of eukaryotic cell cultures such as hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Contaminants may be removed from a cell culture or harvested ascites fluid by conventional techniques, such as chromatography (e.g., size-exclusion, ion-exchange), gel filtration, precipitation, extraction, or the like (see, e.g., Coligan, supra, p. 2.7.1-2.7.12; 2.9.1-2.9.3; Baines et al., Purification of Immunoglobulin G (IgG), *in Methods in Molecular Biology*, 10:9-104 (The Humana Press, Inc. (1992)). Monoclonal antibodies may be purified by affinity chromatography using an appropriate ligand selected based on particular properties of the monoclonal antibody (e.g., heavy or light chain isotype, binding specificity, etc.). Examples of a suitable ligand immobilized on a solid support, include Protein A, Protein G, an anti-constant region (light chain or heavy chain) antibody, an anti-idiotype antibody, or the peptide or polypeptide used for immunizing the animal that is the source of the B cells.

If desired, human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes) (see, e.g., U.S. Pat. No. 4,464,456; Glasky et al., *Hybridoma* 8:377-89 (1989)), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, methods for obtaining human antibodies from transgenic mice are described, for example, by Green et al., *Nature Genet.* 7:13 (1994); Lonberg et al., *Nature* 368:856 (1994); Taylor et al., *Int. Immun.* 6:579 (1994); U.S. Pat. No. 5,877,397; Bruggemann et al., *Curr. Opin. Biotechnol.* 8:455-58 (1997); Jakobovits et al., *Ann. N. Y. Acad. Sci.* 764:525-35 (1995). Other methods comprise cloning the light chain and heavy chain variable regions from B cells according to molecular biology techniques known in the art (WO 92/02551; U.S. Pat. No. 5,627,052; Babcook et al., *Proc. Natl. Acad. Sci. USA* 93:7843-48 (1996)) and described herein. Chimeric antibodies, including humanized antibodies, may also be generated. A chimeric antibody has at least one constant region domain derived from a first mammalian species and at least one variable region domain derived from a second, distinct mammalian species (see, e.g., Morrison et al., *Proc. Natl. Acad. Sci. USA,* 81:6851-55 (1984); Shin et al., *Methods Enzymol.* 178:459-76 (1989); Walls et al., *Nucleic Acids Res.* 21:2921-29 (1993); U.S. Pat. No. 5,482,856). A non-human/human chimeric antibody may be further genetically engineered to create a "humanized" antibody (see, e.g., Jones et al., *Nature* 321:522-25 (1986); Riechmann et al., *Nature* 332:323-27 (1988)). Designing a humanized antibody may include determining CDR loop conformations and structural determinants of the non-human variable regions, for example, by computer modeling, and then comparing the CDR loops and determinants to known human CDR loop structures and determinants (see, e.g., Padlan et al., *FASEB* 9:133-39 (1995); Chothia et al., *Nature,* 342:377-83 (1989); Bajorath et al., *Ther. Immunol.* 2:95-103 (1995); Davies et al., *Ann. Rev. Biochem.* 59:439-73, (1990); EP-0578515-A3).

For particular uses, antigen-binding fragments of antibodies may be desired. Antibody fragments, F(ab')$_2$, Fab, Fab', Fv, and Fd, can be obtained, for example, by proteolytic hydrolysis of the antibody. An antibody fragment may also be any synthetic or genetically engineered protein that acts like an antibody in that it binds to a specific antigen to form a complex according to numerous methods described in the art (see, for example, Larrick et al., *Methods: A Companion to Methods in Enzymology* 2:106, (1991); Courtenay-Luck, "Genetic Manipulation of Monoclonal Antibodies," in *Monoclonal Antibodies: Production, Engineering and Clinical Application,* Ritter et al. (eds.), page 166 (Cambridge University Press 1995); and Ward et al., "Genetic Manipulation and Expression of Antibodies," in *Monoclonal Antibodies: Principles and Applications,* Birch et al., (eds.), page 137 (Wiley-Liss, Inc. 1995))

Antibodies may also be identified and isolated from human immunoglobulin phage libraries, from rabbit immunoglobulin phage libraries, from mouse immunoglobulin phage libraries, and/or from chicken immunoglobulin phage libraries (see, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246: 1275-81 (1989); Schlebusch et al., *Hybridoma* 16:47-52 (1997) and references cited therein; Rader et al., *J. Biol. Chem.* 275:13668-76 (2000); Popkov et al., *J. Mol. Biol.* 325:325-35 (2003); Andris-Widhopf et al., *J. Immunol. Methods* 242:159-31 (2000)). Antibodies isolated from non-human species or non-human immunoglobulin libraries may be genetically engineered according to methods described herein and known in the art to "humanize" the antibody or fragment thereof. Immunoglobulin variable region gene combinatorial libraries may be created in phage vectors that can be screened to select Ig fragments (Fab, Fv, scFv, or multimers thereof) that bind specifically to an immunogenic peptide as described herein (see, e.g., U.S. Pat. No. 5,223, 409; Huse et al., *Science* 246:1275-81 (1989); Sastry et al., *Proc. Natl. Acad. Sci. USA* 86:5728-32 (1989); Alting-Mees et al., *Strategies in Molecular Biology* 3:1-9 (1990); Kang et al., *Proc. Natl. Acad. Sci. USA* 88:4363-66 (1991); Hoogenboom et al., *J. Molec. Biol.* 227:381-388 (1992); Schlebusch et al., *Hybridoma* 16:47-52 (1997) and references cited therein; U.S. Pat. No. 6,703,015).

Immunogenic Compositions

Immunogenic compositions described herein may be used for immunizing a subject (a human or non-human animal) to induce an immune response against beta-hemolytic streptococci, including GAS and SDSE. The immunogenic compositions may be formulated such that the compositions are pharmaceutically or physiologically acceptable or suitable compositions, preparations, or formulations for administration to a human or non-human animal. In certain embodiments, immunogenic compositions are provided that comprise immunogenic polypeptides, peptides, and/or fusion proteins (and variants thereof) derived or obtained from at least at least one, at least two, at least three, or more Mrp(s). In specific embodiments, the at least one, two, or three Mrps are selected from any one, two, or three of Mrp2, Mrp4, and Mrp49. The Mrp polypeptides, peptides, immunogenic fragments thereof, fusion proteins comprising the Mrp polypeptides, peptides, immunogenic fragments, or variants thereof, that may be formulated into immunogenic compositions are described in great detail herein.

In a more specific embodiment, an immunogenic composition is provided that comprises at least an Mrp2 family polypeptide or peptide (e.g., SEQ ID NOS:10-13, 47-54) or immunogenic fragment or variant thereof. In another specific embodiment, an immunogenic composition is provided that comprises at least an Mrp4 family polypeptide or peptide (e.g., SEQ ID NOS:18-20, 28-46) or immunogenic fragment or variant thereof. In still another specific embodiment, an immunogenic composition is provided that comprises at least an Mrp49 family polypeptide or peptide (e.g., SEQ ID NOS:14-17, 55-57) or immunogenic fragment or variant thereof.

In another embodiment, an immunogenic composition comprises at least one, two, three, four, five, six, seven, or eight, or more different Mrp or immunogenic fragments or variants thereof. In a particular embodiment, an immunogenic composition comprises at least two Mrp polypeptides or immunogenic fragments or variants thereof that each belong to two different Mrp families. In another particular embodiment, an immunogenic composition comprises three Mrp polypeptides (or variants thereof) or immunogenic fragments thereof, and each of the three Mrp polypeptides (or variants thereof) or immunogenic fragments belong to one of the three different Mrp families (i.e., Mrp2, Mrp4, and Mrp49 families). In more specific embodiments an immunogenic composition comprises at least two of (1) an Mrp2 family polypeptide (e.g., SEQ ID NOS:10-13, 47-54) or immunogenic fragment or variant thereof; (2) an Mrp4 family polypeptide (e.g., SEQ ID NOS:18-20, 28-46) or immunogenic fragment or variant thereof; and (3) an Mrp49 family polypeptide (e.g., SEQ ID NOS:14-17, 55-57) or immunogenic fragment or variant thereof. In other specific embodiments, an immunogenic composition comprises at least one of an Mrp2 family polypeptide (e.g., SEQ ID NOS:10-13, 47-54) or immunogenic fragment or variant thereof; at least one of an Mrp4 family polypeptide (e.g., SEQ ID NOS:18-20, 28-46) or immunogenic fragment or variant thereof; and at least one of an Mrp49 family polypeptide (e.g., SEQ ID NOS:14-17, 55-57) or immunogenic fragment or variant thereof.

In another embodiment, any one of the aforementioned immunogenic compositions comprising two or more Mrps (or variant or immunogenic fragment thereof) may further comprise a second different group A streptococcus immunogen. In other embodiments, any one of these immunogenic compositions may further comprise at least one immunogenic peptide that comprises at least 25 contiguous amino acids from the amino terminal portion of a group A streptococcus M protein or a group A streptococcus Spa protein. Examples of M and Spa immunogenic peptide- containing compositions that may be combined with at least one Mrp immunogenic polypeptide or peptide are described in greater detail herein. In certain specific embodiments, the at least one M protein is selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18. In still other specific embodiments, the at least one M immunogenic peptide is an M4 immunogenic peptide.

An immunogenic composition comprising any one or more (i.e., one, two, three, etc.) of an Mrp immunogenic polypeptide, peptide, and/or fusion protein (or variant thereof) may further comprise at least one different (i.e., non-Mrp) GAS immunogen. In a specific embodiment, the at least one different GAS immunogen is an immunogenic M peptide or an immunogenic Spa peptide, such as by way of example, an amino terminal immunogenic M peptide and amino terminal immunogenic Spa peptide, which are described herein. By way of non-limiting example, at least one M protein immunogen that may be used in combination (i.e., in a fusion protein and immunogenic composition comprising the fusion protein, immunogenic composition, or immunogenic preparation) with an Mrp is an immunogenic peptide from the M protein of GAS serotype 4 (i.e., M4 immunogenic peptide). GAS serotype 4 causes approximately 9% of uncomplicated pharyngitis in North America and 5% of invasive GAS disease in Europe (see, e.g., Courtney et al., *Molec. Microbiol.* 59:936-47 (2006); Shulman et al., *Clin. Infect. Dis.* 49:78-84 (2009); Luca-Harari et al., *J. Clin. Microbiol.* 47:1155-65 (2009)).

A vaccine or vaccine regimen may comprise one or more different, separate immunogenic compositions. For ease of description herein, an immunogenic preparation comprises two or more separate and different immunogenic compositions. The two, three, or more different immunogenic compositions may be called for convenience a first immunogenic composition, a second immunogenic composition, a third immunogenic composition, etc. The two or more immunogenic compositions may be administered concurrently or sequentially. In certain embodiments, an immunogenic preparation comprises a first immunogenic composition that comprises at least one Mrp related immunogen described herein, and a second immunogenic composition that comprises at least one M immunogenic peptide or Spa polypeptide. As described in detail herein, immunogenic compositions that comprise M and Spa immunogenic peptides may comprise any number of different peptides from one to 31 different peptides, or more.

In another particular embodiment, an immunogenic composition may comprise M and Spa immunogenic peptides and fusion polypeptides comprising same as described in detail herein. These compositions may comprise any number of different peptides from one to 31 different peptides, or more. Immunogenic compositions comprising GAS M and Spa peptides may be used for immunizing a subject against an SDSE infection. In one embodiment, the subject who is immunized is a child, and in other particular embodiments, the immunized subject is an adult.

Immunogenic compositions may be combined with a pharmaceutically acceptable (i.e., physiologically suitable or acceptable) excipient(s). Any physiological or pharmaceutically suitable excipient or carrier (i.e., a non-toxic material that does not interfere with the activity of the active ingredient) known to those of ordinary skill in the art for use in pharmaceutical compositions comprising protein-related immunogens may be employed in the compositions described herein. Exemplary excipients include diluents and carriers that maintain stability and integrity of the component(s) of the composition. Exemplary excipients for inclusion in the compositions described herein include diluents and carriers that maintain stability and integrity of proteins. Excipients for therapeutic use are well known, and are described, for example, in Remington: *The Science and Practice of Pharmacy* (Gennaro, 21$^{st}$ Ed. Mack Pub. Co., Easton, Pa. (2005)). The choice of an excipient depends on several factors, including the stability of the immunogenic polypeptides, peptides, or fusion polypeptides; the route of administration; and the dosing schedule. For example, saline and phosphate buffered saline at physiological pH may be used. Preservatives, stabilizers, dyes and even flavoring agents (if administered orally) may be provided in the composition.

The immunogenic compositions described herein may also comprise a suitable adjuvant. An adjuvant is intended to enhance (or improve, augment) the immune response to the immunogenic polypeptides, peptides or fusion polypeptides comprising one or more of the immunogenic polypeptides or peptides (i.e., increase the level of the specific immune response to the immunogenic polypeptide or peptide in a statistically, biologically, or clinically significant manner compared with the level of the specific immune response in the absence of administering the adjuvant).

For administration in humans, a pharmaceutically acceptable adjuvant is one that has been approved or is approvable for human administration by pertinent regulatory bodies. For example, as discussed herein and known in the art, Complete Freund's adjuvant is not suitable for human administration. Desired adjuvants augment the response to the immunogenic peptide or fusion polypeptide without causing conformational changes in the immunogen that might adversely affect the qualitative immune response. Suitable adjuvants include aluminum salts, such as alum (potassium aluminum sulfate), or other aluminum containing adjuvants such as aluminum hydroxide, aluminum phosphate, or aluminum sulfate. Other pharmaceutically suitable adjuvants include nontoxic lipid A-related adjuvants such as, by way of non-limiting example, nontoxic monophosphoryl lipid A (see, e.g., Persing et al., *Trends Microbiol.* 10:s32-s37 (2002)), for example, 3 De-O-acylated monophosphoryl lipid A (MPL) (see, e.g., United Kingdom Patent Application No. GB 2220211). Other useful adjuvants include QS21 and QuilA that comprise a triterpene glycoside or saponin isolated from the bark of the *Quillaja saponaria* Molina tree found in South America (see, e.g., Kensil et al., in *Vaccine Design: The Subunit and Adjuvant Approach* (eds. Powell and Newman, Plenum Press, NY, 1995); U.S. Pat. No. 5,057,540). Other suitable adjuvants include oil in water emulsions, optionally in combination with immune stimulants, such as monophosphoryl lipid A (see, e.g., Stoute et al., *N. Engl. J. Med.* 336, 86-91 (1997)). Other suitable adjuvants include polymeric or monomeric amino acids such as polyglutamic acid or polylysine, liposomes, and CpG (see, e.g., Klinman,

*Int. Rev. Immunol.* 25(3-4):135-54 (2006); U.S. Pat. No. 7,402,572; European Patent No. 772 619).

The immunogenic compositions described herein may be formulated by combining a plurality of immunogenic polypeptides and/or peptides and/or plurality of fusion polypeptides with at least one pharmaceutically acceptable excipient. As described herein the immunogenic compositions may further comprise a pharmaceutically acceptable adjuvant. In one embodiment, all immunogenic polypeptides, peptides and fusion polypeptides intended to be administered to a host are combined in a single immunogenic composition, which may include at least one pharmaceutically acceptable excipient and which may further include a pharmaceutically acceptable adjuvant. Alternatively, for example, multiple immunogenic compositions may be formulated separately for separate administration, which could be by any route described herein or in the art and which could be sequential or concurrent. By way of example, a first immunogenic composition (e.g., one that comprises at least one Mrp related GAS polypeptide or peptide or fusion polypeptide) and a second immunogenic composition (e.g., one that comprises another different GAS polypeptide, peptide, or fusion polypeptide), and which combination is described herein as a preparation, may be administered concurrently in a single immunogenic composition or may be administered concurrently or sequentially as separate compositions.

The immunogenic compositions described herein may be formulated as sterile aqueous or non-aqueous solutions, suspensions or emulsions, which as described herein may additionally comprise a pharmaceutically acceptable excipient (which may also be called a pharmaceutically acceptable carrier) and/or a pharmaceutically acceptable diluent. The immunogenic compositions may be in the form of a solid, liquid, or gas (aerosol). Alternatively, immunogenic compositions described herein may be formulated as a lyophilate (i.e., a lyophilized composition), or may be encapsulated within liposomes using technology known in the art. Immunogenic compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins (such as albumin), polypeptides or amino acids such as glycine, antioxidants, chelating agents such as EDTA or glutathione, stabilizers, dyes, flavoring agents, and suspending agents and/or preservatives.

The type of excipient may also be selected on the basis of the mode of administration. The compositions and preparations described herein may be formulated for any appropriate manner of administration, including, for example, topical, buccal, lingual, oral, intranasal, intrathecal, rectal, vaginal, intraocular, subconjunctival, transdermal, sublingual or parenteral administration, including subcutaneous, intravenous, intramuscular, intrasternal, intracavernous, intrameatal or intraurethral injection or infusion.

For parenteral administration, such as subcutaneous injection or intramuscular injection, the carrier or excipient preferably comprises water, saline, alcohol, a fat, a wax or a buffer, and the immunogenic composition is sterile. For oral administration, any of the above excipients or a solid carrier, such as mannitol, lactose, starch, magnesium stearate, sodium saccharin, talcum, cellulose, glucose, sucrose, and magnesium carbonate, may be employed. Biodegradable microspheres (e.g., polylactic galactide) as well as nanoparticles may also be used as carriers for the compositions described herein. Suitable biodegradable microspheres are described, for example, in U.S. Pat. Nos. 4,897,268 and 5,075,109. In particular embodiments in which the composition or preparation is combined with a microsphere, the microsphere is larger than approximately 25 microns. An immunogenic composition described herein may be lyophilized or otherwise formulated as a lyophilized product using one or more appropriate excipient solutions (e.g., sucrose, physiological saline) as diluents upon administration. Nanoparticles may be used to deliver the lyphophilized product and appropriate excipient(s).

The immunogenic compositions disclosed herein may be intended for topical administration, such as directly to mucosal tissue, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in an immunogenic composition for topical administration (e.g., oral or vaginal). The immunogenic compositions described herein may be administered topically by using any one of several delivery vehicles described herein and used in the art, including but not limited to a sponge, gel cap, suppository, gauze (or other suitable fabric for application to the tissue to be treated), nanoparticles, and a lozenge. With respect to certain delivery vehicles, such as a sponge, fabric, or gauze, the composition or preparation is attached to, absorbed by, adsorbed to, or in some manner applied to the vehicle that permits release of the composition or preparation upon contact with the tissue to be treated.

An immunogenic composition disclosed herein may be intended for rectal, oral, or vaginal administration, in the form, e.g., of a suppository or lozenge, which will melt in the rectum, oral, or vaginal space, respectively, and release the drug or components of the composition. A composition or preparation described herein that is administered orally may also be in the form of a liquid. The composition or preparation for rectal administration may contain an oleaginous base as a suitable nonirritating excipient. Such bases include, without limitation, lanolin, cocoa butter and polyethylene glycol.

The immunogenic compositions described herein are preferably endotoxin free, particularly when delivered parenterally. An endotoxin free composition is substantially free of endotoxins and/or related pyrogenic substances (i.e., an endotoxin is not detectable by methods accepted by regulatory agencies to demonstrate with sufficient sensitivity whether an endotoxin is present). Endotoxins include toxins that are present in viable microorganisms and include toxins that are released only when the microorganisms lack cell integrity or die. Pyrogenic substances include fever-inducing, thermostable substances (lipopolysaccharides and glycoproteins) located in the outer membrane of bacteria and other microorganisms. These substances can cause fever, hypotension, and shock when administered to humans. Manufacturing compositions that are endotoxin-free can require special equipment, expert artisans, and can be significantly more expensive than making formulations that are not endotoxin-free.

In another embodiment, a method of manufacture of the immunogenic compositions described herein is provided. Methods of manufacture comprise combining or mixing together an immunogenic polypeptide, peptide, or fusion protein or the desired plurality of immunogenic polypeptides, peptides or fusion polypeptides to provide the immunogenic compositions described herein. The methods of manufacture may further comprise combining or mixing one or more physiologically suitable (or pharmaceutically acceptable) excipients as described herein. The methods may further comprise combining or mixing the immunogenic composition with a pharmaceutically suitable adjuvant; at least one pharmaceutically suitable excipient may also be combined or mixed with the immunogenic composition comprising an adjuvant. In still further embodiments, a method of manufacture comprises chemical synthesis or recombinant production of the desired immunogenic polypeptide(s), peptide(s) or fusion polypeptide(s). Chemical synthesis and recombinant production of the polypeptide(s), peptide(s) or fusion polypeptide(s) are described in detail herein. During manufacture of each immunogenic polypeptide, peptide and fusion protein, appropriate manufacturing processes (such as Good Manufacturing Practices (GMP)) as required by a regulatory agency are employed when the immunogenic compositions will be administered to a human subject. In addition, a person skilled in the art is familiar with techniques and steps to be taken to maintain stability and integrity of the polypeptides, peptides, and fusion polypeptides during manufacture of an immunogenic composition.

Methods of Using Immunogenic Polypeptides and Peptides, Fusion Polypeptides, Immunogenic Compositions, and Preparations The at least one, two, three, or more Mrps or immunogenic polypeptides and peptides (or fragments) thereof or a fusion protein comprising same, and immunogenic compositions comprising the immunogenic polypeptide, peptide, or fusion protein may be used for inducing an immune response against the beta-hemolytic streptococci, GAS and SDSE. As described herein, fusion proteins, immunogenic compositions, and immunogenic preparations that comprise at least one Mrp or immunogenic fragment or variant thereof and that further comprise at least one additional GAS immunogen (e.g., at least one M and/or Spa immunogenic peptide or a plurality of GAS immunogenic peptides) also may be used for inducing an immune response against the beta-hemolytic streptococci, GAS and SDSE.

Accordingly, in certain embodiments, methods are provided herein that comprise immunizing a host (or subject), which may be a human host, in a manner appropriate to evoke an immune response (including a humoral response) against the beta-hemolytic streptococci GAS bacteria and SDSE bacteria. These compositions described herein are therefore useful for prophylactic and/or therapeutic treatment of a host in need thereof who has inadequate immunity to GAS and/or SDSE and is susceptible to infection. In addition, induction of secretory or mucosal anti-GAS antibodies in the host may prevent (i.e., reduce or decrease likelihood of occurrence) initial colonization by streptococci.

GAS serotypes represented by immunogenic polypeptides, peptides, and fusion proteins in immunogenic compositions described herein include those that cause non-invasive infections (e.g., pharyngitis, impetigo, erysipelas, and cellulitis) and GAS serotypes that cause invasive infections (e.g., GAS infections of the blood (bacteremia), muscle, and lung (pneumonia), necrotizing fasciitis, and streptococcal toxic shock syndrome), and nonsuppurative sequelae such as acute rheumatic fever, reactive arthritis, and glomerulonephritis (see, e.g., Cunningham, *Clin. Microbiol. Rev.* 13:470 (2000)).

SDSE serotypes to which evoking an immune response is desired by using the immunogens and immunogenic compositions described herein include serotypes that cause a spectrum of disease similar to that of group A streptococci (see, e.g., Efstratiou et al., *Soc. Appl. Bacteriol. Symp. Ser.* 1997; 26: 72S-9S). SDSE serotypes may colonize the human upper respiratory, gastrointestinal, female genital tracts, as well as the skin. The infections caused by SDSE include superficial skin and mucosal infections as well as life-threatening bacteremia and toxic shock syndrome. SDSE have also been associated with outbreaks of pharyngitis in children (see, e.g., Gerber et al., suspra) and are established causes of acute post-streptococcal glomerulonephritis.

Methods for inducing an immune response against beta-hemolytic streptococci such as GAS and SDSE and for preventing (i.e., reducing the likelihood of occurrence) and/or treating a beta-hemolytic streptococci infection such as a GAS infection or a SDSE infection, comprise administering an immunogenic composition or an immunogenic preparation described herein to the host once, twice, three times, four times, or more times at appropriate time intervals to evoke and maintain the desired anti-streptococcal immune response. Because the immunogenic compositions comprising one or more Mrp immunogenic polypeptides or peptides or comprising one or more fusion polypeptides comprising these immunogenic polypeptides and/or peptides (and optionally comprising at least one or a plurality of M and Spa immunogenic peptides) may be used for prevention, amelioration, or treatment of beta-hemolytic streptococci infection such as a GAS infection or an SDSE infection, the immunogenic compositions may also be referred to as vaccines by a person skilled in the art.

The dose of each immunogenic composition, the number of doses administered to the host, and the time intervals between two doses of the composition may be determined by a person skilled in the medical art. The appropriate amount of each immunogenic polypeptide or peptide or the amount of each fusion polypeptide in the immunogenic composition administered to the host may depend upon the host's or patient's (e.g., human's) condition, that is, stage of the disease, general health status, as well as age and weight, and other factors familiar to a person skilled in the medical art. Hosts or subjects who may be immunized with the immunogenic compositions described herein include human and non-human hosts and subjects. Human hosts/subjects include infants, children, and/or adults. Immunogenic compositions suitable for administration to an adult may further be prepared appropriately depending on whether the adult is a young adult, middle-aged, or a senior adult.

Immunogenic compositions may be administered in a manner appropriate to the disease to be treated (or prevented) as determined by persons skilled in the medical art. An appropriate dose and a suitable duration and frequency of administration will be determined by factors such as the condition of the patient, age of the patient, the type and severity of the patient's disease to be treated or prevented, the particular form of the active ingredient, and the method of administration. In general, an appropriate dose and treatment regimen provides the immunogenic composition in an amount sufficient to provide therapeutic and/or prophylactic benefit (e.g., an improved clinical outcome, overall survival, or a lessening of symptom severity). For prophylactic use, a dose should be sufficient to prevent or delay the onset of, and/or to diminish the severity of an infection in a statistically, biologically, or clinically significant manner.

Optimal doses may generally be determined using experimental in vitro assays, in vivo animal models, and/or human clinical trials. The optimal dose may depend upon the body mass, weight, or blood volume of the host. In general, the amount of an immunogenic polypeptide, peptide, or fusion polypeptide as described herein present in a dose, ranges from about 10 µg to about 10 mg, from about 100 µg to 1 mg, from about 150 µg to 500 µg, or from about 200 µg to about 400 µg. The use of the minimum dosage that is sufficient to provide effective therapy and/or prophylaxis is usually preferred. Patients may generally be monitored for therapeutic or prophylactic effectiveness using assays suitable for the condition being treated or prevented, which assays will be familiar to those having ordinary skill in the art and are described herein. When administered in a liquid form, suitable dose sizes may vary with the size (i.e., weight or body mass) of the patient, but will typically range from about 1 ml to about 500 ml (comprising an appropriate dose) for a 10-60 kg subject.

An initial immunization regimen (i.e., protocol) may include an initial administration (i.e., administration of the primary dose) of an immunogenic composition followed by one or more booster immunizations. Booster immunizations may be administered multiple times (e.g., two times or three times or four times or more) at desired time intervals ranging from about 2 weeks to about 26 weeks, such as 2, 4, 8, 12, 16, 20, 24, 26, or 28 week intervals. The time intervals between different doses (e.g., between the primary dose and second dose, or between the second dose and a third dose) may not be the same, and the time interval between each two doses may be determined independently. Additional booster immunizations for prophylaxis of microbial infections, such as group A streptococcus infections, may be administered one year or more years after the initial immunization regimen, such as any time between one and ten years after the initial regimen.

The immunogenic compositions described herein may be administered via a route including oral, enteral, parenteral, transdermal/transmucosal, and inhalation. The term enteral, as used herein, is a route of administration in which the agent is absorbed through the gastrointestinal tract or oral mucosa, including oral, rectal, and sublingual. The term parenteral, as used herein, describes administration routes that bypass the gastrointestinal tract, and are typically administered by injection or infusion, including intraarterial, intradermal, subdermal, intramuscular, intranasal, intraocular, intraperitoneal, intravenous, subcutaneous, submucosal, intravaginal, intrasternal, intracavernous, intrathecal, intrameatal, and intraurethral injection. The term transdermal/transmucosal, as used herein, is a route of administration in which the agent is administered through or by way of the skin, including topical. The term inhalation encompasses techniques of administration in which an agent is introduced into the pulmonary tree, including intrapulmonary or transpulmonary and includes intranasal administration. In more particular embodiments, the immunogenic compositions described herein may be administered orally, intramuscularly, or intranasally. All doses of the immunogenic compositions may not necessarily be administered by the same route. In certain embodiments, different doses of the immunogenic compositions may be delivered by different routes, such as by two or more of oral, intramuscular, and intransal routes.

The immunogenic compositions described herein may be used to reduce the likelihood of occurrence of a beta-hemolytic streptococci, such as GAS or SDSE, infection or to treat a beta-hemolytic infection, such as a GAS or SDSE infection. In one embodiment, the immunogenic compositions described herein may be used to reduce the likelihood of occurrence of a GAS infection or to treat a GAS infection that causes any one of the following: pharyngitis, scarlet fever, necrotizing fasciitis, cellulitis, meningitis, pneumonia, streptococcal toxic shock syndrome, bacteremia, septicemia, septic arthritis, pyoderma, skin infections (invasive and non-invasive), impetigo, erysipelas, soft-tissue infection, nephritis, and GAS pyrogenic reaction. Methods described herein for inducing an immune response against GAS and reducing the likelihood of occurrence of a GAS infection or treating a GAS infection may also effectively reduce the likelihood of occurrence or severity of nonsuppurative sequelae such as acute rheumatic fever, rheumatic heart disease, reactive arthritis, and glomerulonephritis. In other embodiments, the immunogenic compositions described herein may be used to reduce the likelihood of occurrence of a SDSE infection or to treat a SDSE infection, for example an SDSE infection that causes any one of pharyngitis, streptococcal toxic shock syndrome, bacteremia, septicemia, skin infections (invasive and non-invasive), or glomerulonephritis.

Immunized subjects may be monitored for therapeutic or prophylactic effectiveness using assays suitable for the infection or condition being treated or prevented, which assays will be familiar to those having ordinary skill in the art and which are described herein. The immune response evoked by administering the immunogenic compositions described herein according to the methods described above comprises an adaptive immune response that includes a humoral response and may also include a cellular response (which comprises a CD4 immune response and a CD8 immune response) specific for each immunogen polypeptide or peptide represented in the immunogenic composition. The humoral immune response (i.e., antibody response) can be monitored throughout an immunization protocol using any one of the immunoassays (e.g., ELISA, immunoblotting), in vitro functional assays (e.g., opsonic, phagocytic and killing assays, indirect bactericidal assays) and the like. Such methods are useful for monitoring and determining the level of binding (i.e., titer) of specific antibodies present in a biological sample (e.g., sera) from an immunized host. Based on the results from one or more of these assays, the dose or timing of the next dose or the necessity for an additional dose may be determined.

A cell-mediated immune response involves various types of T cells (i.e., T lymphocytes). In a cell mediated response, T cells act to eliminate an antigen by a number of mechanisms. For example, helper T cells that are capable of recognizing specific antigens may respond by releasing soluble mediators such as cytokines to recruit additional cells of the immune system to participate in an immune response. Also, cytotoxic T cells are capable of specifically recognizing an antigen and may respond by binding to and destroying or damaging an antigen-bearing cell, such as a GAS bacterial cell.

Assays routinely practiced in the art to examine a cellular immune response include determining the presence and level of soluble mediators such as cytokines, lymphokines, chemokines, hormones, growth factors, as well as other mediators. Immunoassays also include determining cellular activation state changes of immune cells by analyzing altered functional or structural properties of the immune cells, for example, cell proliferation, altered motility, induction of specialized activities such as specific gene expression or cytolytic behavior; cell maturation, and alteration in relationship between a Th1 response and a Th2 response. Procedures for performing these and similar assays are may be found, for example, in Lefkovits (*Immunology Methods Manual: The Comprehensive Sourcebook of Techniques,* 1998). See also *Current Protocols in Immunology*; Weir, *Handbook of Experimental Immunology*, Blackwell Scientific, Boston, Mass. (1986); Mishell and Shigii (eds.)

Selected Methods in Cellular Immunology, Freeman Publishing, San Francisco, Calif. (1979); Green and Reed, Science 281:1309 (1998) and references cited therein).

As described briefly herein, a biological sample may be obtained from the subject for determining the presence and level of an immune response to immunogenic polypeptide(s) or peptide(s), to a fusion polypeptide comprising same, and/or to a full-length or mature GAS polypeptide, or GAS bacteria in the subject who has received the immunogenic compositions described herein. Similarly, to determine the immune response against other beta-hemolytic streptococci such as SDSE, a biological sample may be obtained from the subject for determining the presence and level of an immune response to immunogenic polypeptide(s) or peptide(s), to a fusion polypeptide comprising same, and/or to a full-length or mature SDSE polypeptide, or SDSE bacteria in the subject who has received the immunogenic compositions described herein. A "biological sample" may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

Determining the effectiveness of immunization with the immunogenic compositions described herein may also include clinical evaluation. By way of example, the presence of a GAS infection or an SDSE infection may be determined by performing routine assays (bacteria cell culture; immunofluorescence assays) available to the clinician to determine quickly if streptococci are present in a body fluid or at a site on the body, such as the throat, mucosal tissue, or skin. Symptomatology, such as fever, inflammation, pain, and various other and numerous symptoms of beta-hemolytic streptococcal infections (e.g., a GAS or an SDSE infection) can be monitored by persons skilled in the clinical art.

Immunogenic polypeptide, peptides, and fusion polypeptides described herein may be used as reagents for detecting the presence and level of specific antibody in a sample. A biological sample, such as by way of non-limiting example, a biological sample described herein from an immunized host, or a cell supernatant or cell lysate from cell lines that are known to or suspected of producing a specific monoclonal antibody is obtained. The biological sample is contacted with (i.e., mixed with, combined with, or in some manner permitted to interact with) an immunogenic polypeptide or peptide (or fusion polypeptide, mature or full-length protein, or streptococcal bacteria (such as GAS or SDSE) which each may comprise the immunogenic polypeptide or peptide) for a time sufficient and under conditions suitable to permit an antibody in the biological sample and the immunogenic polypeptide or peptide (alone or as part of a larger protein) to interact. The level of interaction between the biological sample and the immunogenic peptide is detected and compared with the level of interaction of the immunogenic polypeptide or peptide with a control biological sample that serves as a baseline or negative control. The level of interaction (i.e., binding of an antibody and immunogenic polypeptide or peptide) can be determined by any one of the numerous immunoassay methods described herein and the art and with which a person skilled in the art is familiar.

The following examples are provided for purposes of illustration, not limitation.

EXAMPLES

Example 1

M-Related Proteins of GAS

M-related proteins (Mrps) range from 38-42 kDa in size, are largely alpha-helical, and are anchored to the cell wall via an LPSTGE (SEQ ID NO:1) motif as shown in FIG. 1 (see FIGS. 1A, 1C, and 1E). N-terminal peptides of three polypeptides, Mrp2, Mrp4 and Mrp49, representing the three families, were cloned and purified.

Sequencing Mrp Genes.

Mrp genes are located in the same position of all GAS chromosomes sequenced to date and all have nearly identical leader sequences, which facilitated the design of PCR primers to amplify the structural genes. The amplified DNA was either sequenced directly from PCR amplicons or after cloning into plasmids. Mrp genes were amplified using one set of the following PCR primers:

Primers for complete mrp genes: FT1B: aaa gga tcc gat ttg aca gtt ttg (SEQ ID NO:2); and FB1B: aaa gga tcc tta gtt ttc ttc ttt gcg (SEQ ID NO:3). Primers for mrp4U had the following sequences: T16B: ctt gga tcc gag agt cgt cgt tat cag gca cct (SEQ ID NO:4) and B27B: tac gga tcc taa atc tga gat ttg ctt (SEQ ID NO:5). Primers for mrp2U had the following sequences: GTAAccatgGAGACCGTAG-GTCGCTTTAGTG (SEQ ID NO:6), which includes an NcoI site; and gcaagcttAGCATTTTCTGACT-CAATCTTTTT (SEQ ID NO:7), which includes a Hind III site. Primers for mrp49U had the following sequences: GTAAccatgGACTTAAGTACTCAGGAACATCCTAG (SEQ ID NO:8), which includes an NcoI site; and gcaagct-tCTTGTCGCTAGATTCTCTATATTTTTT (SEQ ID NO:9), which includes a Hind III site. The restriction enzyme sites are shown as non-capitalized bases.

Sequence Comparisons and Clustal Analysis.

Mrp sequences were analyzed for sequence identities, and clustal alignments were created using the MegAlign program from DNASTAR Inc. (Madison, Wis.). Sequences of Mrp polypeptides from serotypes 2, 4, 8, 9, 13, 15, 22, 28, 49, 50, and 76 were obtained from references (see, e.g., O'Toole et al., Proc. Natl. Acad. Sci. USA 1992; 89(18): 8661-65; Heath et al., Proc. Natl. Acad. Sci. USA 1989; 86(12):4741-45; Yung et al., Infect. Immun. 1996; 64(6): 2193-200; Krebs et al., supra; Yung et al. supra; Podbielski et al., Med. Microbiol. Immunol. 1994; 183(1):33-42; Podbielski et al., Infect. Immun. 1995; 63(1):9-20; Green et al., J. Infect. Dis. 2005; 192(5):760-70) and from GenBank accession numbers X78482.1, X78483.1, X78484.1, X73159.1, X75750.1, X69324.1, M87831.1, S75411.1, AAB06612.1, CP000056.1, and A33939. Mrp nucleotide sequences from serotypes 101, Ala49, 100.2, 80, 64, 116, 121, NS88.2, 15Mali, ST4547, 25, 81.2, 67, 124, 42, 65, 123, 52, and 59 were obtained as described herein. The phylogenetic tree of Mrp was generated with Geneious software (Biomatters Ltd., Auckland, New Zealand) using the neighbor joining and bootstrap methods using Mrp sequences listed above and sequences obtained as described herein.

Analysis of the sequences of 30 Mrp's from heterologous serotypes of GAS indicates that the sequences at the C-terminal end are highly conserved and share almost 100% identity, which is likely the result of conservation of function defined by fibrinogen and IgG binding. However, the N-terminal 80-90 amino acids of the mature proteins are semi-conserved and can be divided into three structurally related families (see FIGS. 1A, 1B, and 2). Particular Mrp polypeptides, Mrp4, Mrp2, and Mrp49, have been selected as representative members of each family for study (see FIG. 3). Mrp amino acid sequence identity within each family is as follows: Mrp4 family, percent identity ranged from 77-100% with an average of 90%; Mrp2 family, percent identity ranged from 72-100% with an average of 94%; and Mrp49 family, range 74-100% with an average of 90% (see Table 3). Pileup and clustal analyses depict three main branches representing each family of Mrp polypeptides (see FIG. 3).

TABLE 3

AMINO ACID SEQUENCE IDENTITY AMONG THE
N-TERMINAL SEQUENCES OF MRP'S
FROM HETEROLOGOUS EMM-TYPES
OF GAS (DERIVED FROM FIG. 2)

| | % Sequence Identity | | |
|---|---|---|---|
| | N Mrp4 | N Mrp2 | N Mrp49 |
| N Mrp101 | 94.3 | 14.7 | 16.3 |
| N MrpAlab49 | 94.3 | 14.7 | 16.3 |
| N Mrp100.2 | 94.3 | 14.7 | 16.3 |
| N Mrp80 | 94.3 | 14.7 | 16.3 |
| N Mrp64 | 94.3 | 14.7 | 16.3 |
| N Mrp116 | 95.7 | 14.7 | 16.3 |
| N Mrp121 | 95.7 | 14.7 | 16.3 |
| N MrpNS88.2 | 95.7 | 14.7 | 16.3 |
| N Mrp15 | 91.4 | 14.7 | 16.3 |
| N Mrp15B106 | 94.3 | 14.7 | 16.3 |
| N MrpST4547 | 95.7 | 14.7 | 16.3 |
| N Mrp4 | 100 | 14.7 | 16.3 |
| N Mrp22 | 100 | 14.7 | 16.3 |
| N Mrp25 | 77.1 | 13.7 | 14 |
| N Mrp81.2 | 77.1 | 13.7 | 14 |
| N Mrp8 | 81.4 | 13.7 | 14 |
| N Mrp28 | 81.4 | 13.7 | 14 |
| N Mrp67 | 80 | 14.7 | 15.1 |
| N Mrp124 | 80 | 14.7 | 15.1 |
| N Mrp2 | 14.7 | 100 | 39.3 |
| N Mrp76 | 14.7 | 100 | 39.3 |
| N Mrp50 | 15.8 | 99.1 | 39.3 |
| N Mrp42 | 14.7 | 96.3 | 39.3 |
| N Mrp65 | 15.8 | 96.3 | 40.2 |
| N Mrp13 | 13.8 | 72 | 36.4 |
| N Mrp9 | 19.8 | 39.3 | 76.3 |
| N Mrp123 | 19.8 | 38.3 | 74.2 |
| N Mrp49 | 16.3 | 39.3 | 100 |
| N Mrp52 | 16.3 | 39.3 | 100 |
| N Mrp59 | 16.3 | 39.3 | 97.9 |

Cloning, Expression and Purification of Mrp N-Terminal Unique Peptides (MrpU).

Based on mrp gene sequences, primers were designed to amplify the DNA encoding the desired polypeptide fragments of Mrp2, Mrp4 and Mrp49. The mrp4U amplicon was ligated into pTrcHis, and introduced into *E. coli* Top10. The mrp2 and mrp49 PCR products were ligated into pET28, transformed into C3016, expressed as histidine fusion products, and purified by metal affinity chromatography as previously described (see, e.g., Courtney et al., 2006, supra). The recombinant proteins consisted of Mrp2U (93 amino acids, which includes a MET in the first position; (see residues 1-93 of SEQ ID NO:11; SEQ ID NO:12, which provides the sequence without the methionine)); Mrp4U (145 amino acids, some of which is derived from plasmid sequence (SEQ ID NO:19); residues 37-116 of SEQ ID NO:19 correspond to Mrp2U sequences (see also, e.g., residues 42-122 of SEQ ID NO:18)); and Mrp49U (83 amino acids; (see residues 1-83 of SEQ ID NO:15)).

The 5' mrp gene fragments containing the unique (family-specific) sequences (see FIGS. 1G, 1H, and 1I) were cloned into expression plasmids as PCR products using primers to specify the unique regions of the genes. The three proteins were purified from extracts of *E. coli* by nickel affinity using standard procedures. SDS-PAGE showed that Mrp2U and Mrp49U migrated with an apparent Mr of approximately 10 kDa. Mrp4U had an Mr of 14 kDa. Intact Mrp4b was approximately 50 kDa.

Example 2

Cross-Reactivity of Rabbit M-Related Protein Antisera

The purified proteins prepared as described in Example 1 were adsorbed to alum and used to immunize rabbits for the production of antisera. Rabbits were immunized intramuscularly (I.M.) with 200 µg of Mrp2U or 200 µg Mrp49U that was conjugated in equal ratios (wt/wt) to KLH and 150 µg of unconjugated Mrp4U adsorbed to an equal amount of alum (wt/wt) at time 0, 4 weeks, and 8 weeks. Booster injections were given at 12 weeks, and sera were obtained 2 weeks after the final injection.

Antibody titers were determined by ELISA (see, e.g., Penfound et al., *Vaccine* 2010; 28(31):5017-22) using the homologous and heterologous Mrp's as solid-phase antigens (see Table 4). Because both the immunizing antigens and the ELISA antigens were purified from extracts of *E. coli*, the antisera were diluted using an extract of host *E. coli* to inhibit non-specific antibody binding (see, e.g., Sambrook et al., editors; Molecular cloning: A Laboratory Manual. 3rd ed. Cold Spring Harbor, N.Y.: Cold Spring Harbor Laboratory Press, 2001). Each immune serum reacted in high titer with the immunizing antigen. Cross-reactive antibodies were detected between Mrp2U and Mrp49U antisera (see Table 4, which refers to the N terminal region of the Mrp), which is consistent with the presence of some shared sequence between the two proteins (see FIG. 2).

TABLE 4

MRP-SPECIFIC AND CROSS-REACTIVE ANTIBODIES EVOKED
IN RABBITS BY N-TERMINAL PEPTIDES OF MRP

| | Antiserum | | | |
|---|---|---|---|---|
| ELISA Ag | Pre-immune | Mrp2U (1-93) | Mrp4U (1-82) | Mrp49U (1-83) |
| Mrp2U(1-93) | <200 | 6,400 | <200 | 1,600 |
| Mrp4U(1-82) | <200 | <200 | 1,600 | <200 |
| Mrp49U(1-83) | <200 | 1,600 | <200 | 12,800 |

Example 3

Rabbit M-Related Protein Antisera Promotes Bactericidal Killing of GAS

Mrp antisera promoted bactericidal killing of heterologous M serotypes of GAS. Previous studies showed that Mrp4 antisera opsonized type 4 GAS and promoted bactericidal killing of the organisms in whole human blood. Bactericidal antibodies have previously been shown to correlate with protection against infection in animals (see, e.g., Lancefield, *J. Immunol.* 1962; 89:307-13) and humans (see, e.g., Wannamaker et al., *AMA Am. J. Dis. Child* 1953; 86(3):347-48). Three heterologous M serotypes of GAS (M52, M65, and M124) that expressed Mrp's were selected from each of the three structurally related families of Mrp (Mrp49, Mrp2, and Mrp4, respectively), and bactericidal assays were performed using the immune sera against the MrpU peptides (see FIG. 4). Bactericidal assays were performed as previously described (see, e.g., Pendfound et al., *Vaccine*, supra). In each instance, the MrpU immune sera resulted in significant bactericidal killing of the test organism. These results indicated that the conservation of amino acid sequence within the Mrp families resulted in functional bactericidal antibody activity that correlated with protection against infection.

Mrp and M Protein Antibodies in Combination Resulted in Enhanced Bactericidal Killing of the Homologous M Serotype of GAS.

Figure 5:
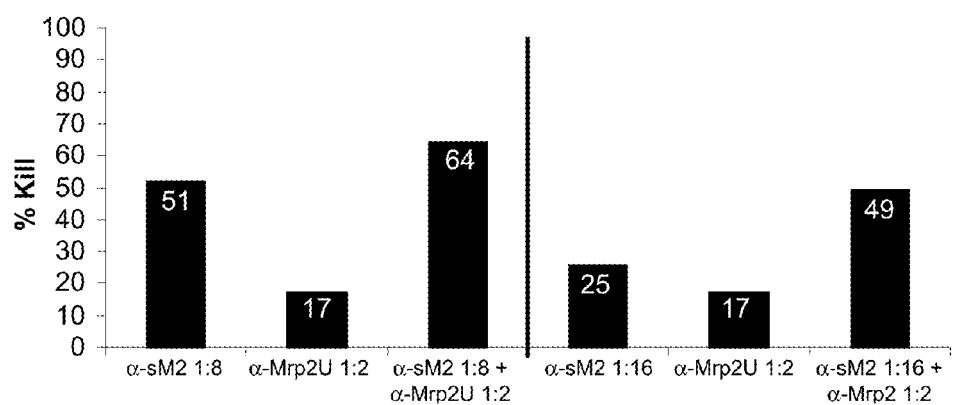
FIG. 5 illustrates that M2 antibodies in combination with Mrp2 antibodies promoted enhanced bactericidal activity against type M2 GAS. Specific rabbit antisera were diluted for each antiserum as shown. The percent killing is indicated in each bar of the graph.

Because M protein antibodies as well as Mrp antibodies promote opsonization of GAS serotypes that express both surface proteins, bactericidal assays were performed with M and Mrp antisera alone and in combination (see results in FIG. 5). The antiserum against an N-terminal synthetic peptide of M2 (anti-sM2(1-35) (α-sM2)) was strongly bactericidal when used undiluted. Therefore, the antiserum was titrated to achieve approximately 50% and 25% killing when used alone. When the M2 and Mrp2U antisera were added to the assay together, they demonstrated an additive bactericidal effect that was greater than either diluted antiserum used alone. These results suggested that the combination of M and Mrp may be more effective as vaccine antigens than either alone when both antigens are expressed by the infecting serotype of GAS.

MrpU Antibodies were Sufficient to Promote Bactericidal Killing of Non-Vaccine Serotypes of GAS that were not Opsonized by the 30-Valent M Protein-Based Vaccine.

Figure 6:
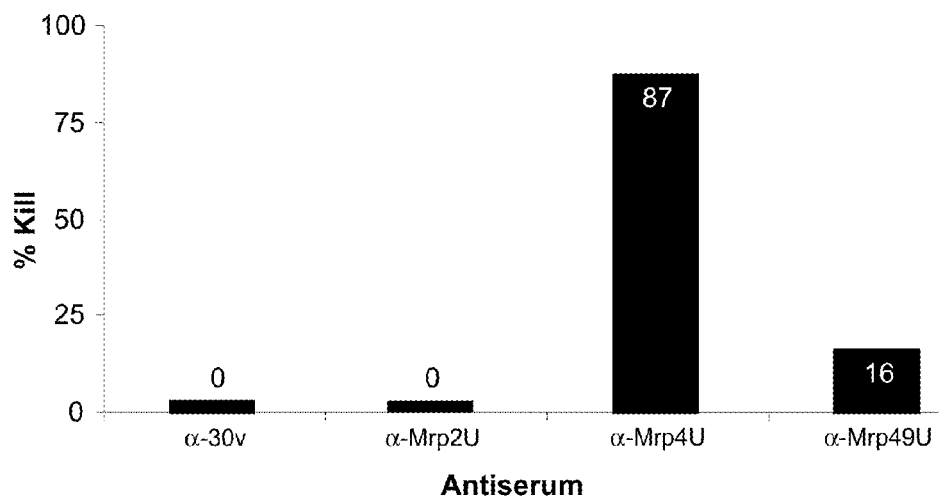
FIG. 6 shows that Mrp4U antibodies are bactericidal against M116 GAS, a serotype of GAS that expresses an Mrp that belongs to the Mrp4 family but that is not opsonized by a 30-valent vaccine (α-30v). Antisera specific for Mrp2U and Mrp49U also were not bactericidal against M116 GAS. The percent killing is indicated in each bar of the graph.

Some non-vaccine serotypes of GAS are not killed in the presence of 30-valent antisera while others are opsonized and killed (see, e.g., Dale et al., *Vaccine* 2011; 29(46):8175-78). To determine whether the addition of Mrp peptides to current multivalent M protein-based vaccines may afford broader coverage, the Mrp4U antisera were tested in bactericidal assays using a serotype of GAS that was not killed in the presence of 30-valent vaccine antiserum (see FIG. 6). The M116 serotype of GAS expresses both a type-specific M protein and an Mrp that shares 96% sequence identity with Mrp4 (see Table 3). The 30-valent vaccine antiserum, as well as the Mrp2U and Mrp49U antisera, resulted in bactericidal killing of the M116 strain ranging from 0-16%. The Mrp4U antiserum added to the test mixture produced 87% killing of the test organism, indicating that Mrp antibodies alone are sufficient to promote significant opsonization and bactericidal activity (see FIG. 6).

Conserved Epitopes within the C-Terminus of Mrp Evoked Cross-Opsonic Antibodies that Promoted Bactericidal Killing of GAS Expressing a Heterologous Mrp.

Figure 4:
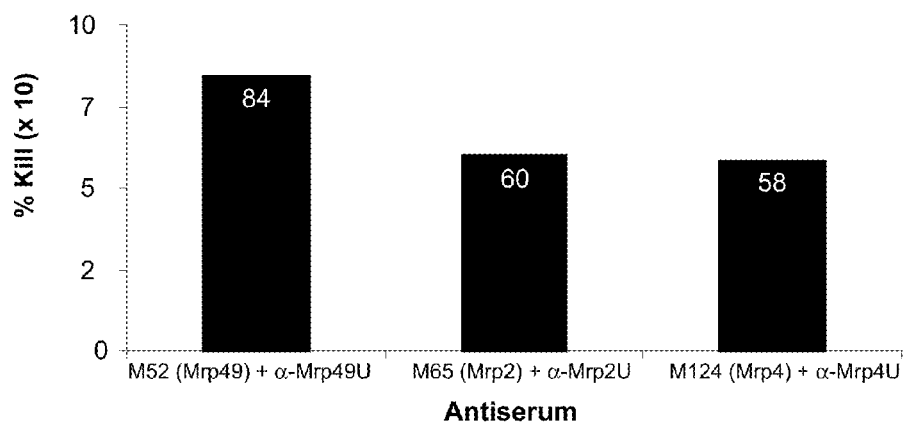
FIG. 4 shows that Mrp antisera promoted bactericidal killing of heterologous M-types of GAS expressing Mrp's in the same family. M52, M65, and M124 signify the three M protein serotypes of GAS. The percent killing is represented by the number in each bar of the graph.
Figure 7:
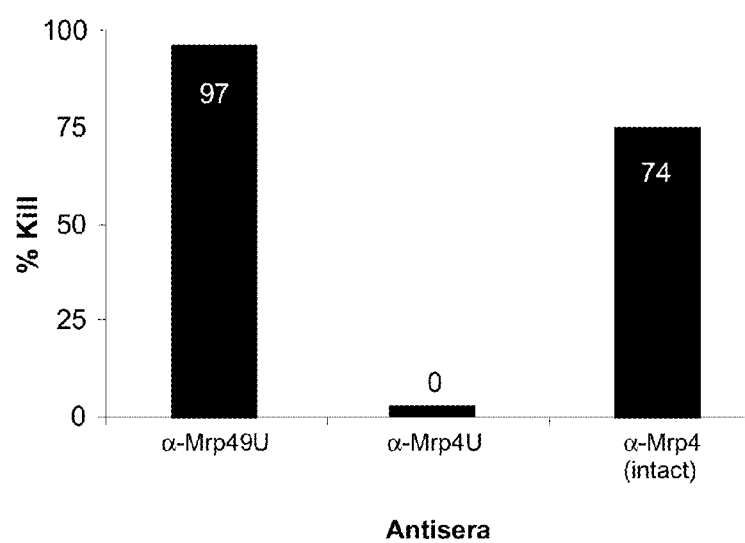
FIG. 7 shows that antibodies against the conserved regions of intact Mrp4 are bactericidal against heterologous M49 GAS.

The N-terminal peptides of Mrp evoked bactericidal antibodies against GAS that express Mrp from the same family (see FIG. 4). To identify potential protective epitopes that may reside in the conserved C-terminal regions of Mrp, rabbits were immunized with intact (i.e., mature Mrp4) and the immune sera were assayed for bactericidal activity against M49 GAS, which express Mrp49 (see FIG. 7). As expected, anti-Mrp49U resulted in 97% killing of M49 GAS and anti-Mrp4U demonstrated no bactericidal activity. However, antiserum against mature Mrp4 resulted in 74% killing of M49 GAS. Taken together, these results indicate that Mrp4U evoked family-specific antibodies that did not cross-react with Mrp49 (see Table 4) and mature Mrp4, which contains epitopes that are conserved among all Mrp's, evoked cross-opsonic antibodies that promoted significant bactericidal activity against M49 GAS.

Example 4

MRP Immunized Animals Were Protected From Lethal Group A Streptococcus Infection Mrp is a Cross Protective GAS Vaccine Antigen.

Figure 8:
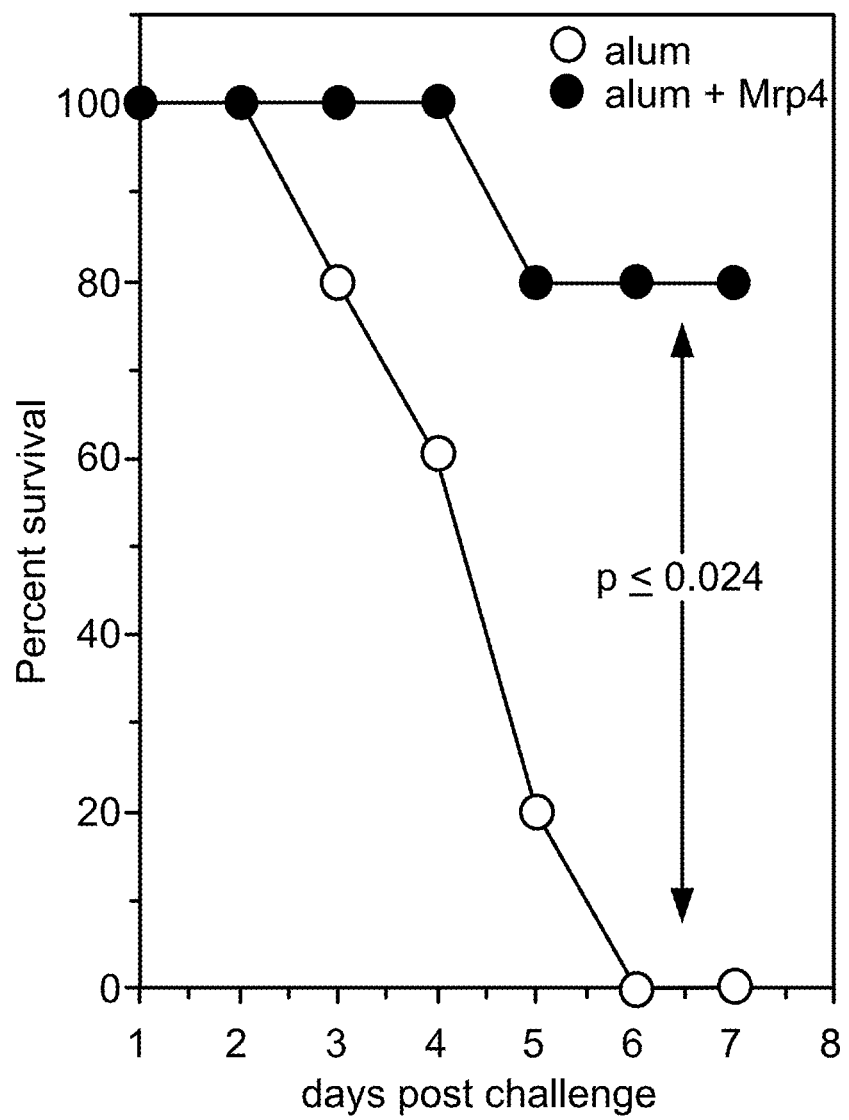
FIG. 8 demonstrates that immunization with Mrp4 protected mice against lethal infections by M serotype 28 GAS, which expresses an Mrp in the Mrp4 family.

The cross-protective efficacy of Mrp was demonstrated after immunizing mice with Mrp4 or alum alone and then challenging both groups of mice with the heterologous M28 GAS strain. Groups of 5 mice each were immunized with Mrp4 and then challenged with virulent M type 28 GAS. Mice received 30 μg Mrp4 on alum via the I.M. route on days 0, 14, and 28. Control mice received alum alone. Challenge infections with $6\times10^8$ CFU type 28 GAS were administered via the intraperitoneal route 3 weeks after the final injection. Mice immunized with Mrp4 were significantly protected against lethal challenge infections (80% survival) compared to control mice (0% survival, $p \leq 0.024$) (see FIG. 8).

Example 5

Immunogenicity of MRP in Humans

Mrp is Immunogenic in Humans Following Natural Infection.

Figure 9:
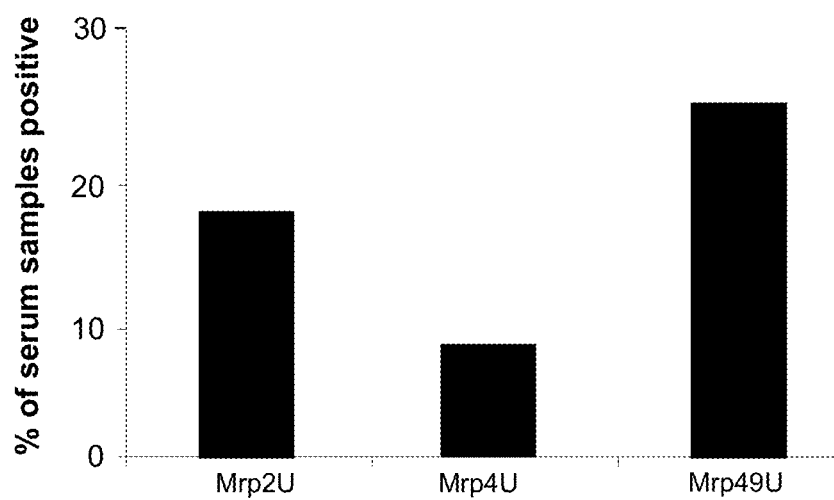
FIG. 9 illustrates that serum from normal adult volunteers contains antibodies against N-terminal peptides of Mrp2, Mrp4, and Mrp49.

Serum samples from 71 normal adult volunteers were screened for the presence of antibodies against Mrp2U, Mrp4U, and Mrp49U by ELISA. Serum samples were diluted 1:1000 and those with significant reactivity (O.D.>1.000) were considered positive. A significant percentage of serum samples reacted with one or more of the Mrp peptides, ranging from 9-25%. Altogether, 30/71 serum samples (42%) contained high levels of Mrp antibodies. Three serum samples were highly reactive with two of the Mrp proteins and one sample reacted with all three. These results indicated that Mrp is immunogenic in humans following natural infection with GAS (see FIG. 9).

Example 6

Immunogenicity of MRP in Children

Mrp is Immunogenic in Human Children Following Natural Infection.

The prevalence and age-related acquisition of Mrp antibodies in children is described in this example. Serum samples from 174 subjects (ages 1-15) were obtained from the clinical laboratories of Le Bonheur Children's Hospital (Memphis, Tenn.). Purified, recombinant N-terminal peptides of Mrp2, 4, and 49 were used to assess Mrp antibody levels by ELISA.

Figure 10:
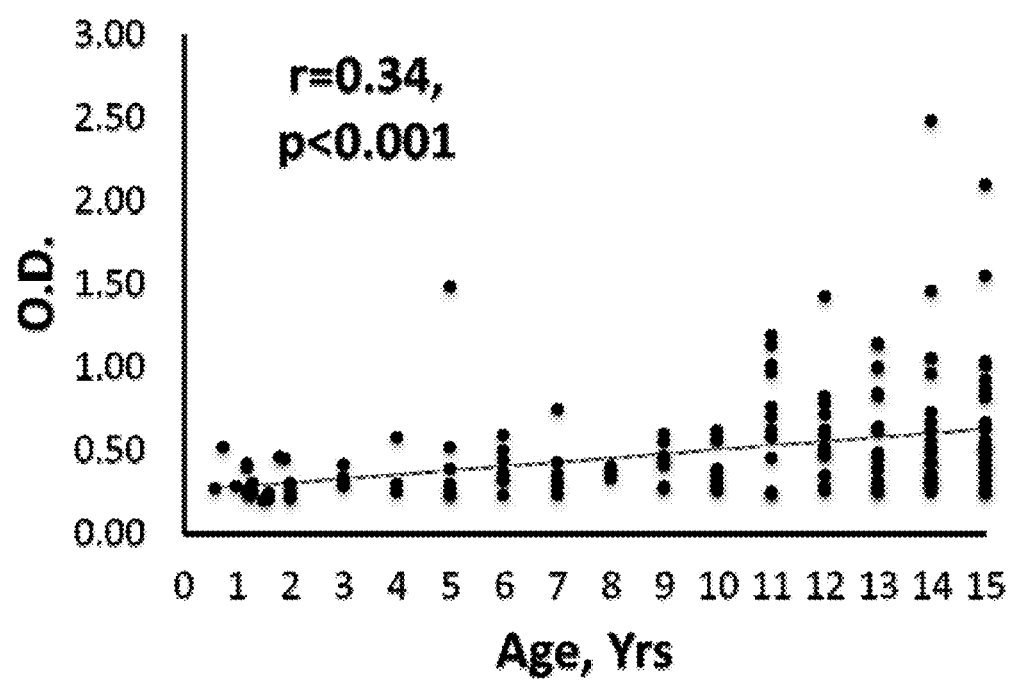
FIG. 10 presents a graph demonstrating the antibody titers against three Mrp proteins (Mrp2, Mrp4, Mrp49) in children (N=174) by age (<1 year-15 years). R=0.34, p<0.001
Figure 11:
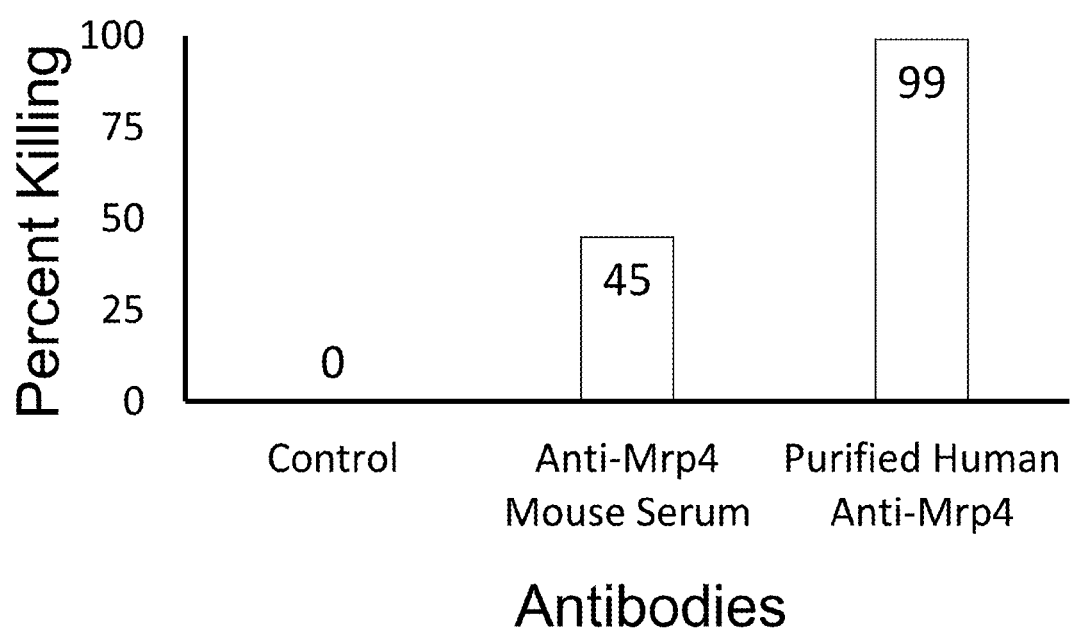
FIG. 11 shows that affinity purified human antibodies specific for Mrp4 promotes bactericidal killing of Type 28 GAS, which is a Mrp4 positive M serotype.

Significant levels of antibodies against any of the three Mrp's were observed in 91/174 serum samples (52%). Mrp4 specific antibodies were the most prevalent (53/174) ($r=0.3$, $p<0.001$), followed by Mrp2 (24/174) ($r=0.21$, $p<0.05$), and Mrp49 (14/174) ($r=0.19$, $p<0.05$). 38% of serum samples contained antibodies against one Mrp, 12% against two, and 3% against all three. FIG. 10 illustrates an association between the subjects' age and prevalence of antibodies against Mrp's ($r=0.34$, $p<0.0001$). The "r" value is the correlation coefficient determined using Pearson's product moment correlation. Significant age-related trends in antibody levels against the individual Mrp's were also observed. In addition, as shown in FIG. 11, affinity-purified human Mrp4 antibodies were bactericidal against M28 GAS, a heterologous serotype that expresses Mrp4, showing that N-terminal peptides of Mrp proteins contain opsonic epitopes.

Example 7

Protective Immunogenicity of MRP

Mrp is Highly Immunogenic in Mice and Evokes Bactericidal Antibodies Against GAS.

Four groups of 25 Swiss white mice each were immunized with four injections of 30 µg of Mrp2U, Mrp4U, or Mrp49U (each combined with the adjuvant alum) or alum alone. Immunogenicity was determined by ELISA and bactericidal tests. Protective efficacy and $LD_{50}$ were assessed after i.p. challenge infections with 10-fold increasing doses of M2 GAS.

Recombinant Mrp peptides were immunogenic in mice and evoked high levels of antibodies against the immunizing antigen as well as variable levels of antibodies that cross-reacted with heterologous Mrp's. The antibody titers in pooled sera from each group of 25 mice immunized with Mrp2U, Mrp4U, or Mrp49U is presented in Table 5 below.

TABLE 5

| | ELISA Antigen | | |
|---|---|---|---|
| Immunizing Antigen | Mrp2 | Mrp4 | Mrp49 |
| Mrp2u | 3,200 | 200 | 3,200 |
| Mrp4u | 800 | 25,600 | 200 |
| Mrp49u | 1,600 | <200 | 6,400 |

Figure 12:
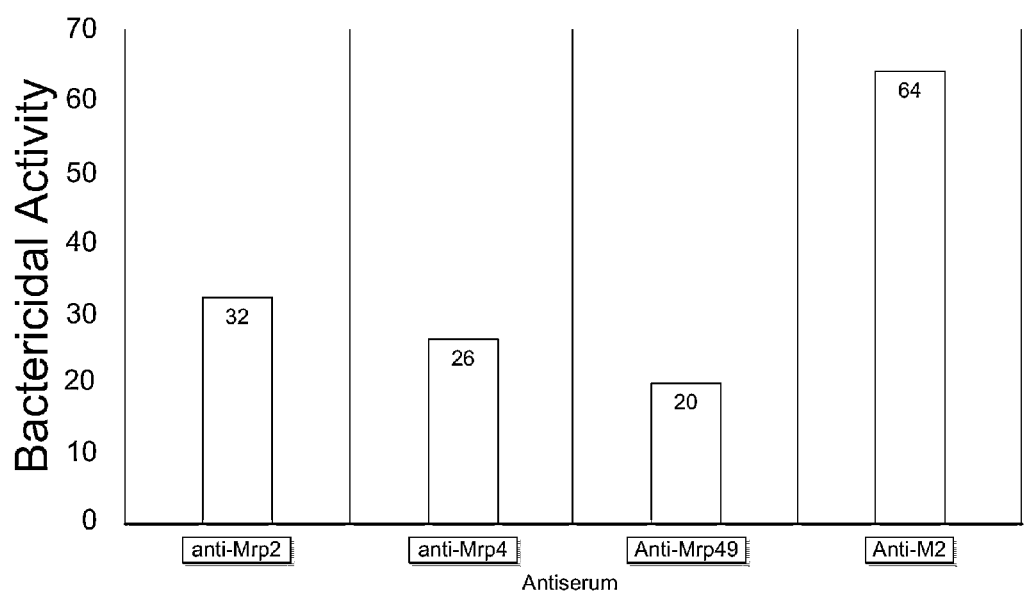
FIG. 12 illustrates that GAS bactericidal antibodies against Type M2 GAS are evoked in mice immunized with Mrp polypeptides.
Figure 13:
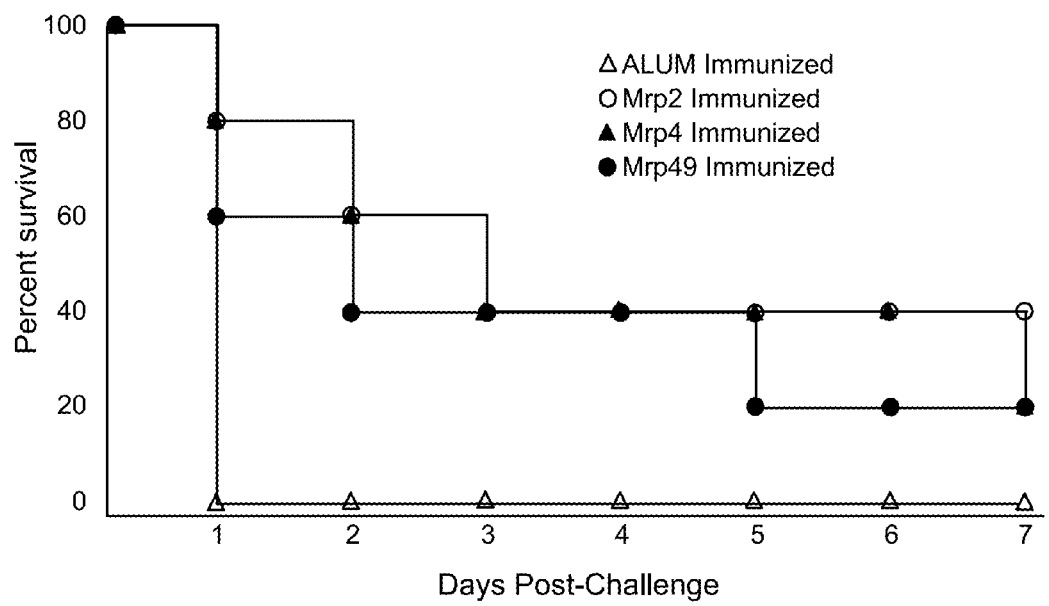
FIG. 13 presents results from animal studies in which mice were immunized with Mrp2, Mrp4, or Mrp49 (each in combination with the adjuvant Alum) or Alum alone and then challenged with $10^7$ colony forming units (CFU) of Type M2 GAS.

Sera from animals immunized with each of Mrp2U, Mrp4U, or Mrp49U were examined in a bactericidal assay in which GAS M serotype 2 was the test strain. Sera from animals immunized with an M2 antigen were included in the assay as a positive control. The data are presented in FIG. 12. Indirect bactericidal tests of pooled immune sera using M serotype 2 GAS resulted in 20-32% killing (see FIG. 12). The mice were challenged i.p. with 10-fold increasing doses of virulent type 2 GAS. The $LD_{50}$ of the M2 strain seven days post-challenge was not significantly different between immunized and control mice. However, all three Mrp vaccines showed a protective effect as determined by improved survival and delayed deaths as shown in FIG. 13. Statistical significance was achieved only on day one post-challenge in the Mrp2U immunized groups.

Example 8

Bactericidal Activity of Anti-GAS M Protein 30-Valent Immunogen and MRP Immunogens Against SDSE Clinical Isolates Rabbits were immunized with Mrp proteins as described in Example 2. Animals were immunized intramuscularly (I.M.) with either 200 µg of Mrp2U or Mrp49U that was conjugated in equal ratios (wt/wt) to KLH and 150 µg of unconjugated Mrp4U adsorbed to an equal amount of alum (wt/wt) at time 0, 4 weeks and 8 weeks. Booster injections were given at 12 weeks, and sera were obtained 2 weeks after the final injection. Additional rabbits were immunized with 600 µg of the 30-valent GAS vaccine proteins (150 µg of each of four fusion proteins (SEQ ID NO:24-27); Dale et al., *Vaccine* 2011; 29(46): 8175-78; U.S. Patent Appl. Publ. No. 2012-0321657; Int'l Patent Appl. Publ. No. WO 2012/174455) adsorbed to 600 µg alum at times 0, 4, and 8 weeks. Serum was obtained 10 weeks following the first immunization.

Without wishing to be bound by theory, SDSE may have likely acquired virulence genes via horizontal transfer of DNA from GAS. To determine whether vaccines designed to protect against GAS infections may evoke cross-reactive opsonic antibodies against clinical isolates of SDSE, anti-MRP antisera and anti-M protein antisera were tested in bactericidal assays. Indirect bactericidal assays were performed as described herein for GAS (see also, e.g., Lancefield R C. *J. Exp. Med.* 1957; 106: 525-44). Data are presented in Tables 6 and 7. Antiserum raised in rabbits against the N-terminal fragments of Mrp2, Mrp4, and Mrp49 showed significant bactericidal activity against a number of SDSE sequence types when rotated in fresh human blood (Table 6). The level of bactericidal killing ranged from 0-89% with a mean of 57% killing against all strains. At least one Mrp antisera killed at least 70% of at least one SDSE isolate.

Rabbit antisera against the 30-valent M protein-based vaccine also showed significant bactericidal activity against SDSE strains (Table 7). The range of bactericidal activity was 0-94% with a mean of 61%. Some strains of SDSE that were killed in the presence of Mrp antisera were also killed when rotated with antiserum against the 30-valent vaccine (e.g., stL1929 and stG652).

TABLE 6

BACTERICIDAL KILLING OF SDSE STRAINS PROMOTED BY RABBIT ANTISERA AGAINST M-RELATED PROTEINS OF GAS.

| | Percent Bactericidal Killing with Antiserum Against SDSE | | |
|---|---|---|---|
| SDSE Sequence Type | Mrp2U | Mrp4U | Mrp49U |
| stG652 | 47 | 82 | 77 |
| stC6979 | 75 | 0 | 11 |
| stG6792 | 89 | 71 | 81 |
| stG7882 | 82 | 70 | 28 |
| stL1929 | 39 | 92 | 5 |

TABLE 7

BACTERICIDAL KILLING OF SDSE STRAINS PROMOTED BY RABBIT ANTISERA AGAINST 30-VALENT GAS M PROTEIN VACCINE.

| SDSE Sequence Type | Percent Bactericidal Killing with 30-valent Vaccine Antiserum: |
|---|---|
| stG1750 | 62 |
| stG652 | 86 |
| stG643 | 75 |
| stG6 | 73 |
| stL1929 | 94 |
| stG7882 | 39 |
| stC6979 | 0 |

Example 9

Sequence Homology of SDSE M Proteins, GAS MRP and GAS M Proteins

Sequence Homology Among SDSE M Proteins and GAS Mrp and M Proteins.

Cross-opsonic activity between GAS vaccine antigens and SDSE isolates may occur, at least in part, because the SDSE M proteins share homology with GAS M proteins and/or Mrp. Shared sequence comparison was performed to determine if sequences (epitopes) could be identified among the surface proteins of both species of β-hemolytic streptococci. BLAST analyses of the three Mrp sequences against the SDSE emm sequences in the CDC database revealed significant regions of homology with sequence identity ranging from <20% to 55% (Table 8). Examples of homologies within the N-terminal regions of Mrp peptides and SDSE M peptides are shown in FIG. 14. Similarly, a number of GAS M peptides comprising the 30-valent vaccine contained regions of homology with SDSE M sequences, indicating potential cross-opsonic epitopes that could account for cross-reactive bactericidal activity (Table 9). Examples of homologous sequences between GAS M peptides and SDSE M peptides are shown in FIG. 15.

TABLE 8

GROUP C AND G EMM SEQUENCE HOMOLOGIES WITH MRP VACCINE PEPTIDES

| Sequence Type | % identity | | | % similarity | | |
|---|---|---|---|---|---|---|
| | Mrp2u | Mrp4u | Mrp49u | Mrp2u | Mrp4u | Mrp49u |
| stC1400 | 36 | 32 | 28 | 64 | 60 | 60 |
| stC6979 | <20 | 41 | 40 | <50 | 70 | 68 |
| stC839 | <20 | 30 | 36 | <50 | 57 | 60 |
| stG1389 | 33 | 23 | 35 | 74 | 61 | 76 |
| stG485 | 23 | 25 | 31 | 59 | 63 | 56 |
| stG6 | 26 | 26 | 31 | 54 | 65 | 59 |
| stG62647 | <20 | 41 | 34 | <50 | 70 | 73 |
| stG643 | 36 | 29 | 53 | 64 | 74 | 82 |
| stG652 | 36 | 38 | 33 | 58 | 74 | 67 |
| stG6792 | 28 | 28 | 45 | 64 | 74 | 83 |
| stG7882 | 24 | 36 | <20 | 73 | 64 | <50 |
| stL1929 | 55 | 40 | 26 | 86 | 75 | 58 |
| stL1376 | 57 | 30 | 37 | 83 | 75 | 77 |

TABLE 9

GROUP C AND G EMM SEQUENCE HOMOLOGIES WITH 30-VALENT VACCINE PEPTIDES

| Sequence Type | 30-valent peptide | %identity/%similarity |
|---|---|---|
| stG1389 | emm1 | 36/72 |
| stG652 | emm11 | 39/62 |
| stG6792 | emm22 | 32/77 |
| stG6792 | emm92 | 30/62 |
| stG7882 | emm12 | 47/69 |
| stL1929 | emm78 | 44/72 |
| stG866 | emm1 | 76/90 |
| stC7505 | emm1 | 67/89 |
| stC5345 | emm114 | 38/72 |
| stG354 | emm114 | 36/61 |
| stG866 | emm118 | 37/71 |
| stL2764 | emm5 | 44/72 |
| stG507 | emm24 | 52/84 |
| stG245 | emm28 | 52/84 |
| stG211 | emm3.1 | 67/92 |
| stG4831 | emm58 | 38/71 |
| stC9431 | emm6.4 | 58/83 |
| stG840 | emm83.1 | 52/74 |

The disclosure herein provides the following exemplary embodiments.

Embodiment 1. An isolated polypeptide selected from:

(a) an isolated polypeptide consisting of an amino acid sequence at least 70% identical to the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55;

(b) an isolated polypeptide consisting of an amino acid sequence at least 80% identical to the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55;

(c) an isolated polypeptide consisting of an amino acid sequence at least 90% identical to the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55;

(d) an isolated polypeptide consisting of an amino acid sequence at least 95% identical to the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55;

(e) an isolated polypeptide consisting of the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55;

(f) an isolated polypeptide comprising an immunogenic fragment that comprises at least 15 contiguous amino acids of SEQ ID NO:12, SEQ ID NO:13, SEQ ID NO:16, SEQ ID NO:17, SEQ ID NO:20, SEQ ID NO:39, SEQ ID NO:47; or SEQ ID NO:55; and (g) an isolated polypeptide that is a variant of a polypeptide consisting of the amino acid sequence of SEQ ID NO:12, SEQ ID NO:13, SEQ ID NO:16, SEQ ID NO:17, EQ ID NO:20, SEQ ID NO:39, SEQ ID NO:47; or SEQ ID NO:55, wherein the variant has no more than 10 amino acid additions, deletions, or substitutions in the amino acid sequence of SEQ ID NO:12, SEQ ID NO:13, SEQ ID NO:16, SEQ ID NO:17, SEQ ID NO:20, SEQ ID NO:39, SEQ ID NO:47; or SEQ ID NO:55, wherein the isolated polypeptide evokes an immune response specific for (i) group A streptococcus (GAS), (ii) *Streptococcus dysgalactiae* subspecies equisimilus (SDSE), or (iii) GAS and SDSE.

Embodiment 2. The isolated polypeptide of embodiment 1 wherein the isolated polypeptide evokes an immune response specific for group A streptococcus and SDSE.

Embodiment 3. A fusion polypeptide comprising the polypeptide of embodiment 1, wherein the fusion polypeptide evokes an immune response specific for (i) group A streptococcus (GAS), (ii) *Streptococcus dysgalactiae* subspecies equisimilus (SDSE), or (iii) GAS and SDSE.

Embodiment 4. The fusion polypeptide of embodiment 3 selected from:

(a) at least two of (i) the polypeptide consisting of an amino acid sequence at least 70% identical to SEQ ID NO:13 or SEQ ID NO:47, (ii) the polypeptide consisting of an amino acid sequence at least 70% identical to SEQ ID NO:20 or SEQ ID NO:39, and (iii) the polypeptide consisting of an amino acid sequence at least 70% identical to SEQ ID SEQ ID NO:17 or SEQ ID NO:55 are fused in frame to form the fusion polypeptide;

(b) at least two of (i) the polypeptide consisting of an amino acid sequence at least 80% identical to SEQ ID NO:13 or SEQ ID NO:47, (ii) the polypeptide consisting of an amino acid sequence at least 80% identical to SEQ ID NO:20 or SEQ ID NO:39, and (iii) the polypeptide consisting of an amino acid sequence at least 80% identical to SEQ ID NO:17 or SEQ ID NO:55 are fused in frame to form the fusion polypeptide;

(c) at least two of (i) the polypeptide consisting of an amino acid sequence at least 90% identical to SEQ ID NO:13 or SEQ ID NO:47, (ii) the polypeptide consisting of an amino acid sequence at least 90% identical to SEQ ID NO:20 or SEQ ID NO:39, and (iii) the polypeptide consisting of an amino acid sequence at least 90% identical to SEQ ID NO:17 or SEQ ID NO:55 are fused in frame to form the fusion polypeptide;

(d) at least two of (i) the polypeptide consisting of an amino acid sequence at least 95% identical to SEQ ID NO:13 or SEQ ID NO:47, (ii) the polypeptide consisting of an amino acid sequence at least 95% identical to SEQ ID NO:20 or SEQ ID NO:39, and (iii) the polypeptide consisting of an amino acid sequence at least 95% identical to SEQ ID NO:17 or SEQ ID NO:55 are fused in frame to form the fusion polypeptide;

(e) at least two of (i) the polypeptide consisting of the amino acid sequence identical to SEQ ID NO:13 or SEQ ID NO:47, (ii) the polypeptide consisting of the amino acid sequence identical to SEQ ID NO:20 or SEQ ID NO:39, and (iii) the polypeptide consisting of the amino acid sequence identical to SEQ ID NO:17 or SEQ ID NO:55 are fused in frame to form the fusion polypeptide;

(f) at least two of (i) the polypeptide comprising an immunogenic fragment that comprises at least 15 contiguous amino acids of SEQ ID NO:13 or SEQ ID NO:47, (ii) the polypeptide comprising an immunogenic fragment that comprises at least 15 contiguous amino acids of SEQ ID NO:20 or SEQ ID NO:39, and (iii) the polypeptide comprising an immunogenic fragment that comprises at least 15 contiguous amino acids of SEQ ID NO:17 or SEQ ID NO:55 are fused in frame to form the fusion polypeptide; and (g) at least two of (i) the polypeptide that is a variant of a polypeptide consisting of the amino acid sequence of SEQ ID NO:13 or SEQ ID NO:47, wherein the variant has no more than 10 amino acid additions, deletions, or substitutions in the amino acid sequence of SEQ ID NO:13 or SEQ ID NO:47; (ii) the polypeptide that is a variant of a polypeptide consisting of the amino acid sequence of SEQ ID NO:20 or SEQ ID NO:39, wherein the variant has no more than 10 amino acid additions, deletions, or substitutions in the amino acid sequence of SEQ ID NO:20 or SEQ ID NO:39; (iii) the polypeptide that is a variant of a polypeptide consisting of the amino acid sequence of SEQ ID NO:17 or SEQ ID NO:55, wherein the variant has no more than 10 amino acid additions, deletions, or substitutions in the amino acid sequence of SEQ ID NO:17 or SEQ ID NO:55, wherein the fusion polypeptide evokes an immune response specific for (i) group A streptococcus (GAS), (ii) *Streptococcus dysgalactiae* subspecies equisimilus (SDSE), or (iii) GAS and SDSE.

Embodiment 5. The fusion polypeptide of embodiment 3 selected from:

(a) the polypeptide consisting of an amino acid sequence at least 70% identical to SEQ ID NO:13 or SEQ ID NO:47, the polypeptide consisting of an amino acid sequence at least 70% identical to SEQ ID NO:20 or SEQ ID NO:39, and the polypeptide consisting of an amino acid sequence at least 70% identical to SEQ ID NO:17 or SEQ ID NO:55 fused in frame to form the fusion polypeptide;

(b) the polypeptide consisting of an amino acid sequence at least 80% identical to SEQ ID NO:13 or SEQ ID NO:47, the polypeptide consisting of an amino acid sequence at least 80% identical to SEQ ID NO:20 or SEQ ID NO:39, and the polypeptide consisting of an amino acid sequence at least 80% identical to SEQ ID NO:17 or SEQ ID NO:55 fused in frame to form the fusion polypeptide;

(c) the polypeptide consisting of an amino acid sequence at least 90% identical to SEQ ID NO:13 or SEQ ID NO:47, the polypeptide consisting of an amino acid sequence at least 90% identical to SEQ ID NO:20 or SEQ ID NO:39, and the polypeptide consisting of an amino acid sequence at least 90% identical to SEQ ID NO:17 or SEQ ID NO:55 fused in frame to form the fusion polypeptide;

(d) the polypeptide consisting of an amino acid sequence at least 95% identical to SEQ ID NO:13 or SEQ ID NO:47, the polypeptide consisting of an amino acid sequence at least 95% identical to SEQ ID NO:20 or SEQ ID NO:39, and the polypeptide consisting of an amino acid sequence at least 95% identical to SEQ ID NO:17 or SEQ ID NO:55 fused in frame to form the fusion polypeptide;

(e) the polypeptide consisting of the amino acid sequence identical to SEQ ID NO:13 or SEQ ID NO:47, the polypeptide consisting of the amino acid sequence identical to SEQ ID NO:20 or SEQ ID NO:39, and the polypeptide consisting of the amino acid sequence identical to SEQ ID NO:17 or SEQ ID NO:55 fused in frame to form the fusion polypeptide;

(f) the polypeptide comprising an immunogenic fragment that comprises at least 15 contiguous amino acids of SEQ ID NO:13 or SEQ ID NO:47, the polypeptide comprising an immunogenic fragment that comprises at least 15 contiguous amino acids of SEQ ID NO:20 or SEQ ID NO:39, and the polypeptide comprising an immunogenic fragment that comprises at least 15 contiguous amino acids of SEQ ID NO:17 or SEQ ID NO:55 fused in frame to form the fusion polypeptide; and (g) the polypeptide that is a variant of a polypeptide consisting of the amino acid sequence of SEQ ID NO:13 or SEQ ID NO:47, wherein the variant has no more than 10 amino acid additions, deletions, or substitutions in the amino acid sequence of SEQ ID NO:13 or SEQ ID NO:47; the polypeptide that is a variant of a polypeptide consisting of the amino acid sequence of SEQ ID NO:20 or SEQ ID NO:39, wherein the variant has no more than 10 amino acid additions, deletions, or substitutions in the amino acid sequence of SEQ ID NO:20 or SEQ ID NO:39; the polypeptide that is a variant of a polypeptide consisting of the amino acid sequence of SEQ ID NO:17 or SEQ ID NO:55, wherein the variant has no more than 10 amino acid additions, deletions, or substitutions in the amino acid sequence of SEQ ID NO:17 or SEQ ID NO:55, wherein the fusion polypeptide evokes an immune response specific for (i) group A streptococcus (GAS), (ii) *Streptococcus dysgalactiae* subspecies equisimilus (SDSE), or (iii) GAS and SDSE.

Embodiment 6. The fusion polypeptide of any one of embodiments 3-5, further comprising at least one immunogenic peptide that comprises at least 25 contiguous amino acids from the amino terminal portion of a group A streptococcus M protein or a group A streptococcus Spa protein.

Embodiment 7. The fusion polypeptide of embodiment 6, wherein the at least one M protein is selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18.

Embodiment 8. The fusion polypeptide of any one of embodiments 3-7 wherein the isolated polypeptide evokes an immune response specific for group A streptococcus and SDSE.

Embodiment 9. An immunogenic composition comprising a pharmaceutically acceptable excipient and (a) the isolated polypeptide of embodiment 1 or embodiment 2;

(b) the fusion polypeptide of any one of embodiments 3-8;

(c) an isolated polypeptide comprising an amino acid sequence at least 70% identical to the amino acid sequence of SEQ ID NO:10, SEQ ID NO:14, or SEQ ID NO:18, wherein the isolated polypeptide evokes an immune response specific for group A streptococcus (GAS), Streptococcus dysgalactiae subspecies equisimilus (SDSE), or GAS and SDSE;

(d) an isolated polypeptide comprising an amino acid sequence at least 80% identical to the amino acid sequence of SEQ ID NO:10, SEQ ID NO:14, or SEQ ID NO:18, wherein the isolated polypeptide evokes an immune response specific for group A streptococcus (GAS), Streptococcus dysgalactiae subspecies equisimilus (SDSE), or GAS and SDSE;

(e) an isolated polypeptide comprising an amino acid sequence at least 90% identical to the amino acid sequence of SEQ ID NO:10, SEQ ID NO:14, or SEQ ID NO:18, wherein the isolated polypeptide evokes an immune response specific for group A streptococcus (GAS), Streptococcus dysgalactiae subspecies equisimilus (SDSE), or GAS and SDSE;

(f) an isolated polypeptide comprising an amino acid sequence at least 95% identical to the amino acid sequence of SEQ ID NO:10, SEQ ID NO:14, or SEQ ID NO:18; wherein the isolated polypeptide evokes an immune response specific for group A streptococcus (GAS), Streptococcus dysgalactiae subspecies equisimilus (SDSE), or GAS and SDSE;

(g) an isolated polypeptide comprising the amino acid sequence of SEQ ID NO:10, SEQ ID NO:14, or SEQ ID NO:18, wherein the isolated polypeptide evokes an immune response specific for group A streptococcus (GAS), Streptococcus dysgalactiae subspecies equisimilus (SDSE), or GAS and SDSE;

(h) an isolated polypeptide that is a variant of a polypeptide consisting of the amino acid sequence of SEQ ID NO:10, SEQ ID NO:14, or SEQ ID NO:18, wherein the variant has no more than 20 amino acid additions, deletions, or substitutions in the amino acid sequence of SEQ ID NO:10, SEQ ID NO:14, or SEQ ID NO:18, and wherein the isolated polypeptide evokes an immune response specific for group A streptococcus (GAS), Streptococcus dysgalactiae subspecies equisimilus (SDSE), or GAS and SDSE;

(i) the isolated polypeptide of any one of (a)-(h) from which the N-terminal methionine has been deleted;

(j) the isolated polypeptide of any one of (a)-(i) from which the signal peptide sequence has been deleted; or (k) an isolated polypeptide comprising an immunogenic fragment that comprises at least 15 contiguous amino acids of the amino acid sequence of SEQ ID NO:10, SEQ ID NO:14, or SEQ ID NO:18, wherein the isolated polypeptide evokes an immune response specific for group A streptococcus (GAS), Streptococcus dysgalactiae subspecies equisimilus (SDSE), or GAS and SDSE.

Embodiment 10. The immunogenic composition of embodiment 9, comprising:

(a) at least two of (i) the polypeptide consisting of an amino acid sequence at least 70% identical to SEQ ID NO:13 or SEQ ID NO:47, (ii) the polypeptide consisting of an amino acid sequence at least 70% identical to SEQ ID NO:20 or SEQ ID NO:39, and (iii) the polypeptide consisting of an amino acid sequence at least 70% identical to SEQ ID NO:17 or SEQ ID NO:55;

(b) at least two of (i) the polypeptide consisting of an amino acid sequence at least 80% identical to SEQ ID NO:13 or SEQ ID NO:47, (ii) the polypeptide consisting of an amino acid sequence at least 80% identical to SEQ ID NO:20 or SEQ ID NO:39, and (iii) the polypeptide consisting of an amino acid sequence at least 80% identical to SEQ ID NO:17 or SEQ ID NO:55;

(c) at least two of (i) the polypeptide consisting of an amino acid sequence at least 90% identical to SEQ ID NO:13 or SEQ ID NO:47, (ii) the polypeptide consisting of an amino acid sequence at least 90% identical to SEQ ID NO:20 or SEQ ID NO:39, and (iii) the polypeptide consisting of an amino acid sequence at least 90% identical to SEQ ID NO:17 or SEQ ID NO:55;

(d) at least two of (i) the polypeptide consisting of an amino acid sequence at least 95% identical to SEQ ID NO:13 or SEQ ID NO:47, (ii) the polypeptide consisting of an amino acid sequence at least 95% identical to SEQ ID NO:20 or SEQ ID NO:39, and (iii) the polypeptide consisting of an amino acid sequence at least 95% identical to SEQ ID NO:17 or SEQ ID NO:55;

(e) at least two of (i) the polypeptide consisting of the amino acid sequence identical to SEQ ID NO:13 or SEQ ID NO:47, (ii) the polypeptide consisting of the amino acid sequence identical to SEQ ID NO:20 or SEQ ID NO:39, and (iii) the polypeptide consisting of the amino acid sequence identical to SEQ ID NO:17 or SEQ ID NO:55;

(f) at least two of (i) the polypeptide comprising an immunogenic fragment that comprises at least 15 contiguous amino acids of SEQ ID NO:13 or SEQ ID NO:47, (ii) the polypeptide comprising an immunogenic fragment that comprises at least 15 contiguous amino acids of SEQ ID NO:20 or SEQ ID NO:39, and (iii) the polypeptide comprising an immunogenic fragment that comprises at least 15 contiguous amino acids of SEQ ID NO:17 or SEQ ID NO:55; or (g) at least two of (i) the polypeptide that is a variant of a polypeptide consisting of the amino acid sequence of SEQ ID NO:13 or SEQ ID NO:47, wherein the variant has no more than 10 amino acid additions, deletions, or substitutions in the amino acid sequence of SEQ ID NO:13 or SEQ ID NO:47; (ii) the polypeptide that is a variant of a polypeptide consisting of the amino acid sequence of SEQ ID NO:20 or SEQ ID NO:39, wherein the variant has no more than 10 amino acid additions, deletions, or substitutions in the amino acid sequence of SEQ ID NO:20 or SEQ ID NO:39; (iii) the polypeptide that is a variant of a polypeptide consisting of the amino acid sequence of SEQ ID NO:17 or SEQ ID NO:55, wherein the variant has no more than 10 amino acid additions, deletions, or substitutions in the amino acid sequence of SEQ ID NO:17 or SEQ ID NO:55.

Embodiment 11. The immunogenic composition of embodiment 9, comprising:

(a) at least two of (i) the isolated polypeptide comprising an amino acid sequence at least 70% identical to the amino acid sequence of SEQ ID NO:10, (ii) the isolated polypeptide comprising an amino acid sequence at least 70% identical to the amino acid sequence of SEQ ID NO:14, and (iii) the isolated polypeptide comprising an amino acid sequence at least 70% identical to the amino acid sequence of SEQ ID NO:18;

(b) at least two of (i) the isolated polypeptide comprising an amino acid sequence at least 80% identical to the amino acid sequence of SEQ ID NO:10, (ii) the isolated polypeptide comprising an amino acid sequence at least 80% identical to the amino acid sequence of SEQ ID NO:14, and (iii) the isolated polypeptide comprising an amino acid sequence at least 80% identical to the amino acid sequence of SEQ ID NO:18;

(c) at least two of (i) the isolated polypeptide comprising an amino acid sequence at least 90% identical to the amino acid sequence of SEQ ID NO:10, (ii) the isolated polypeptide comprising an amino acid sequence at least 90% identical to the amino acid sequence of SEQ ID NO:14, and (iii) the isolated polypeptide comprising an amino acid sequence at least 90% identical to the amino acid sequence of SEQ ID NO:18;

(d) at least two of (i) the isolated polypeptide comprising an amino acid sequence at least 95% identical to the amino acid sequence of SEQ ID NO:10, (ii) the isolated polypeptide comprising an amino acid sequence at least 95% identical to the amino acid sequence of SEQ ID NO:14, and (iii) the isolated polypeptide comprising an amino acid sequence at least 95% identical to the amino acid sequence of SEQ ID NO:18;

(e) at least two of (i) the isolated polypeptide comprising the amino acid sequence of SEQ ID NO:10, (ii) the isolated polypeptide comprising the amino acid sequence of SEQ ID NO:14, and (iii) the isolated polypeptide comprising the amino acid sequence of SEQ ID NO:18;

(f) at least two of (i) the isolated polypeptide that is a variant of a polypeptide consisting of the amino acid sequence of SEQ ID NO:10, wherein the variant has no more than 20 amino acid additions, deletions, or substitutions in the amino acid sequence of SEQ ID NO:10 (ii) the isolated polypeptide that is a variant of a polypeptide consisting of the amino acid sequence of SEQ ID NO:14, wherein the variant has no more than 20 amino acid additions, deletions, or substitutions in the amino acid sequence of SEQ ID NO:14 and (iii) the isolated polypeptide that is a variant of a polypeptide consisting of the amino acid sequence of SEQ ID NO:18, wherein the variant has no more than 20 amino acid additions, deletions, or substitutions in the amino acid sequence of SEQ ID NO:18; or (g) at least two of (i) the isolated polypeptide comprising an immunogenic fragment that comprises at least 15 contiguous amino acids of the amino acid sequence of SEQ ID NO:10, (ii) the isolated polypeptide comprising an immunogenic fragment that comprises at least 15 contiguous amino acids of the amino acid sequence of SEQ ID NO:14, and (iii) the isolated polypeptide comprising an immunogenic fragment that comprises at least 15 contiguous amino acids of the amino acid sequence of SEQ ID NO:18, wherein the isolated polypeptide evokes an immune response specific for (i) group A streptococcus (GAS), (ii) Streptococcus dysgalactiae subspecies equisimilus (SDSE), or (iii) GAS and SDSE.

Embodiment 12. The immunogenic composition of embodiment 9 comprising:

(a) (i) the polypeptide consisting of an amino acid sequence at least 70% identical to SEQ ID NO:13 or SEQ ID NO:47, (ii) the polypeptide consisting of an amino acid sequence at least 70% identical to SEQ ID NO:20 or SEQ ID NO:39, and (iii) the polypeptide consisting of an amino acid sequence at least 70% identical to SEQ ID NO:17 or SEQ ID NO:55;

(b) (i) the polypeptide consisting of an amino acid sequence at least 80% identical to SEQ ID NO:13 or SEQ ID NO:47, (ii) the polypeptide consisting of an amino acid sequence at least 80% identical to SEQ ID NO:20 or SEQ ID NO:39, and (iii) the polypeptide consisting of an amino acid sequence at least 80% identical to SEQ ID NO:17 or SEQ ID NO:55;

(c) (i) the polypeptide consisting of an amino acid sequence at least 90% identical to SEQ ID NO:13 or SEQ ID NO:47, (ii) the polypeptide consisting of an amino acid sequence at least 90% identical to SEQ ID NO:20 or SEQ ID NO:39, and (iii) the polypeptide consisting of an amino acid sequence at least 90% identical to SEQ ID NO:17 or SEQ ID NO:55;

(d) (i) the polypeptide consisting of an amino acid sequence at least 95% identical to SEQ ID NO:13 or SEQ ID NO:47, (ii) the polypeptide consisting of an amino acid sequence at least 95% identical to SEQ ID NO:20 or SEQ ID NO:39, and (iii) the polypeptide consisting of an amino acid sequence at least 95% identical to SEQ ID NO:17 or SEQ ID NO:55;

(e) (i) the polypeptide consisting of the amino acid sequence identical to SEQ ID NO:13 or SEQ ID NO:47, (ii) the polypeptide consisting of the amino acid sequence identical to SEQ ID NO:20 or SEQ ID NO:39, and (iii) the polypeptide consisting of the amino acid sequence identical to SEQ ID NO:17 or SEQ ID NO:55;

(f) (i) the polypeptide comprising an immunogenic fragment that comprises at least 15 contiguous amino acids of SEQ ID NO:13 or SEQ ID NO:47, (ii) the polypeptide comprising an immunogenic fragment that comprises at least 15 contiguous amino acids of SEQ ID NO:20 or SEQ ID NO:39, and (iii) the polypeptide comprising an immunogenic fragment that comprises at least 15 contiguous amino acids of SEQ ID NO:17 or SEQ ID NO:55; or (g) (i) the polypeptide that is a variant of a polypeptide consisting of the amino acid sequence of SEQ ID NO:13 or SEQ ID NO:47, wherein the variant has no more than 10 amino acid additions, deletions, or substitutions in the amino acid sequence of SEQ ID NO:13 or SEQ ID NO:47; (ii) the polypeptide that is a variant of a polypeptide consisting of the amino acid sequence of SEQ ID NO:20 or SEQ ID NO:39, wherein the variant has no more than 10 amino acid additions, deletions, or substitutions in the amino acid sequence of SEQ ID NO:20 or SEQ ID NO:39; (iii) the polypeptide that is a variant of a polypeptide consisting of the amino acid sequence of SEQ ID NO:17 or SEQ ID NO:55, wherein the variant has no more than 10 amino acid additions, deletions, or substitutions in the amino acid sequence of SEQ ID NO:17 or SEQ ID NO:55.

Embodiment 13. The immunogenic composition of embodiment 9 comprising:

(a) (i) the isolated polypeptide comprising an amino acid sequence at least 70% identical to the amino acid sequence of SEQ ID NO:10, (ii) the isolated polypeptide comprising an amino acid sequence at least 70% identical to the amino acid sequence of SEQ ID NO:14, and (iii) the isolated polypeptide comprising an amino acid sequence at least 70% identical to the amino acid sequence of SEQ ID NO:18;

(b) (i) the isolated polypeptide comprising an amino acid sequence at least 80% identical to the amino acid sequence of SEQ ID NO:10, (ii) the isolated polypeptide comprising an amino acid sequence at least 80% identical to the amino acid sequence of SEQ ID NO:14, and (iii) the isolated polypeptide comprising an amino acid sequence at least 80% identical to the amino acid sequence of SEQ ID NO:18;

(c) (i) the isolated polypeptide comprising an amino acid sequence at least 90% identical to the amino acid sequence of SEQ ID NO:10, (ii) the isolated polypeptide comprising an amino acid sequence at least 90% identical to the amino acid sequence of SEQ ID NO:14, and (iii) the isolated polypeptide comprising an amino acid sequence at least 90% identical to the amino acid sequence of SEQ ID NO:18;

(d) (i) the isolated polypeptide comprising an amino acid sequence at least 95% identical to the amino acid sequence of SEQ ID NO:10, (ii) the isolated polypeptide comprising an amino acid sequence at least 95% identical to the amino acid sequence of SEQ ID NO:14, and (iii) the isolated polypeptide comprising an amino acid sequence at least 95% identical to the amino acid sequence of SEQ ID NO:18;

(e) (i) the isolated polypeptide comprising the amino acid sequence of SEQ ID NO:10, (ii) the isolated polypeptide comprising the amino acid sequence of SEQ ID NO:14, and (iii) the isolated polypeptide comprising the amino acid sequence of SEQ ID NO:18;

(f) (i) the isolated polypeptide that is a variant of a polypeptide consisting of the amino acid sequence of SEQ ID NO:10, wherein the variant has no more than 20 amino acid additions, deletions, or substitutions in the amino acid sequence of SEQ ID NO:10 (ii) the isolated polypeptide that is a variant of a polypeptide consisting of the amino acid sequence of SEQ ID NO:14, wherein the variant has no more than 20 amino acid additions, deletions, or substitutions in the amino acid sequence of SEQ ID NO:14 and (iii) the isolated polypeptide that is a variant of a polypeptide consisting of the amino acid sequence of SEQ ID NO:18, wherein the variant has no more than 20 amino acid additions, deletions, or substitutions in the amino acid sequence of SEQ ID NO:18; or (g) (i) the isolated polypeptide comprising an immunogenic fragment that comprises at least 15 contiguous amino acids of the amino acid sequence of SEQ ID NO:10, (ii) the isolated polypeptide comprising an immunogenic fragment that comprises at least 15 contiguous amino acids of the amino acid sequence of SEQ ID NO:14, and (iii) the isolated polypeptide comprising an immunogenic fragment that comprises at least 15 contiguous amino acids of the amino acid sequence of SEQ ID NO:18, wherein the isolated polypeptide evokes an immune response specific for (i) group A streptococcus (GAS), (ii) Streptococcus dysgalactiae subspecies equisimilus (SDSE), or (iii) GAS and SDSE.

Embodiment 14. The immunogenic composition of any one of embodiments 9-13 further comprising a pharmaceutically acceptable adjuvant.

Embodiment 15. The immunogenic composition of any one of embodiments 9-14 wherein the isolated polypeptide evokes an immune response specific for group A streptococcus and SDSE.

Embodiment 16. A preparation comprising (a) a first immunogenic composition that is the immunogenic composition of any one of embodiments 9-15; and (b) a second immunogenic composition comprising at least one other group A streptococcus immunogen and a pharmaceutically acceptable excipient, wherein the second immunogenic composition evokes an immune response specific for group A streptococcus (GAS), Streptococcus dysgalactiae subspecies equisimilus (SDSE), or GAS and SDSE.

Embodiment 17. The preparation of embodiment 16, wherein the at least one other group A streptococcus immunogen comprises an immunogenic peptide comprising at least 25 contiguous amino acids from the amino terminal portion of a group A streptococcus (GAS) serotype M protein or a Spa protein.

Embodiment 18. The preparation of embodiment 17, wherein the at least one M protein is selected from the M protein of GAS serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18.

Embodiment 19. The preparation of any one of embodiments 16-18, wherein the second immunogenic composition comprises at least 31 immunogenic peptides, wherein each immunogenic peptide is different and comprises at least 25 contiguous amino acids from the amino terminal portion of a different M protein or a Spa protein, wherein each different M protein is independently selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18.

Embodiment 20. The preparation of embodiment 19, wherein at least four of the 31 different immunogenic peptides are linked in tandem to form a fusion polypeptide.

Embodiment 21. The preparation of embodiment 20, wherein the second immunogenic composition comprises a first fusion polypeptide, a second fusion polypeptide, a third fusion polypeptide, and a fourth fusion polypeptide that each comprises at least six of the different immunogenic peptides linked in tandem.

Embodiment 22. The preparation of embodiment 21, wherein the first fusion polypeptide comprises eight of the different immunogenic peptides linked in tandem, wherein each of the eight immunogenic peptides comprises at least 25 contiguous amino acids from the amino terminal portion of a different M protein or the Spa protein, wherein each different M protein is independently selected from the M protein of GAS serotype 1, 2, 3, 6, 12, 18, and 28, and the Spa protein is from GAS serotype 18.

Embodiment 23. The preparation of embodiment 22, wherein the immunogenic peptide located at the carboxy terminal end of the first fusion polypeptide is a duplicate of the immunogenic peptide located at the amino terminal end of the first fusion polypeptide.

Embodiment 24. The preparation of embodiment 23, wherein the immunogenic peptide that is duplicated comprises at least 25 contiguous amino acids from the amino terminal portion of the M protein of GAS serotype 1.

Embodiment 25. The preparation of any one of embodiments 21-24, wherein the second fusion polypeptide comprises eight of the different immunogenic peptides linked in tandem, and wherein each of the eight immunogenic peptides comprises at least 25 contiguous amino acids from the amino terminal portion of a different M protein independently selected from the M protein of GAS serotype 4, 5, 11, 14, 19, 24, 29, and 75.

Embodiment 26. The preparation of embodiment 25, wherein the immunogenic peptide located at the carboxy terminal end of the second fusion polypeptide is a duplicate of the immunogenic peptide located at the amino terminal end of the second fusion polypeptide.

Embodiment 27. The preparation of embodiment 26, wherein the immunogenic peptide that is duplicated comprises at least 25 contiguous amino acids from the amino terminal portion of the M protein of GAS serotype 4.

Embodiment 28. The preparation of any one of embodiments 21-27, wherein the third fusion polypeptide comprises eight of the different immunogenic peptides linked in tandem, and wherein each of the eight immunogenic peptides comprises at least 25 contiguous amino acids from the amino terminal portion of a different M protein independently selected from the M protein of GAS serotype 22, 44, 58, 73, 77, 78, 89, and 118.

Embodiment 29. The preparation of embodiment 28, wherein the immunogenic peptide located at the carboxy terminal end of the third fusion polypeptide is a duplicate of the immunogenic peptide located at the amino terminal end of the third fusion polypeptide.

Embodiment 30. The preparation of embodiment 29, wherein the immunogenic peptide that is duplicated comprises at least 25 contiguous amino acids from the amino terminal portion of the M protein of GAS serotype 77.

Embodiment 31. The preparation of any one of embodiments 21-30, wherein the fourth fusion polypeptide comprises seven of the different immunogenic peptides linked in tandem, and wherein each of the seven immunogenic peptides comprises at least 25 contiguous amino acids from the amino terminal portion of a different M protein independently selected from the M protein of GAS serotype 49, 81, 82, 83, 87, 92, and 114.

Embodiment 32. The preparation of embodiment 31, wherein the immunogenic peptide located at the carboxy terminal end of the fourth fusion polypeptide is a duplicate of the immunogenic peptide located at the amino terminal end of the fourth fusion polypeptide.

Embodiment 33. The preparation of embodiment 32, wherein the immunogenic peptide that is duplicated comprises at least 25 contiguous amino acids from the amino terminal portion of the M protein of GAS serotype 83.

Embodiment 34. The preparation of embodiment 21 wherein (a) the first fusion polypeptide comprises an amino acid sequence at least 70% identical to the amino acid sequence set forth in SEQ ID NO:24; (b) the second fusion polypeptide comprises an amino acid sequence at least 70% identical to the amino acid sequence set forth in SEQ ID NO:25; (c) the third fusion polypeptide comprises an amino acid sequence at least 70% identical to the amino acid sequence set forth in SEQ ID NO:26; and (d) the fourth fusion polypeptide comprises an amino acid sequence at least 70% identical to the amino acid sequence set forth in SEQ ID NO:27.

Embodiment 35. The preparation of embodiment 21 wherein (a) the first fusion polypeptide comprises an amino acid sequence at least 80% identical to the amino acid sequence set forth in SEQ ID NO:24; (b) the second fusion polypeptide comprises an amino acid sequence at least 80% identical to the amino acid sequence set forth in SEQ ID NO:25; (c) the third fusion polypeptide comprises an amino acid sequence at least 80% identical to the amino acid sequence set forth in SEQ ID NO:26; and (d) the fourth fusion polypeptide comprises an amino acid sequence at least 80% identical to the amino acid sequence set forth in SEQ ID NO:27.

Embodiment 36. The preparation of embodiment 21 wherein (a) the first fusion polypeptide comprises an amino acid sequence at least 90% identical to the amino acid sequence set forth in SEQ ID NO:24; (b) the second fusion polypeptide comprises an amino acid sequence at least 90% identical to the amino acid sequence set forth in SEQ ID NO:25; (c) the third fusion polypeptide comprises an amino acid sequence at least 90% identical to the amino acid sequence set forth in SEQ ID NO:26; and (d) the fourth fusion polypeptide comprises an amino acid sequence at least 90% identical to the amino acid sequence set forth in SEQ ID NO:27.

Embodiment 37. The preparation of embodiment 21, wherein (a) the first fusion polypeptide comprises an amino acid sequence at least 95% identical to the amino acid sequence set forth in SEQ ID NO:24; (b) the second fusion polypeptide comprises an amino acid sequence at least 95% identical to the amino acid sequence set forth in SEQ ID NO:25; (c) the third fusion polypeptide comprises an amino acid sequence at least 95% identical to the amino acid sequence set forth in SEQ ID NO:26; and (d) the fourth fusion polypeptide comprises an amino acid sequence at least 95% identical to the amino acid sequence set forth in SEQ ID NO:27.

Embodiment 38. The preparation of embodiment 21, wherein (a) the first fusion polypeptide comprises the amino acid sequence set forth in SEQ ID NO:24; (b) the second fusion polypeptide comprises the amino acid sequence set forth in SEQ ID NO:25; (c) the third fusion polypeptide comprises the amino acid sequence set forth in SEQ ID NO:26; and (d) the fourth fusion polypeptide comprises the amino acid sequence set forth in SEQ ID NO:27.

Embodiment 39. The preparation of any one of embodiments 16-38, wherein the second immunogenic composition further comprises a pharmaceutically acceptable adjuvant.

Embodiment 40. The preparation of any one of embodiments 16-39, wherein the second immunogenic composition evokes an immune response specific for group A streptococcus and SDSE.

Embodiment 41. A method for inducing an immune response against group A streptococcus (GAS), *Streptococcus dysgalactiae* subspecies *equisimilus* (SDSE), or GAS and SDSE in a subject, comprising administering to the subject the immunogenic composition of any one of embodiments 9-15.

Embodiment 42. A method for reducing the likelihood of occurrence of a beta-hemolytic streptococcus infection selected from group A streptococcus infection and *Streptococcus dysgalactiae* subspecies *equisimilus* (SDSE) infection in a subject, comprising administering to the subject the immunogenic composition of any one of embodiments 9-15.

Embodiment 43. A method for preventing or treating a beta-hemolytic streptococcus infection selected from group A streptococcus infection and *Streptococcus* dysgalactiae subspecies *equisimilus* (SDSE) infection in a subject, comprising administering to the subject the immunogenic composition of any one of embodiments 9-15.

Embodiment 44. The immunogenic composition of any one of embodiments 9-15 for use in preventing or treating a beta-hemolytic streptococcus infection selected from group A streptococcus infection and *Streptococcus dysgalactiae* subspecies equisimilus (SDSE) infection.

Embodiment 45. Use of the immunogenic composition of any one of embodiments 9-15 for the manufacture of a vaccine to prevent or treat a beta-hemolytic streptococcus infection selected from group A streptococcus infection and *Streptococcus* dysgalactiae subspecies *equisimilus* (SDSE) infection.

Embodiment 46. The immunogenic composition of any one of embodiments 9-15 for preventing or treating a beta-hemolytic streptococcus infection selected from group A streptococcus (GAS) infection and *Streptococcus dysgalactiae* subspecies *equisimilus* (SDSE) infection.

Embodiment 47. A method for inducing an immune response against a beta-hemolytic streptococcus selected from (i) group A streptococcus (GAS), (ii) *Streptococcus dysgalactiae* subspecies *equisimilus* (SDSE), and (iii) GAS and SDSE in a subject, comprising administering to the subject the preparation of any one of embodiments 16-40.

Embodiment 48. A method for reducing the likelihood of occurrence of a beta-hemolytic streptococcus infection selected from group A streptococcus infection and *Streptococcus dysgalactiae* subspecies *equisimilus* (SDSE) infection in a subject, comprising administering to the subject the preparation of any one of embodiments 16-40.

Embodiment 49. A method for preventing or treating a beta-hemolytic streptococcus infection selected from group A streptococcus infection and *Streptococcus* dysgalactiae subspecies *equisimilus* (SDSE) infection in a subject, comprising administering to the subject the preparation of any one of embodiments 16-40.

Embodiment 50. The method of any one of embodiments 47-49, wherein the first immunogenic composition and the second immunogenic composition are administered concurrently.

Embodiment 51. The method of any one of embodiments 47-49, wherein the first immunogenic composition and the second immunogenic composition are administered sequentially.

Embodiment 52. The preparation of any one of embodiments 16-40 for use in preventing or treating a beta-hemolytic streptococcus infection selected from group A streptococcus infection and *Streptococcus dysgalactiae* subspecies *equisimilus* (SDSE) infection.

Embodiment 53. Use of the preparation of any one of embodiments 16-40 for the manufacture of a vaccine to prevent or treat a beta-hemolytic streptococcus infection selected from group A streptococcus infection and *Streptococcus dysgalactiae* subspecies *equisimilus* (SDSE) infection.

Embodiment 54. The preparation of any one of embodiments 16-40 for preventing or treating a beta-hemolytic streptococcus infection selected from group A streptococcus infection and *Streptococcus dysgalactiae* subspecies *equisimilus* (SDSE) infection.

Embodiment 55. A method for inducing an immune response in a subject against *Streptococcus dysgalactiae* subspecies *equisimilus* (SDSE) with an immunogenic composition comprising a pharmaceutically acceptable excipient and an immunogenic peptide comprising at least 25 contiguous amino acids from the amino terminal portion of a group A streptococcus (GAS) serotype M protein or a Spa protein.

Embodiment 56. A method for treating or preventing a *Streptococcus* dysgalactiae subspecies *equisimilus* (SDSE) infection in a subject, comprising administering an immunogenic composition comprising a pharmaceutically acceptable excipient and an immunogenic peptide comprising at least 25 contiguous amino acids from the amino terminal portion of a group A streptococcus (GAS) serotype M protein or a Spa protein.

Embodiment 57. A method for reducing the likelihood of occurrence of a *Streptococcus dysgalactiae* subspecies *equisimilus* (SDSE) infection in a subject, comprising administering to the subject an immunogenic composition comprising and an immunogenic peptide comprising at least 25 contiguous amino acids from the amino terminal portion of a group A streptococcus (GAS) serotype M protein or a Spa protein.

Embodiment 58. The method of any one of embodiments 55-57, wherein the at least one M protein is selected from the M protein of GAS serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18.

Embodiment 59. The method of any one of embodiments 55-57, wherein the immunogenic composition comprises at least 31 immunogenic peptides, wherein each immunogenic peptide is different and comprises at least 25 contiguous amino acids from the amino terminal portion of a different M protein or a Spa protein, wherein each different M protein is independently selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18.

Embodiment 60. The method of embodiment 59, wherein at least four of the 31 different immunogenic peptides are linked in tandem to form a fusion polypeptide.

Embodiment 61. The method of embodiment 60, wherein the immunogenic composition comprises a first fusion polypeptide, a second fusion polypeptide, a third fusion polypeptide, and a fourth fusion polypeptide that each comprises at least six of the different immunogenic peptides linked in tandem.

Embodiment 62. The method of embodiment 61, wherein the first fusion polypeptide comprises eight of the different immunogenic peptides linked in tandem, wherein each of the eight immunogenic peptides comprises at least 25 contiguous amino acids from the amino terminal portion of a different M protein or the Spa protein, wherein each different M protein is independently selected from the M protein of GAS serotype 1, 2, 3, 6, 12, 18, and 28, and the Spa protein is from GAS serotype 18.

Embodiment 63. The method of embodiment 62, wherein the immunogenic peptide located at the carboxy terminal end of the first fusion polypeptide is a duplicate of the immunogenic peptide located at the amino terminal end of the first fusion polypeptide.

Embodiment 64. The method of embodiment 63, wherein the immunogenic peptide that is duplicated comprises at least 25 contiguous amino acids from the amino terminal portion of the M protein of GAS serotype 1.

Embodiment 65. The method of any one of embodiments 61-64, wherein the second fusion polypeptide comprises eight of the different immunogenic peptides linked in tandem, and wherein each of the eight immunogenic peptides comprises at least 25 contiguous amino acids from the amino terminal portion of a different M protein independently selected from the M protein of GAS serotype 4, 5, 11, 14, 19, 24, 29, and 75.

Embodiment 66. The method of embodiment 65, wherein the immunogenic peptide located at the carboxy terminal end of the second fusion polypeptide is a duplicate of the immunogenic peptide located at the amino terminal end of the second fusion polypeptide.

Embodiment 67. The method of embodiment 66, wherein the immunogenic peptide that is duplicated comprises at least 25 contiguous amino acids from the amino terminal portion of the M protein of GAS serotype 4.

Embodiment 68. The method of any one of embodiments 61-67, wherein the third fusion polypeptide comprises eight of the different immunogenic peptides linked in tandem, and wherein each of the eight immunogenic peptides comprises at least 25 contiguous amino acids from the amino terminal portion of a different M protein independently selected from the M protein of GAS serotype 22, 44, 58, 73, 77, 78, 89, and 118.

Embodiment 69. The method of embodiment 68, wherein the immunogenic peptide located at the carboxy terminal end of the third fusion polypeptide is a duplicate of the immunogenic peptide located at the amino terminal end of the third fusion polypeptide.

Embodiment 70. The method of embodiment 69, wherein the immunogenic peptide that is duplicated comprises at least 25 contiguous amino acids from the amino terminal portion of the M protein of GAS serotype 77.

Embodiment 71. The method of any one of embodiments 61-70, wherein the fourth fusion polypeptide comprises seven of the different immunogenic peptides linked in tandem, and wherein each of the seven immunogenic peptides comprises at least 25 contiguous amino acids from the amino terminal portion of a different M protein independently selected from the M protein of GAS serotype 49, 81, 82, 83, 87, 92, and 114.

Embodiment 72. The method of embodiment 71, wherein the immunogenic peptide located at the carboxy terminal end of the fourth fusion polypeptide is a duplicate of the immunogenic peptide located at the amino terminal end of the fourth fusion polypeptide.

Embodiment 73. The method of embodiment 72, wherein the immunogenic peptide that is duplicated comprises at least 25 contiguous amino acids from the amino terminal portion of the M protein of GAS serotype 83.

Embodiment 74. The method of embodiment 61 wherein (a) the first fusion polypeptide comprises an amino acid sequence at least 70% identical to the amino acid sequence set forth in SEQ ID NO:24; (b) the second fusion polypeptide comprises an amino acid sequence at least 70% identical to the amino acid sequence set forth in SEQ ID NO:25; (c) the third fusion polypeptide comprises an amino acid sequence at least 70% identical to the amino acid sequence set forth in SEQ ID NO:26; and (d) the fourth fusion polypeptide comprises an amino acid sequence at least 70% identical to the amino acid sequence set forth in SEQ ID NO:27.

Embodiment 75. The method of embodiment 61 wherein (a) the first fusion polypeptide comprises an amino acid sequence at least 80% identical to the amino acid sequence set forth in SEQ ID NO:24; (b) the second fusion polypeptide comprises an amino acid sequence at least 80% identical to the amino acid sequence set forth in SEQ ID NO:25; (c) the third fusion polypeptide comprises an amino acid sequence at least 80% identical to the amino acid sequence set forth in SEQ ID NO:26; and (d) the fourth fusion polypeptide comprises an amino acid sequence at least 80% identical to the amino acid sequence set forth in SEQ ID NO:27.

Embodiment 76. The method of embodiment 61 wherein (a) the first fusion polypeptide comprises an amino acid sequence at least 90% identical to the amino acid sequence set forth in SEQ ID NO:24; (b) the second fusion polypeptide comprises an amino acid sequence at least 90% identical to the amino acid sequence set forth in SEQ ID NO:25; (c) the third fusion polypeptide comprises an amino acid sequence at least 90% identical to the amino acid sequence set forth in SEQ ID NO:26; and (d) the fourth fusion polypeptide comprises an amino acid sequence at least 90% identical to the amino acid sequence set forth in SEQ ID NO:27.

Embodiment 77. The method of embodiment 61, wherein (a) the first fusion polypeptide comprises an amino acid sequence at least 95% identical to the amino acid sequence set forth in SEQ ID NO:24; (b) the second fusion polypeptide comprises an amino acid sequence at least 95% identical to the amino acid sequence set forth in SEQ ID NO:25; (c) the third fusion polypeptide comprises an amino acid sequence at least 95% identical to the amino acid sequence set forth in SEQ ID NO:26; and (d) the fourth fusion polypeptide comprises an amino acid sequence at least 95% identical to the amino acid sequence set forth in SEQ ID NO:27.

Embodiment 78. The method of embodiment 61, wherein (a) the first fusion polypeptide comprises the amino acid sequence set forth in SEQ ID NO:24; (b) the second fusion polypeptide comprises the amino acid sequence set forth in SEQ ID NO:25; (c) the third fusion polypeptide comprises the amino acid sequence set forth in SEQ ID NO:26; and (d) the fourth fusion polypeptide comprises the amino acid sequence set forth in SEQ ID NO:27.

Embodiment 79. The method of any one of embodiments 55-78, wherein the immunogenic composition further comprises a pharmaceutically acceptable adjuvant.

Embodiment 80. The method of any one of embodiments 46-51 wherein the preparation evokes an immune response specific for group A streptococcus and SDSE.

Embodiment 81. The preparation of embodiment 52 or embodiment 54 or the use of embodiment 53 wherein the preparation evokes an immune response specific for group A streptococcus and SDSE.

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A fusion polypeptide, comprising at least two of the following polypeptides:

(a) a polypeptide comprising an immunogenic fragment consisting of at least about 20 to about 50 contiguous amino acids that is at least 75% identical to an amino acid sequence of the same length from SEQ ID NO:13 or SEQ ID NO:47, (b) a polypeptide comprising an immunogenic fragment consisting of at least about 20 to about 50 contiguous amino acids that is at least 75% identical to an amino acid sequence of the same length from SEQ ID NO:20 or SEQ ID NO:39, (c) a polypeptide comprising an immunogenic fragment consisting of at least about 20 to about 50 contiguous amino acids that is at least 75% identical to an amino acid sequence of the same length from SEQ ID NO:17 or SEQ ID NO:55, (d) a polypeptide consisting of at least about 20 to about 50 contiguous amino acids from SEQ ID NO:13 or SEQ ID NO:47, (e) a polypeptide consisting of at least about 20 to about 50 contiguous amino acids from SEQ ID NO:20 or SEQ ID NO:39, (f) a polypeptide consisting of least about 20 to about 50 contiguous amino acids from SEQ ID NO:17 or SEQ ID NO:55, wherein the fusion polypeptide is capable of eliciting opsonic antibodies against group A Streptococcus (GAS).

2. The fusion polypeptide of claim 1, comprising at least three of the polypeptides from those listed in subparts (a)-(f) of claim 1 in any one of the following combinations:

(i) a polypeptide of (a), a polypeptide of (b), and a polypeptide of (c);

(ii) a polypeptide of (a), a polypeptide of (b), and a polypeptide of (f);

(iii) a polypeptide of (a), a polypeptide of (c), and a polypeptide of (e);
(iv) a polypeptide of (a), a polypeptide of (e), and a polypeptide of (f);
(v) a polypeptide of (b), a polypeptide of (c), and a polypeptide of (d);
(vi) a polypeptide of (b), a polypeptide of (d), and a polypeptide of (f);
(vii) a polypeptide of (c), a polypeptide of (d), and a polypeptide of (e); and
(viii) a polypeptide of (d), a polypeptide of (e), and a polypeptide of (f).

3. The fusion polypeptide of claim 1, further comprising at least one immunogenic peptide that comprises at least 25 contiguous amino acids from the amino terminal portion of a group A streptococcus M protein or a group A streptococcus Spa protein.

4. The fusion polypeptide of claim 3, wherein the at least one M protein is selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18.

5. An immunogenic composition, comprising a pharmaceutically acceptable adjuvant and
   (a) an isolated polypeptide comprising an amino acid sequence of at least about 20 to about 50 contiguous amino acids that is at least 75% identical to an amino acid sequence of the same length from any one of SEQ ID NO:13, SEQ ID NO:17, SEQ ID NO:20, SEQ ID NO:39, SEQ ID NO:47, or SEQ ID NO:55;
   (b) an isolated polypeptide consisting of at least about 20 to about 50 contiguous amino acids from any one of SEQ ID NO:13, SEQ ID NO:17, SEQ ID NO:20, SEQ ID NO:39, SEQ ID NO:47, or SEQ ID NO:55; or
   (c) any combination thereof,
   wherein any one of the isolated polypeptides is capable of eliciting opsonic antibodies against GAS.

6. The immunogenic composition of claim 5, comprising at least two isolated polypeptides, wherein each of the at least two isolated polypeptides is from a different Mrp family.

7. The immunogenic composition of claim 5, comprising at least three isolated polypeptides, wherein each of the at least two isolated polypeptides is from a different Mrp family.

8. The immunogenic composition of claim 5, further comprising a pharmaceutically acceptable excipient.

9. The immunogenic composition of claim 5, further comprising at least one other group A streptococcus immunogen, wherein the at least one other group A streptococcus immunogen is capable of eliciting opsonic antibodies against GAS.

10. The immunogenic composition of claim 9, wherein the at least one other group A streptococcus immunogen comprises an immunogenic peptide comprising at least 25 contiguous amino acids from the amino terminal portion of a group A streptococcus (GAS) serotype M protein or a Spa protein.

11. The immunogenic composition of claim 10, wherein the at least one M protein is selected from the M protein of GAS serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18.

12. The immunogenic composition of claim 9, comprising at least 31 immunogenic peptides, wherein each immunogenic peptide is different and comprises at least 25 contiguous amino acids from the amino terminal portion of a different M protein or a Spa protein, wherein each different M protein is independently selected from the M protein of group A streptococcus (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18.

13. The immunogenic composition of claim 12, wherein the at least 31 immunogenic peptides comprise a first fusion polypeptide, a second fusion polypeptide, a third fusion polypeptide, and a fourth fusion polypeptide that each comprises at least six of the different immunogenic peptides linked in tandem.

14. The immunogenic composition of claim 13, wherein:
   (a) the first fusion polypeptide comprises the amino acid sequence set forth in SEQ ID NO:24;
   (b) the second fusion polypeptide comprises the amino acid sequence set forth in SEQ ID NO:25;
   (c) the third fusion polypeptide comprises the amino acid sequence set forth in SEQ ID NO:26; and
   (d) the fourth fusion polypeptide comprises the amino acid sequence set forth in SEQ ID NO:27.

15. The immunogenic composition of claim 9, further comprising a pharmaceutically acceptable excipient.

16. A method for inducing an immune response against group A streptococcus (GAS), comprising administering to the subject the immunogenic composition of claim 5.

17. A method for reducing the likelihood of occurrence of a group A streptococcal disease, comprising administering to the subject the immunogenic composition of claim 5.

18. A method for inducing an immune response against group A streptococcus (GAS), comprising administering to the subject the immunogenic composition of claim 9.

19. A method for reducing the likelihood of occurrence of a group A streptococcal disease, comprising administering to the subject the immunogenic composition of claim 9.

20. The immunogenic composition of claim 5, wherein each polypeptide is capable of eliciting cross-opsonic antibodies against GAS and *Streptococcus dysgalactiae* subspecies *equisimilus* (SDSE).

21. An immunogenic composition comprising a pharmaceutically acceptable excipient and (a) the fusion polypeptide of claim 1; or (b) the fusion polypeptide of claim 1 further comprising at least one immunogenic peptide that comprises at least 25 contiguous amino acids from the amino terminal portion of a group A streptococcus M protein or a group A streptococcus Spa protein, wherein the fusion polypeptide is capable of eliciting opsonic antibodies against GAS.

22. The immunogenic composition of claim 21, wherein the fusion polypeptide is capable of eliciting cross-opsonic antibodies against GAS and *Streptococcus dysgalactiae* subspecies *equisimilus* (SDSE).

23. The immunogenic composition of claim 9, wherein the immunogenic composition is capable of eliciting cross-opsonic antibodies against GAS and SDSE.

24. A method for inducing an immune response against *Streptococcus dysgalactiae* subspecies *equisimilus* (SDSE) in a subject, comprising administering to the subject the immunogenic composition of claim 5, wherein the immunogenic composition elicits opsonic antibodies against SDSE.

25. A method for reducing the likelihood of occurrence of a *Streptococcus dysgalactiae* subspecies *equisimilus* (SDSE) disease in a subject, comprising administering to the subject the immunogenic composition of claim 5, wherein the immunogenic composition elicits opsonic antibodies against SDSE.

26. The method of claim 24, wherein the immunogenic composition further comprises at least one other group A streptococcus immunogen, and wherein the at least one other group A streptococcus immunogen elicits opsonic antibodies against GAS.

27. The method of claim 25, wherein the immunogenic composition further comprises at least one other group A streptococcus immunogen, and wherein the at least one other group A streptococcus immunogen is capable of eliciting opsonic antibodies against GAS.

28. The fusion polypeptide of claim 1, wherein:
(i) at least one of the polypeptides is selected from subpart (a) or subpart (d) and at least one of the polypeptides is selected from subpart (b) or subpart (e);
(ii) at least one of the polypeptides is selected from subpart (b) or subpart (e) and at least one of the polypeptides is selected from subpart (c) or subpart (f); or
(iii) at least one of the polypeptides is selected from subpart (a) or subpart (d) and at least one of the polypeptides is selected from subpart (c) or subpart (f).

29. The fusion polypeptide of claim 1, wherein at least one polypeptide of the fusion polypeptide further comprises a spacer polypeptide of about 5 to about 100 amino acid residues disposed between the at least one polypeptide and an adjacent polypeptide.

30. The fusion polypeptide of claim 29, wherein the spacer polypeptide comprises an amino acid sequence of KLAAALE (SEQ ID NO:65), or $(Gly_4Ser)_n$(SEQ ID NO: 99), wherein n=1–12.

31. The immunogenic composition of claim 5, wherein any one of the isolated polypeptides comprises an amino acid sequence from the N-terminal portion of the MRP protein that is carboxy-terminal to SEQ ID NO: 13, SEQ ID NO: 47, SEQ ID NO: 20, SEQ ID NO: 39, SEQ ID NO: 17, or SEQ ID NO: 55.

32. The fusion polypeptide of claim 1, wherein any one of the polypeptides of the fusion protein comprises an amino acid sequence from the N-terminal portion of the MRP protein that is carboxy-terminal to SEQ ID NO: 13, SEQ ID NO: 47, SEQ ID NO: 20, SEQ ID NO: 39, SEQ ID NO: 17, or SEQ ID NO: 55.

* * * * *

SEQUENCE LISTING

<160> NUMBER OF SEQ ID NOS: 127

<210> SEQ ID NO 1
<211> LENGTH: 6
<212> TYPE: PRT

<213> ORGANISM: Artificial Sequence
<220> FEATURE:
<223> OTHER INFORMATION: Mrp anchoring motif

<400> SEQUENCE: 1

Leu Pro Ser Thr Gly Glu
1               5

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
aaaggatccg atttgacagt tttg                                          24

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
aaaggatcct tagttttctt ctttgcg                                       27

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
cttggatccg agagtcgtcg ttatcaggca cct                                33

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
tacggatcct aaatctgaga tttgctt                                       27

<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6
gtaaccatgg agaccgtagg tcgctttagt g                                  31

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7

```
gcaagcttag cattttctga ctcaatcttt tt                               32
```

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8

```
gtaaccatgg acttaagtac tcaggaacat cctag                            35
```

<210> SEQ ID NO 9
<211> LENGTH: 36
<212> TYPE: DNA
<213> ORGANISM: Artificial Sequence
<220> FEATURE:
<223> OTHER INFORMATION: primer

<400> SEQUENCE: 9

```
gcaagcttct tgtcgctaga ttctctatat tttttt                           36
```

<210> SEQ ID NO 10
<211> LENGTH: 425
<212> TYPE: PRT
<213> ORGANISM: Streptococcus pyogenes

<400> SEQUENCE: 10

```
Met Ser Lys Arg Asn Pro Asn Lys His Tyr Ser Leu Arg Lys Leu Lys
1               5                   10                  15
Thr Gly Thr Ala Ser Val Ala Val Ala Leu Thr Val Gly Gly Thr Gly
            20                  25                  30
Leu Ala Asn Thr Thr Asp Val Lys Ala Glu Thr Val Gly Arg Phe Ser
        35                  40                  45
Asp Glu Gln Val Arg Lys Ala Arg Glu Lys Ala Ile Glu Asp Val Phe
    50                  55                  60
Asp Gly Tyr Thr Gly Ala Arg Ser Val Tyr Gln Ser Gly Asn Leu Pro
65                  70                  75                  80
Asn Arg Leu Thr Pro Thr Lys Leu Ser Lys Leu Met Gln Gln Met Tyr
                85                  90                  95
Lys Glu Thr Leu Gln Lys Lys Glu Glu Leu Asp Thr Leu Ser Lys Ala
            100                 105                 110
Leu Thr His Thr Ile Glu Lys Lys Ile Glu Ser Glu Asn Ala Tyr Lys
        115                 120                 125
Lys Glu Leu Gly Gln Leu Lys Ala Ala Ala Glu Ala Glu Ala Gln Lys
    130                 135                 140
Ala Leu Asp Ala Leu Asn Asn Lys Asn Lys Gln Ile Ser Asp Leu Thr
145                 150                 155                 160
Thr Glu Asn Ala Gln Leu Lys Glu Ala Ile Glu Gly Tyr Val Gln Thr
                165                 170                 175
Ile Gln Asn Ala Ser Arg Glu Ile Ala Ala Lys Gln Glu Leu Ala
            180                 185                 190
Ala Ala Lys Ser Gln Leu Glu Ala Lys Asn Ala Glu Ile Glu Ala Leu
        195                 200                 205
Lys Gln Gln Asp Ala Ser Lys Thr Glu Glu Leu Ala Lys Leu Gln Ser
    210                 215                 220
Glu Ala Ala Thr Leu Glu Asn Leu Leu Gly Ser Ala Lys Arg Glu Leu
225                 230                 235                 240
```

```
Thr Glu Leu Gln Ala Lys Leu Asp Thr Ala Thr Glu Lys Ala Lys
            245                 250                 255

Leu Glu Ser Gln Val Thr Thr Leu Glu Asn Leu Leu Gly Ser Ala Lys
        260                 265                 270

Arg Glu Leu Thr Asp Leu Gln Ala Lys Leu Asp Ala Ala Asn Ala Glu
            275                 280                 285

Lys Glu Lys Leu Gln Ser Gln Ala Ala Leu Glu Lys Gln Leu Glu
        290                 295                 300

Ala Thr Lys Lys Glu Leu Ala Asp Leu Gln Ala Lys Leu Ala Ala Thr
305                 310                 315                 320

Asn Gln Gly Lys Glu Lys Leu Glu Ala Glu Lys Ala Leu Lys Glu
            325                 330                 335

Gln Leu Ala Lys Gln Ala Glu Glu Leu Ala Lys Leu Lys Ala Asp Lys
        340                 345                 350

Ala Ser Gly Gly Gln Lys Pro Asp Thr Lys Pro Gly Asn Lys Glu Val
            355                 360                 365

Pro Thr Arg Pro Ser Gln Thr Arg Thr Asn Thr Asn Lys Ala Pro Met
            370                 375                 380

Ala Gln Thr Lys Arg Gln Leu Pro Ser Thr Gly Glu Glu Thr Thr Asn
385                 390                 395                 400

Pro Phe Phe Thr Ala Ala Ala Leu Thr Val Ile Ala Ser Ala Gly Val
            405                 410                 415

Leu Ala Leu Lys Arg Lys Glu Glu Asn
            420                 425

<210> SEQ ID NO 11
<211> LENGTH: 99
<212> TYPE: PRT
<213> ORGANISM: Artificial Sequence
<220> FEATURE:
<223> OTHER INFORMATION: Mrp2U polypeptide

<400> SEQUENCE: 11

Met Glu Thr Val Gly Arg Phe Ser Asp Glu Gln Val Arg Lys Ala Arg
1               5                   10                  15

Glu Lys Ala Ile Glu Asp Val Phe Asp Gly Tyr Thr Gly Ala Arg Ser
            20                  25                  30

Val Tyr Gln Ser Gly Asn Leu Pro Asn Arg Leu Thr Pro Thr Lys Leu
        35                  40                  45

Ser Lys Leu Met Gln Gln Met Tyr Lys Glu Thr Leu Gln Lys Lys Glu
    50                  55                  60

Glu Leu Asp Thr Leu Ser Lys Ala Leu Thr His Thr Ile Glu Lys Lys
65                  70                  75                  80

Ile Glu Ser Glu Asn Ala Lys Leu Ala Ala Ala Leu Glu His His His
            85                  90                  95

His His His

<210> SEQ ID NO 12
<211> LENGTH: 92
<212> TYPE: PRT
<213> ORGANISM: Artificial Sequence
<220> FEATURE:
<223> OTHER INFORMATION: Mrp2U polypeptide without Met and without His 6

<400> SEQUENCE: 12

Glu Thr Val Gly Arg Phe Ser Asp Glu Gln Val Arg Lys Ala Arg Glu
1               5                   10                  15
```

Lys Ala Ile Glu Asp Val Phe Asp Gly Tyr Thr Gly Ala Arg Ser Val
                20                  25                  30

Tyr Gln Ser Gly Asn Leu Pro Asn Arg Leu Thr Pro Thr Lys Leu Ser
            35                  40                  45

Lys Leu Met Gln Gln Met Tyr Lys Glu Thr Leu Gln Lys Lys Glu Glu
        50                  55                  60

Leu Asp Thr Leu Ser Lys Ala Leu Thr His Thr Ile Glu Lys Lys Ile
65                  70                  75                  80

Glu Ser Glu Asn Ala Lys Leu Ala Ala Ala Leu Glu
                85                  90

<210> SEQ ID NO 13
<211> LENGTH: 85
<212> TYPE: PRT
<213> ORGANISM: Artificial Sequence
<220> FEATURE:
<223> OTHER INFORMATION: Mrp2U polypeptide without COH divergent seqs

<400> SEQUENCE: 13

Glu Thr Val Gly Arg Phe Ser Asp Glu Gln Val Arg Lys Ala Arg Glu
1               5                   10                  15

Lys Ala Ile Glu Asp Val Phe Asp Gly Tyr Thr Gly Ala Arg Ser Val
                20                  25                  30

Tyr Gln Ser Gly Asn Leu Pro Asn Arg Leu Thr Pro Thr Lys Leu Ser
            35                  40                  45

Lys Leu Met Gln Gln Met Tyr Lys Glu Thr Leu Gln Lys Lys Glu Glu
        50                  55                  60

Leu Asp Thr Leu Ser Lys Ala Leu Thr His Thr Ile Glu Lys Lys Ile
65                  70                  75                  80

Glu Ser Glu Asn Ala
                85

<210> SEQ ID NO 14
<211> LENGTH: 415
<212> TYPE: PRT
<213> ORGANISM: Streptococcus pyogenes

<400> SEQUENCE: 14

Met Ser Thr Arg Asn Pro Asn Lys His Tyr Ser Leu Arg Lys Leu Lys
1               5                   10                  15

Thr Gly Thr Ala Ser Val Ala Val Ala Leu Thr Val Leu Gly Thr Gly
                20                  25                  30

Leu Ala Asn Thr Thr Asp Val Lys Ala Asp Leu Ser Thr Gln Glu His
            35                  40                  45

Pro Arg Val Thr Lys Ala Arg Glu Glu Ala Leu Glu Glu Val Leu Arg
        50                  55                  60

Ser Trp Asp Tyr Gly Ser Val Lys Ala Ala Leu Ala Gly Ser Tyr Arg
65                  70                  75                  80

Lys Asn Leu Gln Leu Glu Asn Thr Ile Lys Gln Lys Asp Lys Glu Leu
                85                  90                  95

Ser Phe Leu Ser Lys Val Leu Asp Glu Ala Ala Lys Lys Tyr Arg Glu
                100                 105                 110

Ser Ser Asp Lys Tyr Lys Gln Glu Ile Gly Gln Leu Lys Ala Ala Ala
            115                 120                 125

Glu Ala Glu Ala Gln Lys Ala Leu Asp Ala Leu Asn Asn Lys Asn Lys
        130                 135                 140

Gln Ile Ser Asp Leu Thr Asn Glu Asn Ala Gln Leu Lys Glu Ala Ile

```
             145                 150                 155                 160
        Glu Gly Tyr Val Gln Thr Ile Gln Asn Ala Ser Arg Glu Ile Ala Ala
                         165                 170                 175
        Lys Gln Gln Glu Leu Ala Ala Val Lys Ser Gln Leu Glu Ala Lys Asn
                         180                 185                 190
        Ala Glu Ile Glu Asp Leu Lys Gln Gln Asp Ala Ser Lys Thr Glu Glu
                         195                 200                 205
        Ile Ala Asn Leu Gln Ser Glu Ala Ala Thr Leu Glu Asn Leu Leu Gly
                         210                 215                 220
        Ser Ala Lys His Glu Leu Thr Asp Leu Gln Ala Lys Leu Asp Thr Ala
        225                 230                 235                 240
        Thr Ala Glu Lys Ala Lys Leu Glu Ser Gln Glu Thr Thr Leu Glu Asn
                         245                 250                 255
        Leu Leu Gly Ser Ala Lys Arg Glu Leu Thr Asp Leu Gln Ala Lys Leu
                         260                 265                 270
        Asp Asp Ala Asn Ala Glu Lys Glu Lys Leu Gln Ser Gln Ala Ala Ala
                         275                 280                 285
        Leu Glu Lys Gln Leu Glu Ala Thr Lys Lys Glu Leu Ala Asp Leu Gln
                         290                 295                 300
        Ala Lys Leu Ala Ala Thr Asn Gln Glu Lys Glu Lys Leu Glu Ala Glu
        305                 310                 315                 320
        Ala Lys Ala Leu Lys Glu Gln Leu Ala Lys Gln Val Glu Glu Leu Ala
                         325                 330                 335
        Lys Leu Lys Ala Asp Lys Ala Ser Gly Ala Gln Lys Pro Asp Thr Lys
                         340                 345                 350
        Pro Asp Asn Lys Glu Val Pro Thr Arg Pro Ser Gln Thr Arg Thr Asn
                         355                 360                 365
        Thr Asn Lys Ala Pro Met Pro Gln Thr Lys Arg Gln Leu Pro Ser Thr
                         370                 375                 380
        Gly Glu Glu Thr Thr Asn Pro Phe Phe Thr Ala Ala Ala Leu Thr Val
        385                 390                 395                 400
        Ile Ala Ser Ala Gly Val Leu Ala Leu Lys Arg Lys Glu Glu Asn
                         405                 410                 415

<210> SEQ ID NO 15
<211> LENGTH: 89
<212> TYPE: PRT
<213> ORGANISM: Artificial Sequence
<220> FEATURE:
<223> OTHER INFORMATION: Mrp49U polypeptide

<400> SEQUENCE: 15

Met Asp Leu Ser Thr Gln Glu His Pro Arg Val Thr Lys Ala Arg Glu
1               5                   10                  15

Glu Ala Leu Glu Glu Val Leu Arg Ser Trp Asp Tyr Gly Ser Val Lys
                20                  25                  30

Ala Ala Leu Ala Gly Ser Tyr Arg Lys Asn Leu Gln Leu Glu Asn Thr
            35                  40                  45

Ile Lys Gln Lys Asp Lys Glu Leu Ser Phe Leu Ser Lys Val Leu Asp
        50                  55                  60

Glu Ala Ala Lys Lys Tyr Arg Glu Ser Ser Asp Lys Lys Leu Ala Ala
65                  70                  75                  80

Ala Leu Glu His His His His His His
                85
```

<210> SEQ ID NO 16
<211> LENGTH: 82
<212> TYPE: PRT
<213> ORGANISM: Artificial Sequence
<220> FEATURE:
<223> OTHER INFORMATION: Mrp49U polypeptide without Met and 6 His

<400> SEQUENCE: 16

Asp Leu Ser Thr Gln Glu His Pro Arg Val Thr Lys Ala Arg Glu Glu
1               5                   10                  15

Ala Leu Glu Glu Val Leu Arg Ser Trp Asp Tyr Gly Ser Val Lys Ala
            20                  25                  30

Ala Leu Ala Gly Ser Tyr Arg Lys Asn Leu Gln Leu Glu Asn Thr Ile
        35                  40                  45

Lys Gln Lys Asp Lys Glu Leu Ser Phe Leu Ser Lys Val Leu Asp Glu
    50                  55                  60

Ala Ala Lys Lys Tyr Arg Glu Ser Ser Asp Lys Lys Leu Ala Ala Ala
65                  70                  75                  80

Leu Glu

<210> SEQ ID NO 17
<211> LENGTH: 75
<212> TYPE: PRT
<213> ORGANISM: Artificial Sequence
<220> FEATURE:
<223> OTHER INFORMATION: Mrp49U polypeptide without divergent COH
      terminal aa

<400> SEQUENCE: 17

Asp Leu Ser Thr Gln Glu His Pro Arg Val Thr Lys Ala Arg Glu Glu
1               5                   10                  15

Ala Leu Glu Glu Val Leu Arg Ser Trp Asp Tyr Gly Ser Val Lys Ala
            20                  25                  30

Ala Leu Ala Gly Ser Tyr Arg Lys Asn Leu Gln Leu Glu Asn Thr Ile
        35                  40                  45

Lys Gln Lys Asp Lys Glu Leu Ser Phe Leu Ser Lys Val Leu Asp Glu
    50                  55                  60

Ala Ala Lys Lys Tyr Arg Glu Ser Ser Asp Lys
65                  70                  75

<210> SEQ ID NO 18
<211> LENGTH: 388
<212> TYPE: PRT
<213> ORGANISM: Streptococcus pyogenes

<400> SEQUENCE: 18

Met Ser Lys Arg Asn Pro Asn Lys Leu Tyr Ser Leu Arg Lys Leu Lys
1               5                   10                  15

Thr Gly Thr Ala Ser Val Ala Val Ala Leu Thr Val Leu Gly Thr Gly
            20                  25                  30

Leu Ala Asn Thr Thr Asp Val Lys Ala Glu Ser Arg Arg Tyr Gln Ala
        35                  40                  45

Pro Pro Arg Val Leu Leu Gln Gly Lys Glu Ala Asn Lys Val Phe Glu
    50                  55                  60

Glu Arg Lys Ala Leu Glu Lys Gln Ala Arg Asp Leu Gly Asp Thr Ile
65                  70                  75                  80

Asn His Met Ser Gln Thr Ile Ser Glu Gln Ser Arg Lys Ile Ala Ala
                85                  90                  95

Leu Lys Ser Glu Ala Glu Leu Lys Asn Gln Gln Ala Leu Glu Ala Leu
            100                 105                 110

```
Asn Asn Lys Asn Lys Gln Ile Ser Asp Leu Thr Asn Glu Asn Ala Gln
            115                 120                 125

Leu Lys Glu Ala Ile Glu Gly Tyr Val Gln Thr Ile Gln Asn Ala Ser
        130                 135                 140

Arg Glu Ile Ala Ala Lys Gln Gln Leu Ala Ala Lys Ser Gln
145                 150                 155                 160

Leu Glu Ala Lys Asn Ala Glu Ile Glu Ala Leu Lys Gln Gln Asp Ala
                165                 170                 175

Ser Lys Thr Glu Glu Ile Ala Lys Leu Gln Ser Glu Ala Ala Thr Leu
            180                 185                 190

Glu Asn Leu Leu Gly Ser Ala Lys Arg Glu Leu Thr Glu Leu Gln Ala
        195                 200                 205

Lys Leu Asp Thr Ala Thr Ala Glu Lys Ala Lys Leu Glu Ser Gln Val
    210                 215                 220

Thr Thr Leu Glu Asn Leu Leu Gly Ser Ala Lys Arg Glu Leu Thr Asp
225                 230                 235                 240

Leu Gln Ala Lys Leu Asp Ala Ala Asn Ala Glu Lys Glu Lys Leu Gln
                245                 250                 255

Ser Gln Ala Ala Thr Leu Glu Lys Gln Leu Glu Ala Thr Lys Lys Glu
            260                 265                 270

Leu Ala Asp Leu Gln Ala Lys Leu Ala Ala Thr Asn Gln Glu Lys Glu
        275                 280                 285

Lys Leu Glu Ala Glu Ala Lys Ala Leu Lys Glu Gln Leu Ala Lys Gln
    290                 295                 300

Ala Glu Glu Leu Ala Lys Leu Lys Ala Asp Lys Ala Ser Gly Ala Gln
305                 310                 315                 320

Lys Pro Asp Thr Lys Pro Gly Asn Lys Glu Val Pro Thr Arg Pro Ser
                325                 330                 335

Gln Thr Arg Thr Asn Thr Asn Lys Ala Pro Met Ala Gln Thr Lys Arg
            340                 345                 350

Gln Leu Pro Ser Thr Gly Glu Thr Thr Asn Pro Phe Phe Thr Ala
        355                 360                 365

Ala Ala Leu Thr Val Ile Ala Ser Ala Gly Val Leu Ala Leu Lys Arg
    370                 375                 380

Lys Glu Glu Asn
385

<210> SEQ ID NO 19
<211> LENGTH: 145
<212> TYPE: PRT
<213> ORGANISM: Artificial Sequence
<220> FEATURE:
<223> OTHER INFORMATION: Mrp4U polypeptide

<400> SEQUENCE: 19

Met Gly Gly Ser His His His His His His Gly Met Ala Ser Met Thr
1               5                   10                  15

Gly Gly Gln Gln Met Gly Arg Asp Leu Tyr Asp Asp Asp Lys Asp
        20                  25                  30

Arg Trp Gly Ser Glu Ser Arg Arg Tyr Gln Ala Pro Pro Arg Val Leu
    35                  40                  45

Leu Gln Gly Lys Glu Ala Asn Lys Val Phe Glu Glu Arg Lys Ala Leu
50                  55                  60

Glu Lys Gln Ala Arg Asp Leu Gly Asp Thr Ile Asn His Met Ser Gln
65                  70                  75                  80
```

```
Thr Ile Ser Glu Gln Ser Arg Lys Ile Ala Ala Leu Lys Ser Glu Ala
                85                  90                  95

Glu Leu Lys Asn Gln Gln Ala Leu Glu Ala Leu Asn Asn Lys Asn Lys
            100                 105                 110

Gln Ile Ser Asp Leu Gly Ser Glu Leu Glu Ile Cys Ser Trp Tyr His
        115                 120                 125

Met Gly Ile Arg Ser Leu Ala Val Leu Ala Asp Glu Arg Arg Phe Ser
    130                 135                 140

Ala
145

<210> SEQ ID NO 20
<211> LENGTH: 81
<212> TYPE: PRT
<213> ORGANISM: Artificial Sequence
<220> FEATURE:
<223> OTHER INFORMATION: MRP4U polypeptide without plasmid amino acids

<400> SEQUENCE: 20

Glu Ser Arg Arg Tyr Gln Ala Pro Pro Arg Val Leu Leu Gln Gly Lys
1               5                   10                  15

Glu Ala Asn Lys Val Phe Glu Glu Arg Lys Ala Leu Glu Lys Gln Ala
            20                  25                  30

Arg Asp Leu Gly Asp Thr Ile Asn His Met Ser Gln Thr Ile Ser Glu
        35                  40                  45

Gln Ser Arg Lys Ile Ala Ala Leu Lys Ser Glu Ala Glu Leu Lys Asn
    50                  55                  60

Gln Gln Ala Leu Glu Ala Leu Asn Asn Lys Asn Lys Gln Ile Ser Asp
65                  70                  75                  80

Leu

<210> SEQ ID NO 21
<211> LENGTH: 300
<212> TYPE: DNA
<213> ORGANISM: Artificial Sequence
<220> FEATURE:
<223> OTHER INFORMATION: polynucleotide encoding mrp2U polypeptide with
      initiating Met spacer sequence and His tag

<400> SEQUENCE: 21
atggagaccg taggtcgctt tagtgatgaa caagttagaa aggctcgtga aaaagcaatc      60
gaagacgtgt ttgatggcta tactggagct cgttctgttt atcaatctgg gaatctgcct     120
aataggttaa ctcctacaaa acttagcaaa ttaatgcaac agatgtataa ggagactttta    180 caaagaaag aagaactgga tacccctatct aaagctctta cgcacactat tgagaaaaag    240
attgagtcag aaaatgctct cgagttggcc gcactcgagc accaccacca ccaccactga    300

<210> SEQ ID NO 22
<211> LENGTH: 438
<212> TYPE: DNA
<213> ORGANISM: Artificial Sequence
<220> FEATURE:
<223> OTHER INFORMATION: Polynucleotide encoding mrp4U polypeptide and
      plasmid related amino acids

<400> SEQUENCE: 22
atggggggtt ctcatcatca tcatcatcat ggtatggcta gcatgactgg tggacagcaa      60
atgggtcggg atctgtacga cgatgacgat aaggatcgat ggggatccga gagtcgtcgt     120
tatcaggcac ctcctcgtgt gttactgcaa ggcaaagaag ctaacaaagt attcgaagag     180
```

```
cgcaaagcct tggaaaaaca agcacgtgat ttgggtgaca ctattaacca catgtcacaa      240
accattagcg agcaaagccg caagattgca gcactaaagt ctgaagcaga acttaaaaac      300
caacaagctc ttgaagcttt aaacaataaa acaagcaaa tctcagattt aggatccgag      360
ctcgagatct gcagctggta ccatatggga attcgaagct tggctgtttt ggcggatgag      420
agaagatttt cagcctga                                                   438

<210> SEQ ID NO 23
<211> LENGTH: 270
<212> TYPE: DNA
<213> ORGANISM: Artificial Sequence
<220> FEATURE:
<223> OTHER INFORMATION: Polynucleotide encoding mrp49U polypeptide with
      initiating Met spacer sequence and His tag

<400> SEQUENCE: 23
atggacttaa gtactcagga acatcctaga gtaacaaaag cgagagaaga agctctcgag      60
gaagttttac gtagttggga ttatggatct gtaaaagctg ctttggcagg ctcttatcgt     120
aaaaacttac aacttgaaaa cactattaag cagaaagata agaattatc tttcttatcc     180 aaagttttgg atgaggctgc aaaaaaatat agagaatcta gcgacaagaa gcttgcggcc     240
gcactcgagc accaccacca ccaccactga                                      270

<210> SEQ ID NO 24
<211> LENGTH: 450
<212> TYPE: PRT
<213> ORGANISM: Artificial Sequence
<220> FEATURE:
<223> OTHER INFORMATION: Fusion protein of group A streptococcus M
      proteins

<400> SEQUENCE: 24

Asn Gly Asp Gly Asn Pro Arg Glu Val Ile Glu Asp Leu Ala Ala Asn
1               5                   10                  15

Asn Pro Ala Ile Gln Asn Ile Arg Leu Arg His Glu Asn Lys Asp Leu
            20                  25                  30

Lys Ala Arg Leu Glu Asn Ala Met Glu Val Ala Gly Arg Asp Phe Lys
        35                  40                  45

Arg Ala Leu Leu Asp Gln Val Thr Gln Leu Tyr Thr Lys His Asn Ser
    50                  55                  60

Asn Tyr Gln Gln Tyr Asn Ala Gln Ala Gly Arg Leu Asp Leu Arg Gln
65                  70                  75                  80

Lys Ala Glu Tyr Leu Lys Gly Leu Asn Asp Trp Ala Glu Arg Leu Leu
                85                  90                  95

Gln Glu Leu Asn Arg Val Phe Pro Arg Gly Thr Val Glu Asn Pro Asp
            100                 105                 110

Lys Ala Arg Glu Leu Leu Asn Lys Tyr Asp Val Glu Asn Arg Val Phe
        115                 120                 125

Pro Arg Gly Thr Val Glu Asn Pro Asp Lys Ala Arg Glu Leu Leu Asn
    130                 135                 140

Lys Tyr Asp Val Glu Asn Ser Lys Asn Pro Val Pro Val Lys Lys Glu
145                 150                 155                 160

Ala Lys Leu Ser Glu Ala Glu Leu His Asp Lys Ile Lys Asn Leu Ser
                165                 170                 175

Lys Asn Pro Val Pro Val Lys Lys Glu Ala Lys Leu Ser Glu Ala Glu
            180                 185                 190
```

-continued

```
Leu His Asp Lys Ile Lys Asn Leu Ala Pro Leu Thr Arg Ala Thr Ala
        195                 200                 205

Asp Asn Lys Asp Glu Leu Ile Lys Arg Ala Asn Asp Tyr Glu Ile Gln
        210                 215                 220

Asn His Gln Leu Thr Val Glu Asn Lys Lys Leu Lys Thr Asp Lys Glu
225                 230                 235                 240

Gln Leu Thr Lys Glu Asn Asp Leu Lys Ala Glu Ser Pro Lys Ser
            245                 250                 255

Thr Glu Thr Ser Ala Asn Gly Ala Asp Lys Leu Ala Asp Ala Tyr Asn
                260                 265                 270

Thr Leu Leu Thr Glu His Glu Lys Leu Arg Asp Glu Tyr Tyr Thr Leu
                275                 280                 285

Ile Asp Ala Lys Glu Glu Pro Arg Tyr Lys Ala Asp His Ser Asp
        290                 295                 300

Leu Val Ala Glu Lys Gln Arg Leu Glu Asp Leu Gly Gln Lys Phe Glu
305                 310                 315                 320

Arg Leu Lys Gln Arg Ser Glu Leu Tyr Leu Gln Gln Tyr Tyr Asp Asn
                325                 330                 335

Lys Ser Asn Gly Tyr Lys Gly Asp Trp Tyr Val Gln Gln Leu Asp Ser
                340                 345                 350

Val Ser Gly Leu Glu Val Ala Asp Pro Ser Asp Ser Lys Lys Leu Ile
            355                 360                 365

Glu Leu Gly Leu Ala Lys Tyr Leu Asn Asp Lys Leu Pro Phe Lys Thr
        370                 375                 380

Lys Glu Asp Ser Glu Ile Leu Ser Glu Leu Arg Asp Val Leu Lys Asn
385                 390                 395                 400

Asn Gly Asp Gly Asn Pro Arg Glu Val Ile Glu Asp Leu Ala Ala Asn
                405                 410                 415

Asn Pro Ala Ile Gln Asn Ile Arg Leu Arg His Glu Asn Lys Asp Leu
            420                 425                 430

Lys Ala Arg Leu Glu Asn Ala Met Glu Val Ala Gly Arg Asp Phe Lys
        435                 440                 445

Arg Ala
    450

<210> SEQ ID NO 25
<211> LENGTH: 450
<212> TYPE: PRT
<213> ORGANISM: Artificial Sequence
<220> FEATURE:
<223> OTHER INFORMATION: Fusion protein of group A streptococcus M
      proteins

<400> SEQUENCE: 25

Ala Glu Ile Lys Lys Pro Gln Ala Asp Ser Ala Trp Asn Trp Pro Lys
1               5                   10                  15

Glu Tyr Asn Ala Leu Leu Lys Glu Asn Glu Glu Leu Lys Val Glu Arg
                20                  25                  30

Glu Lys Tyr Leu Ser Tyr Ala Asp Asp Lys Glu Lys Asp Pro Gln Tyr
            35                  40                  45

Arg Ala Ala Val Thr Arg Gly Thr Ile Asn Asp Pro Gln Arg Ala Lys
        50                  55                  60

Glu Ala Leu Asp Lys Tyr Glu Leu Glu Asn His Ala Val Thr Arg Gly
65                  70                  75                  80

Thr Ile Asn Asp Pro Gln Arg Ala Lys Glu Ala Leu Asp Lys Tyr Glu
                85                  90                  95
```

Leu Glu Asn His Thr Glu Val Lys Ala Ala Gly Gln Ser Ala Pro Lys
            100                 105                 110

Gly Thr Asn Val Ser Ala Asp Leu Tyr Asn Ser Leu Trp Asp Glu Asn
            115                 120                 125

Lys Thr Leu Arg Glu Lys Gln Glu Glu Tyr Ile Thr Lys Ile Gln Asn
            130                 135                 140

Glu Glu Thr Lys Asn Lys Glu Glu Glu Arg Thr Phe Thr Glu Leu Pro
145                 150                 155                 160

Tyr Glu Ala Arg Tyr Lys Ala Trp Lys Ser Glu Asn Asp Glu Leu Arg
                165                 170                 175

Glu Asn Tyr Arg Arg Thr Leu Asp Lys Phe Asn Thr Glu Gln Gly Lys
            180                 185                 190

Thr Thr Arg Leu Glu Glu Gln Asn Arg Val Arg Tyr Thr Arg His Thr
            195                 200                 205

Pro Glu Asp Lys Leu Lys Lys Ile Ile Asp Asp Leu Asp Ala Lys Glu
            210                 215                 220

His Arg Val Arg Tyr Thr Arg His Thr Pro Glu Asp Lys Leu Lys Lys
225                 230                 235                 240

Ile Ile Asp Asp Leu Asp Ala Lys Glu His Arg Val Tyr Ile Thr Arg
                245                 250                 255

Arg Met Thr Lys Glu Asp Val Glu Lys Ile Ala Asn Asp Leu Asp Thr
            260                 265                 270

Glu Asn His Gly Leu Lys Gln Gln Asn Glu Gln Leu Ser Thr Glu Lys
            275                 280                 285

Gln Gly Leu Glu Glu Gln Asn Lys Gln Leu Ser Thr Asp Arg Val Ser
            290                 295                 300

Arg Ser Met Ser Arg Asp Asp Leu Leu Asn Arg Ala Gln Asp Leu Glu
305                 310                 315                 320

Ala Lys Asn His Gly Leu Glu His Gln Asn Thr Lys Leu Ser Thr Glu
                325                 330                 335

Asn Lys Thr Leu Gln Glu Gln Ala Glu Ala Arg Gln Lys Glu Val Ala
            340                 345                 350

Thr Arg Ser Gln Thr Asp Thr Leu Glu Lys Val Gln Glu Arg Ala Asp
            355                 360                 365

Lys Phe Glu Ile Glu Asn Asn Thr Leu Lys Leu Lys Asn Ser Asp Leu
370                 375                 380

Ser Phe Asn Asn Lys Ala Leu Lys Asp His Asn Asp Glu Leu Thr Glu
385                 390                 395                 400

Ala Glu Ile Lys Lys Pro Gln Ala Asp Ser Ala Trp Asn Trp Pro Lys
                405                 410                 415

Glu Tyr Asn Ala Leu Leu Lys Glu Asn Glu Glu Leu Lys Val Glu Arg
            420                 425                 430

Glu Lys Tyr Leu Ser Tyr Ala Asp Asp Lys Glu Lys Asp Pro Gln Tyr
            435                 440                 445

Arg Ala
    450

<210> SEQ ID NO 26
<211> LENGTH: 450
<212> TYPE: PRT
<213> ORGANISM: Artificial Sequence
<220> FEATURE:
<223> OTHER INFORMATION: Fusion protein of group A streptococcus M
      proteins

```
<400> SEQUENCE: 26

Glu Gly Val Ser Val Gly Ser Asp Ala Ser Leu His Asn Arg Ile Thr
1               5                   10                  15

Asp Leu Glu Glu Arg Glu Lys Leu Leu Asn Lys Leu Asp Lys Val
            20                  25                  30

Glu Glu Glu His Lys Lys Asp His Glu Gln Leu Glu Lys Lys Ser Glu
            35                  40                  45

Asp Val Glu Ser Ser Asn Asn Ala Glu Ser Ser Asn Ile Ser Gln Glu
50                      55                  60

Ser Lys Leu Ile Asn Thr Leu Thr Asp Glu Asn Glu Lys Leu Arg Glu
65                  70                  75                  80

Glu Leu Gln Gln Tyr Tyr Ala Leu Ser Asp Ala Lys Glu Glu Glu Pro
                85                  90                  95

Arg Tyr Lys Ala Asp Asn Gln Ser Pro Ala Pro Val Lys Lys Glu Ala
            100                 105                 110

Lys Lys Leu Asn Glu Ala Glu Leu Tyr Asn Lys Ile Gln Glu Leu Glu
            115                 120                 125

Glu Gly Lys Ala Glu Leu Phe Asp Lys Leu Glu Lys Val Glu Glu Glu
        130                 135                 140

Asn Lys Lys Val Lys Glu Asp Ser Asp Asn Ile Asn Arg Ser Val Ser
145                 150                 155                 160

Val Lys Asp Asn Glu Lys Glu Leu His Asn Lys Ile Ala Asp Leu Glu
                165                 170                 175

Glu Glu Arg Gly Glu His Leu Asp Lys Ile Asp Glu Leu Lys Glu Glu
            180                 185                 190

Leu Lys Ala Lys Glu Lys Ser Ser Asp Ser Ser Arg Glu Val Thr Asn
        195                 200                 205

Glu Leu Thr Ala Ser Met Trp Lys Ala Gln Ala Asp Ser Ala Lys Ala
210                 215                 220

Lys Ala Lys Glu Leu Glu Lys Gln Val Glu Glu Tyr Lys Lys Asn Tyr
225                 230                 235                 240

Glu Thr Leu Glu Lys Gly Tyr Asp Asp Leu Ala Glu Ser Arg Ser Val
                245                 250                 255

Ser Gln Gly Ser Val Ser Leu Glu Leu Tyr Asp Lys Leu Ser Asp Glu
            260                 265                 270

Asn Asp Ile Leu Arg Glu Lys Gln Asp Glu Tyr Leu Thr Lys Ile Asp
        275                 280                 285

Gly Leu Asp Lys Glu Asn Lys Glu Tyr Ala Ser Gln Glu Ser Gln Asn
290                 295                 300

Ser Arg Ser Ile Thr Asn Glu Gln Leu Ile Asp Lys Leu Val Glu Glu
305                 310                 315                 320

Asn Asn Asp Leu Lys Glu Glu Arg Ala Lys Tyr Leu Asp Leu Leu Asp
                325                 330                 335

Asn Arg Glu Lys Asp Pro Gln Tyr Arg Ala Leu Met Gly Glu Ala Glu
            340                 345                 350

Lys Lys Val Glu Val Ala Asp Ser Asn Ala Ser Ser Val Ala Lys Leu
        355                 360                 365

Tyr Asn Gln Ile Ala Asp Leu Thr Asp Lys Asn Gly Glu Tyr Leu Glu
370                 375                 380

Arg Ile Glu Glu Leu Glu Glu Arg Gln Lys Asn Leu Glu Lys Leu Glu
385                 390                 395                 400

Glu Gly Val Ser Val Gly Ser Asp Ala Ser Leu His Asn Arg Ile Thr
                405                 410                 415
```

```
Asp Leu Glu Glu Glu Arg Glu Lys Leu Leu Asn Lys Leu Asp Lys Val
            420                 425                 430

Glu Glu Glu His Lys Lys Asp His Glu Gln Leu Glu Lys Lys Ser Glu
        435                 440                 445

Asp Val
    450

<210> SEQ ID NO 27
<211> LENGTH: 400
<212> TYPE: PRT
<213> ORGANISM: Artificial Sequence
<220> FEATURE:
<223> OTHER INFORMATION: Fusion protein of group A streptococcus M
      proteins

<400> SEQUENCE: 27

Asp Asn Pro Arg Tyr Thr Asp Ala His Asn Ala Val Thr Gln Gly Arg
1               5                   10                  15

Thr Val Pro Leu Gln Asn Leu Leu His Glu Met Asp Lys Asn Gly Lys
            20                  25                  30

Leu Arg Ser Glu Asn Glu Glu Leu Lys Ala Asp Leu Gln Lys Lys Glu
        35                  40                  45

Gln Glu Asp Ser Ser Ser Arg Asp Ile Thr Glu Ala Gly Val Ser Lys
    50                  55                  60

Phe Trp Lys Ser Lys Phe Asp Ala Glu Gln Asn Arg Ala Asn Glu Leu
65                  70                  75                  80

Glu Lys Lys Leu Ser Gly Tyr Glu Lys Asp Tyr Lys Thr Leu Glu Gln
                85                  90                  95

Glu Tyr Glu Asn Ala Gly Ser Glu Glu Asn Val Pro Lys Gln Gln Tyr
            100                 105                 110

Asn Ala Leu Trp Glu Glu Asn Glu Asp Leu Arg Gly Arg Glu Arg Lys
        115                 120                 125

Tyr Ile Ala Lys Leu Glu Lys Glu Glu Ile Gln Asn Gly Glu Leu Asn
    130                 135                 140

Glu Lys Asn Arg Lys Leu Glu Ser Pro Arg Glu Val Thr Asn Glu Leu
145                 150                 155                 160

Ala Ala Ser Val Trp Lys Lys Lys Val Glu Glu Ala Lys Glu Lys Ala
                165                 170                 175

Ser Lys Leu Glu Lys Gln Leu Glu Glu Ala Gln Lys Asp Tyr Ser Glu
            180                 185                 190

Ile Glu Gly Lys Leu Glu Gln Phe Val Glu Lys Lys Val Glu Ala Ala
        195                 200                 205

Glu Asn Asn Val Ser Ser Val Ala Arg Arg Glu Lys Glu Leu Tyr Asp
    210                 215                 220

Gln Ile Ala Asp Leu Thr Asp Lys Asn Gly Glu Tyr Leu Glu Arg Ile
225                 230                 235                 240

Gly Glu Leu Glu Glu Arg Gln Lys Asn Leu Asp Asp Arg Ser Val Ser
                245                 250                 255

Thr Asn Ser Gly Ser Val Ser Thr Pro Tyr Asn Asn Leu Leu Asn Glu
            260                 265                 270

Tyr Asp Asp Leu Leu Ala Lys His Gly Glu Leu Leu Ser Glu Tyr Asp
        275                 280                 285

Ala Leu Lys Glu Lys Gln Asp Lys Asn Gln Glu Glu Asn Ser Lys Asn
    290                 295                 300

Pro Ala Pro Ala Pro Ala Ser Ala Val Pro Val Lys Lys Glu Ala Thr
```

```
                305                 310                 315                 320
Lys Leu Ser Glu Ala Glu Leu Tyr Asn Lys Ile Gln Glu Leu Glu Glu
                325                 330                 335

Gly Lys Ala Glu Leu Phe Asp Lys Leu Glu Lys Val Glu Glu Asp Asn
                340                 345                 350

Pro Arg Tyr Thr Asp Ala His Asn Ala Val Thr Gln Gly Arg Thr Val
                355                 360                 365

Pro Leu Gln Asn Leu Leu His Glu Met Asp Lys Asn Gly Lys Leu Arg
        370                 375                 380

Ser Glu Asn Glu Glu Leu Lys Ala Asp Leu Gln Lys Lys Glu Gln Glu
385                 390                 395                 400

<210> SEQ ID NO 28
<211> LENGTH: 70
<212> TYPE: PRT
<213> ORGANISM: Artificial Sequence
<220> FEATURE:
<223> OTHER INFORMATION: N terminal amino acid sequences of Mrp
      polypeptide from heterologus emm types of group A streptococcus

<400> SEQUENCE: 28

Glu Ser Arg Gly Tyr Gln Val Pro Pro Arg Val Leu Leu Pro Gly Lys
1               5                   10                  15

Glu Ala Asn Lys Val Phe Glu Glu Arg Lys Ala Leu Glu Lys Gln Ala
                20                  25                  30

Arg Glu Leu Gly Asp Thr Ile Asn His Met Ser Gln Thr Ile Ser Glu
            35                  40                  45

Gln Ser Arg Lys Ile Ala Ala Leu Lys Ser Glu Ala Glu Leu Lys Asn
        50                  55                  60

Gln Gln Ala Leu Glu Ala
65                  70

<210> SEQ ID NO 29
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologus emm types of group A streptococcus

<400> SEQUENCE: 29

Glu Ser Arg Gly Tyr Gln Val Pro Pro Arg Val Leu Leu Pro Gly Lys
1               5                   10                  15

Glu Ala Asn Lys Val Phe Glu Glu Arg Lys Ala Leu Glu Lys Gln Ala
                20                  25                  30

Arg Glu Leu Gly Asp Thr Ile Asn His Met Ser Gln Thr Ile Ser Glu
            35                  40                  45

Gln Ser Arg Lys Ile Ala Ala Leu Lys Ser Glu Ala Glu Leu Lys Asn
        50                  55                  60

Gln Gln Ala Leu Glu Ala
65                  70

<210> SEQ ID NO 30
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologus emm types of group A streptococcus

<400> SEQUENCE: 30
```

```
Glu Ser Arg Gly Tyr Gln Val Pro Pro Arg Val Leu Pro Gly Lys
1               5                   10                  15

Glu Ala Asn Lys Val Phe Glu Glu Arg Lys Ala Leu Glu Lys Gln Ala
            20                  25                  30

Arg Glu Leu Gly Asp Thr Ile Asn His Met Ser Gln Thr Ile Ser Glu
        35                  40                  45

Gln Ser Arg Lys Ile Ala Ala Leu Lys Ser Glu Ala Glu Leu Lys Asn
    50                  55                  60

Gln Gln Ala Leu Glu Ala
65              70

<210> SEQ ID NO 31
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 31

Glu Ser Arg Gly Tyr Gln Val Pro Pro Arg Val Leu Pro Gly Lys
1               5                   10                  15

Glu Ala Asn Lys Val Phe Glu Glu Arg Lys Ala Leu Glu Lys Gln Ala
            20                  25                  30

Arg Glu Leu Gly Asp Thr Ile Asn His Met Ser Gln Thr Ile Ser Glu
        35                  40                  45

Gln Ser Arg Lys Ile Ala Ala Leu Lys Ser Glu Ala Glu Leu Lys Asn
    50                  55                  60

Gln Gln Ala Leu Glu Ala
65              70

<210> SEQ ID NO 32
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 32

Glu Ser Arg Gly Tyr Gln Val Pro Pro Arg Val Leu Pro Gly Lys
1               5                   10                  15

Glu Ala Asn Lys Val Phe Glu Glu Arg Lys Ala Leu Glu Lys Gln Ala
            20                  25                  30

Arg Glu Leu Gly Asp Thr Ile Asn His Met Ser Gln Thr Ile Ser Glu
        35                  40                  45

Gln Ser Arg Lys Ile Ala Ala Leu Lys Ser Glu Ala Glu Leu Lys Asn
    50                  55                  60

Gln Gln Ala Leu Glu Ala
65              70

<210> SEQ ID NO 33
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 33
```

```
Glu Ser Arg Gly Tyr Gln Ala Pro Pro Arg Val Leu Leu Pro Gly Lys
1               5                   10                  15

Glu Ala Asn Lys Val Phe Glu Glu Arg Lys Ala Leu Glu Lys Gln Ala
            20                  25                  30

Arg Glu Leu Gly Asp Thr Ile Asn His Met Ser Gln Thr Ile Ser Glu
        35                  40                  45

Gln Ser Arg Lys Ile Ala Ala Leu Lys Ser Glu Ala Glu Leu Lys Asn
    50                  55                  60

Gln Gln Ala Leu Glu Ala
65                  70

<210> SEQ ID NO 34
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 34

Glu Ser Arg Gly Tyr Gln Ala Pro Pro Arg Val Leu Leu Pro Gly Lys
1               5                   10                  15

Glu Ala Asn Lys Val Phe Glu Glu Arg Lys Ala Leu Glu Lys Gln Ala
            20                  25                  30

Arg Glu Leu Gly Asp Thr Ile Asn His Met Ser Gln Thr Ile Ser Glu
        35                  40                  45

Gln Ser Arg Lys Ile Ala Ala Leu Lys Ser Glu Ala Glu Leu Lys Asn
    50                  55                  60

Gln Gln Ala Leu Glu Ala
65                  70

<210> SEQ ID NO 35
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 35

Glu Ser Arg Gly Tyr Gln Ala Pro Pro Arg Val Leu Leu Pro Gly Lys
1               5                   10                  15

Glu Ala Asn Lys Val Phe Glu Glu Arg Lys Ala Leu Glu Lys Gln Ala
            20                  25                  30

Arg Glu Leu Gly Asp Thr Ile Asn His Met Ser Gln Thr Ile Ser Glu
        35                  40                  45

Gln Ser Arg Lys Ile Ala Ala Leu Lys Ser Glu Ala Glu Leu Lys Asn
    50                  55                  60

Gln Gln Ala Leu Glu Ala
65                  70

<210> SEQ ID NO 36
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 36

Glu Gly Arg Gly Tyr Gln Val Pro Pro Arg Ala Pro Leu Pro Gly Lys
```

```
                1               5                   10                  15
Glu Ala Asn Lys Val Phe Glu Glu Arg Lys Ala Leu Glu Lys Gln Ala
                20                  25                  30
Arg Asp Leu Gly Asp Thr Ile Asn His Met Ser Gln Thr Ile Ser Glu
            35                  40                  45
Gln Ser Arg Lys Ile Ala Ala Leu Lys Ser Glu Ala Glu Leu Lys Asn
    50                  55                  60
Gln Gln Ala Leu Glu Ala
65                  70

<210> SEQ ID NO 37
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 37

Glu Gly Arg Gly Tyr Gln Val Pro Pro Arg Val Leu Leu Pro Gly Lys
1               5                   10                  15
Glu Ala Asn Lys Val Phe Glu Glu Arg Lys Ala Leu Glu Lys Gln Ala
                20                  25                  30
Arg Asp Leu Gly Asp Thr Ile Asn His Met Ser Gln Thr Ile Ser Glu
            35                  40                  45
Gln Ser Arg Lys Ile Ala Ala Leu Lys Ser Glu Ala Glu Leu Lys Asn
    50                  55                  60
Gln Gln Ala Leu Glu Ala
65                  70

<210> SEQ ID NO 38
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 38

Glu Ser Arg Gly Tyr Gln Val Pro Pro Arg Val Leu Leu Pro Gly Lys
1               5                   10                  15
Glu Ala Asn Lys Val Phe Glu Glu Arg Lys Ala Leu Glu Lys Gln Ala
                20                  25                  30
Arg Asp Leu Gly Asp Thr Ile Asn His Met Ser Gln Thr Ile Ser Glu
            35                  40                  45
Gln Ser Arg Lys Ile Ala Ala Leu Lys Ser Glu Ala Glu Leu Lys Asn
    50                  55                  60
Gln Gln Ala Leu Glu Ala
65                  70

<210> SEQ ID NO 39
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 39

Glu Ser Arg Arg Tyr Gln Ala Pro Pro Arg Val Leu Leu Gln Gly Lys
1               5                   10                  15
```

```
Glu Ala Asn Lys Val Phe Glu Glu Arg Lys Ala Leu Glu Lys Gln Ala
            20                  25                  30

Arg Asp Leu Gly Asp Thr Ile Asn His Met Ser Gln Thr Ile Ser Glu
        35                  40                  45

Gln Ser Arg Lys Ile Ala Ala Leu Lys Ser Glu Ala Glu Leu Lys Asn
    50                  55                  60

Gln Gln Ala Leu Glu Ala
65                  70

<210> SEQ ID NO 40
<211> LENGTH: 70
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 40

Glu Ser Arg Arg Tyr Gln Ala Pro Pro Arg Val Leu Leu Gln Gly Lys
1               5                   10                  15

Glu Ala Asn Lys Val Phe Glu Glu Arg Lys Ala Leu Glu Lys Gln Ala
            20                  25                  30

Arg Asp Leu Gly Asp Thr Ile Asn His Met Ser Gln Thr Ile Ser Glu
        35                  40                  45

Gln Ser Arg Lys Ile Ala Ala Leu Lys Ser Glu Ala Glu Leu Lys Asn
    50                  55                  60

Gln Gln Ala Leu Glu Ala
65                  70

<210> SEQ ID NO 41
<211> LENGTH: 66
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 41

Glu Thr Glu His Leu Asp Val Val Leu Ser Ala Lys Glu Ala Asn Lys
1               5                   10                  15

Val Phe Glu Arg Lys Ala Leu Glu Lys Gln Ala His Asp Leu Gly
            20                  25                  30

Asp Thr Ile Asn His Met Ser Gln Ile Ile Ser Glu Lys Ser Arg Lys
        35                  40                  45

Ile Ala Ala Leu Lys Ser Glu Ala Glu Leu Lys Asn Gln Gln Ala Leu
    50                  55                  60

Glu Ala
65

<210> SEQ ID NO 42
<211> LENGTH: 66
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 42

Glu Thr Glu His Leu Asp Val Val Leu Ser Ala Lys Glu Ala Asn Lys
1               5                   10                  15
```

```
Val Phe Glu Glu Arg Lys Ala Leu Glu Lys Gln Ala His Asp Leu Gly
            20                  25                  30

Asp Thr Ile Asn His Met Ser Gln Ile Ser Glu Lys Ser Arg Lys
        35                  40                  45

Ile Ala Ala Leu Lys Ser Glu Ala Glu Leu Lys Asn Gln Gln Ala Leu
    50                  55                  60

Glu Ala
65

<210> SEQ ID NO 43
<211> LENGTH: 66
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 43

Glu Thr Glu His Leu Asp Val Val Leu Ser Ala Lys Glu Ala Asn Lys
1               5                   10                  15

Val Phe Glu Glu Arg Lys Ala Leu Glu Lys Gln Ala Arg Asp Leu Gly
            20                  25                  30

Asp Thr Ile Asn His Met Ser Gln Thr Ile Ser Glu Gln Ser Arg Lys
        35                  40                  45

Ile Ala Ala Leu Lys Ser Glu Ala Glu Leu Lys Asn Gln Gln Ala Leu
    50                  55                  60

Glu Ala
65

<210> SEQ ID NO 44
<211> LENGTH: 66
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 44

Glu Thr Glu His Val Asp Val Val Leu Ser Ala Lys Glu Ala Asn Lys
1               5                   10                  15

Val Phe Glu Glu Arg Lys Ala Leu Glu Lys Gln Ala Arg Asp Leu Gly
            20                  25                  30

Asp Thr Ile Asn His Met Ser Gln Thr Ile Ser Glu Gln Ser Arg Lys
        35                  40                  45

Ile Ala Ala Leu Lys Ser Glu Ala Glu Leu Lys Asn Gln Gln Ala Leu
    50                  55                  60

Glu Ala
65

<210> SEQ ID NO 45
<211> LENGTH: 66
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 45

Lys Thr Glu His Leu Asp Val Val Leu Ser Ala Lys Glu Ala Asn Lys
1               5                   10                  15

Val Phe Glu Glu Arg Lys Ala Leu Glu Lys Gln Ala Arg Asp Leu Gly
```

```
                20                  25                  30

Asp Thr Ile Asn His Met Ser Gln Thr Ile Ser Glu Gln Ser Arg Lys
         35                  40                  45

Ile Ala Ala Leu Lys Ser Glu Ala Glu Leu Lys Asn Gln Gln Ala Leu
     50                  55                  60

Glu Ala
65

<210> SEQ ID NO 46
<211> LENGTH: 66
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 46

Lys Thr Glu His Leu Asp Val Val Leu Ser Ala Lys Glu Ala Asn Lys
1               5                  10                  15

Val Phe Glu Glu Arg Lys Ala Leu Glu Lys Gln Ala Arg Asp Leu Gly
                20                  25                  30

Asp Thr Ile Asn His Met Ser Gln Thr Ile Ser Glu Gln Ser Arg Lys
         35                  40                  45

Ile Ala Ala Leu Lys Ser Glu Ala Glu Leu Lys Asn Gln Gln Ala Leu
     50                  55                  60

Glu Ala
65

<210> SEQ ID NO 47
<211> LENGTH: 107
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 47

Glu Thr Val Gly Arg Phe Ser Asp Glu Gln Val Arg Lys Ala Arg Glu
1               5                  10                  15

Lys Ala Ile Glu Asp Val Phe Asp Gly Tyr Thr Gly Ala Arg Ser Val
                20                  25                  30

Tyr Gln Ser Gly Asn Leu Pro Asn Arg Leu Thr Pro Thr Lys Leu Ser
         35                  40                  45

Lys Leu Met Gln Gln Met Tyr Lys Glu Thr Leu Gln Lys Lys Glu Glu
     50                  55                  60

Leu Asp Thr Leu Ser Lys Ala Leu Thr His Thr Ile Glu Lys Lys Ile
65                  70                  75                  80

Glu Ser Glu Asn Ala Tyr Lys Lys Glu Leu Gly Gln Leu Lys Ala Ala
                85                  90                  95

Ala Glu Ala Glu Ala Gln Lys Ala Leu Asp Ala
            100                 105

<210> SEQ ID NO 48
<211> LENGTH: 107
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 48
```

Glu Thr Val Gly Arg Phe Ser Asp Glu Gln Val Arg Lys Ala Arg Glu
1               5                   10                  15

Lys Ala Ile Glu Asp Val Phe Asp Gly Tyr Thr Gly Ala Arg Ser Val
            20                  25                  30

Tyr Gln Ser Gly Asn Leu Pro Asn Arg Leu Thr Pro Thr Lys Leu Ser
        35                  40                  45

Lys Leu Met Gln Gln Met Tyr Lys Glu Thr Leu Gln Lys Lys Glu Glu
    50                  55                  60

Leu Asp Thr Leu Ser Lys Ala Leu Thr His Thr Ile Glu Lys Lys Ile
65                  70                  75                  80

Glu Ser Glu Asn Ala Tyr Lys Lys Glu Leu Gly Gln Leu Lys Ala Ala
                85                  90                  95

Ala Glu Ala Glu Ala Gln Lys Ala Leu Asp Ala
            100                 105

<210> SEQ ID NO 49
<211> LENGTH: 107
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 49

Glu Thr Val Gly Arg Phe Ser Asp Glu Gln Val Arg Lys Ala Arg Glu
1               5                   10                  15

Lys Ala Ile Glu Asp Val Phe Asp Gly Tyr Thr Gly Ala Arg Ser Val
            20                  25                  30

Tyr Gln Ser Gly Asn Leu Pro Asn Arg Leu Thr Pro Thr Lys Leu Ser
        35                  40                  45

Lys Leu Met Gln Gln Met Tyr Lys Glu Thr Leu Gln Lys Lys Glu Glu
    50                  55                  60

Leu Asp Thr Leu Ser Lys Ala Leu Thr Asp Thr Ile Glu Lys Lys Ile
65                  70                  75                  80

Glu Ser Glu Asn Ala Tyr Lys Lys Glu Leu Gly Gln Leu Lys Ala Ala
                85                  90                  95

Ala Glu Ala Glu Ala Gln Lys Ala Leu Asp Ala
            100                 105

<210> SEQ ID NO 50
<211> LENGTH: 107
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 50

Glu Thr Leu Gly Arg Phe Ser Asp Glu Gln Val Arg Lys Ala Arg Glu
1               5                   10                  15

Lys Ala Ile Glu Asp Val Phe Asp Gly Tyr Thr Gly Ala Arg Ser Val
            20                  25                  30

Tyr Gln Ser Gly Asp Leu Pro Asn Arg Leu Thr Pro Thr Lys Leu Ser
        35                  40                  45

Lys Leu Met Gln Gln Met Tyr Lys Glu Thr Leu Gln Lys Lys Glu Glu
    50                  55                  60

Leu Asp Thr Leu Ser Lys Ala Pro Thr Asp Thr Ile Glu Lys Lys Ile
65                  70                  75                  80

```
Glu Ser Glu Asn Ala Tyr Lys Lys Glu Leu Gly Gln Leu Lys Ala Ala
                85                  90                  95

Ala Glu Ala Glu Ala Gln Lys Ala Leu Asp Ala
            100                 105

<210> SEQ ID NO 51
<211> LENGTH: 107
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 51

Glu Thr Leu Gly Arg Phe Ser Asp Glu Gln Val Arg Lys Ala Arg Glu
1               5                   10                  15

Lys Ala Ile Glu Asp Val Phe Asp Gly Tyr Thr Gly Ala Arg Ser Val
                20                  25                  30

Tyr Gln Ser Gly Asp Leu Pro Asn Arg Leu Thr Pro Thr Lys Leu Ser
            35                  40                  45

Lys Leu Met Gln Gln Met Tyr Lys Glu Thr Leu Gln Lys Lys Glu Glu
        50                  55                  60

Leu Asp Thr Leu Ser Lys Ala Leu Thr Asp Thr Ile Glu Lys Lys Ile
65                  70                  75                  80

Glu Ser Glu Asn Val Tyr Lys Lys Glu Leu Gly Gln Leu Lys Ala Ala
                85                  90                  95

Ala Glu Ala Glu Ala Gln Lys Ala Leu Asp Ala
            100                 105

<210> SEQ ID NO 52
<211> LENGTH: 107
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 52

Glu Asn Arg Thr Pro Arg Phe Thr Ala Glu Glu Phe Lys Lys Ala Arg
1               5                   10                  15

Glu Lys Val Ile Lys Glu Met Phe Asp Asp Tyr Thr Gly Ala Thr Ser
                20                  25                  30

Arg His Tyr Ser Asn Gly Tyr Gln Arg Met Thr Pro Ser Gln Leu Ser
            35                  40                  45

Asn Leu Met Gln Gly Met Phe Arg Glu Thr Leu Gln Lys Lys Glu Glu
        50                  55                  60

Leu Asp Thr Leu Ser Lys Ala Leu Thr His Thr Ile Glu Lys Lys Ile
65                  70                  75                  80

Glu Ser Glu Asn Ala Tyr Lys Lys Glu Leu Gly Gln Leu Lys Ala Ala
                85                  90                  95

Ala Glu Ala Glu Ala Gln Lys Ala Leu Asp Ala
            100                 105

<210> SEQ ID NO 53
<211> LENGTH: 97
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus
```

```
<400> SEQUENCE: 53

Asp Leu Ser Thr Gln Glu Asn Pro Arg Val Thr Glu Ala Arg Glu Lys
1               5                   10                  15

Ala Leu Glu Glu Val Ile Ala Lys Met Pro Phe Glu Glu Leu Gln His
            20                  25                  30

Thr Leu Ala Gly Ser Tyr Arg Lys Asn Arg Glu Leu Glu Lys Thr Ile
        35                  40                  45

Glu Lys Lys Asp Ser Glu Ala Ser Phe Leu Ser Lys Val Leu Asp Glu
    50                  55                  60

Thr Ala Lys Lys Tyr Arg Glu Ser Ser Asp Lys Tyr Lys Gln Glu Ile
65                  70                  75                  80

Gly Gln Leu Lys Ala Ala Ala Glu Ala Glu Ala Gln Lys Ala Leu Asp
                85                  90                  95

Ala

<210> SEQ ID NO 54
<211> LENGTH: 97
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 54

Asp Phe Ser Thr Gln Glu Asn Pro Arg Val Thr Glu Ala Arg Glu Lys
1               5                   10                  15

Ala Leu Glu Glu Val Ile Thr Asn Met Ser Leu Glu Glu Leu Gln His
            20                  25                  30

Thr Leu Ala Gly Ser Tyr Arg Lys Asn Arg Glu Leu Glu Lys Thr Ile
        35                  40                  45

Glu Lys Lys Asp Gly Glu Ala Ser Phe Leu Ser Lys Val Leu Asp Glu
    50                  55                  60

Thr Ala Lys Arg Tyr Arg Glu Ser Ser Asp Lys Tyr Lys Gln Glu Ile
65                  70                  75                  80

Gly Gln Leu Lys Ala Ala Ala Glu Ala Glu Ala Gln Lys Ala Leu Asp
                85                  90                  95

Ala

<210> SEQ ID NO 55
<211> LENGTH: 97
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 55

Asp Leu Ser Thr Gln Glu His Pro Arg Val Thr Lys Ala Arg Glu Glu
1               5                   10                  15

Ala Leu Glu Glu Val Leu Arg Ser Trp Asp Tyr Gly Ser Val Lys Ala
            20                  25                  30

Ala Leu Ala Gly Ser Tyr Arg Lys Asn Leu Gln Leu Glu Asn Thr Ile
        35                  40                  45

Lys Gln Lys Asp Lys Glu Leu Ser Phe Leu Ser Lys Val Leu Asp Glu
    50                  55                  60

Ala Ala Lys Lys Tyr Arg Glu Ser Ser Asp Lys Tyr Lys Gln Glu Ile
65                  70                  75                  80
```

```
Gly Gln Leu Lys Ala Ala Ala Glu Ala Glu Ala Gln Lys Ala Leu Asp
                85                  90                  95

Ala

<210> SEQ ID NO 56
<211> LENGTH: 97
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 56

Asp Leu Ser Thr Gln Glu His Pro Arg Val Thr Lys Ala Arg Glu Glu
1               5                   10                  15

Ala Leu Glu Glu Val Leu Arg Ser Trp Asp Tyr Gly Ser Val Lys Ala
                20                  25                  30

Ala Leu Ala Gly Ser Tyr Arg Lys Asn Leu Gln Leu Glu Asn Thr Ile
            35                  40                  45

Lys Gln Lys Asp Lys Glu Leu Ser Phe Leu Ser Lys Val Leu Asp Glu
    50                  55                  60

Ala Ala Lys Lys Tyr Arg Glu Ser Ser Asp Lys Tyr Lys Gln Glu Ile
65                  70                  75                  80

Gly Gln Leu Lys Ala Ala Ala Glu Ala Glu Ala Gln Lys Ala Leu Asp
                85                  90                  95

Ala

<210> SEQ ID NO 57
<211> LENGTH: 97
<212> TYPE: PRT
<213> ORGANISM: Artificial Sequence
<220> FEATURE:
<223> OTHER INFORMATION: N terminal amino acid sequence of Mrp
      polypeptide from heterologous emm types of group A streptococcus

<400> SEQUENCE: 57

Asp Leu Ser Thr Gln Glu Asn Pro Arg Val Thr Lys Ala Arg Glu Glu
1               5                   10                  15

Ala Leu Glu Glu Val Leu Arg Ser Trp Asp Tyr Gly Ser Val Arg Ala
                20                  25                  30

Ala Leu Ala Gly Ser Tyr Arg Lys Asn Leu Gln Leu Glu Asn Thr Ile
            35                  40                  45

Lys Gln Lys Asp Lys Glu Leu Ser Phe Leu Ser Lys Val Leu Asp Glu
    50                  55                  60

Ala Ala Lys Lys Tyr Arg Glu Ser Ser Asp Lys Tyr Lys Gln Glu Ile
65                  70                  75                  80

Gly Gln Leu Lys Ala Ala Ala Glu Ala Glu Ala Gln Lys Ala Leu Asp
                85                  90                  95

Ala

<210> SEQ ID NO 58
<211> LENGTH: 1463
<212> TYPE: DNA
<213> ORGANISM: Artificial Sequence
<220> FEATURE:
<223> OTHER INFORMATION: Polynucleotide encoding a fusion protein of
      group A streptococcus M proteins

<400> S

```
agatctcgat cccgcgaaat taatacgact cactataggg gaattgtgag cggataacaa     60
ttcccctcta gaaataattt tgtttaactt taagaaggag atatcatatg aacggtgacg    120
gtaacccgcg tgaagttatc gaagacctgg ctgctaacaa cccggctatc cagaacatcc    180
gtctgcgtca cgaaaacaaa gacctgaaag ctcgtctgga aaacgctatg gaagttgctg    240
gtcgtgactt caaacgtgct ctgctggacc aggttaccca gctgtacacc aaacacaact    300
ccaactacca gcagtacaac gctcaggctg gtcgtctgga cctgcgtcag aaagctgaat    360
acctgaaagg tctgaacgac tgggctgaac gtctgctgca ggaactgaac cgtgttttcc    420
cgcgtggtac cgttgaaaac ccggacaaag ctcgtgaact gctgaacaaa tacgacgttg    480
aaaaccgtgt tttcccgcgt ggtaccgttg aaaacccgga caaagctcgt gaactgctga    540
acaaatacga cgttgaaaac tccaaaaacc cggttccggt taaaaaagaa gctaaactgt    600
ccgaagctga actgcacgac aaaatcaaaa acctgtccaa aaacccggtt ccggttaaaa    660
aagaagctaa actgtccgaa gctgaactgc acgacaaaat caaaaacctg gctccgctga    720
cccgtgctac cgctgacaac aaagacgaac tgatcaaacg tgctaacgac tacgaaatcc    780
agaaccacca gctgaccgtt gaaaacaaaa aactgaaaac cgacaaagaa cagctgacca    840
aagaaaacga cgacctgaaa gctgaatccc cgaaatccac cgaaacctcc gctaacggtg    900
ctgacaaact ggctgacgct tacaacaccc tgctgaccga acacgaaaaa ctgcgtgacg    960
aatactacac cctgatcgac gctaaagaag aagaaccgcg ttacaaagct gaccactccg   1020
acctggttgc tgaaaaacag cgtctggaag acctgggtca gaaattcgaa cgtctgaaac   1080
agcgttccga actgtacctg cagcagtact acgacaacaa atccaacggt tacaaaggtg   1140
actggtacgt tcagcagctg gactccgttt ccggtctgga agttgctgac ccgtccgact   1200
ccaaaaaact gatcgaactg ggtctggcta aatacctgaa cgacaaactg ccgttcaaaa   1260
ccaaagaaga ctccgaaatc ctgtccgaac tgcgtgacgt tctgaaaaac aacggtgacg   1320
gtaacccgcg tgaagttatc gaagacctgg ctgctaacaa cccggctatc cagaacatcc   1380
gtctgcgtca cgaaaacaaa gacctgaaag ctcgtctgga aaacgctatg gaagttgctg   1440
gtcgtgactt caaacgtgct tag                                           1463
```

<210> SEQ ID NO 59
<211> LENGTH: 1463
<212> TYPE: DNA
<213> ORGANISM: Artificial Sequence
<220> FEATURE:
<223> OTHER INFORMATION: Polynucleotide encoding a fusion protein of group A streptococcus M proteins

<400> SEQUENCE: 59

```
agatctcgat cccgcgaaat taatacgact cactataggg gaattgtgag cggataacaa     60
ttcccctcta gaaataattt tgtttaactt taagaaggag atataccatg gctgaaatca    120
aaaaaccgca ggctgactcc gcttggaact ggccgaaaga atacaacgct ctgctgaaag    180
aaaacgaaga actgaaagtt gaacgtgaaa aatacctgtc ctacgctgac gacaaagaaa    240
aagacccgca gtaccgtgct gctgttaccc gtggtaccat caacgacccg cagcgtgcta    300
aagaagctct ggacaaatac gaactggaaa accacgctgt tacccgtggt accatcaacg    360
acccgcagcg tgctaaagaa gctctggaca aatacgaact ggaaaaccac accgaagtta    420
aagctgctgg tcagtccgct ccgaaaggta ccaacgtttc cgctgacctg tacaactccc    480
tgtgggacga aaacaaaacc ctgcgtgaaa aacaggaaga atacatcacc aaaatccaga    540
```

```
acgaagaaac caaaaacaaa gaagaagaac gtaccttcac cgaactgccg tacgaagctc    600
gttacaaagc ttggaaatcc gaaaacgacg aactgcgtga aaactaccgt cgtaccctgg    660
acaaattcaa caccgaacag ggtaaaacca cccgtctgga agaacagaac cgtgttcgtt    720
acacccgtca cacccccggaa gacaaactga aaaaaatcat cgacgacctg gacgctaaag    780
aacaccgtgt tcgttacacc cgtcacaccc cggaagacaa actgaaaaaa atcatcgacg    840
acctggacgc taaagaacac cgtgtttaca tcacccgtcg tatgaccaaa gaagacgttg    900
aaaaaatcgc taacgacctg gacaccgaaa accacggtct gaaacagcag aacgaacagc    960
tgtccaccga aaacagggt ctggaagaac agaacaaaca gctgtccacc gaccgtgttt    1020
cccgttccat gtcccgtgac gacctgctga accgtgctca ggacctggaa gctaaaaacc    1080
acggtctgga acaccagaac accaaactgt ccaccgaaaa caaaaccctg caggaacagg    1140
ctgaagctcg tcagaaagaa gttgctaccc gttcccagac cgacacccctg gaaaaagttc    1200 aggaacgtgc tgacaaattc gaaatcgaaa acaaacccct gaaactgaaa aactccgacc    1260
tgtccttcaa caacaaagct ctgaaagacc acaacgacga actgaccgaa gctgaaatca    1320
aaaaaccgca ggctgactcc gcttggaact ggccgaaaga atacaacgct ctgctgaaag    1380
aaaacgaaga actgaaagtt gaacgtgaaa atacctgtc ctacgctgac gacaaagaaa    1440
aagacccgca gtaccgtgct tag                                            1463
```

<210> SEQ ID NO 60
<211> LENGTH: 1463
<212> TYPE: DNA
<213> ORGANISM: Artificial Sequence
<220> FEATURE:
<223> OTHER INFORMATION: Polynucleotide encoding a fusion protein of group A streptococcus M proteins

<400> SEQUENCE: 60
agatctcgat cccgcgaaat taatacgact cactataggg gaattgtgag cggataacaa 60
ttcccctcta gaaataattt tgtttaactt taagaaggag atataccatg gaaggtgttt 120
ccgttggttc cgacgcttcc ctgcacaacc gtatcaccga cctggaagaa gaacgtgaaa 180
aactgctgaa caaactggac aaagttgaag aagaacacaa aaaagaccac gaacagctgg 240
aaaaaaaatc cgaagacgtt gaatcctcca acaacgctga atcctccaac atctcccagg 300
aatccaaact gatcaacacc ctgaccgacg aaaacgaaaa actgcgtgaa gaactgcagc 360
agtactacgc tctgtccgac gctaaagaag aagaaccgcg ttacaaagct gacaaccagt 420
ccccggctcc ggttaaaaaa gaagctaaaa aactgaacga agctgaactg tacaacaaaa 480
tccaggaact ggaagaaggt aaagctgaac tgttcgacaa actggaaaaa gttgaagaag 540
aaaacaaaaa agttaaagaa gactccgaca acatcaaccg ttccgtttcc gttaaagaca 600
acgaaaaaga actgcacaac aaaatcgctg acctggaaga agaacgtggt gaacacctgg 660
acaaaatcga cgaactgaaa gaagaactga aagctaaaga aaaatcctcc gactcctccc 720
gtgaagttac caacgaactg accgcttcca tgtggaaagc tcaggctgac tccgctaaag 780
ctaaagctaa agaactggaa aaacaggttg aagaatacaa aaaaaactac gaaaccctgg 840
aaaaaggtta cgacgacctg gctgaatccc gttccgtttc ccagggttcc gtttccctgg 900
aactgtacga caaactgtcc gacgaaaacg acatcctgcg tgaaaaacag gacgaatacc 960
tgaccaaaat cgacggtctg gacaaagaaa acaaagaata cgcttcccag gaatcccaga 1020
actcccgttc catcaccaac gaacagctga tcgacaaact ggttgaagaa aacaacgacc 1080

| | | | | |
|---|---|---|---|---|
| tgaaagaaga | acgtgctaaa | tacctggacc | tgctggacaa | ccgtgaaaaa | gacccgcagt | 1140 |
| accgtgctct | gatgggtgaa | gctgaaaaaa | aagttgaagt | tgctgactcc | aacgcttcct | 1200 |
| ccgttgctaa | actgtacaac | cagatcgctg | acctgaccga | caaaaacggt | gaatacctgg | 1260 |
| aacgtatcga | agaactggaa | gaacgtcaga | aaaacctgga | aaaactggaa | gaaggtgttt | 1320 |
| ccgttggttc | cgacgcttcc | ctgcacaacc | gtatcaccga | cctggaagaa | gaacgtgaaa | 1380 |
| aactgctgaa | caaactggac | aaagttgaag | aagaacacaa | aaaagaccac | gaacagctgg | 1440 |
| aaaaaaaatc | cgaagacgtt | tag | | | | 1463 |

<210> SEQ ID NO 61
<211> LENGTH: 1313
<212> TYPE: DNA
<213> ORGANISM: Artificial Sequence
<220> FEATURE:
<223> OTHER INFORMATION: Polynucleotide encoding a fusion protein of
      group A streptococcus M proteins

<400> SEQUENCE: 61

```
agatctcgat cccgcgaaat taatacgact cactataggg gaattgtgag cggataacaa     60
ttcccctcta gaaataattt tgtttaactt taagaaggag atataccatg gacaacccgc    120
gttacaccga cgctcacaac gctgttaccc agggtcgtac cgttccgctg cagaacctgc    180
tgcacgaaat ggacaaaaac ggtaaactgc gttccgaaaa cgaagaactg aaagctgacc    240
tgcagaaaaa agaacaggaa gactcctcct cccgtgacat caccgaagct ggtgtttcca    300
aattctggaa atccaaattc gacgctgaac agaaccgtgc taacgaactg gaaaaaaaac    360
tgtccggtta cgaaaaagac tacaaaaccc tggaacagga atacgaaaac gctggttccg    420
aagaaaacgt tccgaaacag cagtacaacg ctctgtggga agaaaacgaa gacctgcgtg    480
gtcgtgaacg taaatacatc gctaaactgg aaaaagaaga aatccagaac ggtgaactga    540
acgaaaaaaa ccgtaaactg gaatccccgc gtgaagttac caacgaactg gctgcttccg    600
tttggaaaaa aaaagttgaa gaagctaaag aaaaagcttc caaactggaa aaacagctgg    660
aagaagctca gaaagactac tccgaaatcg aaggtaaact ggaacagttc gttgaaaaaa    720
aagttgaagc tgctgaaaac aacgtttcct ccgttgctcg tcgtgaaaaa gaactgtacg    780
accagatcgc tgacctgacc gacaaaaacg gtgaatacct ggaacgtatc ggtgaactgg    840
aagaacgtca gaaaaacctg gacgaccgtt ccgtttccac caactccggt tccgtttcca    900
ccccgtacaa caacctgctg aacgaatacg acgacctgct ggctaaacac ggtgaactgc    960
tgtccgaata cgacgctctg aaagaaaaac aggacaaaaa ccaggaagaa aactccaaaa   1020
acccggctcc ggctccggct tccgctgttc cggttaaaaa agaagctacc aaactgtccg   1080
aagctgaact gtacaacaaa atccaggaac tggaagaagg taaagctgaa ctgttcgaca   1140
aactggaaaa agttgaagaa gacaacccgc gttacaccga cgctcacaac gctgttaccc   1200
agggtcgtac cgttccgctg cagaacctgc tgcacgaaat ggacaaaaac ggtaaactgc   1260
gttccgaaaa cgaagaactg aaagctgacc tgcagaaaaa agaacaggaa tag          1313
```

<210> SEQ ID NO 62
<211> LENGTH: 255
<212> TYPE: DNA
<213> ORGANISM: Artificial Sequence
<220> FEATURE:
<223> OTHER INFORMATION: mrp2U nucleotide

<400> SEQUENCE: 62

```
gagaccgtag gtcgctttag tgatgaacaa gttagaaagg ctcgtgaaaa agcaatcgaa    60
gacgtgtttg atggctatac tggagctcgt tctgtttatc aatctgggaa tctgcctaat   120
aggttaactc ctacaaaact tagcaaatta atgcaacaga tgtataagga gactttacaa   180
aagaaagaag aactggatac cctatctaaa gctcttacgc acactattga gaaaaagatt   240
gagtcagaaa atgct                                                    255

<210> SEQ ID NO 63
<211> LENGTH: 243
<212> TYPE: DNA
<213> ORGANISM: Artificial Sequence
<220> FEATURE:
<223> OTHER INFORMATION: mrp4U nucleotide

<400> SEQUENCE: 63
gagagtcgtc gttatcaggc acctcctcgt gtgttactgc aaggcaaaga agctaacaaa    60
gtattcgaag agcgcaaagc cttggaaaaa caagcacgtg atttgggtga cactattaac   120
cacatgtcac aaaccattag cgagcaaagc cgcaagattg cagcactaaa gtctgaagca   180
gaacttaaaa accaacaagc tcttgaagct ttaaacaata aaaacaagca aatctcagat   240
tta                                                                 243

<210> SEQ ID NO 64
<211> LENGTH: 225
<212> TYPE: DNA
<213> ORGANISM: Artificial Sequence
<220> FEATURE:
<223> OTHER INFORMATION: mrp49U nucleotide

<400> SEQUENCE: 64
gacttaagta ctcaggaaca tcctagagta acaaaagcga gagaagaagc tctcgaggaa    60
gttttacgta gttgggatta tggatctgta aaagctgctt tggcaggctc ttatcgtaaa   120
aacttacaac ttgaaaacac tattaagcag aaagataaag aattatcttt cttatccaaa   180
gttttggatg aggctgcaaa aaaatataga gaatctagcg acaag                   225

<210> SEQ ID NO 65
<211> LENGTH: 7
<212> TYPE: PRT
<213> ORGANISM: Artificial Sequence
<220> FEATURE:
<223> OTHER INFORMATION: spacer

<400> SEQUENCE: 65

Lys Leu Ala Ala Ala Leu Glu
1               5

<210> SEQ ID NO 66
<211> LENGTH: 50
<212> TYPE: PRT
<213> ORGANISM: Streptococcus pyogenes

<400> SEQUENCE: 66

Asn Gly Asp Gly Asn Pro Arg Glu Val Ile Glu Asp Leu Ala Ala Asn
1               5                   10                  15

Asn Pro Ala Ile Gln Asn Ile Arg Leu Arg His Glu Asn Lys Asp Leu
            20                  25                  30

Lys Ala Arg Leu Glu Asn Ala Met Glu Val Ala Gly Arg Asp Phe Lys
        35                  40                  45

Arg Ala
```

50

<210> SEQ ID NO 67
<211> LENGTH: 50
<212> TYPE: PRT
<213> ORGANISM: Streptococcus pyogenes

<400> SEQUENCE: 67

Leu Leu Asp Gln Val Thr Gln Leu Tyr Thr Lys His Asn Ser Asn Tyr
1               5                   10                  15

Gln Gln Tyr Asn Ala Gln Ala Gly Arg Leu Asp Leu Arg Gln Lys Ala
            20                  25                  30

Glu Tyr Leu Lys Gly Leu Asn Asp Trp Ala Glu Arg Leu Leu Gln Glu
        35                  40                  45

Leu Asn
    50

<210> SEQ ID NO 68
<211> LENGTH: 50
<212> TYPE: PRT
<213> ORGANISM: Streptococcus pyogenes

<400> SEQUENCE: 68

Arg Val Phe Pro Arg Gly Thr Val Glu Asn Pro Asp Lys Ala Arg Glu
1               5                   10                  15

Leu Leu Asn Lys Tyr Asp Val Glu Asn Arg Val Phe Pro Arg Gly Thr
            20                  25                  30

Val Glu Asn Pro Asp Lys Ala Arg Glu Leu Leu Asn Lys Tyr Asp Val
        35                  40                  45

Glu Asn
    50

<210> SEQ ID NO 69
<211> LENGTH: 50
<212> TYPE: PRT
<213> ORGANISM: Streptococcus pyogenes

<400> SEQUENCE: 69

Ser Lys Asn Pro Val Pro Val Lys Lys Glu Ala Lys Leu Ser Glu Ala
1               5                   10                  15

Glu Leu His Asp Lys Ile Lys Asn Leu Ser Lys Asn Pro Val Pro Val
            20                  25                  30

Lys Lys Glu Ala Lys Leu Ser Glu Ala Glu Leu His Asp Lys Ile Lys
        35                  40                  45

Asn Leu
    50

<210> SEQ ID NO 70
<211> LENGTH: 50
<212> TYPE: PRT
<213> ORGANISM: streptococcus pyogenes

<400> SEQUENCE: 70

Ala Pro Leu Thr Arg Ala Thr Ala Asp Asn Lys Asp Glu Leu Ile Lys
1               5                   10                  15

Arg Ala Asn Asp Tyr Glu Ile Gln Asn His Gln Leu Thr Val Glu Asn
            20                  25                  30

Lys Lys Leu Lys Thr Asp Lys Glu Gln Leu Thr Lys Glu Asn Asp Asp
        35                  40                  45

-continued

```
Leu Lys
    50

<210> SEQ ID NO 71
<211> LENGTH: 50
<212> TYPE: PRT
<213> ORGANISM: streptococcus pyogenes

<400> SEQUENCE: 71

Ala Glu Ser Pro Lys Ser Thr Glu Thr Ser Asn Gly Ala Asp Lys
1               5                   10                  15

Leu Ala Asp Ala Tyr Asn Thr Leu Leu Thr Glu His Glu Lys Leu Arg
            20                  25                  30

Asp Glu Tyr Tyr Thr Leu Ile Asp Ala Lys Glu Glu Glu Pro Arg Tyr
        35                  40                  45

Lys Ala
    50

<210> SEQ ID NO 72
<211> LENGTH: 50
<212> TYPE: PRT
<213> ORGANISM: Streptococcus pyogenes

<400> SEQUENCE: 72

Asp His Ser Asp Leu Val Ala Glu Lys Gln Arg Leu Glu Asp Leu Gly
1               5                   10                  15

Gln Lys Phe Glu Arg Leu Lys Gln Arg Ser Glu Leu Tyr Leu Gln Gln
            20                  25                  30

Tyr Tyr Asp Asn Lys Ser Asn Gly Tyr Lys Gly Asp Trp Tyr Val Gln
        35                  40                  45

Gln Leu
    50

<210> SEQ ID NO 73
<211> LENGTH: 50
<212> TYPE: PRT
<213> ORGANISM: Streptococcus pyogenes

<400> SEQUENCE: 73

Asp Ser Val Ser Gly Leu Glu Val Ala Asp Pro Ser Asp Ser Lys Lys
1               5                   10                  15

Leu Ile Glu Leu Gly Leu Ala Lys Tyr Leu Asn Asp Lys Leu Pro Phe
            20                  25                  30

Lys Thr Lys Glu Asp Ser Glu Ile Leu Ser Glu Leu Arg Asp Val Leu
        35                  40                  45

Lys Asn
    50

<210> SEQ ID NO 74
<211> LENGTH: 50
<212> TYPE: PRT
<213> ORGANISM: Streptococcus pyogenes

<400> SEQUENCE: 74

Ala Glu Ile Lys Lys Pro Gln Ala Asp Ser Ala Trp Asn Trp Pro Lys
1               5                   10                  15

Glu Tyr Asn Ala Leu Leu Lys Glu Asn Glu Glu Leu Lys Val Glu Arg
            20                  25                  30

Glu Lys Tyr Leu Ser Tyr Ala Asp Lys Glu Lys Asp Pro Gln Tyr
        35                  40                  45
```

Arg Ala
    50

<210> SEQ ID NO 75
<211> LENGTH: 50
<212> TYPE: PRT
<213> ORGANISM: Steptococcus pyogenes

<400> SEQUENCE: 75

Ala Val Thr Arg Gly Thr Ile Asn Asp Pro Gln Arg Ala Lys Glu Ala
1               5                   10                  15

Leu Asp Lys Tyr Glu Leu Glu Asn His Ala Val Thr Arg Gly Thr Ile
            20                  25                  30

Asn Asp Pro Gln Arg Ala Lys Glu Ala Leu Asp Lys Tyr Glu Leu Glu
        35                  40                  45

Asn His
    50

<210> SEQ ID NO 76
<211> LENGTH: 50
<212> TYPE: PRT
<213> ORGANISM: Streptococcus pyogenes

<400> SEQUENCE: 76

Thr Glu Val Lys Ala Ala Gly Gln Ser Ala Pro Lys Gly Thr Asn Val
1               5                   10                  15

Ser Ala Asp Leu Tyr Asn Ser Leu Trp Asp Glu Asn Lys Thr Leu Arg
            20                  25                  30

Glu Lys Gln Glu Glu Tyr Ile Thr Lys Ile Gln Asn Glu Glu Thr Lys
        35                  40                  45

Asn Lys
    50

<210> SEQ ID NO 77
<211> LENGTH: 50
<212> TYPE: PRT
<213> ORGANISM: Streptococcus pyogenes

<400> SEQUENCE: 77

Glu Glu Glu Arg Thr Phe Thr Glu Leu Pro Tyr Glu Ala Arg Tyr Lys
1               5                   10                  15

Ala Trp Lys Ser Glu Asn Asp Glu Leu Arg Glu Asn Tyr Arg Arg Thr
            20                  25                  30

Leu Asp Lys Phe Asn Thr Glu Gln Gly Lys Thr Thr Arg Leu Glu Glu
        35                  40                  45

Gln Asn
    50

<210> SEQ ID NO 78
<211> LENGTH: 50
<212> TYPE: PRT
<213> ORGANISM: Streptococcus pyogenes

<400> SEQUENCE: 78

Arg Val Arg Tyr Thr Arg His Thr Pro Glu Asp Lys Leu Lys Lys Ile
1               5                   10                  15

Ile Asp Asp Leu Asp Ala Lys Glu His Arg Val Arg Tyr Thr Arg His
            20                  25                  30

Thr Pro Glu Asp Lys Leu Lys Lys Ile Ile Asp Asp Leu Asp Ala Lys

-continued

```
                35                  40                  45

Glu His
    50

<210> SEQ ID NO 79
<211> LENGTH: 50
<212> TYPE: PRT
<213> ORGANISM: streptococcus pyogenes

<400> SEQUENCE: 79

Arg Val Tyr Ile Thr Arg Arg Met Thr Lys Glu Asp Val Glu Lys Ile
1               5                   10                  15

Ala Asn Asp Leu Asp Thr Glu Asn His Gly Leu Lys Gln Gln Asn Glu
            20                  25                  30

Gln Leu Ser Thr Glu Lys Gln Gly Leu Glu Glu Gln Asn Lys Gln Leu
        35                  40                  45

Ser Thr
    50

<210> SEQ ID NO 80
<211> LENGTH: 50
<212> TYPE: PRT
<213> ORGANISM: streptococcus pyogenes

<400> SEQUENCE: 80

Asp Arg Val Ser Arg Ser Met Ser Arg Asp Asp Leu Leu Asn Arg Ala
1               5                   10                  15

Gln Asp Leu Glu Ala Lys Asn His Gly Leu Glu His Gln Asn Thr Lys
            20                  25                  30

Leu Ser Thr Glu Asn Lys Thr Leu Gln Glu Gln Ala Glu Ala Arg Gln
        35                  40                  45

Lys Glu
    50

<210> SEQ ID NO 81
<211> LENGTH: 50
<212> TYPE: PRT
<213> ORGANISM: streptococcus pyogenes

<400> SEQUENCE: 81

Val Ala Thr Arg Ser Gln Thr Asp Thr Leu Glu Lys Val Gln Glu Arg
1               5                   10                  15

Ala Asp Lys Phe Glu Ile Glu Asn Asn Thr Leu Lys Leu Lys Asn Ser
            20                  25                  30

Asp Leu Ser Phe Asn Asn Lys Ala Leu Lys Asp His Asn Asp Glu Leu
        35                  40                  45

Thr Glu
    50

<210> SEQ ID NO 82
<211> LENGTH: 50
<212> TYPE: PRT
<213> ORGANISM: streptococcus pyogenes

<400> SEQUENCE: 82

Glu Gly Val Ser Val Gly Ser Asp Ala Ser Leu His Asn Arg Ile Thr
1               5                   10                  15

Asp Leu Glu Glu Glu Arg Glu Lys Leu Leu Asn Lys Leu Asp Lys Val
            20                  25                  30
```

-continued

```
Glu Glu Glu His Lys Lys Asp His Glu Gln Leu Glu Lys Lys Ser Glu
            35                  40                  45

Asp Val
    50

<210> SEQ ID NO 83
<211> LENGTH: 50
<212> TYPE: PRT
<213> ORGANISM: streptococcus pyogenes

<400> SEQUENCE: 83

Glu Ser Ser Asn Asn Ala Glu Ser Ser Asn Ile Ser Gln Glu Ser Lys
1               5                   10                  15

Leu Ile Asn Thr Leu Thr Asp Glu Asn Glu Lys Leu Arg Glu Glu Leu
            20                  25                  30

Gln Gln Tyr Tyr Ala Leu Ser Asp Ala Lys Glu Glu Pro Arg Tyr
            35                  40                  45

Lys Ala
    50

<210> SEQ ID NO 84
<211> LENGTH: 50
<212> TYPE: PRT
<213> ORGANISM: streptococcus pyogenes

<400> SEQUENCE: 84

Asp Asn Gln Ser Pro Ala Pro Val Lys Lys Glu Ala Lys Lys Leu Asn
1               5                   10                  15

Glu Ala Glu Leu Tyr Asn Lys Ile Gln Glu Leu Glu Glu Gly Lys Ala
            20                  25                  30

Glu Leu Phe Asp Lys Leu Glu Lys Val Glu Glu Asn Lys Lys Val
            35                  40                  45

Lys Glu
    50

<210> SEQ ID NO 85
<211> LENGTH: 50
<212> TYPE: PRT
<213> ORGANISM: streptococcus pyogenes

<400> SEQUENCE: 85

Asp Ser Asp Asn Ile Asn Arg Ser Val Ser Val Lys Asp Asn Glu Lys
1               5                   10                  15

Glu Leu His Asn Lys Ile Ala Asp Leu Glu Glu Arg Gly Glu His
            20                  25                  30

Leu Asp Lys Ile Asp Glu Leu Lys Glu Glu Leu Lys Ala Lys Glu Lys
            35                  40                  45

Ser Ser
    50

<210> SEQ ID NO 86
<211> LENGTH: 50
<212> TYPE: PRT
<213> ORGANISM: streptococcus pyogenes

<400> SEQUENCE: 86

Asp Ser Ser Arg Glu Val Thr Asn Glu Leu Thr Ala Ser Met Trp Lys
1               5                   10                  15

Ala Gln Ala Asp Ser Ala Lys Ala Lys Ala Lys Glu Leu Glu Lys Gln
            20                  25                  30
```

Val Glu Glu Tyr Lys Lys Asn Tyr Glu Thr Leu Glu Lys Gly Tyr Asp
        35                  40                  45

Asp Leu
    50

<210> SEQ ID NO 87
<211> LENGTH: 50
<212> TYPE: PRT
<213> ORGANISM: streptococcus pyogenes

<400> SEQUENCE: 87

Ala Glu Ser Arg Ser Val Ser Gln Gly Ser Val Ser Leu Glu Leu Tyr
1               5                   10                  15

Asp Lys Leu Ser Asp Glu Asn Asp Ile Leu Arg Glu Lys Gln Asp Glu
            20                  25                  30

Tyr Leu Thr Lys Ile Asp Gly Leu Asp Lys Glu Asn Lys Glu Tyr Ala
        35                  40                  45

Ser Gln
    50

<210> SEQ ID NO 88
<211> LENGTH: 50
<212> TYPE: PRT
<213> ORGANISM: streptococcus pyogenes

<400> SEQUENCE: 88

Glu Ser Gln Asn Ser Arg Ser Ile Thr Asn Glu Gln Leu Ile Asp Lys
1               5                   10                  15

Leu Val Glu Glu Asn Asn Asp Leu Lys Glu Glu Arg Ala Lys Tyr Leu
            20                  25                  30

Asp Leu Leu Asp Asn Arg Glu Lys Asp Pro Gln Tyr Arg Ala Leu Met
        35                  40                  45

Gly Glu
    50

<210> SEQ ID NO 89
<211> LENGTH: 50
<212> TYPE: PRT
<213> ORGANISM: streptococcus pyogenes

<400> SEQUENCE: 89

Ala Glu Lys Lys Val Glu Val Ala Asp Ser Asn Ala Ser Ser Val Ala
1               5                   10                  15

Lys Leu Tyr Asn Gln Ile Ala Asp Leu Thr Asp Lys Asn Gly Glu Tyr
            20                  25                  30

Leu Glu Arg Ile Glu Glu Leu Glu Glu Arg Gln Lys Asn Leu Glu Lys
        35                  40                  45

Leu Glu
    50

<210> SEQ ID NO 90
<211> LENGTH: 50
<212> TYPE: PRT
<213> ORGANISM: streptococcus pyogenes

<400> SEQUENCE: 90

Asp Asn Pro Arg Tyr Thr Asp Ala His Asn Ala Val Thr Gln Gly Arg
1               5                   10                  15

Thr Val Pro Leu Gln Asn Leu Leu His Glu Met Asp Lys Asn Gly Lys 20              25              30

Leu Arg Ser Glu Asn Glu Glu Leu Lys Ala Asp Leu Gln Lys Lys Glu
        35                  40                  45

Gln Glu
    50

<210> SEQ ID NO 91
<211> LENGTH: 50
<212> TYPE: PRT
<213> ORGANISM: streptococcus pyogenes

<400> SEQUENCE: 91

Asp Ser Ser Ser Arg Asp Ile Thr Glu Ala Gly Val Ser Lys Phe Trp
1               5                   10                  15

Lys Ser Lys Phe Asp Ala Glu Gln Asn Arg Ala Asn Glu Leu Glu Lys
            20                  25                  30

Lys Leu Ser Gly Tyr Glu Lys Asp Tyr Lys Thr Leu Glu Gln Glu Tyr
        35                  40                  45

Glu Asn
    50

<210> SEQ ID NO 92
<211> LENGTH: 50
<212> TYPE: PRT
<213> ORGANISM: steptococcus pyogenes

<400> SEQUENCE: 92

Ala Gly Ser Glu Glu Asn Val Pro Lys Gln Gln Tyr Asn Ala Leu Trp
1               5                   10                  15

Glu Glu Asn Glu Asp Leu Arg Gly Arg Glu Arg Lys Tyr Ile Ala Lys
            20                  25                  30

Leu Glu Lys Glu Glu Ile Gln Asn Gly Glu Leu Asn Glu Lys Asn Arg
        35                  40                  45

Lys Leu
    50

<210> SEQ ID NO 93
<211> LENGTH: 50
<212> TYPE: PRT
<213> ORGANISM: streptococcus pyogenes

<400> SEQUENCE: 93

Glu Ser Pro Arg Glu Val Thr Asn Glu Leu Ala Ala Ser Val Trp Lys
1               5                   10                  15

Lys Lys Val Glu Glu Ala Lys Glu Lys Ala Ser Lys Leu Glu Lys Gln
            20                  25                  30

Leu Glu Glu Ala Gln Lys Asp Tyr Ser Glu Ile Glu Gly Lys Leu Glu
        35                  40                  45

Gln Phe
    50

<210> SEQ ID NO 94
<211> LENGTH: 50
<212> TYPE: PRT
<213> ORGANISM: streptococcus pyogenes

<400> SEQUENCE: 94

Val Glu Lys Lys Val Glu Ala Ala Glu Asn Asn Val Ser Ser Val Ala
1               5                   10                  15

```
Arg Arg Glu Lys Glu Leu Tyr Asp Gln Ile Ala Asp Leu Thr Asp Lys
            20                  25                  30

Asn Gly Glu Tyr Leu Glu Arg Ile Gly Glu Leu Glu Arg Gln Lys
        35                  40                  45

Asn Leu
    50

<210> SEQ ID NO 95
<211> LENGTH: 50
<212> TYPE: PRT
<213> ORGANISM: streptococcus pyogenes

<400> SEQUENCE: 95

Asp Asp Arg Ser Val Ser Thr Asn Ser Gly Ser Val Ser Thr Pro Tyr
1               5                   10                  15

Asn Asn Leu Leu Asn Glu Tyr Asp Leu Leu Ala Lys His Gly Glu
            20                  25                  30

Leu Leu Ser Glu Tyr Asp Ala Leu Lys Glu Lys Gln Asp Lys Asn Gln
        35                  40                  45

Glu Glu
    50

<210> SEQ ID NO 96
<211> LENGTH: 50
<212> TYPE: PRT
<213> ORGANISM: streptococcus pyogenes

<400> SEQUENCE: 96

Asn Ser Lys Asn Pro Ala Pro Ala Pro Ala Ser Ala Val Pro Val Lys
1               5                   10                  15

Lys Glu Ala Thr Lys Leu Ser Glu Ala Glu Leu Tyr Asn Lys Ile Gln
            20                  25                  30

Glu Leu Glu Glu Gly Lys Ala Glu Leu Phe Asp Lys Leu Lys Val
        35                  40                  45

Glu Glu
    50

<210> SEQ ID NO 97
<211> LENGTH: 8
<212> TYPE: PRT
<213> ORGANISM: Artificial Sequence
<220> FEATURE:
<223> OTHER INFORMATION: FLAG epitope tag

<400> SEQUENCE: 97

Asp Tyr Lys Asp Asp Asp Asp Lys
1               5

<210> SEQ ID NO 98
<211> LENGTH: 8
<212> TYPE: PRT
<213> ORGANISM: Artificial Sequence
<220> FEATURE:
<223> OTHER INFORMATION: XPRESS  epitope tag

<400> SEQUENCE: 98

Asp Leu Tyr Asp Asp Asp Asp Lys
1               5

<210> SEQ ID NO 99
<211> LENGTH: 5
<212> TYPE: PRT
```

<213> ORGANISM: Artificial Sequence
<220> FEATURE:
<223> OTHER INFORMATION: Gly Ser spacer

<400> SEQUENCE: 99

Gly Gly Gly Gly Ser
1               5

<210> SEQ ID NO 100
<211> LENGTH: 1353
<212> TYPE: DNA
<213> ORGANISM: Artificial Sequence
<220> FEATURE:
<223> OTHER INFORMATION: Polynucleotide encoding a fusion protein of
      group A streptococcus M proteins

<400> SEQUENCE: 100

```
aacggtgacg gtaacccgcg tgaagttatc g

-continued

```
ctgctgaaag aaaacgaaga actgaaagtt gaacgtgaaa aatacctgtc ctacgctgac    120
gacaaagaaa aagacccgca gtaccgtgct gctgttaccc gtggtaccat caacgacccg    180
cagcgtgcta aagaagctct ggacaaatac gaactggaaa accacgctgt tacccgtggt    240
accatcaacg acccgcagcg tgctaaagaa gctctggaca aatacgaact ggaaaaccac    300
accgaagtta aagctgctgg tcagtccgct ccgaaaggta ccaacgtttc cgctgacctg    360
tacaactccc tgtgggacga aaacaaaacc ctgcgtgaaa aacaggaaga atacatcacc    420
aaaatccaga acgaagaaac caaaaacaaa gaagaagaac gtaccttcac cgaactgccg    480
tacgaagctc gttacaaagc ttggaaatcc gaaaacgacg aactgcgtga aaactaccgt    540
cgtaccctgg acaaattcaa caccgaacag ggtaaaacca cccgtctgga agaacagaac    600
cgtgttcgtt acacccgtca caccccggaa gacaaactga aaaaaatcat cgacgacctg    660
gacgctaaag aacaccgtgt tcgttacacc cgtcacaccc cggaagacaa actgaaaaaa    720
atcatcgacg acctggacgc taaagaacac cgtgtttaca tcacccgtcg tatgaccaaa    780
gaagacgttg aaaaaatcgc taacgacctg gacaccgaaa accacggtct gaaacagcag    840
aacgaacagc tgtccaccga aaaacagggt ctggaagaac agaacaaaca gctgtccacc    900
gaccgtgttt cccgttccat gtcccgtgac gacctgctga accgtgctca ggacctggaa    960
gctaaaaacc acggtctgga acaccagaac accaaactgt ccaccgaaaa caaaaccctg   1020
caggaacagg ctgaagctcg tcagaaagaa gttgctaccc gttcccagac cgacaccctg   1080
gaaaaagttc aggaacgtgc tgacaaattc gaaatcgaaa acaacaccct gaaactgaaa   1140
aactccgacc tgtccttcaa caacaaagct ctgaaagacc acaacgacga actgaccgaa   1200
gctgaaatca aaaaaccgca ggctgactcc gcttggaact ggccgaaaga atacaacgct   1260
ctgctgaaag aaaacgaaga actgaaagtt gaacgtgaaa aatacctgtc ctacgctgac   1320
gacaaagaaa aagacccgca gtaccgtgct tag                               1353
```

<210> SEQ ID NO 102
<211> LENGTH: 1353
<212> TYPE: DNA
<213> ORGANISM: Artificial Sequence
<220> FEATURE:
<223> OTHER INFORMATION: Polynucleotide encoding a fusion protein of
      group A streptococcus M proteins

<400> SEQUENCE: 102

```
gaaggtgttt ccgttggttc cgacgcttcc ctgcacaacc gtatcaccga cctggaagaa     60
gaacgtgaaa aactgctgaa caaactggac aaagttgaag aagaacacaa aaaagaccac    120
gaacagctgg aaaaaaaatc cgaagacgtt gaatcctcca acaacgctga atcctccaac    180
atctcccagg aatccaaact gatcaacacc ctgaccgacg aaaacgaaaa actgcgtgaa    240
gaactgcagc agtactacgc tctgtccgac gctaaagaag aagaaccgcg ttacaaagct    300
gacaaccagt ccccggctcc ggttaaaaaa gaagctaaaa aactgaacga agctgaactg    360
tacaacaaaa tccaggaact ggaagaaggt aaagctgaac tgttcgacaa actggaaaaa    420
gttgaagaag aaaacaaaaa agttaaagaa gactccgaca acatcaaccg ttccgtttcc    480
gttaaagaca acgaaaaaga actgcacaac aaaatcgctg acctggaaga agaacgtggt    540
gaacacctgg acaaaatcga cgaactgaaa gaagaactga aagctaaaga aaaatcctcc    600
gactcctccc gtgaagttac caacgaactg accgcttcca tgtggaaagc tcaggctgac    660
tccgctaaag ctaaagctaa agaactggaa aaacaggttg aagaatacaa aaaaaactac    720
```

| | |
|---|---|
| gaaaccctgg aaaaaggtta cgacgacctg gctgaatccc gttccgtttc ccagggttcc | 780 |
| gtttccctgg aactgtacga caaactgtcc gacgaaaacg acatcctgcg tgaaaaacag | 840 |
| gacgaatacc tgaccaaaat cgacggtctg acaaagaaa acaaagaata cgcttcccag | 900 |
| gaatcccaga actcccgttc catcaccaac gaacagctga tcgacaaact ggttgaagaa | 960 |
| aacaacgacc tgaaagaaga acgtgctaaa tacctggacc tgctggacaa ccgtgaaaaa | 1020 |
| gacccgcagt accgtgctct gatgggtgaa gctgaaaaaa aagttgaagt tgctgactcc | 1080 |
| aacgcttcct ccgttgctaa actgtacaac cagatcgctg acctgaccga caaaaacggt | 1140 |
| gaatacctgg aacgtatcga gaactggaaa gaacgtcaga aaacctggaa aaactggaa | 1200 |
| gaaggtgttt ccgttggttc cgacgcttcc ctgcacaacc gtatcaccga cctggaagaa | 1260 |
| gaacgtgaaa aactgctgaa caaactggac aaagttgaag aagaacacaa aaagaccac | 1320 |
| gaacagctgg aaaaaaaatc cgaagacgtt tag | 1353 |

<210> SEQ ID NO 103
<211> LENGTH: 1203
<212> TYPE: DNA
<213> ORGANISM: Artificial Sequence
<220> FEATURE:
<223> OTHER INFORMATION: Polynucleotide encoding a fusion protein of
    group A streptococcus M proteins

<400> SEQUENCE: 103
gacaacccgc gttacaccga cgctcacaac gctgttaccc agggtcgtac cgttccgctg 60
cagaacctgc tgcacgaaat ggacaaaaac ggtaaactgc gttccgaaaa cgaagaactg 120
aaagctgacc tgcagaaaaa agaacaggaa gactcctcct cccgtgacat caccgaagct 180
ggtgtttcca aattctggaa atccaaattc gacgctgaac agaaccgtgc taacgaactg 240
gaaaaaaaac tgtccggtta cgaaaaagac tacaaaaccc tggaacagga atacgaaaac 300
gctggttccg aagaaaacgt tccgaaacag cagtacaacg ctctgtggga agaaaacgaa 360
gacctgcgtg gtcgtgaacg taaatacatc gctaaactgg aaaaagaaga aatccagaac 420
ggtgaactga acgaaaaaaa ccgtaaactg gaatccccgc gtgaagttac caacgaactg 480
gctgcttccg tttggaaaaa aaaagttgaa gaagctaaag aaaaagcttc caaactggaa 540
aaacagctgg aagaagctca gaaagactac tccgaaatcg aaggtaaact ggaacagttc 600
gttgaaaaaa aagttgaagc tgctgaaaac aacgtttcct ccgttgctcg tcgtgaaaaa 660
gaactgtacg accagatcgc tgacctgacc gacaaaaacg gtgaatacct ggaacgtatc 720
ggtgaactgg aagaacgtca gaaaaacctg gacgaccgtt ccgtttccac caactccggt 780
tccgtttcca ccccgtacaa caacctgctg aacgaatacg acgacctgct ggctaaacac 840
ggtgaactgc tgtccgaata cgacgctctg aaagaaaaac aggacaaaaa ccaggaagaa 900
aactccaaaa acccggctcc ggctccggct tccgctgttc cggttaaaaa agaagctacc 960
aaactgtccg aagctgaact gtacaacaaa atccaggaac tggaagaagg taaagctgaa 1020
ctgttcgaca aactggaaaa agttgaagaa gacaacccgc gttacaccga cgctcacaac 1080
gctgttaccc agggtcgtac cgttccgctg cagaacctgc tgcacgaaat ggacaaaaac 1140
ggtaaactgc gttccgaaaa cgaagaactg aaagctgacc tgcagaaaaa agaacaggaa 1200
tag 1203

<210> SEQ ID NO 104
<211> LENGTH: 85
<212> TYPE: PRT

```
<213> ORGANISM: Artificial Sequence
<220> FEATURE:
<223> OTHER INFORMATION: Mrp2 group A streptococcus peptide

<400> SEQUENCE: 104

Glu Thr Val Gly Arg Phe Ser Asp Glu Gln Val Arg Lys Ala Arg Glu
1               5                   10                  15

Lys Ala Ile Glu Asp Val Phe Asp Gly Tyr Thr Gly Ala Arg Ser Val
            20                  25                  30

Tyr Gln Ser Gly Asn Leu Pro Asn Arg Leu Thr Pro Thr Lys Leu Ser
        35                  40                  45

Lys Leu Met Gln Gln Met Tyr Lys Glu Thr Leu Gln Lys Lys Glu Glu
    50                  55                  60

Leu Asp Thr Leu Ser Lys Ala Leu Thr His Thr Ile Glu Lys Lys Ile
65                  70                  75                  80

Glu Ser Glu Asn Ala
                85

<210> SEQ ID NO 105
<211> LENGTH: 84
<212> TYPE: PRT
<213> ORGANISM: Artificial Sequence
<220> FEATURE:
<223> OTHER INFORMATION: stL1929 Streptococcus dysgalactiae subsp.
      Equisimilus peptide

<400> SEQUENCE: 105

Gln Ser Val Gly Arg Phe Asn Glu Asp Gln Ile Arg Glu Ala Arg Asp
1               5                   10                  15

Lys Val Leu Lys Glu Met Phe Asp Asp Tyr Thr Gly Ala Thr Ser Ile
            20                  25                  30

Tyr Asn Ser Asn Gly Tyr Gly Arg Lys Thr Pro Thr Glu Leu Ser Asn
        35                  40                  45

Leu Met Gln Gly Met Tyr Arg Asp Leu Leu Ala Lys Lys Glu Glu Leu
    50                  55                  60

Ser Phe Leu Asn Asp Glu Leu Ser Arg Thr Ile Asp Lys Lys Ile Glu
65                  70                  75                  80

Ser Asp Asn Ala

<210> SEQ ID NO 106
<211> LENGTH: 42
<212> TYPE: PRT
<213> ORGANISM: Artificial Sequence
<220> FEATURE:
<223> OTHER INFORMATION: Mrp2 group A streptococcus peptide

<400> SEQUENCE: 106

Leu Thr Pro Thr Lys Leu Ser Lys Leu Met Gln Gln Met Tyr Lys Glu
1               5                   10                  15

Thr Leu Gln Lys Lys Glu Glu Leu Asp Thr Leu Ser Lys Ala Leu Thr
            20                  25                  30

His Thr Ile Glu Lys Lys Ile Glu Ser Glu
        35                  40

<210> SEQ ID NO 107
<211> LENGTH: 42
<212> TYPE: PRT
<213> ORGANISM: Artificial Sequence
<220> FEATURE:
<223> OTHER INFORMATION: stg1389 Streptococcus dysgalactiae subsp.
      Equisimilus peptide
```

<400> SEQUENCE: 107

Leu Leu Asn Lys Arg Ile Asn Lys Leu Gln Glu Asp Leu Ala Asn Lys
1               5                   10                  15

Glu Gln Glu Ser Lys Glu Thr Ile Asp Thr Leu Asn Lys Ile Leu Asp
            20                  25                  30

Glu Thr Val Lys Asp Lys Ile Ala Lys Glu
        35                  40

<210> SEQ ID NO 108
<211> LENGTH: 50
<212> TYPE: PRT
<213> ORGANISM: Artificial Sequence
<220> FEATURE:
<223> OTHER INFORMATION: Mrp4 group A streptococcus peptide

<400> SEQUENCE: 108

Gln Ala Arg Asp Leu Gly Asp Thr Ile Asn His Met Ser Gln Thr Ile
1               5                   10                  15

Ser Glu Gln Ser Arg Lys Ile Ala Ala Leu Lys Ser Glu Ala Glu Leu
            20                  25                  30

Lys Asn Gln Gln Ala Leu Glu Ala Leu Asn Asn Lys Asn Lys Gln Ile
        35                  40                  45

Ser Asp
    50

<210> SEQ ID NO 109
<211> LENGTH: 50
<212> TYPE: PRT
<213> ORGANISM: Artificial Sequence
<220> FEATURE:
<223> OTHER INFORMATION: stg7882 Streptococcus dysgalactiae subsp.
      Equisimilus peptide

<400> SEQUENCE: 109

Arg Ala Asn Asp Leu Asn Ser Gln Arg Asn His Glu Ile Glu Arg Leu
1               5                   10                  15

Glu Asp Leu Lys Ser Lys Phe Glu Lys Leu Lys Ala His Ser Glu Lys
            20                  25                  30

Tyr Phe Gln Glu Ala Leu Glu Ala Glu Glu Asn Phe Asp Lys Tyr Thr
        35                  40                  45

Ser Asp
    50

<210> SEQ ID NO 110
<211> LENGTH: 75
<212> TYPE: PRT
<213> ORGANISM: Artificial Sequence
<220> FEATURE:
<223> OTHER INFORMATION: Mrp49 group A streptococcus peptide

<400> SEQUENCE: 110

Asp Leu Ser Thr Gln Glu His Pro Arg Val Thr Lys Ala Arg Glu Glu
1               5                   10                  15

Ala Leu Glu Glu Val Leu Arg Ser Trp Asp Tyr Gly Ser Val Lys Ala
            20                  25                  30

Ala Leu Ala Gly Ser Tyr Arg Lys Asn Leu Gln Leu Glu Asn Thr Ile
        35                  40                  45

Lys Gln Lys Asp Lys Glu Leu Ser Phe Leu Ser Lys Val Leu Asp Glu
    50                  55                  60

Ala Ala Lys Lys Tyr Arg Glu Ser Ser Asp Lys
65                  70                  75

<210> SEQ ID NO 111
<211> LENGTH: 75
<212> TYPE: PRT
<213> ORGANISM: Artificial Sequence
<220> FEATURE:
<223> OTHER INFORMATION: stG6792 Streptococcus dysgalactiae subsp.
      equisimilus   peptide

<400> SEQUENCE: 111

Glu Val Lys Ala Glu Glu Asn Glu Arg Leu Arg Gln Ala Lys Glu Gln
1               5                   10                  15

Ala Leu Gln Glu Val Leu Arg Asn Thr Pro Tyr Asp Asp Leu Lys Asn
                20                  25                  30

Ala Tyr Ala Gly Ala Phe Arg Lys Asn Asp Glu Leu Glu Lys Thr Ile
            35                  40                  45

Gln Glu Lys Asn Arg Asp Leu Glu Ser Leu Ser Gln Glu Leu Asp Lys
        50                  55                  60

Thr Val Ser Lys His Ile Glu Ser Ser Asp Lys
65                  70                  75

<210> SEQ ID NO 112
<211> LENGTH: 66
<212> TYPE: PRT
<213> ORGANISM: Artificial Sequence
<220> FEATURE:
<223> OTHER INFORMATION: Mpr49 group A streptococcus peptide

<400> SEQUENCE: 112

Val Thr Lys Ala Arg Glu Glu Ala Leu Glu Glu Val Leu Arg Ser Trp
1               5                   10                  15

Asp Tyr Gly Ser Val Lys Ala Ala Leu Ala Gly Ser Tyr Arg Lys Asn
                20                  25                  30

Leu Gln Leu Glu Asn Thr Ile Lys Gln Lys Asp Lys Glu Leu Ser Phe
            35                  40                  45

Leu Ser Lys Val Leu Asp Glu Ala Ala Lys Lys Tyr Arg Glu Ser Ser
        50                  55                  60

Asp Lys
65

<210> SEQ ID NO 113
<211> LENGTH: 66
<212> TYPE: PRT
<213> ORGANISM: Artificial Sequence
<220> FEATURE:
<223> OTHER INFORMATION: stG643 Streptococcus dysgalactiae subsp.
      equisimilus peptide

<400> SEQUENCE: 113

Ile Glu Lys Ile Arg Glu Glu Ala Leu Lys Glu Val Ile Gly Arg Met
1               5                   10                  15

Asp Tyr Gly Gln Leu Ser Asn Thr Leu Ala Gly Ser Phe Arg Glu Asn
                20                  25                  30

Ser Ala Leu Lys Glu Thr Ile Lys Gln Lys Gly Asp Leu Glu Phe
            35                  40                  45

Leu Ser Gln Glu Leu Asp Lys Thr Val Ser Lys His Ile Glu Ser Ser
        50                  55                  60

Asp Lys
65

<210> SEQ ID NO 114
<211> LENGTH: 46
<212> TYPE: PRT
<213> ORGANISM: Artificial Sequence
<220> FEATURE:
<223> OTHER INFORMATION: M1 group A streptococcus peptide

<400> SEQUENCE: 114

Asn Gly Asp Gly Asn Pro Arg Glu Val Ile Glu Asp Leu Ala Ala Asn
1               5                   10                  15

Asn Pro Ala Ile Gln Asn Ile Arg Leu Arg His Glu Asn Lys Asp Leu
            20                  25                  30

Lys Ala Arg Leu Glu Asn Ala Met Glu Val Ala Gly Arg Asp
        35                  40                  45

<210> SEQ ID NO 115
<211> LENGTH: 60
<212> TYPE: PRT
<213> ORGANISM: Artificial Sequence
<220> FEATURE:
<223> OTHER INFORMATION: stG866 Streptococcus dysgalactiae subsp.
      equisimilus peptide

<400> SEQUENCE: 115

Val Leu Gly Ala Gly Phe Thr Asn Gln Thr Glu Val Lys Ala Asn Glu
1               5                   10                  15

Asn Gly Ser Pro Arg Glu Val Ile Glu Leu Ala Ala Lys Asn Pro
            20                  25                  30

Val Ile Gln Asn Ile Arg Leu Arg Ser Glu Asn Gln Lys Leu Lys Glu
        35                  40                  45

Ser Leu Glu Asn Ala Met Asp Val Ala Gly Arg Asp
    50                  55                  60

<210> SEQ ID NO 116
<211> LENGTH: 43
<212> TYPE: PRT
<213> ORGANISM: Artificial Sequence
<220> FEATURE:
<223> OTHER INFORMATION: M1 group A streptoccus peptide

<400> SEQUENCE: 116

Asn Gly Asp Gly Asn Pro Arg Glu Val Ile Glu Asp Leu Ala Ala Asn
1               5                   10                  15

Asn Pro Ala Ile Gln Asn Ile Arg Leu Arg His Glu Asn Lys Asp Leu
            20                  25                  30

Lys Ala Arg Leu Glu Asn Ala Met Glu Val Ala
        35                  40

<210> SEQ ID NO 117
<211> LENGTH: 60
<212> TYPE: PRT
<213> ORGANISM: Artificial Sequence
<220> FEATURE:
<223> OTHER INFORMATION: stC7505 Streptococcus dysgalactiae subsp.
      Equisimilus peptide

<400> SEQUENCE: 117

Val Ala Val Ala Leu Cys Val Leu Gly Ala Gly Leu Ala Ser Gln Thr
1               5                   10                  15

Glu Val Lys Ala Gln Asp Pro Arg Glu Val Thr Glu Glu Ile Ala Ala
            20                  25                  30

```
Arg Asn Pro Val Val Gln Asn Ile Arg Leu Arg Ser Glu Asn Glu Lys
            35                  40                  45

Leu Lys Ala Ser Leu Glu Asn Ala Ile Asp Ile Ala
    50                  55                  60

<210> SEQ ID NO 118
<211> LENGTH: 48
<212> TYPE: PRT
<213> ORGANISM: Artificial Sequence
<220> FEATURE:
<223> OTHER INFORMATION: M114 group A streptococcus peptide

<400> SEQUENCE: 118

Asn Ser Lys Asn Pro Ala Pro Ala Pro Ala Ser Ala Val Pro Val Lys
1               5                   10                  15

Lys Glu Ala Thr Lys Leu Ser Glu Ala Glu Leu Tyr Asn Lys Ile Gln
            20                  25                  30

Glu Leu Glu Glu Gly Lys Ala Glu Leu Phe Asp Lys Leu Glu Lys Val
        35                  40                  45

<210> SEQ ID NO 119
<211> LENGTH: 60
<212> TYPE: PRT
<213> ORGANISM: Artificial Sequence
<220> FEATURE:
<223> OTHER INFORMATION: stC5345 Streptococcus dysgalactiae subsp.
      Equisimilus peptide

<400> SEQUENCE: 119

Val Ala Leu Thr Val Leu Gly Ala Gly Leu Ala Ser Gly Gln Ile Val
1               5                   10                  15

Lys Ala Asp Ser Ser Asp Val Ala Ile Val Val Gln Pro Gln Ser Ile
            20                  25                  30

Glu Lys Glu Ile Ala Asp Leu Asn Asn Lys Ile Gln Lys Leu Glu Lys
        35                  40                  45

Glu Asn Ser Leu Leu Asn Asp Ser Leu Leu Lys Thr
    50                  55                  60

<210> SEQ ID NO 120
<211> LENGTH: 46
<212> TYPE: PRT
<213> ORGANISM: Artificial Sequence
<220> FEATURE:
<223> OTHER INFORMATION: M118 group A  streptococcus

<400> SEQUENCE: 120

Ala Glu Lys Lys Val Glu Val Ala Asp Ser Asn Ala Ser Ser Val Ala
1               5                   10                  15

Lys Leu Tyr Asn Gln Ile Ala Asp Leu Thr Asp Lys Asn Gly Glu Tyr
            20                  25                  30

Leu Glu Arg Ile Glu Glu Leu Glu Glu Arg Gln Lys Asn Leu
        35                  40                  45

<210> SEQ ID NO 121
<211> LENGTH: 60
<212> TYPE: PRT
<213> ORGANISM: Artificial Sequence
<220> FEATURE:
<223> OTHER INFORMATION: stG866 Streptococcus dysgalactiae subsp.
      Equisimilus peptide

<400> SEQUENCE: 121

Asn Glu Asn Gly Ser Pro Arg Glu Val Ile Glu Glu Leu Ala Ala Lys
```

```
                1               5                  10                 15
Asn Pro Val Ile Gln Asn Ile Arg Leu Arg Ser Glu Asn Gln Lys Leu
            20                  25                  30

Lys Glu Ser Leu Glu Asn Ala Met Asp Val Ala Gly Arg Asp Phe Lys
        35                  40                  45

Arg Ala Glu Glu Leu Glu Lys Ala Lys Gln Asp Leu
    50                  55                  60

<210> SEQ ID NO 122
<211> LENGTH: 37
<212> TYPE: PRT
<213> ORGANISM: Artificial Sequence
<220> FEATURE:
<223> OTHER INFORMATION: M12 group A streptococcus peptide

<400> SEQUENCE: 122

Asp His Ser Asp Leu Val Ala Glu Lys Gln Arg Leu Glu Asp Leu Gly
1               5                   10                  15

Gln Lys Phe Glu Arg Leu Lys Arg Ser Glu Leu Tyr Leu Gln Gln
            20                  25                  30

Tyr Tyr Asp Asn Lys
        35

<210> SEQ ID NO 123
<211> LENGTH: 60
<212> TYPE: PRT
<213> ORGANISM: Artificial Sequence
<220> FEATURE:
<223> OTHER INFORMATION: stG7882 Streptococcus dysgalactiae subsp.
      Equisimilus peptide

<400> SEQUENCE: 123

Ser Val Ala Val Ala Leu Thr Val Leu Gly Ala Gly Leu Val Ala Gly
1               5                   10                  15

Gln Thr Val Arg Ala Asn Asp Leu Asn Ser Gln Arg Asn His Glu Ile
            20                  25                  30

Glu Arg Leu Glu Asp Leu Lys Ser Lys Phe Glu Lys Leu Lys Ala His
        35                  40                  45

Ser Glu Lys Tyr Phe Gln Glu Ala Leu Glu Ala Glu
    50                  55                  60

<210> SEQ ID NO 124
<211> LENGTH: 42
<212> TYPE: PRT
<213> ORGANISM: Artificial Sequence
<220> FEATURE:
<223> OTHER INFORMATION: M3 group A streptoccocus peptide

<400> SEQUENCE: 124

Asp Ala Arg Ser Val Asn Gly Glu Phe Pro Arg His Val Lys Leu Lys
1               5                   10                  15

Asn Glu Ile Glu Asn Leu Leu Asp Gln Val Thr Gln Leu Tyr Thr Lys
            20                  25                  30

His Asn Ser Asn Tyr Gln Gln Tyr Asn Ala
        35                  40

<210> SEQ ID NO 125
<211> LENGTH: 60
<212> TYPE: PRT
<213> ORGANISM: Artificial Sequence
<220> FEATURE:
<223> OTHER INFORMATION: stG211 Streptococcus dysgalactiae subsp.
```

Equisimilus peptide

<400> SEQUENCE: 125

```
Gly Ala Leu Ser Val Leu Gly Ala Gly Leu Val Ala Gly Gln Thr Val
1               5                   10                  15

Lys Ala Asp Val Gly Asn Val Asn Gly Glu Tyr His Arg His Thr Lys
            20                  25                  30

Leu Lys Ser Glu Ile Glu Asp Leu Leu Asp Gln Val Thr Glu Leu Tyr
        35                  40                  45

Ser Thr His Asn His Asn Tyr Gln Arg Tyr Asp Ser
    50                  55                  60
```

<210> SEQ ID NO 126
<211> LENGTH: 25
<212> TYPE: PRT
<213> ORGANISM: Artificial Sequence
<220> FEATURE:
<223> OTHER INFORMATION: M6 group A streptococcus peptide

<400> SEQUENCE: 126

```
Arg Val Phe Pro Arg Gly Thr Val Glu Asn Pro Asp Lys Ala Arg Glu
1               5                   10                  15

Leu Leu Asn Lys Tyr Asp Val Glu Asn
            20                  25
```

<210> SEQ ID NO 127
<211> LENGTH: 60
<212> TYPE: PRT
<213> ORGANISM: Artificial Sequence
<220> FEATURE:
<223> OTHER INFORMATION: stC9431 Streptococcus dysgalactiae subsp.
      Equisimilus peptide

<400> SEQUENCE: 127

```
Ala Ser Val Ala Val Ala Leu Ser Val Leu Gly Ala Gly Leu Val Val
1               5                   10                  15

Asn Thr Asn Glu Val Ser Ala Arg Val Tyr Thr Arg Ser Val Val Asn
            20                  25                  30

Asn Pro Glu Lys Ala Arg Glu Leu Ile Tyr Lys Leu Asp Ser Glu Val
        35                  40                  45

Ile Ala Leu Glu Lys Glu Lys Glu Ser Leu Asn Lys
    50                  55                  60
```

UNITED STATES PATENT AND TRADEMARK OFFICE
CERTIFICATE OF CORRECTION

PATENT NO.        : 9,650,425 B2
APPLICATION NO.   : 14/178021
DATED             : May 16, 2017
INVENTOR(S)       : James B. Dale et al.

It is certified that error appears in the above-identified patent and that said Letters Patent is hereby corrected as shown below:

In the Claims

Column 174, Line 55:
"(f) a polypeptide consisting of least about 20 to about 50" should read, --(f) a polypeptide consisting of at least about 20 to about 50--.

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*